US012773692B2

(12) United States Patent
Johnson et al.

(10) Patent No.: US 12,773,692 B2
(45) Date of Patent: Oct. 27, 2026

(54) SELF-CONTAINED NUCLEIC ACID PROCESSING

(71) Applicants: BioFire Diagnostics, LLC., Salt Lake City, UT (US); BioFire Defense, LLC., Salt Lake City, UT (US)

(72) Inventors: Kyle K. Johnson, Eagle Mountain, UT (US); Owen D. Brimhall, South Jordan, UT (US); Jonathan J. Politis, Riverton, UT (US)

(73) Assignees: BIOFIRE DIAGNOSTICS, LLC, Salt Lake City, UT (US); BIOFIRE DEFENSE, LLC, Salt Lake City, UT (US)

( * ) Notice: Subject to any disclaimer, the term of this patent is extended or adjusted under 35 U.S.C. 154(b) by 1057 days.

(21) Appl. No.: 17/372,082

(22) Filed: Jul. 9, 2021

(65) Prior Publication Data

US 2022/0055033 A1 Feb. 24, 2022

Related U.S. Application Data

(63) Continuation of application No. 15/769,044, filed as application No. PCT/US2017/044333 on Jul. 28, 2017, now Pat. No. 11,090,652.

(Continued)

(51) Int. Cl.
*B01L 3/00* (2006.01)
*B01L 7/00* (2006.01)
(Continued)

(52) U.S. Cl.
CPC ......... *B01L 3/502738* (2013.01); *B01L 3/527* (2013.01); *B01L 7/525* (2013.01); *C12N 1/066* (2013.01); *C12Q 1/6806* (2013.01); *B01L 2200/027* (2013.01); *B01L 2200/0621* (2013.01); *B01L 2200/0647* (2013.01); *B01L 2200/14* (2013.01); *B01L 2300/044* (2013.01); *B01L 2300/0627* (2013.01); *B01L 2300/0861* (2013.01); *B01L 2300/1822* (2013.01);
(Continued)

(58) Field of Classification Search
None
See application file for complete search history.

(56) References Cited

U.S. PATENT DOCUMENTS

| | | | |
|---|---|---|---|
| 3,286,939 | A | 11/1966 | Karpenko et al. |
| 5,557,154 | A | 9/1996 | Erhart |

(Continued)

FOREIGN PATENT DOCUMENTS

| | | | |
|---|---|---|---|
| JP | H07284679 | A | 10/1995 |
| JP | 2004535200 | A | 11/2004 |

(Continued)

OTHER PUBLICATIONS

Carley et al. Choosing the Right Camshaft for a performance engine import car, 2013.

(Continued)

*Primary Examiner* — Maris R Kessel
*Assistant Examiner* — Mickey Huang
(74) *Attorney, Agent, or Firm* — Kenneth E. Horton; Barnes & Thornburg LLP

(57) ABSTRACT

Instruments and methods for amplifying nucleic acids in a sample provided in a flexible, self-contained, substantially closed sample container.

16 Claims, 59 Drawing Sheets

Related U.S. Application Data

(60) Provisional application No. 62/508,163, filed on May 18, 2017, provisional application No. 62/368,095, filed on Jul. 28, 2016.

(51) Int. Cl.
*C12N 1/066* (2026.01)
*C12Q 1/6806* (2018.01)

(52) U.S. Cl.
CPC .................. *B01L 2300/1827* (2013.01); *B01L 2400/0481* (2013.01); *B01L 2400/0683* (2013.01)

(56) References Cited

U.S. PATENT DOCUMENTS

| | | | | |
|---|---|---|---|---|
| 7,972,315 | B2 | 7/2011 | Birk et al. | |
| 10,413,905 | B2 | 9/2019 | Ririe | |
| 2004/0209331 | A1 | 10/2004 | Ririe | |
| 2006/0178646 | A1 | 8/2006 | Harris et al. | |
| 2010/0056383 | A1 | 3/2010 | Ririe et al. | |
| 2010/0285578 | A1 | 11/2010 | Selden et al. | |
| 2013/0137172 | A1 | 5/2013 | Ririe et al. | |
| 2014/0194305 | A1 | 7/2014 | Kayyem et al. | |
| 2014/0263945 | A1 | 9/2014 | Huang et al. | |
| 2014/0283945 | A1 | 9/2014 | Jones et al. | |
| 2015/0099291 | A1* | 4/2015 | Ririe | B01L 3/50273 435/287.2 |
| 2015/0141291 | A1* | 5/2015 | Zhou | G01N 35/10 435/6.12 |
| 2015/0308931 | A1* | 10/2015 | Toogood | B01L 7/00 435/7.1 |
| 2015/0346097 | A1* | 12/2015 | Battrell | G01N 21/6428 702/19 |
| 2016/0138010 | A1* | 5/2016 | Yu | G01N 35/0098 435/309.1 |

FOREIGN PATENT DOCUMENTS

| | | | |
|---|---|---|---|
| JP | 2007216103 | A | 8/2007 |
| JP | 2008083018 | A | 4/2008 |
| JP | 2010509918 | A | 4/2010 |
| JP | 2014533176 | A | 12/2014 |
| WO | 2017165269 | A1 | 9/2017 |

OTHER PUBLICATIONS

International Search Report and Written Opinion for corresponding International Application No. PCT/US2017/044333, 28 pages (Dec. 4, 2017).

Sessitsch, A., et al. (2002). RNA isolation from soil for bacterial community and functional analysis: evaluation of different extraction and soil conservation protocols. Journal of Microbiological Methods, 51(2), 171-179. doi: 10.1016/s0167-7012(02)00065-9.

* cited by examiner

SELF-CONTAINED NUCLEIC ACID PROCESSING

RELATED APPLICATIONS

This is a continuation of U.S. Utility patent application Ser. No. 15/769,044, filed Apr. 17, 2018 and entitled Self-Contained Nucleic Acid Processing, which is a National Stage Application of PCTUS2017044333, filed Jul. 28, 2017 and entitled Self-Contained Nucleic Acid Processing, which claims the benefit of and priority to U.S. Prov. App. Ser. No. 62/368,095, filed Jul. 28, 2016, and U.S. Prov. App. Ser. No. 62/508,163, filed May 18, 2017, the entireties of which are incorporated by reference herein.

GOVERNMENT INTEREST

This invention was made with government support under W911QY-13-D-0080 awarded by the U.S. Department of Defense. The government has certain rights in the invention.

BACKGROUND

1. Technical Field

Embodiments of the present disclosure relate generally to methods and devices for extraction and amplification of nucleic acids from a sample.

2. Background

In the United States, Canada, and Western Europe infectious disease accounts for approximately 7% of human mortality, while in developing regions infectious disease accounts for over 40% of human mortality. Infectious diseases lead to a variety of clinical manifestations. Among common overt manifestations are fever, pneumonia, meningitis, diarrhea, and diarrhea containing blood. While the physical manifestations suggest some pathogens and eliminate others as the etiological agent, a variety of potential causative agents remain, and clear diagnosis often requires a variety of assays be performed. Traditional microbiology techniques for diagnosing pathogens can take days or weeks, often delaying a proper course of treatment.

In recent years, the polymerase chain reaction (PCR) has become a method of choice for rapid diagnosis of infectious agents. PCR can be a rapid, sensitive, and specific tool to diagnose infectious disease. A challenge to using PCR as a primary means of diagnosis is the variety of possible causative organisms or viruses and the low levels of organism or virus present in some pathological specimens. It is often impractical to run large panels of PCR assays, one for each possible causative organism or viruses, most of which are expected to be negative. The problem is exacerbated when pathogen nucleic acid is at low concentration and requires a large volume of sample to gather adequate reaction templates. In some cases there is inadequate sample to assay for all possible etiological agents. A solution is to run "multiplex PCR" wherein the sample is concurrently assayed for multiple targets in a single reaction. While multiplex PCR has proved to be valuable in some systems, shortcomings exist concerning robustness of high level multiplex reactions and difficulties for clear analysis of multiple products. To solve these problems, the assay may be subsequently divided into multiple secondary PCRs. Nesting secondary reactions within the primary product increases robustness. Closed systems such as the FilmArray® (BioFire Diagnostics, LLC, Salt Lake City, UT) reduce handling, thereby diminishing contamination risk.

Sample preparation is needed for many sample types in many amplification systems. Sample preparation is often a balance between harsh extraction and lysing conditions for releasing nucleic acids from tougher materials such as spores and paraffin preserved samples, and gentler lysing conditions that may minimize nucleic acid degradation, particularly in contaminants that lyse more easily and have longer chromosomes. It would be desirable to be able to extract nucleic acids from tougher materials without degrading other nucleic acids that may be present in the sample.

The present invention addresses various improvements relating to preparation of a sample and for processing and detecting nucleic acids in that sample.

BRIEF SUMMARY

Disclosed herein are instruments and methods for amplifying nucleic acids in a sample provided in a flexible, self-contained, substantially closed sample container. In one aspect, the sample container includes a loading attachment that includes a sample zone and a plurality of reagent zones in fluid communication with one or more sealable flow paths. In one embodiment, the sealable flow paths are connected to exterior loading ports that facilitate loading of sample and a rehydration solution into the loading attachment. The sealable flow paths providing the only access from an exterior of the container to the sample zone and the plurality of reagent zones such that when all of the one or more sealable paths are sealed, the container is fully closed. The loading attachment of the sample container includes a sample loading zone and a reagent loading zone in fluid connection with a plurality of fluidly connected reaction zones. The plurality of fluidly connected reaction zones include a first plurality of reaction blisters, a second plurality of reaction blisters, and a plurality of sealable channels fluidly connecting first and second pluralities of reaction blisters. The plurality of sealable channels are divided into a first plurality of channels and a second plurality of channels. In one aspect, an instrument for amplifying nucleic acids in a sample includes a first support member and a second support member, and an opening for receiving a sample container between the first and second support members.

In one embodiment, the instrument includes a seal bar positioned and configured in the instrument for heat sealing the one or more sealable flow paths such that the container may be sealed from the exterior of the container. In one aspect, the seal bar includes a number of individually controlled heater elements associated with each of the one or more sealable flow paths and the sample zone and the plurality of reagent zones.

In one embodiment, the instrument includes a plunging system including a plurality of mechanically actuated pistons positioned and configured in the instrument for moving sample and reagents from the sample and reagent zones into the fluidly connected reaction zones.

In one embodiment, the sample container further includes a quantity of lysis beads in a lysis blister and the instrument includes a bead milling component including a drive motor and three or more beater elements that are positioned and configured in the instrument for contacting the lysis blister for generating a lysate in the lysis blister.

In one embodiment, the sample container further includes a quantity of magnetic beads configured for recovery of a nucleic acid from the lysate and the instrument further includes a moving magnet system including a drive system for moving a magnet on a defined path between at least the lysis blister and a downstream nucleic acid recovery blister for recovery and isolation of the magnetic beads from the lysate. Likewise, the moving magnet system is configured for recovery and isolation of the magnetic beads for washing of the magnetic beads to remove debris from the lysate and for elution of the recovered nucleic acids from the beads. In one embodiment, the drive system for the magnet may include a drive motor, a holder for the magnet, and other optional components such as, but not limited to, one or more position sensors for sensing the position of the magnet relative to the sample container and drive control systems (e.g., system firmware) for controlling the position of the magnet relative to the sample container.

In one embodiment, the instrument includes a plurality of compression members and a plurality of seal members provided on at least one of the support members. The compression members are associated with the reaction zones, and the seal members are associated with the channels connecting the reaction zones. In one embodiment, the compression members and the seal members are configured to work together to provide directional movement of fluid between the fluidly connected reaction zones. In one embodiment the compression members include a first set of mutually actuated compression members associated with the first plurality of reaction blisters, and a second set of mutually actuated compression members associated with the second plurality of reaction blisters. In one embodiment, the plurality of seal members include a first set and a second set of coupled but individually actuatable seals. In one embodiment, each seal of the first set being downstream of a reaction blister of the first plurality and upstream of a reaction blister of the second plurality, and each seal of the second set being downstream of a reaction blister of the second plurality and upstream of a reaction blister of the first plurality.

In one embodiment, the instrument includes at least one heater configured for performing a first thermal cycling reaction in one of the reaction zones and at least one additional heater configured for performing a second, downstream thermal cycling reaction in another one of the reaction zones.

In one embodiment, the instrument includes an optical array configured for exciting and recording fluorescence in at least one area of the container.

In another embodiment, a method for nucleic acid extraction from a sample is described. The method includes (1) placing the sample in a cell lysis zone, (2) bead milling the sample in the lysis zone for a first period of time to release a first portion of nucleic acids that may be present in the sample, (3) capturing the first portion of nucleic acids and storing the captured nucleic acids in a nucleic acid extraction zone, (3) bead milling the sample in the lysis zone for a second period of time to release a second portion of nucleic acids that may be present in the sample, and (4) capturing the second portion of nucleic acids and storing the captured nucleic acids in the nucleic acid extraction zone. In one embodiment, the method further includes (5) bead milling the sample in the lysis zone for a third period of time to release a third portion of nucleic acids that may be present in the sample, and (6) capturing the third portion of nucleic acids and storing the captured nucleic acids in the nucleic acid extraction zone.

In another embodiment, a container for conducting a reaction is described. The container includes a flexible material defining a plurality of fluidly connected zones therein, the zones fluidly connected by channels, wherein at least a first zone includes a plurality of beads contained therein, and a second zone does not contain any beads therein, a port configured to receive a sample, and a filter element in one or more of the plurality of channels, wherein the filter element is configured to prevent the beads from proceeding through the channel and into the adjacent zone. In one embodiment, the flexible material comprises at least two layers of flexible material bonded together.

In another embodiment, an instrument for amplifying nucleic acids in a sample is described. The instrument includes an opening having a first side and a second side, the opening for receiving a closed reaction container between the first side and the second side, wherein the container is configured for nucleic acid amplification. The container includes a plurality of fluidly connected reaction zones, the reaction zones including a lysis zone comprising a plurality of lysis beads and a downstream nucleic acid amplification zone. The instrument further includes at least one compression member associated with the lysis zone provided at one of the sides, and a bead milling component provided at one of the sides, wherein the bead milling component includes a drive motor and three or more beater elements that are positioned and configured in the instrument for contacting the lysis zone for generating a lysate.

In another embodiment, a method for nucleic acid amplification using the foregoing instrument in described. The method includes (1) providing the closed reaction container containing a sample to be analyzed and a plurality of reagents, (2) bead milling the sample in the lysis zone for a period of time to release a portion of nucleic acids that may be present in the sample, wherein the bead milling includes bead milling the sample with the bead milling device while pulsing the sample with the compression member associated with the lysis zone, (3) recovering nucleic acids released from the sample, (4) washing nucleic acids, and (5) performing a PCR reaction. In one embodiment, the method further includes recovering the nucleic acids from the sample in the lysis zone using a quantity of magnetic beads provided in the closed reaction container and a moving magnet system, wherein the method further includes: dispersing the magnetic beads in the lysate, sweeping the moving magnet adjacent to the lysis zone to recover the magnetic beads, and compressing the lysis zone with the compression member associated with the lysis zone to flush the magnetic beads to the downstream nucleic acid recovery zone.

In another embodiment, an instrument for processing a sample is described. The instrument includes a first support member and a second support member, an opening for receiving a flexible reaction container between the first support member and the second support member, wherein the container is configured for receiving the sample. In one embodiment, the container includes a loading attachment that includes a sample zone and a plurality of reagent zones, and a plurality of fluidly connected reaction zones. The instrument further includes a plunging system including a plurality of mechanically actuated pistons positioned and configured in the instrument for moving the sample and reagents from the loading attachment and into the fluidly connected reaction zones.

In another embodiment an instrument for measuring fluorescence in a sample is described. The instrument includes a first support member and a second support member an opening for receiving a container between the first and second support members. In one embodiment, the container includes a plurality of fluidly connected zones comprising a sample processing zone and a reaction zone, the zones being defined by two flexible membranes positioned substantially parallel to one another, a plurality of channels connecting the zones, and one or more sealable ports fluidly connected to the zones, the sealable ports providing the only access from an exterior of the container to the zones such that when all of the one or more sealable ports is sealed, the container is fully closed. The instrument further includes a heating/cooling device provided at one of the first or second supports, the heating/cooling device configured for controlling temperature of contents of the reaction zone, an optics system mounted in the instrument and positioned to produce and detect fluorescence in the reaction zone, and a window bladder associated with the reaction zone and the optics system, wherein the window bladder comprises an optically clear window comprised of a first layer and a second layer of material bonded together on an edge of each layer to form an inflatable envelope between the two layers, and a nipple fluidly connected to a compressed gas source, wherein the first support member and the second support member are separable such that the nipple is user accessible and the window bladder is user replaceable.

In another embodiment, an instrument for amplifying nucleic acids in a sample is described. The instrument includes an opening for receiving a container that includes a plurality of fluidly connected reaction zones including a lysis zone, an extraction zone, and an amplification zone, and one or more sealable ports fluidly connected to the reaction zones, the sealable ports providing the only access from an exterior of the container to the reaction blisters such that when all of the one or more sealable ports is sealed, the container is fully closed, and a plurality of heaters, wherein each of the heaters is configured to be set at a different temperature, and wherein the heaters are positioned on a movable mount such that each heater is configured to move sequentially into position to apply heat to a reaction zone.

In another embodiment, an instrument for processing a sample is described. The instrument includes a first support member and a second support member, an opening for receiving a closed reaction container between the first support member and the second support member. The container includes a plurality of fluidly connected reaction zones comprising a first plurality of reaction blisters and a second plurality of reaction blisters, and a plurality of sealable channels fluidly connecting the reaction zones, wherein the plurality of sealable channels includes a first plurality of channels and a second plurality of channels. The instrument includes a plurality of compression members provided on at least one of the support members, the compression members including a first set of mutually actuated compression members associated with the first plurality of reaction blisters, and a second set of mutually actuated compression members associated with the second plurality of reaction blisters, a plurality of seal members provided on at least one of the support members, wherein the seal members are associated with the channels connecting the reaction zones, wherein activation of the compression members provides directional movement of fluid between the fluidly connected reaction zones.

In another embodiment, an instrument for processing a sample is described. The instrument includes a first support member and a second support member and an opening for receiving a flexible reaction container between the first support member and the second support member. The container includes a loading attachment that includes a sample zone and a plurality of reagent zones, a plurality of fluidly connected reaction zones, and one or more sealable flow paths having a first side connecting the loading attachment to one or more fill ports and a second side connected to the plurality of fluidly connected reaction zones, the sealable flow paths providing the only access from the one or more fill ports to the sample zone and the plurality of reagent zones such that when the first side of all of the one or more sealable paths are sealed, the container is fully closed. The instrument further includes a plurality of heat seal elements provided on at least one of the support members so as to contact the loading attachment and the one or more sealable flow paths, wherein the heat seal elements include a number of individually controlled heater elements associated with each of the first side of the one or more sealable flow paths.

In another embodiment, an instrument for processing nucleic acids in a sample is described. The instrument includes a first support member and a second support member and an opening for receiving a closed reaction container between the first support member and the second support member. The container includes a plurality of fluidly connected reaction zones, the reaction zones including a lysis zone comprising a plurality of lysis beads, and a nucleic acid recovery zone, and the container is provided with nucleic acid-binding magnetic beads therein. The instrument further includes a bead milling component provided on at least one of the support members for generating a lysate in the lysis blister, and a moving magnet component provided on at least one of the support members, wherein the moving magnet component may include a holder, a driver, and other components such as, but not limited to, one or more position sensors for sweeping a magnet between at least the lysis zone and the nucleic acid recovery zone.

In another embodiment, a bead beating instrument for preparing a sample lysate is described. In one embodiment, the bead beating instrument includes an opening for receiving a flexible sample container containing a fluid sample between a first between a first support member and a second support member, and a bead milling component associated with the first or second support member. In one embodiment, the bead milling component includes a reciprocating drive member operatively coupled to at least two alternating paddle elements that extend from the first or second support member to repeatedly and serially contact the flexible sample container to generate a lysate from the sample.

In another embodiment, an instrument for amplifying nucleic acids in a sample is described. The instrument includes an opening for receiving a container that includes a plurality of fluidly connected reaction zones including a lysis zone, an extraction zone, and an amplification zone, and one or more sealable ports fluidly connected to the reaction zones, a bead milling component comprising a reciprocating drive member operatively coupled to at least two alternating paddle elements that repeatedly and serially contact the lysis zone to generate a lysate from the sample, an extraction zone for extracting the nucleic acids from the lysate in the extraction zone, and moving the extracted nucleic acids to the amplification blister, and a heater positioned for controlling temperature of the nucleic acids in the amplification zone. In one embodiment, the at least two paddles are sized and positioned contact substantially the entire lysis zone. In one embodiment, one or more of the paddles comprise a temperature control element. In one embodiment, the at least two paddles are configured to extend together to plunge fluid from the lysis zone.

1. An instrument for processing a sample in a reaction container, comprising a first support member and a second support member;

an opening for receiving the reaction container between the first support member and the second support member, the container comprising:

a plurality of fluidly connected reaction zones comprising a first plurality of reaction blisters and a second plurality of reaction blisters, the reaction blisters being configured for cell lysis, nucleic acid recovery, and at least one nucleic acid amplification reaction in the closed reaction container;

a plurality of sealable channels fluidly connecting the reaction zones, wherein the plurality of sealable channels includes a first plurality of channels and a second plurality of channels;

a plurality of compression members extendable from at least one of the support members, the compression members including:

a first set of mutually actuated compression members associated with the first plurality of reaction blisters, and a second set of mutually actuated compression members associated with the second plurality of reaction blisters;

a plurality of seal members extendable from at least one of the support members, wherein the seal members are associated with the channels connecting the reaction zones, wherein actuation of the compression members and the seal members provides directional movement of fluid between the fluidly connected reaction zones.

2. The instrument of clause 1, wherein the plurality of seal members are coupled to a drive cam that includes actuation members at a plurality of angular positions on the drive cam for releasing or activating each of the seal members.

3. The instrument of clause 1 and/or 2, wherein the actuation members are positioned on the drive cam for releasing or activating zero, one, or two or more seal members at each angular position.

4. The instrument of any of clauses 1-3, wherein each seal member is individually released.

5. The instrument of any of clauses 1-4, wherein the first plurality of reaction blisters are arranged in a first row and the second plurality of reaction blisters are arranged in a second row.

6. The instrument of any of clauses 1-5, wherein the reaction blisters of the first row and the reaction blisters of the second row are connected via the sealable channels in a zig-zag fashion relative to one another.

7. The instrument of any of clauses 1-6, wherein the first set of mutually actuated compression members are configured to provide directional movement of fluid between at least one of the plurality of first row blisters and at least one of the plurality of second row blisters, and the second set of mutually actuated compression members are configured to provide directional movement of fluid between at least one of the plurality of second row blisters and at least one of the plurality of first row blisters.

8. The instrument of any of clauses 1-7, wherein the first and second pluralities of channels fluidly connect the first row and the second row of reaction blisters so that fluid can flow between the first row and the second row of reaction blisters.

9. The instrument of any of clauses 1-8, wherein the first set of compression members moves fluid from one blister of the first plurality of reaction blisters to one blister of the second plurality of reaction blisters by compressing all of the first plurality of reaction blisters substantially simultaneously.

10. The instrument of any of clauses 1-9 wherein release of one or more selected seal members permits fluid to flow from the first blister of the first plurality of reaction blisters to the one blister of the second plurality of reaction blisters, and wherein one or more selected seal members that are not released prevents the fluid from flowing into another blister of the first plurality of reaction blisters.

11. The instrument of any of clauses 1-10, wherein the second set of compression members moves fluid from a one blister of the second plurality of reaction blisters to a blister of the first set of reaction members by compressing each of the second plurality of reaction blisters substantially simultaneously.

12. The instrument of any of clauses 1-11, wherein when one or more selected seal members are released fluid can flow from the one blister of the second plurality of reaction blisters to one or more of the blisters of the first plurality of reaction blisters, and one or more selected seal members are not released so that the fluid cannot flow into other blisters of the first plurality of reaction blisters.

13. The instrument of any of clauses 1-12, wherein the first set of mutually actuated compression members and the second set of mutually actuated compression members are spring driven for compressing the reaction blisters and are coupled to a drive cam that includes actuation members at a plurality of angular positions on the drive cam for separately actuating the first set of mutually actuated compression members and the second set of mutually actuated compression members.

14. The instrument of any of clauses 1-13, wherein compression of the reaction blisters is driven by a drive cam coupled to the first set of mutually actuated compression members and the second set of mutually actuated compression members, and the compression members further comprise position sensors and a feedback control system for controlling actuation of the first set of mutually actuated compression members and the second set of mutually actuated compression members.

15. The instrument of any of clauses 1-14, further comprising a bead milling component including a drive motor and a beater element that is positioned and configured in the instrument for contacting a portion of the closed reaction container for generating a lysate from the sample.

16. The instrument of any of clauses 1-15, further comprising a magnet system for recovery and isolation of a quantity of magnetic beads provided in one or more reaction blisters of the reaction container, wherein the magnetic beads are used for nucleic acid recovery in the reaction container.

17. The instrument of any of clauses 1-16, further comprising at least one heater positioned in the instrument to contact one or more reaction blisters of the reaction container, wherein the at least one heater is configured for performing a thermal cycling reaction in the reaction container.

18. The instrument of any of clauses 1-17, further comprising an optical array positioned in the instrument and configured for exciting fluorescence in one or more reaction blisters of the reaction container and for recording fluorescence from the one or more reaction blisters of the reaction container.

19. The instrument of any of clauses 1-18 wherein one of the first support member and the second support member comprises a door that may be opened for receiving the closed reaction container therebetween.

20. The instrument of any of clauses 1-19, further comprising a computing device configured for controlling the compression members and the seal members.

21. A bead beating instrument for preparing a sample lysate, comprising an opening for receiving a flexible sample container containing a fluid sample between a first between a first support member and a second support member, a bead milling component associated with the first or second support member, the bead milling component comprising a reciprocating drive member operatively coupled to at least two alternating paddle elements that extend from the first or second support member to repeatedly and serially contact the flexible sample container to generate a lysate from the sample.

22. The bead beating instrument of clause 21 wherein the reciprocating drive member comprises a motor driven cam shaft with at least two off-center drive lobes mechanically coupled to the at least two paddles.

23. The bead beating instrument clause 21 and/or 22 wherein the cam shaft comprises bearing members that contact the paddles.

24. The bead beating instrument any of clauses 21-23 wherein the paddles each comprise a cam follower that contacts a corresponding off-center drive lobe of the cam shaft.

25. The bead beating instrument of any of clauses 21-24 the reciprocating drive member comprising a mechanical actuator associated with each paddle, wherein the mechanical actuator extends to extend the associated paddle.

26. The bead beating instrument of any of clauses 21-25 wherein each paddle includes a biasing member positioned and configured to bias each paddle toward or away from the lysis zone.

27. The bead beating instrument of any of clauses 21-26 wherein the at least two paddles are sized and positioned contact substantially the entire flexible sample container.

28. The bead beating instrument of any of clauses 21-27 wherein the fluid sample comprises a quantity of zirconium lysis beads.

29. The bead beating instrument of any of clauses 21-28, wherein the opening is further comprised to receive a container that includes a plurality of fluidly connected reaction zones including a lysis zone, an extraction zone for extraction of nucleic acids from a lysate produced in the lysis zone, a nucleic acid amplification zone, and one or more sealable ports fluidly connected to the reaction zones.

30. The bead beating instrument of any of clauses 21-29, further comprising a heater positioned for controlling temperature of a nucleic acid amplification zone.

31. The bead beating instrument of any of clauses 21-30, further comprising a magnet system for recovery and isolation of a quantity of magnetic beads provided in the container, wherein the magnetic beads are configured for recovery of nucleic acids from the lysate in the container.

32. The bead beating instrument of any of clauses 21-31, further comprising an optical array configured for exciting and recording fluorescence in at least one area of the flexible sample container.

33. The bead beating instrument of any of clauses 21-32, further comprising a computing device.

34. An instrument for amplifying nucleic acids in a sample, comprising an opening for receiving a container, the container comprising a plurality of fluidly connected reaction zones including a lysis zone, an extraction zone, and an amplification zone, and one or more sealable ports fluidly connected to the reaction zones, the sealable ports providing the only access from an exterior of the container to the reaction blisters such that when all of the one or more sealable ports is sealed, the container is fully closed, a bead milling component for generating a lysate in the lysis blister, an extraction zone for extracting the nucleic acids from the sample in the extraction zone, and moving the extracted nucleic acids to the amplification blister, and a heater positioned for controlling temperature of the nucleic acids in the amplification zone.

35. The instrument of clause 34 wherein the bead milling component is a motor driving a housing including plurality of bearings located in the housing, such that when the motor is activated, the plurality of bearings are forced axially to contact the lysis zone.

36. The instrument of clause 34 and/or 35 wherein the bearings are spring loaded.

37. The instrument of any of clauses 34-36 wherein the bead milling component is a motor driving at least three beater bars.

38. The instrument of any of clauses 34-37 further comprising a barrier between the container and the bead milling component, wherein the barrier comprises a flexible membrane.

39. The instrument of any of clauses 34-38 wherein each of the one or more sealable ports is in communication with a loading attachment, the loading attachment comprising a loading cylinder, an opening defined by a rim of the loading cylinder, a clip for attaching the loading attachment to the sealable port, and a hollow, beveled needle in connection with the loading cylinder.

40. The instrument of clause 39 wherein the beveled needle further comprises a blunted heel.

41. The instrument of any of clauses 39-40 wherein the beveled needle is configured for insertion into the sealable port upon attachment using the attaching clip.

42. The instrument of any of clauses 34-41 wherein the bead milling component comprises a reciprocating drive member operatively coupled to at least two alternating paddle elements that extend from the first or second support member to repeatedly and serially contact the flexible sample container to generate a lysate from the sample.

43. A method for nucleic acid extraction from a sample comprising:

placing the sample in a cell lysis zone, bead milling the sample in the lysis zone for a first period of time to release a first portion of nucleic acids that may be present in the sample, capturing the first portion of nucleic acids and storing the captured nucleic acids in a nucleic acid extraction zone, bead milling the sample in the lysis zone for a second period of time to release a second portion of nucleic acids that may be present in the sample, and capturing the second portion of nucleic acids and storing the captured nucleic acids in the nucleic acid extraction zone.

44. The method of clause 43, further comprising:

bead milling the sample in the lysis zone for a third period of time to release a third portion of nucleic acids that may be present in the sample, and capturing the third portion of nucleic acids and storing the captured nucleic acids in the nucleic acid extraction zone.

45. The method of clause 43 and/or 44, wherein the cell lysis zone and the nucleic acid zone are chambers within a sealed container.

46. A container for conducting a reaction, the container comprising:

a flexible material comprising at least two layers of flexible material bonded together to define a plurality of fluidly connected zones therein, the zones fluidly connected by channels, wherein at least a first zone includes a plurality of a type of beads contained therein, and a second zone does not contain any of the type of beads therein;

a port configured to receive a sample, and a filter element in one or more of the plurality of channels, wherein the filter element is bonded in the channel to prevent liquid and beads from flowing around the filter to permit liquid to through the channel and into the adjacent zone and to prevent the type of beads from proceeding through the channel and into the adjacent zone.

47. The container of clause 46, wherein the type of beads is selected from the group consisting of lysis beads and magnetic beads.

48. The container of clause 46 and/or 47, wherein the filter element filter has a pore size in a range of about 5 to 100 μm, such that the filter element is large enough to pass substantially all material in a liquid in the container except the beads.

49. The container of any of clauses 46-48, wherein the filter element is fabricated from a material that is compatible with the material(s) used to form the container such that the filter element can be heat sealed in the one or more of the plurality of channels without compromising either the container or the filter.

50. The container of any of clauses 46-49, wherein the filter element is sealed in the channel between the at least two layers of flexible material at a top edge, at a bottom edge, and over top and bottom surfaces of the filter element to prevent liquid and beads from flowing around the filter element.

51. The container of any of clauses 46-50, wherein the filter element is sealed in the channel between the at least two layers of flexible material at a top edge, at a bottom edge, a first seal applied to a first end of the filter element on one of the at least two layers of flexible material, and a second seal applied to a second, opposite end of the filter element on the opposite of the at least two layers of flexible material.

52. The container of any of clauses 46-51, wherein the first and second ends or the top and bottom edges of the filter element are sealed to one or more additional layers of flexible material prior to bonding the filter element between the at least two layers of flexible material to form the channel and the container.

53. The container of any of clauses 46-52, wherein the filter element is fabricated from a polyethylene material.

54. An instrument for amplifying nucleic acids in a sample, comprising an opening having a first side and a second side, the opening for receiving a closed reaction container between the first side and the second side, wherein the container is configured for nucleic acid amplification, the container comprising:

a plurality of fluidly connected reaction zones, the reaction zones including a lysis zone comprising a plurality of lysis beads and a downstream nucleic acid amplification zone; at least one compression member associated with the lysis zone provided at one of the sides; and a bead milling component provided at one of the sides, wherein the bead milling component includes a drive motor and three or more beater elements that are positioned and configured in the instrument for contacting the lysis zone for generating a lysate.

55. A method for nucleic acid amplification using the instrument of clause 54, comprising the steps of:

providing the closed reaction container containing a sample to be analyzed and a plurality of reagents;

bead milling the sample in the lysis zone for a period of time to release a portion of nucleic acids that may be present in the sample, wherein the bead milling includes bead milling the sample with the bead milling device while pulsing the sample with the compression member associated with the lysis zone;

recovering nucleic acids released from the sample, washing nucleic acids, and performing a PCR reaction.

56. The method of clause 55, further comprising recovering the nucleic acids from the sample in the lysis zone using a quantity of magnetic beads provided in the closed reaction container and a moving magnet system, wherein the method further comprises:

dispersing the magnetic beads in the lysate;

sweeping the moving magnet adjacent to the lysis zone to recover the magnetic beads; and compressing the lysis zone with the compression member associated with the lysis zone to flush the magnetic beads to the downstream nucleic acid recovery zone.

57. An instrument for processing a sample, comprising a first support member and a second support member;

an opening for receiving a flexible reaction container between the first support member and the second support member, wherein the container is configured for receiving the sample, the container comprising:

a loading attachment that includes a sample zone and a plurality of reagent zones; and a plurality of fluidly connected reaction zones; and a plunging system including a plurality of mechanically actuated pistons positioned and configured in the instrument for moving the sample and reagents from the loading attachment and into the fluidly connected reaction zones.

58. The instrument of clause 57, wherein the plunging system comprises:

a housing comprising plurality of pistons;

an opening for receiving at least the loading attachment of the container;

a rotatable cam shaft and a plurality of cam lobes, wherein one cam lobe corresponds to each of the plurality of pistons, wherein rotation of the cam shaft actuates the plurality of pistons sequentially to plunge fluid from the loading attachment and into selected reaction zones of the reaction container.

59. The instrument of clauses 57 and/or 58, wherein the cam shaft is positioned within the housing substantially perpendicular to a proximal end of the plurality of pistons and wherein each of the cam lobes is positioned such that a plane of each of the cam lobes is substantially parallel to an elongate axis of each of the pistons.

60. The instrument of any of clauses 57-59, wherein each of the pistons is configured to come in contact with a corresponding plunger of the loading attachment.

61. The instrument of any of clauses 57-60 wherein the tab in contact with the distal end of the plunger is configured to apply rotational force on the distal end of the plunger as the rod is made to rotate thereby causing the plunger to be actuated.

62. The instrument of any of clauses 57-61, wherein the plunging system comprises:

a threaded member;

a shuttle mechanism threaded onto the threaded member; and the plurality of pistons are actuated by horizontal translation of the shuttle mechanism along the threaded member, wherein rotation of the threaded member causes the shuttle mechanism to sequentially contact a proximal end of each of the pistons, causing a distal end of each of the pistons to sequentially plunge a corresponding plurality of plungers in the loading attachment to move fluid from the loading attachment into selected reaction zones of the reaction container.

63. The instrument of any of clauses 57-62, wherein the plunging system comprises:

a plurality of threaded bolts, each comprising;

a proximal and a distal end, and wherein the proximal end is in communication with a cross-bar and the distal end is in communication with a piston;

wherein rotation of each cross-bar causes a distal end of each of the pistons to sequentially plunge a corresponding plurality of plungers in the loading attachment to move fluid from the loading attachment into selected reaction zones of the reaction container.

64. The instrument of any of clauses 57-63 wherein the cross-bar on a first threaded bolt is configured to come in contact with the cross-bar on an adjacent threaded bolt as the first threaded bolt is made to rotate, thereby causing the adjacent threaded bolt to rotate, and wherein this process is repeated sequentially with each threaded bolt and each adjacent threaded bolt.

65. The instrument of any of clauses 57-64, wherein the plunging system comprises:

a housing comprising a plurality of pistons, a track, a chain positioned around the perimeter of the track, and a drive system to drive movement of the chain around the track to sequentially actuate each of the plurality of pistons;

the chain further comprising at least one raised link configured to contact a proximal end of one of the pistons and to push the one piston out of the housing, wherein movement of the chain around the track causes the raised link to contact a proximal end of each piston to push each piston out of the housing to sequentially contact a corresponding one of a plurality of plungers in the loading attachment to move fluid from the loading attachment into selected reaction zones of the reaction container.

66. The instrument of any of clauses 57-65, a first piston of the plurality of pistons further comprising, a column, the column comprising a proximal end and a distal end, a substantially flat platform in communication with the proximal end, and a piston in contact with the distal end.

67. The instrument of any of clauses 57-66, wherein the first piston has a longer plunging stroke than the rest of the plurality of pistons.

68. The instrument of any of clauses 57-67, wherein a plurality of additional pistons of the plurality of pistons further comprises:

a column, the column comprising, a proximal end and a distal end, a substantially ramped platform in communication with the proximal end, and a piston in contact with the distal end.

69. The instrument of any of clauses 57-68, wherein the at least one raised link is configured to sequentially come into contact with the substantially flat platform and each of the substantially ramped platforms when the chain is made to rotate around the track to sequentially push the pistons out of the housing.

70. The instrument of clause 65, further comprising a return cam and a return pin on the chain, wherein the return pin is configured to come in contact with the inner perimeter of the cam when the chain is made to continue to rotate after actuating all of the pistons, thereby causing the cam to move in a direction that is substantially opposite the direction of movement of the actuated pistons, and causing the cam to sequentially come in contact with the shelf of each of the angled platforms thereby causing the angled platform and plunger to return toward its position prior to being actuated.

71. An instrument for measuring fluorescence in a sample, comprising a first support member and a second support member;

an opening for receiving a container between the first and second support members, the container comprising a plurality of fluidly connected zones comprising a sample processing zone and a reaction zone, the zones being defined by two flexible membranes positioned substantially parallel to one another, a plurality of channels connecting the zones; and one or more sealable ports fluidly connected to the zones, the sealable ports providing the only access from an exterior of the container to the zones such that when all of the one or more sealable ports is sealed, the container is fully closed, a heating/cooling device provided at one of the first or second supports, the heating/cooling device configured for controlling temperature of contents of the reaction zone;

an optics system mounted in the instrument and positioned to produce and detect fluorescence in the reaction zone; and a window bladder associated with the reaction zone and the optics system, wherein the window bladder comprises an optically clear window comprised of a first layer and a second layer of material bonded together on an edge of each layer to form an inflatable envelope between the two layers; and a nipple fluidly connected to a compressed gas source;

wherein the first support member and the second support member are separable such that the nipple is user accessible and the window bladder is user replaceable.

72. The instrument of clause 71, wherein the window bladder is configured to expand to evacuate excess fluid from the reaction zone when inflated by the compressed gas source.

73. The instrument of clauses 71 and/or 72, wherein the window bladder is configured to open from a lower edge toward an upper edge to wipe excess fluid from the reaction zone when inflated by the compressed gas source.

74. The instrument of any of clauses 71-73, wherein the window bladder is comprised of a self-adherent material, and wherein the window bladder includes an engineered gradient of modifications that cause the window bladder to open from a lower edge toward an upper edge to wipe excess fluid from the reaction zone when inflated by the compressed gas source.

75. The instrument of any of clauses 71-74, wherein the window bladder includes an engineered gradient of modifications that cause the window bladder to adhere to itself such that the window bladder opens from a lower edge toward an upper edge to wipe excess fluid from the reaction zone when inflated by the compressed gas source.

76. An instrument for amplifying nucleic acids in a sample, comprising an opening for receiving a container, the container comprising a plurality of fluidly connected reaction zones including a lysis zone, an extraction zone, and an amplification zone, and one or more sealable ports fluidly connected to the reaction zones, the sealable ports providing the only access from an exterior of the container to the reaction blisters such that when all of the one or more sealable ports is sealed, the container is fully closed, and a plurality of heaters, wherein each of the heaters is configured to be set at a different temperature, and wherein the heaters are positioned on a movable mount such that each heater is configured to move sequentially into position to apply heat to a reaction zone.

77. The instrument of clause 76, wherein the movable mount comprises a circular mount that is configured to be driven circularly by a power source.

78. The instrument of clauses 76 and/or 77, wherein the power source is configured to drive the movable mount in both clockwise and counterclockwise directions.

79. An instrument for amplifying nucleic acids in a sample, comprising an opening for receiving a container, the container comprising:

a sample zone and a plurality of reagent zones, all in fluid communication, the reagent zones including a lysis blister, downstream first and second nucleic acid recovery blisters, downstream first and second nucleic acid amplification blisters, a downstream dilution blister, and a downstream nucleic acid amplification zone;

one or more sealable flow paths connected to the sample zone and the plurality of reagent zones, the sealable flow paths providing the only access from an exterior of the container to the sample zone and the plurality of reagent zones such that when all of the one or more sealable paths are sealed, the container is fully closed;

a sample loading zone and a reagent loading zone in fluid connection with a plurality of fluidly connected reaction zones;

a plunging system including a plurality of mechanically actuated pistons positioned and configured in the instrument for moving sample and reagents from the sample and reagent zones into the fluidly connected reaction zones;

the container further comprising a quantity of lysis beads in the lysis blister and a bead milling component including a drive motor and three or more beater elements that are positioned and configured in the instrument for contacting the lysis blister for generating a lysate in the lysis blister;

the container further comprising a quantity of magnetic beads configured for recovery of a nucleic acid from the lysate and a moving magnet system including a driver for moving a magnet on a defined path for recovery and isolation of the magnetic beads and for moving the magnetic beads between at least the lysis blister and the first and second nucleic acid recovery blisters;

a plurality of compression members and seal members associated with the fluidly connected reaction zones, the plurality of compression members and seal members being configured to provide directional movement of fluid between the fluidly connected reaction zones, the compression members including:

a compression member associated with the lysis blister, a first set of mutually actuated compression members associated with the first nucleic acid recovery blister, the first nucleic acid amplification blister, and the dilution blister, and a second set of mutually actuated compression members associated with the second nucleic acid recovery blister and the second nucleic acid amplification blister;

the seal members including:

a first set of coupled but individually actuated seals between the lysis blister and the first nucleic acid recovery blister, between the second nucleic acid recovery blister and the first nucleic acid amplification blister, and between the second nucleic acid amplification blister and the dilution blister, and a second set of coupled but individually actuated seals between the first nucleic acid recovery blister and the second nucleic acid recovery blister, between the first nucleic acid amplification blister and the second nucleic acid amplification blister, and between the dilution blister and the third nucleic acid amplification zone; and at least one heater configured for performing a thermal cycling reaction associated with the first and second nucleic acid amplification blisters and at least one heater configured for performing a thermal cycling reaction associated with the third nucleic acid amplification zone.

80. The instrument of clause 79, further comprising a seal bar positioned and configured in the instrument for heat sealing the one or more sealable flow paths, wherein the seal bar includes a number of individually controlled heater elements associated with each of the one or more sealable flow paths and the sample zone and the plurality of reagent zones.

81. An instrument for processing a sample, comprising a first support member and a second support member;

an opening for receiving a closed reaction container between the first support member and the second support member, the container comprising:

a plurality of fluidly connected reaction zones comprising a first plurality of reaction blisters and a second plurality of reaction blisters;

a plurality of sealable channels fluidly connecting the reaction zones;

a plurality of compression members provided on at least one of the support members, the compression members including:

a first set of mutually actuated compression members associated with the first plurality of reaction blisters, and a second set of mutually actuated compression members associated with the second plurality of reaction blisters;

a plurality of seal members provided on at least one of the support members, wherein the seal members are associated with the channels connecting the reaction zones, wherein activation of the compression members provides directional movement of fluid between the fluidly connected reaction zones.

82. The instrument of clause 81, wherein the plurality of seal members includes a first set of mechanically coupled, each seal of the first set being downstream of a reaction blister of the first plurality and upstream of a reaction blister of the second plurality, and a second set of mechanically coupled, each seal of the second set being downstream of a reaction blister of the second plurality and upstream of a reaction blister of the first plurality.

83. The instrument of clause 81 and/or 82, wherein each seal of the first set and the second set is individually actuatable.

84. The instrument of any of clauses 81-83, wherein the first plurality of reaction blisters are arranged in a first row and the second plurality of reaction blisters are arranged in a second row.

85. The instrument of any of clauses 81-84, wherein the reaction blisters of the first row and the reaction blisters of the second row are connected via the sealable channels in a zig-zag fashion relative to one another.

86. The instrument of any of clauses 81-85, wherein the first set of mutually actuated compression members are configured to provide directional movement of fluid between at least one of the plurality of first row blisters and at least one of the plurality of second row blisters, and the second set of mutually actuated compression members are configured to provide directional movement of fluid between at least one of the plurality of second row blisters and at least one of the plurality of first row blisters.

87. The instrument of any of clauses 81-86, wherein the first and second pluralities of channels fluidly connect the first row and the second row of reaction blisters so that fluid can flow between the first row and the second row of reaction blisters.

88. The instrument of any of clauses 81-87, wherein the first set of compression members moves fluid from one blister of the first plurality of reaction blisters to one blister of the second plurality of reaction blisters by compressing all of the first plurality of reaction blisters.

89. The instrument of any of clauses 81-88, wherein only one blister of the first plurality of reaction blisters has fluid therein and the rest of the blisters of the first plurality of reaction blisters are substantially dry when compressed by the compression members.

90. The instrument of any of clauses 81-89, wherein release of the first set of seals permits fluid to flow from the one blister of the first plurality of reaction blisters to one blister of the second plurality of reaction blisters, and actuation of the second set of seals prevents fluid from flowing into another blister of the first plurality of reaction blisters.

91. The instrument of any of clauses 81-90, wherein the second set of compression members moves fluid from a one blister of the second plurality of reaction blisters to a blister of the first set of reaction members by compressing each of the second plurality of reaction blisters substantially simultaneously.

92. The instrument of any of clauses 81-91, wherein only one blister of the second plurality of reaction blisters has fluid therein and the rest of the blisters of the second plurality of reaction blisters are substantially dry when compressed by the compression members.

93. The instrument of any of clauses 81-92, wherein when the second set of seals is released fluid can flow from the one blister of the second plurality of reaction blisters to one or more of the blisters of the first plurality of reaction blisters, and when the first set of seals is actuated fluid cannot flow into another blister of the second plurality of reaction blisters.

94. An instrument for processing a sample, comprising a first support member and a second support member;

an opening for receiving a flexible reaction container between the first support member and the second support member, the container comprising:

a loading attachment, a plurality of reaction zones, and one or more sealable flow paths, each having a first side connecting the loading attachment to one or more fill ports, at least one of which is configured for receiving the sample, and a second side connected to at least one of the plurality of reaction zones, the sealable flow paths providing the only access from the one or more fill ports to the plurality of reagent zones such that when the first side of all of the one or more sealable paths are sealed, the container is fully closed;

a plurality of heat seal elements provided on at least one of the support members so as to contact the loading attachment and the one or more sealable flow paths, wherein the heat seal elements include a number of individually controlled heater elements associated with each of the first side of the one or more sealable flow paths.

95. The instrument of clause 94, wherein the individually controlled heater elements are ceramic heater elements.

96. The instrument of clause 94 and/or 95, wherein the ceramic heater elements are self-regulating heater elements.

97. The instrument of any of clauses 94-96, wherein the self-regulating heater elements include positive thermal coefficient (PTC) heating elements.

98. The instrument of any of clauses 94-97, wherein the PTC heating elements are self-limiting.

99. The instrument of any of clauses 94-98, wherein the individually controlled heater elements are selected from the group consisting of resistance wire heating elements, ceramic heating elements, etched foil heating elements, and combinations thereof.

100. The instrument of any of clauses 94-99, wherein the individually controlled heater elements are disposed in at least one of the support members and further comprise an electric heater element, a housing, an electrical connection to a power source, and a connection to a control unit.

101. The instrument of any of clauses 94-100, further comprising:

a plunging system including a plurality of pistons positioned and configured in the instrument for moving the sample from the loading attachment into the reaction zones, and wherein the container is sealed with the sealing system prior to actuation of the plunging system.

102. The instrument of any of clauses 94-101, further comprising a sample preparation system associated with one of the first or second supports, the sample preparation system including components to effect cell lysis and nucleic acid recovery in one or more of the reaction zones the flexible reaction container.

103. The instrument of any of clauses 94-102, further comprising an optics system mounted in the instrument and positioned to produce and detect fluorescence in at least one of the reaction zones of the container.

104. The instrument of any of clauses 94-103, further comprising:

a first heating/cooling device provided on one of the first or second supports, the first heating/cooling device configured for thermal cycling contents of at least one of the reaction zones; and a second heating/cooling device provided on one of the first or second supports, the second heating/cooling device configured for thermal cycling contents of another one of the reaction zones.

105. The instrument of any of clauses 94-104, further comprising a computer for controlling one or more of the plurality of heat seal elements, the plunging system, the sample preparation system, the optics system, the first heating/cooling device, or the second heating/cooling device.

106. An instrument for processing nucleic acids in a sample, comprising a first support member and a second support member;

an opening for receiving a closed reaction container between the first support member and the second support member, the container comprising a plurality of fluidly connected reaction zones, the reaction zones including a lysis zone comprising a plurality of lysis beads, and a nucleic acid recovery zone, and wherein the container is provided with nucleic acid-binding magnetic beads therein a bead milling component provided on at least one of the support members for generating a lysate in the lysis blister;

a moving magnet component provided on at least one of the support members, wherein the moving magnet component includes a magnet that is movable between a position adjacent at least the lysis zone and a position adjacent the nucleic acid recovery zone.

107. The instrument of clause 106, wherein the moving magnet component moves magnetic beads from the lysate to the nucleic acid recovery zone.

108. The instrument of clause 106 and/or 107 105, wherein the moving magnet component comprises a driver and a magnet pathway between the lysis zone and the nucleic acid recovery zone.

109. The instrument of any of clauses 106-108, further comprising at least one compression member associated with the lysis zone provided on at least one of the support members, wherein the compression member is activated when the driver is activated.

110. The instrument of any of clauses 106-109, wherein the moving magnet component further comprises a sensor system configured for sensing a position of the magnet relative to one or more of the lysis zone and the nucleic acid recovery zone.

111. The instrument of any of clauses 106-110, wherein the sensing system is an optical sensing system associated with a pathway between the lysis zone and the nucleic acid recovery zone, and the zone outside the lysis zone and the nucleic acid recovery zone.

112. The instrument of any of clauses 106-111, wherein the bead milling component includes a drive motor and three or more beater elements that are positioned and configured in the instrument for contacting the lysis zone.

113. An instrument for amplifying nucleic acids in a sample, comprising an opening for receiving a container, the container comprising a plurality of fluidly connected reaction zones including a lysis zone, an extraction zone, and an amplification zone, and one or more sealable ports fluidly connected to the reaction zones, a bead milling component, an extraction zone for extracting the nucleic acids from the lysate in the extraction zone, and moving the extracted nucleic acids to the amplification blister, and a heater positioned for controlling temperature of the nucleic acids in the amplification zone.

114. The instrument of clause 113 wherein the bead milling component comprises a reciprocating drive member operatively coupled to at least two alternating paddle elements that repeatedly and serially contact the lysis zone to generate a lysate from the sample.

115. The instrument of clause 113 and/or 114 wherein the reciprocating drive member comprises a motor driven cam shaft with at least two off-center drive lobes mechanically coupled to the at least two paddles.

116. The instrument of any of clauses 113-115 wherein the cam shaft comprises bearing members that contact the paddles.

117. The instrument of any of clauses 113-116 wherein the paddles are each operably connected to a cam follower that contacts a corresponding off-center drive lobe of the cam shaft.

118. The instrument of any of clauses 113-117 the reciprocating drive member comprising a mechanical actuator associated with each paddle, wherein the mechanical actuator extends to extend the associated paddle.

119. The instrument of any of clauses 113-118 wherein each paddle includes a biasing member positioned and configured to bias each paddle toward or away from the lysis zone.

120. The instrument of any of clauses 113-119 wherein the at least two paddles are sized and positioned contact substantially the entire lysis zone.

121. The instrument of any of clauses 113-120 wherein one or more of the paddles comprise a temperature control element.

122. The instrument of any of clauses 113-121 wherein the temperature control element is one or more of a heater, cooler, Peltier device, resistance heater, induction heater, electromagnetic heater, thin film heater, printed element heater, or positive temperature coefficient heater.

123. The instrument of any of clauses 113-122 wherein the at least two paddles are configured to extend together to plunge fluid from the lysis zone.

124. The instrument of any of clauses 113-123 wherein the bead milling component comprises a plurality of at least three beater arms arranged asymmetrically around a central axis and driven by a motor.

Additional features and advantages of the embodiments of the invention will be set forth in the description which follows or may be learned by the practice of such embodiments. The features and advantages of such embodiments may be realized and obtained by means of the instruments and combinations particularly pointed out in the appended claims. These and other features will become more fully apparent from the following description and appended claims, or may be learned by the practice of such embodiments as set forth hereinafter.

BRIEF DESCRIPTION OF THE DRAWINGS

In order to describe the manner in which the above-recited and other advantages and features of the invention can be obtained, a more particular description of the invention briefly described above will be rendered by reference to specific embodiments thereof which are illustrated in the appended drawings. Understanding that these drawings depict only typical embodiments of the invention and are not therefore to be considered to be limiting of its scope, the invention will be described and explained with additional specificity and detail through the use of the accompanying drawings in which:

FIG. 6A illustrates a front view of the heat sealing system and FIG. 6B illustrates a top view of the heat sealing system rotated 90° relative to the view of FIG. 6A.

DETAILED DESCRIPTION

Figure 1:
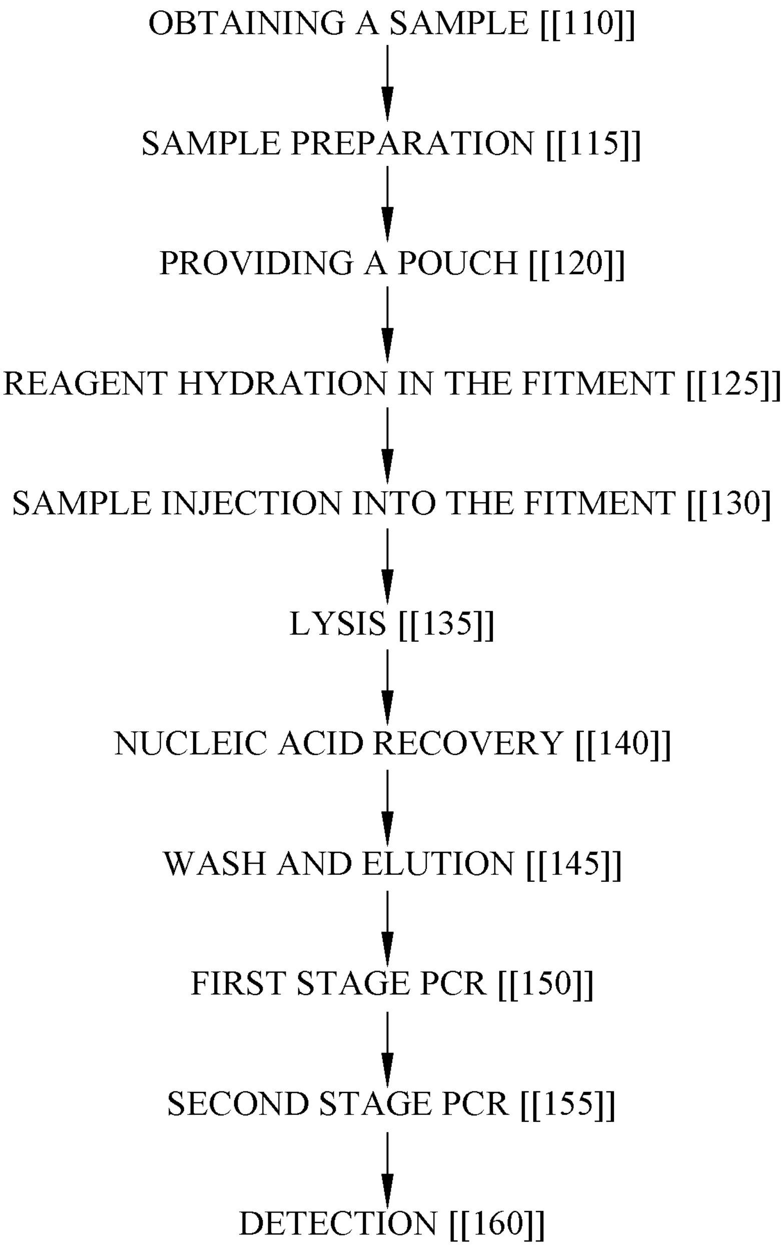
FIG. 1 is a flowchart illustrating a typical workflow for rapid extraction and analysis or identification of a microbe or nucleic acid, according to an embodiment of the present invention.

Example embodiments are described below with reference to the accompanying drawings. Many different forms and embodiments are possible without deviating from the spirit and teachings of this disclosure and so the disclosure should not be construed as limited to the example embodiments set forth herein. Rather, these example embodiments are provided so that this disclosure will be thorough and complete, and will convey the scope of the disclosure to those skilled in the art. In the drawings, the sizes and relative sizes of layers and regions may be exaggerated for clarity. Like reference numbers refer to like elements throughout the description.

Unless defined otherwise, all terms (including technical and scientific terms) used herein have the same meaning as commonly understood by one of ordinary skill in the art to which the present disclosure pertains. It will be further understood that terms, such as those defined in commonly used dictionaries, should be interpreted as having a meaning that is consistent with their meaning in the context of the present application and relevant art and should not be interpreted in an idealized or overly formal sense unless expressly so defined herein. The terminology used in the description of the invention herein is for the purpose of describing particular embodiments only and is not intended to be limiting of the invention. While a number of methods and materials similar or equivalent to those described herein can be used in the practice of the present disclosure, only certain exemplary materials and methods are described herein.

All publications, patent applications, patents or other references mentioned herein are incorporated by reference for in their entirety. In case of a conflict in terminology, the present specification is controlling.

Various aspects of the present disclosure, including devices, systems, methods, etc., may be illustrated with reference to one or more exemplary implementations. As used herein, the terms "exemplary" and "illustrative" mean "serving as an example, instance, or illustration," and should not necessarily be construed as preferred or advantageous over other implementations disclosed herein. In addition, reference to an "implementation" or "embodiment" of the present disclosure or invention includes a specific reference to one or more embodiments thereof, and vice versa, and is intended to provide illustrative examples without limiting the scope of the invention, which is indicated by the appended claims rather than by the following description.

It will be noted that, as used in this specification and the appended claims, the singular forms "a," "an," and "the" include plural referents unless the content clearly dictates otherwise. Thus, for example, reference to "a tile" includes one, two, or more tiles. Similarly, reference to a plurality of referents should be interpreted as comprising a single referent and/or a plurality of referents unless the content and/or context clearly dictate otherwise. Thus, reference to "tiles" does not necessarily require a plurality of such tiles. Instead, it will be appreciated that independent of conjugation; one or more tiles are contemplated herein.

As used throughout this application the words "can" and "may" are used in a permissive sense (i.e., meaning having the potential to), rather than the mandatory sense (i.e., meaning must). Additionally, the terms "including," "having," "involving," "containing," "characterized by," variants thereof (e.g., "includes," "has," "involves," "contains," etc.), and similar terms as used herein, including the claims, shall be inclusive and/or open-ended, shall have the same meaning as the word "comprising" and variants thereof (e.g., "comprise" and "comprises"), and do not exclude additional, un-recited elements or method steps, illustratively.

As used herein, directional and/or arbitrary terms, such as "top," "bottom," "left," "right," "up," "down," "upper," "lower," "inner," "outer," "internal," "external," "interior," "exterior," "proximal," "distal," "forward," "reverse," and the like can be used solely to indicate relative directions and/or orientations and may not be otherwise intended to limit the scope of the disclosure, including the specification, invention, and/or claims.

It will be understood that when an element is referred to as being "coupled," "connected," or "responsive" to, or "on," another element, it can be directly coupled, connected, or responsive to, or on, the other element, or intervening elements may also be present. In contrast, when an element is referred to as being "directly coupled," "directly connected," or "directly responsive" to, or "directly on," another element, there are no intervening elements present.

Example embodiments of the present inventive concepts are described herein with reference to cross-sectional illustrations that are schematic illustrations of idealized embodiments (and intermediate structures) of example embodiments. As such, variations from the shapes of the illustrations as a result, for example, of manufacturing techniques and/or tolerances, are to be expected. Thus, example embodiments of the present inventive concepts should not be construed as limited to the particular shapes of regions illustrated herein but are to include deviations in shapes that result, for example, from manufacturing. Accordingly, the regions illustrated in the Figures are schematic in nature and their shapes are not intended to illustrate the actual shape of a region of a device and are not intended to limit the scope of example embodiments.

It will be understood that although the terms "first," "second," etc. may be used herein to describe various elements, these elements should not be limited by these terms. These terms are only used to distinguish one element from another. Thus, a "first" element could be termed a "second" element without departing from the teachings of the present embodiments.

It is also understood that various implementations described herein can be utilized in combination with any other implementation described or disclosed, without departing from the scope of the present disclosure. Therefore, products, members, elements, devices, apparatus, systems, methods, processes, compositions, and/or kits according to certain implementations of the present disclosure can include, incorporate, or otherwise comprise properties, features, components, members, elements, steps, and/or the like described in other implementations (including systems, methods, apparatus, and/or the like) disclosed herein without departing from the scope of the present disclosure. Thus, reference to a specific feature in relation to one implementation should not be construed as being limited to applications only within said implementation.

The headings used herein are for organizational purposes only and are not meant to be used to limit the scope of the description or the claims. To facilitate understanding, like reference numerals have been used, where possible, to designate like elements common to the Figures. Furthermore, where possible, like numbering of elements have been used in various Figures. Furthermore, alternative configurations of a particular element may each include separate letters appended to the element number.

The term "about" is used herein to mean approximately, in the region of, roughly, or around. When the term "about" is used in conjunction with a numerical range, it modifies that range by extending the boundaries above and below the numerical values set forth. In general, the term "about" is used herein to modify a numerical value above and below the stated value by a variance of 5%. When such a range is expressed, another embodiment includes from the one particular value and/or to the other particular value. Similarly, when values are expressed as approximations, by use of the antecedent "about," it will be understood that the particular value forms another embodiment. It will be further understood that the endpoints of each of the ranges are significant both in relation to the other endpoint, and independently of the other endpoint.

The word "or" as used herein means any one member of a particular list and also includes any combination of members of that list.

By "sample" is meant an animal; a tissue or organ from an animal; a cell (either within a subject, taken directly from a subject, or a cell maintained in culture or from a cultured cell line); a cell lysate (or lysate fraction) or cell extract; a solution containing one or more molecules derived from a cell, cellular material, or viral material (e.g. a polypeptide or nucleic acid); or a solution containing a non-naturally occurring nucleic acid, which is assayed as described herein. A sample may also be any body fluid or excretion (for example, but not limited to, blood, urine, stool, saliva, tears, bile, or cerebrospinal fluid) that may or may not contain host or pathogen cells, cell components, or nucleic acids.

The phrase "nucleic acid" as used herein refers to a naturally occurring or synthetic oligonucleotide or polynucleotide, whether DNA or RNA or DNA-RNA hybrid, single-stranded or double-stranded, sense or antisense, which is capable of hybridization to a complementary nucleic acid by Watson-Crick base-pairing. Nucleic acids of the invention can also include nucleotide analogs (e.g., BrdU), and non-phosphodiester internucleoside linkages (e.g., peptide nucleic acid (PNA) or thiodiester linkages). In particular, nucleic acids can include, without limitation, DNA, RNA, cDNA, gDNA, ssDNA, dsDNA or any combination thereof By "probe," "primer," or "oligonucleotide" is meant a single-stranded nucleic acid molecule of defined sequence that can base-pair to a second nucleic acid molecule that contains a complementary sequence (the "target"). The stability of the resulting hybrid depends upon the length, GC content, and the extent of the base-pairing that occurs. The extent of base-pairing is affected by parameters such as the degree of complementarity between the probe and target molecules and the degree of stringency of the hybridization conditions. The degree of hybridization stringency is affected by parameters such as temperature, salt concentration, and the concentration of organic molecules such as formamide, and is determined by methods known to one skilled in the art. Probes, primers, and oligonucleotides may be detectably-labeled, either radioactively, fluorescently, or non-radioactively, by methods well-known to those skilled in the art. dsDNA binding dyes may be used to detect dsDNA. It is understood that a "primer" is specifically configured to be extended by a polymerase, whereas a "probe" or "oligonucleotide" may or may not be so configured.

By "dsDNA binding dyes" is meant dyes that fluoresce differentially when bound to double-stranded DNA than when bound to single-stranded DNA or free in solution, usually by fluorescing more strongly. While reference is made to dsDNA binding dyes, it is understood that any suitable dye may be used herein, with some non-limiting illustrative dyes described in U.S. Pat. No. 7,387,887, herein incorporated by reference. Other signal producing substances may be used for detecting nucleic acid amplification and melting, illustratively enzymes, antibodies, etc., as are known in the art.

By "specifically hybridizes" is meant that a probe, primer, or oligonucleotide recognizes and physically interacts (that is, base-pairs) with a substantially complementary nucleic acid (for example, a sample nucleic acid) under high stringency conditions, and does not substantially base pair with other nucleic acids.

By "high stringency conditions" is meant typically occur at about melting temperature (Tm) minus 5° C. (i.e. 5° below the Tm of the probe). Functionally, high stringency conditions are used to identify nucleic acid sequences having at least 80% sequence identity.

As used herein, the term "crossing point" (Cp) (or, alternatively, cycle threshold (Ct), quantification cycle (Cq), or a synonymous term used in the art) refers to the number of cycles of PCR required to obtain a fluorescence signal above some threshold value for a given PCR product (e.g., target or internal standard(s)), as determined experimentally. The cycle where each reaction rises above the threshold is dependent on the amount of target (i.e., reaction template) present at the beginning of the PCR reaction. The threshold value may typically be set at the point where the product's fluorescence signal is detectable above background fluorescence; however, other threshold values may be employed. As an alternative to setting a somewhat arbitrary threshold value, Cp may be determined by calculating the point for a reaction at which a first, second, or nth order derivative has its maximum value, which determines the cycle at which the curvature of the amplification curve is maximal. An illustrative derivative method was taught in U.S. Pat. No. 6,303,305, herein incorporated by reference in its entirety. Nevertheless, it usually does not matter much where or how the threshold is set, so long as the same threshold is used for all reactions that are being compared. Other points may be used as well, as are known in the art, and any such point may be substituted for Cp, Ct, or Cq in any of the methods discussed herein.

While PCR is the amplification method used in the examples herein, it is understood that any amplification method that uses a primer may be suitable. Such suitable procedures include polymerase chain reaction (PCR); strand displacement amplification (SDA); nucleic acid sequence-based amplification (NASBA); cascade rolling circle amplification (CRCA), loop-mediated isothermal amplification of DNA (LAMP); isothermal and chimeric primer-initiated amplification of nucleic acids (ICAN); target based-helicase dependent amplification (HDA); transcription-mediated amplification (TMA), and the like. Therefore, when the term PCR is used, it should be understood to include other alternative amplification methods. For amplification methods without discrete cycles, reaction time may be used where measurements are made in cycles or Cp, and additional reaction time may be added where additional PCR cycles are added in the embodiments described herein. It is understood that protocols may need to be adjusted accordingly.

As used herein, the term "temperature control element" refers to a device that adds heat to or removes heat from a sample. Illustrative examples of a temperature control element include, but are not limited to, heaters, coolers, Peltier devices, resistance heaters, induction heaters, electromagnetic heaters, thin film heaters, printed element heaters, positive temperature coefficient heaters, and combinations thereof. A temperature control element may include multiple heaters, coolers, Peltiers, etc. In one aspect, a given temperature control element may include more than one type of heater or cooler. For instance, an illustrative example of a temperature control element may include a Peltier device with a separate resistive heater applied to the top and/or the bottom face of the Peltier. While the term "heater" is used throughout the specification, it is understood that other temperature control elements may be used to adjust the temperature of the sample.

While various examples herein reference human targets and human pathogens, these examples are illustrative only. Methods, kits, and devices described herein may be used to detect and sequence a wide variety of nucleic acid sequences from a wide variety of samples, including, human, veterinary, industrial, and environmental.

Various embodiments disclosed herein use a self-contained nucleic acid analysis pouch to assay a sample for the presence of various biological substances, illustratively antigens and nucleic acid sequences, illustratively in a single closed system. Such systems, including pouches and instruments for use with the pouches, are disclosed in more detail in U.S. Pat. Nos. 8,394,608; and 8,895,295; and U.S. Patent Application No. 2014-0283945, herein incorporated by reference. However, it is understood that such pouches are illustrative only, and the nucleic acid preparation and amplification reactions discussed herein may be performed in any of a variety of open or closed system sample vessels as are known in the art, including 96-well plates, plates of other configurations, arrays, carousels, and the like, using a variety of nucleic acid purification and amplification systems, as are known in the art. While the terms "sample well", "amplification well", "amplification container", or the like are used herein, these terms are meant to encompass wells, tubes, and various other reaction containers, as are used in these amplification systems. In one embodiment, the pouch is used to assay for multiple pathogens. The pouch may include one or more blisters used as sample wells, illustratively in a closed system. Illustratively, various steps may be performed in the optionally disposable pouch, including nucleic acid preparation, primary large volume multiplex PCR, dilution of primary amplification product, and secondary PCR, culminating with optional real-time detection or post-amplification analysis such as melting-curve analysis. Further, it is understood that while the various steps may be performed in pouches of the present invention, one or more of the steps may be omitted for certain uses, and the pouch configuration may be altered accordingly.

Various parts, components, and subassemblies are described herein. While many of these parts, components, and subassemblies are described with reference to either instrument 800 of FIG. 3A or instrument 900 of FIG. 3B, it is contemplated that various parts, components, and subassemblies are interchangeable and may be used with the other instrument or with other instruments. All compatible combinations are contemplated herein.

Referring now to FIG. 1 an overview of a general workflow 100 is illustrated for rapid extraction and analysis and identification of a microbe or nucleic acid (e.g., an unknown microbe or nucleic acid) that may be present in a sample. The steps of the workflow 100 may be performed manually using a variety of independent instruments and devices. Preferably, however, some or all of the steps may be automated using the self-contained nucleic acid assay device (i.e., the "pouch") that is described in detail herein with reference to the following Figures and their accompanying description. Such automated systems, including pouches and instruments for use with the pouches, are disclosed in more detail in U.S. Pat. Nos. 8,394,608; and 8,895,295; and U.S. Patent Application No. 2014-0283945, which were incorporated by reference above. Each of the steps described in the flow chart for workflow 100 will be described in greater detail herein.

In a first step, workflow 100 includes a step 110 of providing a sample. As defined in detail in the definitions section above, a sample may be essentially any material (e.g., a body fluid, a surface swab, an environmental sample, etc.) that is suspected of containing an organism or a nucleic acid or an allele of a nucleic acid that can be identified according to the assays and systems described herein.

In a second step, the workflow 100 includes a step 115 of sample preparation. Sample preparation can vary according to the sample type provided in step 110. For instance, a blood sample may be prepared different than a stool sample and a sputum or saliva sample may be treated differently still. Depending on workflow, water, a sample buffer, or another fluid may be provided for hydration or dilution of the sample prior to analysis. Likewise, preparation of the sample may include addition of components such as, but not limited to, buffering agents, stabilizers, proteases, DNAses, DNAse inhibitors, RNases, RNase inhibitors, lysozymes, reducing agents, and the like. Alternatively, such components may be included in the sample buffer, or may be added downstream, after the sample has been subjected to further sample preparation, such as downstream sample preparation in the pouch. It is understood that the selection of such additives depends on the sample type and on the further processing desired. It is understood that certain sample types in some embodiments may not require any sample preparation prior to the following steps, and that the sample preparation step may be omitted.

In a third step, the workflow 100 includes a step 120 of providing a sample container, illustratively a pouch. The pouch and the exterior and interior components of the pouch will be described in detail below. In brief, however, the illustrative pouch is a self-contained assay device that is configured for analysis and identification of target microbes and/or nucleic acids that may be in the sample. Preferably, the pouch contains freeze dried reagents, enzymes, primers, etc. for analysis and identification of target microbes and/or nucleic acids that may be in the sample. In one embodiment, the pouch includes a so-called "fitment" that is configured to receive the sample and a hydration buffer in the isolated interior envelope defined by the pouch. In one embodiment, the fitment may include discrete fluid handling areas for containing the sample and the reagents for performing the analysis and identification of the target microbes and/or nucleic acids.

In a fourth and a fifth step, the workflow 100 includes steps 125 and 130 of injecting the sample and a hydration solution (e.g., water) into the fitment. In one embodiment, the fitment is configured such that it autoloads with the sample and the hydration solution into the discrete fluid handling areas for containing the sample and the reagents. The configuration of an illustrative fitment and an illustrative procedure for loading the pouch will be described in detail below in Example 2.

With the sample and the hydration solution loaded into the pouch, the pouch may be loaded into an instrument for subsequent automated processing. Various systems and methods for processing and analyzing the sample once it is in the pouch are described in detail herein below. In brief, however, the illustrative workflow 100 includes a step 135 of lysis of the microbes or cells (if present) to liberate the nucleic acids (e.g., DNA and/or RNA) for downstream amplification and detection. As will be discussed in detail below, lysis may be accomplished in the pouch with a bead beating step. Further, the workflow 100 includes a step 140 of nucleic acid recovery in which the nucleic acids liberated from the microbes or cells are recovered from their milieu. As will be discussed in detail below, nucleic acids may be recovered from the lysis with specially coated magnetic beads; magnetic beads may be recovered with a magnet that is included in the instrument. Further, the workflow 100 includes a step 145 wherein the recovered nucleic acids are washed to remove debris from the lysis and, subsequently, nucleic acids are eluted from the beads. As will be discussed in detail below, the wash and elution procedures may be accomplished using the combination of the magnetic beads and the magnet. After elution, the workflow 100 includes a first PCR step 150 in which the nucleic acids are amplified, and a second, separate PCR step 155 where the amplified nucleic acids from step 150 are diluted and then further specifically amplified and assayed for detection 160 of the presence of target nucleic acids from the sample obtained in step 110. The first and second PCR steps and detection of target nucleic acids from the sample are discussed in detail below and in the patent applications incorporated by reference above.

It is understood that the workflow of FIG. 1 is illustrative only, and that some of the steps may be omitted or combined.

Figure 2:
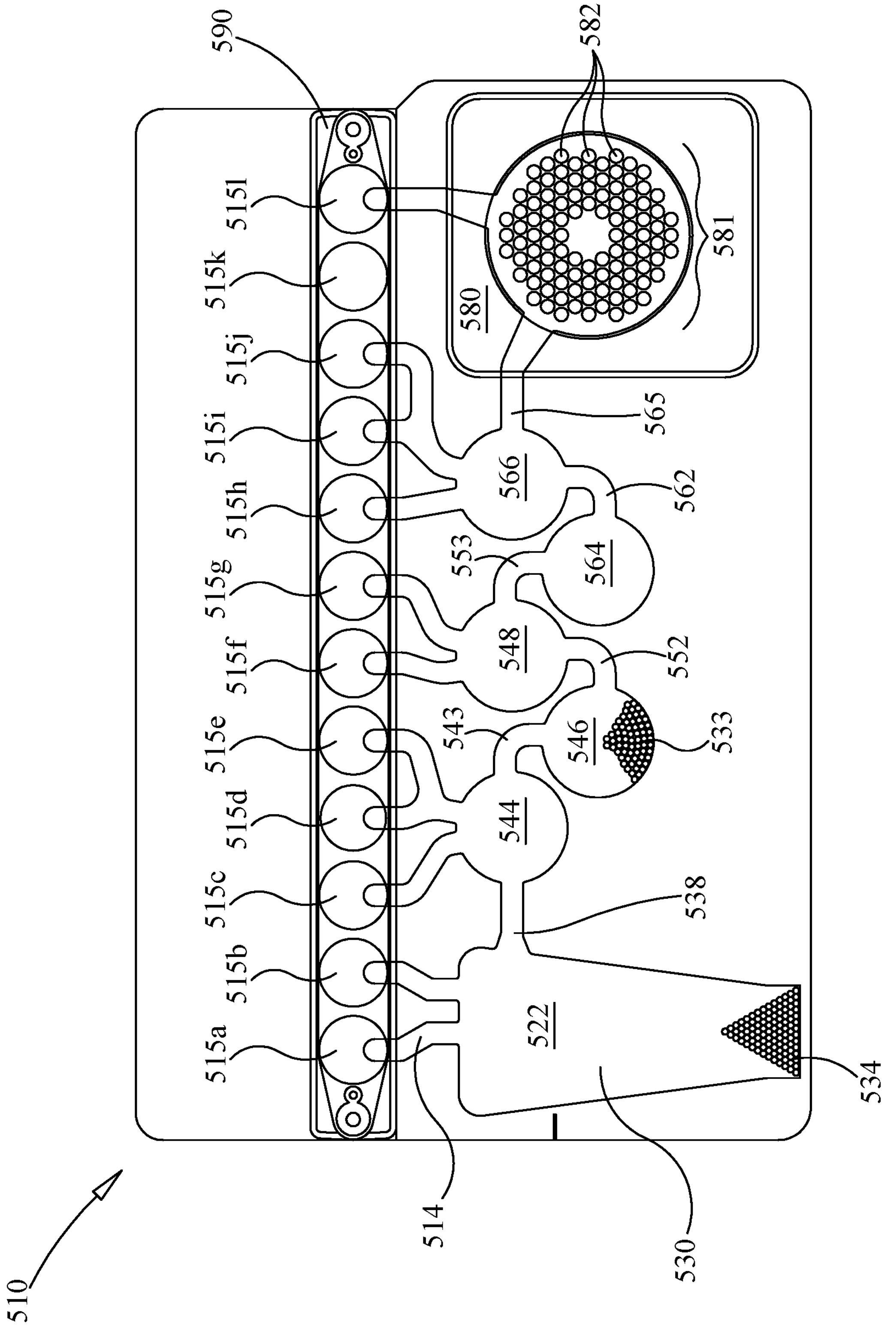
FIG. 2 shows a flexible pouch useful for self-contained PCR.

Referring now to FIG. 2, an illustrative pouch 510 is shown that may be used in various embodiments, or may be reconfigured for various embodiments. Pouch 510 is similar to FIG. 15 of U.S. Pat. No. 8,895,295, with like items numbered the same. Fitment 590 is provided with entry channels 515*a* through 515*l*, which also serve as reagent reservoirs or waste reservoirs. As will be explained in detail below, the fitment 590 serves as a loading attachment for introducing sample and reagents from the fitment into the closed pouch environment. Illustratively, reagents may be freeze dried in fitment 590 and rehydrated prior to use. Blisters 522, 544, 546, 548, 564, and 566, with their respective channels 514, 538, 543, 552, 553, 562, and 565 are similar to blisters of the same number of FIG. 15 of U.S. Pat. No. 8,895,295. Second-stage reaction zone 580 of FIG. 2 is similar to that of U.S. Pat. No. 8,895,295, but the second-stage wells 582 of high density array 581 are arranged in a somewhat different pattern. The more circular pattern of high density array 581 of FIG. 2 eliminates wells in corners and may result in more uniform filling of second-stage wells 582. As shown, the high density array 581 is provided with 102 second-stage wells 582. Pouch 510 is suitable for use in the FilmArray® instrument (BioFire Diagnostics, LLC, Salt Lake City, UT). However, it is understood that the pouch embodiment is illustrative only.

While other containers may be used, illustratively, pouch 510 is formed of two layers of a flexible plastic film or other flexible material such as polyester, polyethylene terephthalate (PET), polycarbonate, polypropylene, polymethylmethacrylate, and mixtures thereof that can be made by any process known in the art, including extrusion, plasma deposition, and lamination. Metal foils or plastics with aluminum lamination also may be used. Other barrier materials are known in the art that can be sealed together to form the blisters and channels. If plastic film is used, the layers may be bonded together, illustratively by heat sealing. Illustratively, the material has low nucleic acid binding capacity.

For embodiments employing fluorescent monitoring, plastic films that are adequately low in absorbance and auto-fluorescence at the operative wavelengths are preferred. Such material could be identified by testing different plastics, different plasticizers, and composite ratios, as well as different thicknesses of the film. For plastics with aluminum or other foil lamination, the portion of the pouch that is to be read by a fluorescence detection device can be left without the foil. For example, if fluorescence is monitored in second-stage wells 582 of the second-stage reaction zone 580 of pouch 510, then one or both layers at wells 582 would be left without the foil. In the example of PCR, film laminates composed of polyester (Mylar, Dupont, Wilmington DE) of about 0.0048 inch (0.1219 mm) thick and polypropylene films of 0.001-0.003 inch (0.025-0.076 mm) thick perform well. Illustratively, pouch 510 is made of a clear material capable of transmitting approximately 80%-90% of incident light.

In the illustrative embodiment, the materials are moved between blisters by the application of pressure, illustratively pneumatic pressure, upon the blisters and channels. Accordingly, in embodiments employing pressure, the pouch material illustratively is flexible enough to allow the pressure to have the desired effect. The term "flexible" is herein used to describe a physical characteristic of the material of pouch. The term "flexible" is herein defined as readily deformable by the levels of pressure used herein without cracking, breaking, crazing, or the like. For example, thin plastic sheets, such as Saran™ wrap and Ziploc® bags, as well as thin metal foil, such as aluminum foil, are flexible. However, only certain regions of the blisters and channels need be flexible, even in embodiments employing pneumatic pressure. Further, only one side of the blisters and channels need to be flexible, as long as the blisters and channels are readily deformable. Other regions of the pouch 510 may be made of a rigid material or may be reinforced with a rigid material.

Illustratively, a plastic film is used for pouch 510. A sheet of metal, illustratively aluminum, or other suitable material, may be milled or otherwise cut, to create a die having a pattern of raised surfaces. When fitted into a pneumatic press (illustratively A-5302-PDS, Janesville Tool Inc., Milton WI), illustratively regulated at an operating temperature of 195° C., the pneumatic press works like a printing press, melting the sealing surfaces of plastic film only where the die contacts the film. Various components, such as PCR primers (illustratively spotted onto the film and dried or provided in dried powder or pill form), antigen binding substrates, magnetic beads, and zirconium silicate beads may be sealed inside various blisters as the pouch 510 is formed. Reagents for sample processing can be spotted onto the film prior to sealing, either collectively or separately. In one embodiment, nucleotide tri-phosphates (NTPs) are provided separately from polymerase and primers, essentially eliminating activity of the polymerase until the reaction is hydrated by an aqueous sample. If the aqueous sample has been heated prior to hydration, this creates the conditions for a true hot-start PCR and reduces or eliminates the need for expensive chemical hot-start components.

Pouch 510 may be used in a manner similar to that described in U.S. Pat. No. 8,895,295. In one illustrative embodiment, a 300 μl mixture comprising the sample to be tested (100 μl) and lysis buffer (200 μl) is injected into an injection port (not shown) in fitment 590 near entry channel 515*a*, and the sample mixture is drawn into entry channel 515*a*. Water is also injected into a second injection port (not shown) of the fitment 590 adjacent entry channel 515*l*, and is distributed via a channel (not shown) provided in fitment 590, thereby hydrating up to eleven different reagents, each of which were previously provided in dry form at entry channels 515*b* through 515*l*. These reagents illustratively may include freeze-dried PCR reagents, DNA extraction reagents, wash solutions, immunoassay reagents, or other chemical entities. Illustratively, the reagents are for nucleic acid extraction, first-stage multiplex PCR, dilution of the multiplex reaction, and preparation of second-stage PCR reagents, as well as control reactions. In the embodiment shown in FIG. 2, all that need be injected is the sample solution in one injection port and water in the other injection port. After injection, the two injection ports may be sealed. For more information on various configurations of pouch 510 and fitment 590, see U.S. Pat. No. 8,895,295, already incorporated by reference.

Figure 3A:
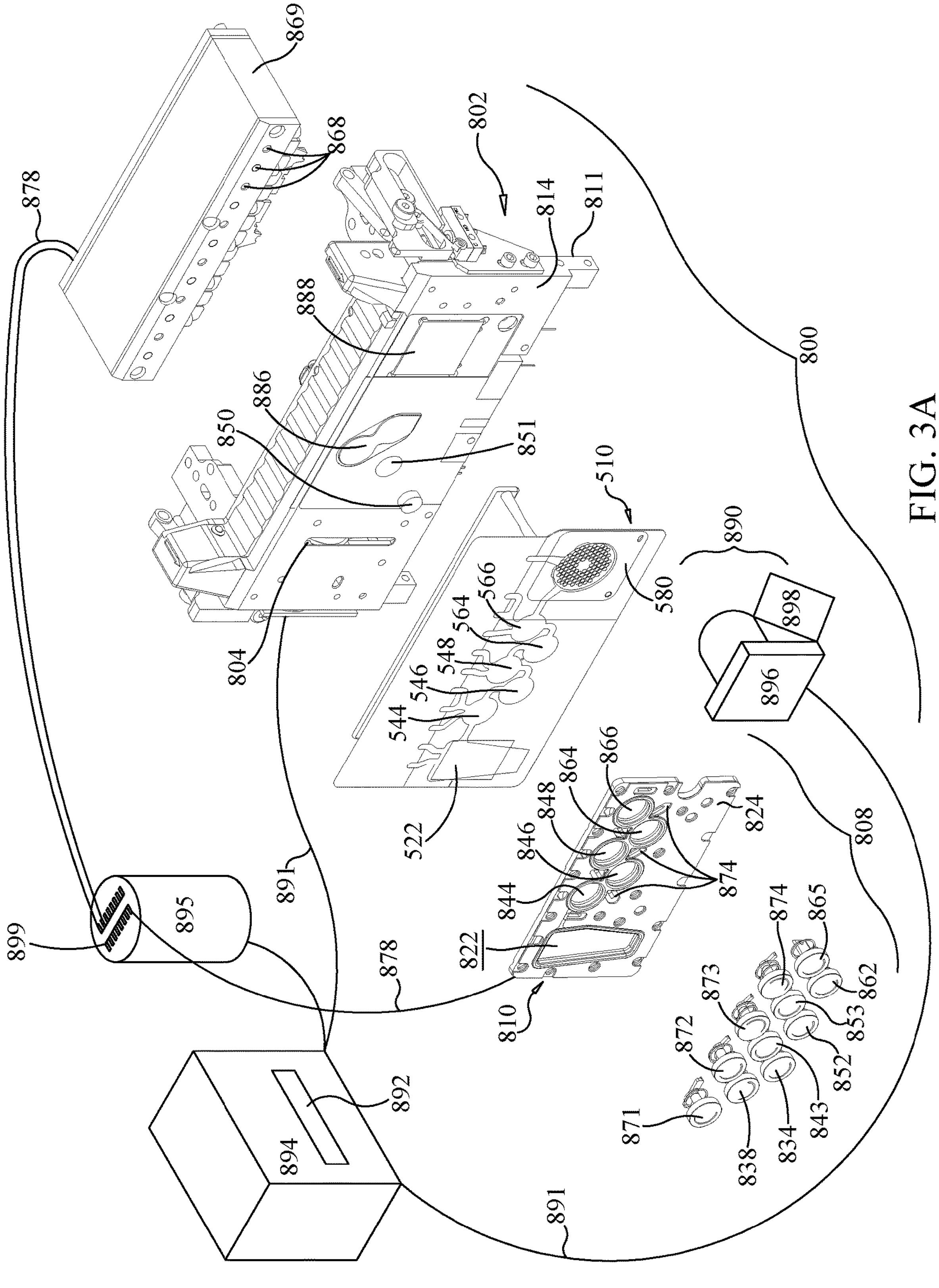
FIG. 3A is an exploded perspective view of an instrument for use with the pouch of FIG. 2, including the pouch of FIG. 2.

FIG. 3A shows an exploded view of an illustrative instrument 800 that could be used with pouch 510. Instrument 800 includes a support member 802 that could form a wall of a casing or be mounted within a casing. Instrument 800 may also include a second support member (not shown) that may be positioned opposite support member 802 such that the pouch may be held in place by the support members. In one embodiment, the second support member is optionally movable with respect to support member 802, to allow insertion and withdrawal of pouch 510. Illustratively, a lid (not shown) may cover pouch 510 once pouch 510 has been inserted into instrument 800. In another embodiment, both support members may be fixed, with pouch 510 held into place by other mechanical means or by pneumatic pressure.

As will be discussed in detail below, instrument 800 includes a piston array 869 (e.g., a pneumatic piston array) that can be used to move sample and reagents from the fitment of pouch 510 into the pouch blisters, and a bladder assembly 808 that can be used to move fluids between blisters in the pouch 510. The piston array 869 and the bladder assembly 808 may be fluidly coupled to a compressed gas source 895. Instrument 800 also includes optical array that can be used, for example, to excite fluorescence in one or more areas of pouch 510 and collect fluorescence data. Instrument 800 also includes a computer 894 that can be linked to one or more components of instrument 800 for control and data collection. It is understood that the computer can be a stand-alone device, or may be an onboard CPU.

Procedures for filling a pouch (e.g., pouch 510) with sample and hydration buffer for the reagents in the fitment are discussed in detail below in Example 2. When the pouch 510 is placed in the instrument 800, the pouch 510 can be contacted by the various systems and subassemblies of the instrument that, for example, effect fluid movement, cell lysis, nucleic acid recovery, first-stage PCR, second-stage PCR, and fluorescent detection. After inserting the pouch 510 into the instrument, the injection ports and the fitment may be sealed with a heat sealing device in order to prevent fluid from flowing back out of the injection ports and to prevent mixing of reagents in the fitment. After sealing, the sample may be injected from the fitment into the lysis blister using piston array 869.

FIG. 3A illustrates a portion of a bead beater assembly that extends through slot 804 to contact pouch 510. The bead beater assembly is positioned adjacent to lysis blister 522 and may be used to lyse cells in a sample. The bead beater assembly may be mounted on a first side 811 of support member 802, of instrument 800 shown in FIG. 3A. Blades, beater arms, or the like may extend through slot 804 to contact pouch 510. The bead beater assembly includes a drive motor that is configured for driving the bladed or beater arms. In one illustrative embodiment, the motor is a Mabuchi RC-280SA-2865 DC Motor (Chiba, Japan), mounted on support member 802. In one illustrative embodiment, the motor is turned at 5,000 to 25,000 rpm, more illustratively 10,000 to 20,000 rpm, and still more illustratively approximately 15,000 to 18,000 rpm. For the Mabuchi motor, it has been found that 7.2V provides sufficient rpm for lysis. It is understood, however, that the actual speed may be somewhat slower when the blades are impacting pouch 510. Other voltages and speeds may be used for lysis depending on the motor and paddles used. Optionally, controlled, small volumes of air may be provided into the bladder 822 adjacent lysis blister 522. It has been found that in some embodiments, partially filling the adjacent bladder with one or more small volumes of air aids in positioning and supporting lysis blister during the lysis process. Alternatively, other structure, illustratively a rigid or compliant gasket or other retaining structure around lysis blister 522, can be used to restrain pouch 510 during lysis. It is also understood that a bead beater motor is illustrative only, and other devices may be used for milling, shaking, or vortexing the sample.

While impaction using rotating blades or paddles is discussed above, it is understood that other embodiments for a bead milling component for shaking or vortexing the sample are contemplated. In one embodiment, beater bars may be replaced with bearings, including ball bearings and roller bearings.

Once the sample material has been adequately lysed, the sample is moved to a nucleic acid extraction zone, illustratively through channel 538, blister 544, and channel 543, to blister 546, where the sample is mixed with a nucleic acid-binding substance, such as silica-coated magnetic beads 533. Alternatively, magnetic beads 533 may be moved through channel 543 to blister 544, and then through channel 538 to blister 522. The mixture is allowed to incubate for an appropriate length of time, illustratively approximately 10 seconds to 10 minutes. A retractable magnet located within the instrument adjacent blister 546 captures the magnetic beads 533 from the solution, forming a pellet against the interior surface of blister 546. If incubation takes place in blister 522, multiple portions of the solution may need to be moved to blister 546 for capture. The liquid is then moved out of blister 546 and back through blister 544 and into blister 522, which is now used as a waste receptacle. One or more wash buffers from one or more of injection channels 515*c* to 515*e* are provided via blister 544 and channel 543 to blister 546. Optionally, the magnet is retracted and the magnetic beads 533 are washed by moving the beads back and forth from blisters 544 and 546 via channel 543. Once the magnetic beads 533 are washed, the magnetic beads 533 are recaptured in blister 546 by activation of the magnet, and the wash solution is then moved to blister 522. This process may be repeated as necessary to wash the lysis buffer and sample debris from the nucleic acid-binding magnetic beads 533.

It is understood that each sample type presents different challenges. Spores may require significant bead beating for lysis, but this may create a problem for genomic DNA, which may be sheered by that same amount of bead beating. In a syndromic panel approach, one may be testing for viruses, gram positive bacteria, gram negative bacteria, and eukaryotes, all in the same mixture. Moreover, even for bacterial testing, one may be testing for both genomic and plasmid-borne sequences. A single bead beating protocol may be inappropriate for all sample types.

Accordingly, a bead beating protocol may be used that employs a plurality of bead milling steps, each followed by a collection step. In this embodiment, bead milling takes place in blister 522 for a first length of time sufficient to lyse a large portion of the more easily lysed structures. Some or all of the sample may then be moved to blister 546 for capture of the released nucleic acids onto magnetic beads 533. The remaining sample may then be subjected to bead milling for an additional length of time, optionally at a higher speed, to lyse tougher samples, with subsequent capture. If desired, further bead beating followed by capture on magnetic beads may take place until tougher samples, such as spores and oocysts, are lysed and nucleic acids captured. Such multiple bead milling steps allows for capture of longer nucleic acids, while still providing for lysis of tougher samples. It is understood that the length and intensity of bead milling, along with the number of bead milling and capture cycles, may be adjusted based on sample type and type of targets that may be present in the sample. It is also understood that such a method may be used in any sample vessel, with collection in any other sample vessel. While a closed system, where bead milling takes place in a lysis zone and collection takes place in a nucleic acid extraction zone is illustrative only.

After washing, elution buffer stored at injection channel 515*f* is moved to blister 548, and the magnet is retracted. The solution is cycled between blisters 546 and 548 via channel 552, breaking up the pellet of magnetic beads 533 in blister 546 and allowing the captured nucleic acids to dissociate from the beads and come into solution. The magnet is once again activated, capturing the magnetic beads 533 in blister 546, and the eluted nucleic acid solution is moved into blister 548.

Referring again to FIG. 2, first-stage PCR master mix from injection channel 515*g* is mixed with the nucleic acid sample in blister 548. Optionally, the mixture is mixed by forcing the mixture between 548 and 564 via channel 553. After several cycles of mixing, the solution is contained in blister 564, where a pellet of first-stage PCR primers is provided, at least one set of primers for each target, and first-stage multiplex PCR is performed. If RNA targets are present, an RT step may be performed prior to or simultaneously with the first-stage multiplex PCR. First-stage multiplex PCR temperature cycling in the instrument is illustratively performed for 15-20 cycles, although other levels of amplification may be desirable, depending on the requirements of the specific application. The first-stage PCR master mix may be any of various master mixes, as are known in the art. In one illustrative example, the first-stage PCR master mix may be any of the chemistries disclosed in US2015/0118715, herein incorporated by reference, for use with PCR protocols taking 20 seconds or less per cycle.

After first-stage PCR has proceeded for the desired number of cycles, the sample may be diluted, illustratively by forcing most of the sample back into blister 548, leaving only a small amount in blister 564, and adding second-stage PCR master mix from injection channel 515*i*. Alternatively, a dilution buffer from 515*i* may be moved to blister 566 then mixed with the amplified sample in blister 564 by moving the fluids back and forth between blisters 564 and 566. If desired, dilution may be repeated several times, using dilution buffer from injection channels 515*j* and 515*k*, or injection channel 515*k* may be reserved for sequencing or for other post-PCR analysis, and then adding second-stage PCR master mix from injection channel 515*h* to some or all of the diluted amplified sample. It is understood that the level of dilution may be adjusted by altering the number of dilution steps or by altering the percentage of the sample discarded prior to mixing with the dilution buffer or second-stage PCR master mix comprising components for amplification, illustratively a polymerase, dNTPs, and a suitable buffer, although other components may be suitable, particularly for non-PCR amplification methods. If desired, this mixture of the sample and second-stage PCR master mix may be pre-heated in blister 564 prior to movement to second-stage wells 582 for second-stage amplification. Such preheating may obviate the need for a hot-start component (antibody, chemical, or otherwise) in the second-stage PCR mixture.

The illustrative second-stage PCR master mix is incomplete, lacking primer pairs, and each of the 102 second-stage wells 582 is pre-loaded with a specific PCR primer pair. If desired, second-stage PCR master mix may lack other reaction components, and these components may be pre-loaded in the second-stage wells 582 as well. Each primer pair may be similar to or identical to a first-stage PCR primer pair or may be nested within the first-stage primer pair. Movement of the sample from blister 564 to the second-stage wells 582 completes the PCR reaction mixture. Once high density array 581 is filled, the individual second-stage reactions are sealed in their respective second-stage blisters by any number of means, as is known in the art. Illustrative ways of filling and sealing the high density array 581 without cross-contamination are discussed in U.S. Pat. No. 8,895,295, already incorporated by reference. Illustratively, the various reactions in wells 582 of high density array 581 are simultaneously thermal cycled, illustratively with one or more peltier devices, although other means for thermal cycling are known in the art. For instance, a pair of heating/cooling devices, illustratively Peltier heaters, are mounted on a second side 814 of support 802. First-stage heater 886 is positioned to heat and cool the contents of one or both of blisters 548, 564 for first-stage PCR. Second-stage heater 888 is positioned to heat and cool the contents of second-stage blisters 582 of pouch 510, for second-stage PCR. It is understood, however, that these heaters could also be used for other heating purposes, and that other heaters may be included, as appropriate for the particular application.

In certain embodiments, second-stage PCR master mix contains the dsDNA binding dye LCGreen® Plus (BioFire Diagnostics, LLC) to generate a signal indicative of amplification. However, it is understood that this dye is illustrative only, and that other signals may be used, including other dsDNA binding dyes and probes that are labeled fluorescently, radioactively, chemiluminescently, enzymatically, or the like, as are known in the art. Alternatively, wells 582 of array 581 may be provided without a signal, with results reported through subsequent processing.

Figure 4:
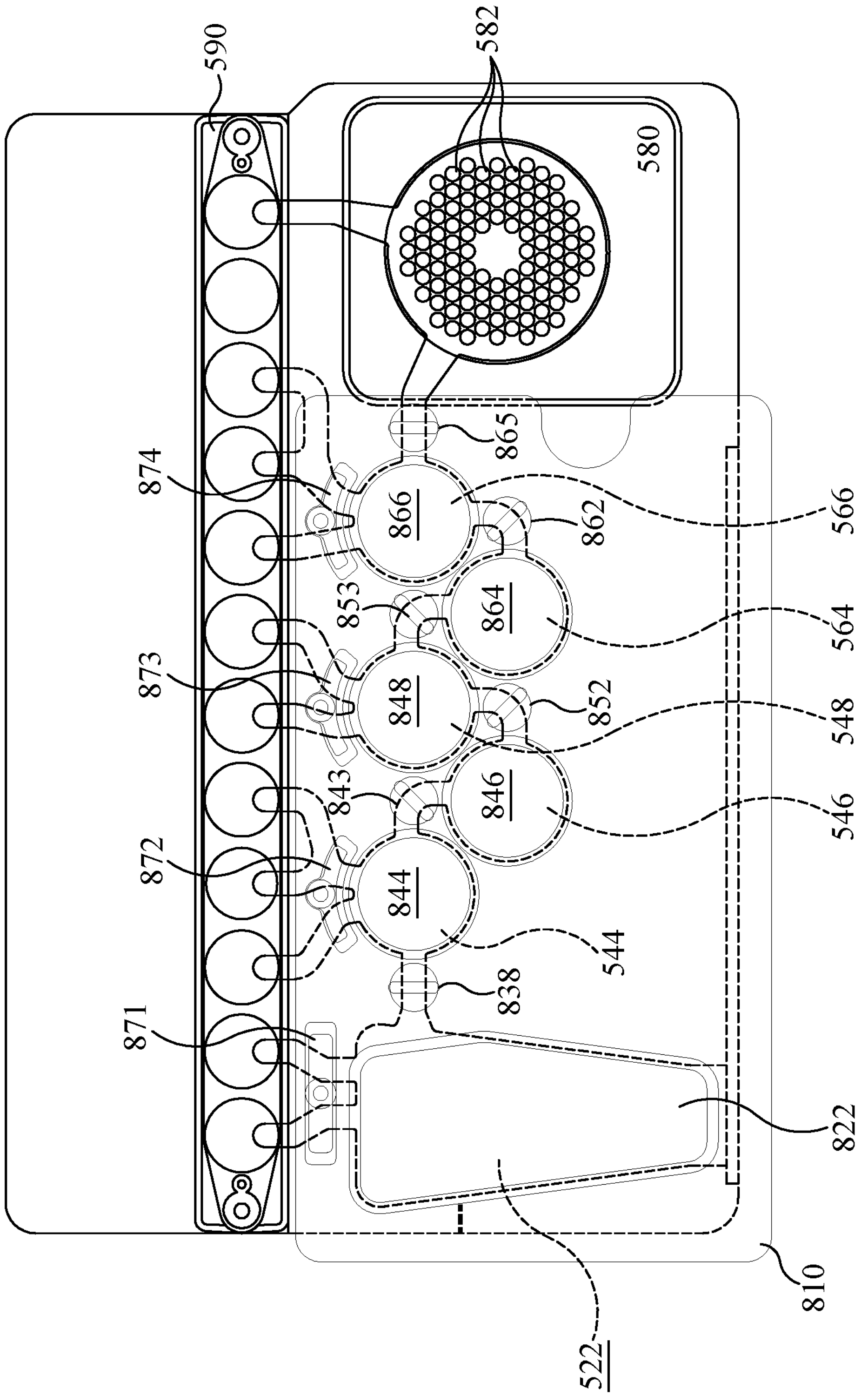
FIG. 4 shows a partial cross-sectional view of the instrument of FIG. 3A, including the bladder components of FIG. 3A, with the pouch of FIG. 2.

When pneumatic pressure is used to move materials within pouch 510, in one embodiment a "bladder" may be employed. The bladder assembly 810, a portion of which is shown in FIGS. 3A and 4, includes a bladder plate 824 housing a plurality of inflatable bladders 822, 844, 846, 848, 864, and 866, each of which may be individually inflatable, illustratively by a compressed gas source. Because the bladder assembly 810 may be subjected to compressed gas and used multiple times, the bladder assembly 810 may be made from tougher or thicker material than the pouch. Alternatively, bladders 822, 844, 846, 848, 864, and 866 may be formed from a series of plates fastened together with gaskets, seals, valves, and pistons. Other arrangements are within the scope of this invention.

Success of the secondary PCR reactions is dependent upon template generated by the multiplex first-stage reaction. Typically, PCR is performed using DNA of high purity. Methods such as phenol extraction or commercial DNA extraction kits provide DNA of high purity. Samples processed through the pouch 510 may require accommodations be made to compensate for a less pure preparation. PCR may be inhibited by components of biological samples, which is a potential obstacle. Illustratively, hot-start PCR, higher concentration of taq polymerase enzyme, adjustments in $MgCl_2$ concentration, adjustments in primer concentration, and addition of adjuvants (such as DMSO, TMSO, or glycerol) optionally may be used to compensate for lower nucleic acid purity. While purity issues are likely to be more of a concern with first-stage amplification, it is understood that similar adjustments may be provided in the second-stage amplification as well.

When pouch 510 is placed within the instrument 800, the bladder assembly 810 is pressed against one face of the pouch 510, so that if a particular bladder is inflated, the pressure will force the liquid out of the corresponding blister in the pouch 510. In addition to bladders corresponding to many of the blisters of pouch 510, the bladder assembly 810 may have additional pneumatic actuators, such as bladders or pneumatically-driven pistons, corresponding to various channels of pouch 510. FIGS. 3A and 4 show an illustrative plurality of pistons or hard seals 838, 843, 852, 853, and 865 that correspond to channels 538, 543, 553, and 565 of pouch 510, as well as seals 871, 872, 873, 874 that minimize backflow into fitment 590. When activated, hard seals 838, 843, 852, 853, and 865 form pinch valves to pinch off and close the corresponding channels. To confine liquid within a particular blister of pouch 510, the hard seals are activated over the channels leading to and from the blister, such that the actuators function as pinch valves to pinch the channels shut. Illustratively, to mix two volumes of liquid in different blisters, the pinch valve actuator sealing the connecting channel is activated, and the pneumatic bladders over the blisters are alternately pressurized, forcing the liquid back and forth through the channel connecting the blisters to mix the liquid therein. The pinch valve actuators may be of various shapes and sizes and may be configured to pinch off more than one channel at a time. While pneumatic actuators are discussed herein, it is understood that other ways of providing pressure to the pouch are contemplated, including various electromechanical actuators such as linear stepper motors, motor-driven cams, rigid paddles driven by pneumatic, hydraulic or electromagnetic forces, rollers, rocker-arms, and in some cases, cocked springs. In addition, there are a variety of methods of reversibly or irreversibly closing channels in addition to applying pressure normal to the axis of the channel. These include kinking the bag across the channel, heat-sealing, rolling an actuator, and a variety of physical valves sealed into the channel such as butterfly valves and ball valves. Additionally, small Peltier devices or other temperature regulators may be placed adjacent the channels and set at a temperature sufficient to freeze the fluid, effectively forming a seal. Also, while the design of FIG. 3A is adapted for an automated instrument featuring actuator elements positioned over each of the blisters and channels, it is also contemplated that the actuators could remain stationary, and the pouch 510 could be transitioned in one or two dimensions such that a small number of actuators could be used for several of the processing stations including sample disruption, nucleic-acid capture, first and second-stage PCR, and other applications of the pouch 510 such as immuno-assay and immuno-PCR. Rollers acting on channels and blisters could prove particularly useful in a configuration in which the pouch 510 is translated between stations. Thus, while pneumatic actuators are used in the presently disclosed embodiments, when the term "pneumatic actuator" is used herein, it is understood that other actuators and other ways of providing pressure may be used, depending on the configuration of the pouch and the instrument.

Other prior art instruments teach PCR within a sealed flexible container. See, e.g., U.S. Pat. Nos. 6,645,758 and 6,780,617, and U.S. Patent Application No. 2014/0038272, herein incorporated by reference. However, including the cell lysis within the sealed PCR vessel can improve ease of use and safety, particularly if the sample to be tested may contain a biohazard. In the embodiments illustrated herein, the waste from cell lysis, as well as that from all other steps, remains within the sealed pouch. However, it is understood that the pouch contents could be removed for further testing.

In the illustrative instrument 800, heaters 886 and 888 are mounted on support member 802. However, it is understood that this arrangement is illustrative only and that other arrangements are possible. Bladder plate 810, with bladders 822, 844, 846, 848, 864, 866, hard seals 838, 843, 852, 853, seals 871, 872, 873, 874 form bladder assembly 808 may illustratively be mounted on a movable support structure that may be moved toward pouch 510, such that the pneumatic actuators are placed in contact with pouch 510. When pouch 510 is inserted into instrument 800 and the movable support member is moved toward support member 802, the various blisters of pouch 510 are in a position adjacent to the various bladders of bladder assembly 810 and the various seals of assembly 808, such that activation of the pneumatic actuators may force liquid from one or more of the blisters of pouch 510 or may form pinch valves with one or more channels of pouch 510. The relationship between the blisters and channels of pouch 510 and the bladders and seals of assembly 808 is illustrated in more detail in FIG. 4.

Each pneumatic actuator is connected to compressed air source 895 via valves 899. While only several hoses 878 are shown in FIG. 3A, it is understood that each pneumatic fitting is connected via a hose 878 to the compressed gas source 895. Compressed gas source 895 may be a compressor, or, alternatively, compressed gas source 895 may be a compressed gas cylinder, such as a carbon dioxide cylinder. Compressed gas cylinders are particularly useful if portability is desired. Other sources of compressed gas are within the scope of this invention.

Assembly 808 is illustratively mounted on a movable support member, although it is understood that other configurations are possible.

Several other components of instrument 810 are also connected to compressed gas source 895. A magnet 850, which may be mounted on a second side 814 of support member 802, is illustratively deployed and retracted using gas from compressed gas source 895 via hose 878, although other methods of extending and retracting the magnet are known in the art. It is understood that recess 851 can be a passageway through support member 802, so that magnet 850 can contact blister 546 of pouch 510. However, depending on the material of support member 802, it is understood that recess 851 need not extend all the way through support member 802, as long as when magnet 850 is deployed, magnet 850 is close enough to provide a sufficient magnetic field at blister 546, and when magnet 850 is retracted, magnet 850 does not significantly affect any magnetic beads 533 present in blister 546. While reference is made to a retracting magnet, it is understood that an electromagnet may be used and the electromagnet may be activated and inactivated by controlling flow of electricity through the electromagnet. Thus, while this specification discusses withdrawing or retracting the magnet, it is understood that these terms are broad enough to incorporate other ways of withdrawing the magnetic field. It is understood that the pneumatic connections may be pneumatic hoses or pneumatic air manifolds, thus reducing the number of hoses or valves required.

The various pneumatic pistons 868 of pneumatic piston array 869 are also connected to compressed gas source 895 via hoses 878. While only two hoses 878 are shown connecting pneumatic pistons 868 to compressed gas source 895, it is understood that each of the pneumatic pistons 868 are connected to compressed gas source 895. Twelve pneumatic pistons 868 are shown.

When fluorescent detection is desired, an optical array 890 may be provided. As shown in FIG. 3A, optical array 890 includes a light source 898, illustratively a filtered LED light source, filtered white light, or laser illumination, and a camera 896. Camera 896 illustratively has a plurality of photodetectors each corresponding to a second-stage well 582 in pouch 510. Alternatively, camera 896 may take images that contain all of the second-stage wells 582, and the image may be divided into separate fields corresponding to each of the second-stage wells 582. Depending on the configuration, optical array 890 may be stationary, or optical array 890 may be placed on movers attached to one or more motors and moved to obtain signals from each individual second-stage well 582. It is understood that other arrangements are possible.

As shown, a computer 894 controls valves 899 of compressed air source 895, and thus controls all of the pneumatics of instrument 800. Computer 894 also controls heaters 886 and 888, and optical array 890. Each of these components is connected electrically, illustratively via cables 891, although other physical or wireless connections are within the scope of this invention. It is understood that computer 894 may be housed within instrument 800 or may be external to instrument 800. Further, computer 894 may include built-in circuit boards that control some or all of the components, and may also include an external computer, such as a desktop or laptop PC, to receive and display data from the optical array. An interface, illustratively a keyboard interface, may be provided including keys for inputting information and variables such as temperatures, cycle times, etc. Illustratively, a display 892 is also provided. Display 892 may be an LED, LCD, or other such display, for example.

Figure 3B:
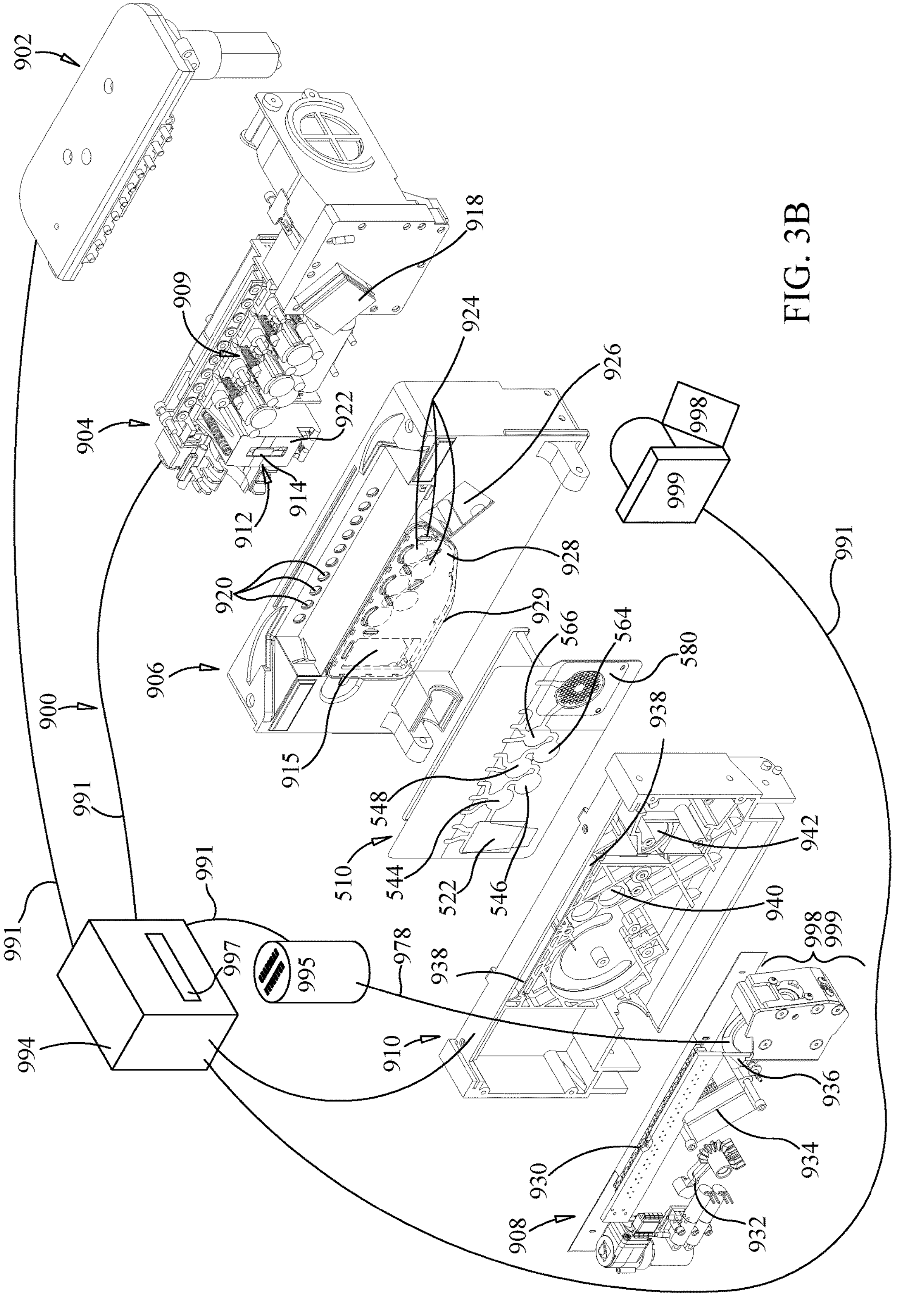
FIG. 3B is an exploded perspective view of another instrument for use with the pouch of FIG. 2, including the pouch of FIG. 2, according to an embodiment of the present invention.

FIG. 3B shows an exploded view of another illustrative embodiment of an instrument 900 that could be used with pouch 510. The instrument 900 includes many features similar to instrument 800 and both instruments are designed to run the same pouches (i.e., pouch 510). However, the various components in instrument 900 have been redesigned and rearranged to, for example, increase the robustness of the instrument, reduce power consumption by the instrument, or to better use the space within the instrument. Some redesigned components achieve several of these goals. In addition, some of the components in instrument 900 may be utilized to reduce the pouch run time relative to instrument 800.

Notable differences between instrument 900 and instrument 800 include, but are not limited to, replacement of the pneumatic systems for liquid movement with purpose built mechanical systems, addition of a moving magnet system for enhanced magnetic bead recovery, and replacement of the single Peltier device for second-stage PCR with a multi-zone rotary heater (e.g., a three zone rotary heater). The subsystems of instrument 900 will be introduced briefly in reference to FIG. 3B and will be discussed in detail in reference to the additional Figures.

When the pouch 510 is placed in instrument 900, the pouch 510 can be contacted by the various systems and subassemblies of the instrument that, for example, effect fluid movement, cell lysis, nucleic acid recovery, first-stage PCR, second-stage PCR, and fluorescent detection. Instrument 900 includes a piston subassembly 902 that can be used to move sample and reagents from the fitment of pouch 510 into the pouch blisters. Embodiments of the plunging system are illustrated in FIGS. 9-9D, 10A-10C, 11A-11B, and 12A-12B and are discussed in detail below.

Figure 13:
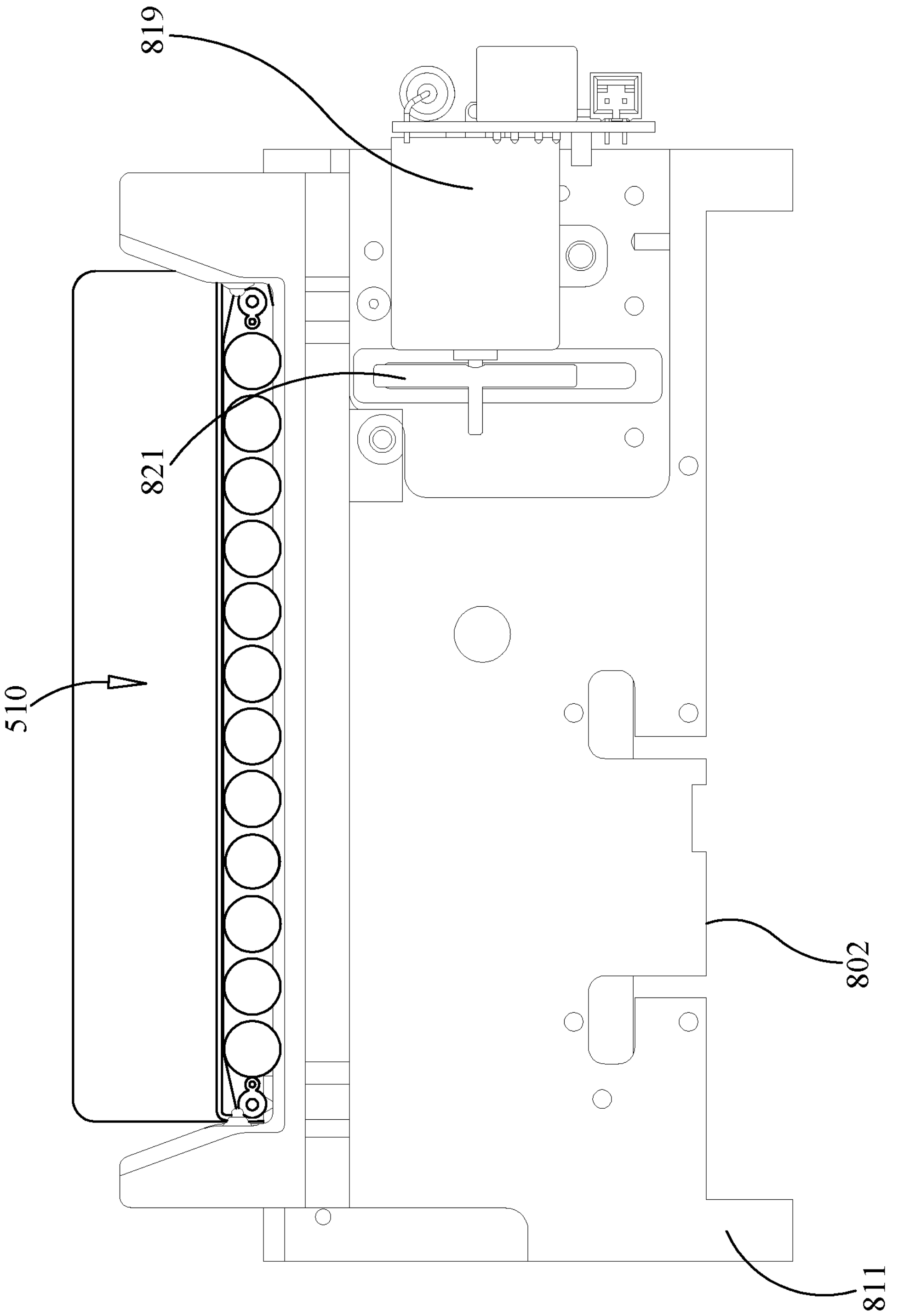
FIG. 13 shows a motor used in one illustrative embodiment of the instrument of FIGS. 3A and 3B.
Figure 14:
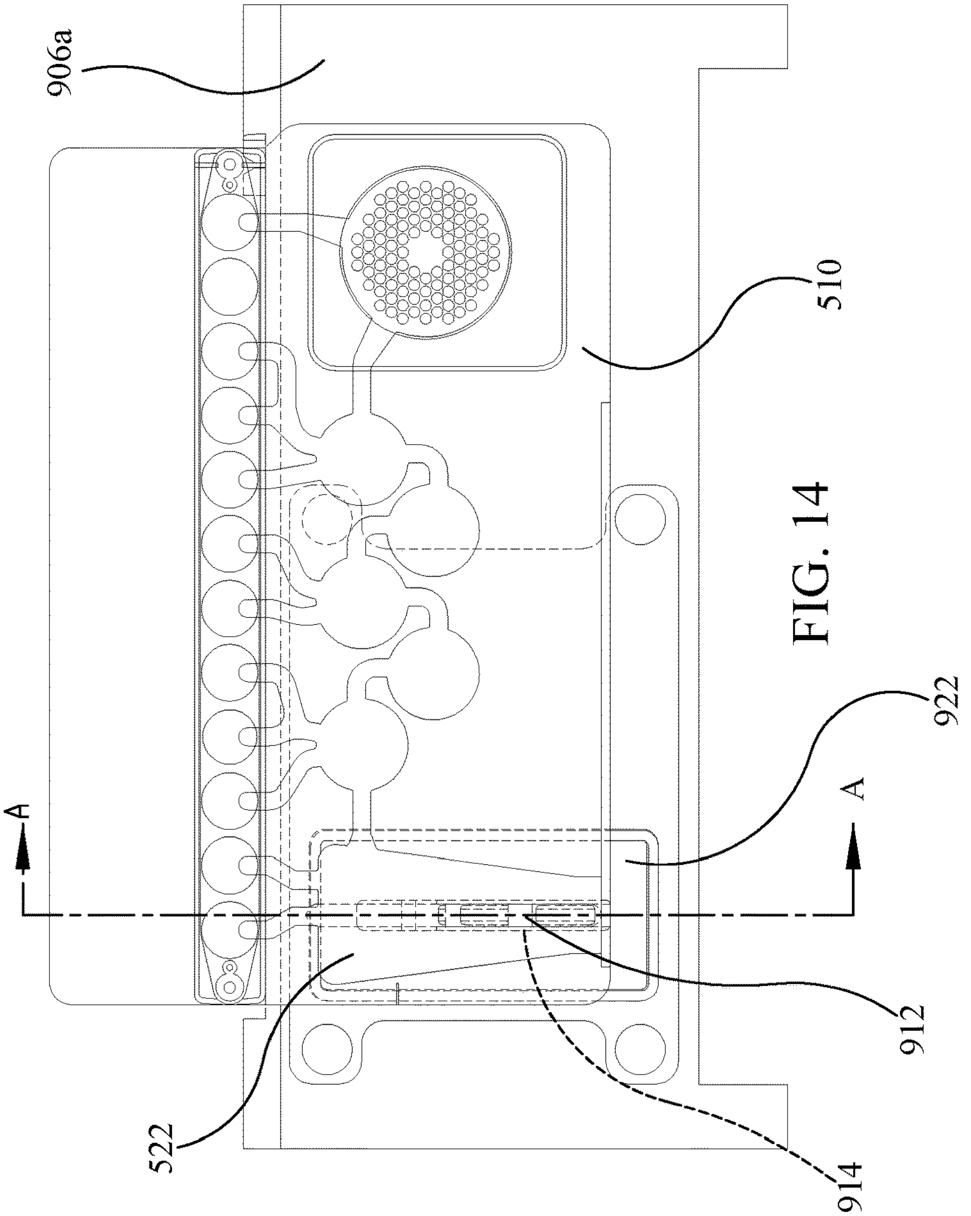
FIG. 14 shows an alternative embodiment of a motor used in one illustrative embodiment of the instrument of FIGS. 3A and 3B.
Figure 14A:
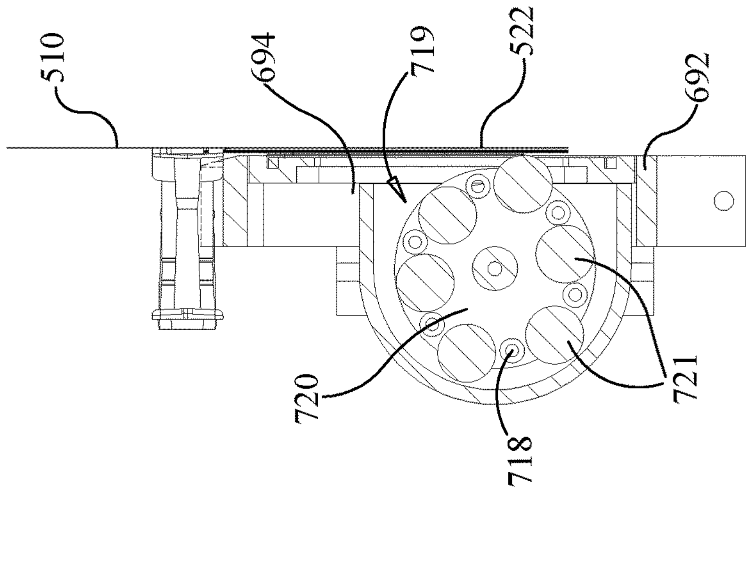
FIG. 14A is a cross-sectional view of the motor of FIG. 14.

Instrument 900 also includes a core subassembly 904 that includes many of the physical components in the interior of the instrument. The core subassembly includes a bead beater assembly 912. In the illustrated embodiment, the bead beater assembly 912 partially extends through a slot 914 in a compression plate 922; the bead beater assembly 912 and the compression plate 922 are positioned in the instrument 900 such that they can contact lysis blister 522 when the pouch 510 is installed in the instrument 900. Embodiments of the bead beater assembly 912 and compression plate 922 are illustrated in FIGS. 13-14E and are discussed in detail below.

The core subassembly 904 also includes a compression member/seal subassembly 909 that, along with compression plate 922, can be used to control movement of fluids between blisters in the pouch 510. Embodiments of the compression plate 922 compression member/seal subassembly 909 are illustrated in FIGS. 20A-20H and 21A-21C and are discussed in detail below. The core subassembly 904 also includes a heater 918 (e.g., a Peltier) that may be configured for second-stage PCR. An alternative embodiment of a second stage heater that may be used in the instrument of FIG. 3B is illustrated and discussed in reference to FIG. 29.

Instrument 900 also includes a support member 906 that is sized and configured for covering the core subassembly 904. The support member 906 includes a plurality of openings 920 to receive the pistons of the plunging system 902, opening 915 for the bead beater assembly 912, openings 924 for the compression members and seals 909, and an opening 926 for the second-stage PCR heater 918. The support member 906 also includes an opening 928 that is sized and configured for receiving a front panel gasket 929. Because pouch 510 may be made of a flexible material, the flexible material may rupture inside the instrument. In one embodiment, the front panel gasket 929 may define a flexible membrane or barrier, e.g., a polyurethane or silicone membrane, although it is understood that these materials are illustrative only, and that other materials may be used as are known in the art. It is desirable that front panel gasket 929 be cleanable, that is withstand multiple cleanings with bleach, RNAse Out, or other cleaners that are typical for cleaning or decontaminating nucleic acid amplification devices. Additionally or alternatively, in one embodiment it is desirable for front panel gasket 929 to be easily removable and replaceable. Front panel gasket 929 also provides a barrier layer between the compression members and seals 909 that operate on blisters 522, 544, 546, 548, 564, and 566 of pouch 510. However, this is illustrative only and front panel gasket 929 may provide a barrier layer for any part of pouch 510, or multiple smaller membranes may be used. Embodiments of the front panel gasket 929 are illustrated in FIGS. 22A and 22B and 23A and 23B and are discussed in detail below.

Instrument 900 also includes a door subassembly 908 and a second support member 910 that may form the front portion of the instrument 900 and may, for instance, be opened in order to insert a pouch (e.g., pouch 510) into the instrument 900 for a run. Door subassembly 908 includes a seal bar 930, a mag lift system 932, Peltier heaters 934 for first-stage PCR, and an inflatable window bladder 936. Embodiments of the seal bar 930 are illustrated in FIGS. 5-8, embodiments of the mag lift system 932 are illustrated in FIGS. 15A-K and 16A-19B, and embodiments of the window bladder 936 are illustrated in FIGS. 24-28B, and are discussed in detail below. Window bladder 936 is fluidly connected to a compressed gas source 995 that can be used to inflate the window bladder 936. Support member 910 provides a support structure for the door subassembly 908 and includes an opening 938 for the seal bar 930, openings 940 for the first-stage heaters, and an opening 942 for the window bladder. The support member 910 also presents a surface 944 that presses against the pouch 510 and holds it in place when it is in the instrument 900. While door assembly 908 is movable to allow insertion of pouch 510 into instrument 900, it is understood that this configuration is illustrative only and that many of the subassemblies provided on door assembly 908 may be stationary relative to pouch 510.

As with instrument 800, instrument 900 includes a light source 998, illustratively a filtered LED light source, filtered white light, or laser illumination, and a camera 999. Camera 999 illustratively has a plurality of photodetectors each corresponding to a second-stage well 582 in pouch 510. Alternatively, camera 999 may take images that contain all of the second-stage wells 582, and the image may be divided into separate fields corresponding to each of the second-stage wells 582. Depending on the configuration, the camera 999 and the light source 998 may be stationary or they may be placed on movers attached to one or more motors and moved to obtain signals from each individual second-stage well 582. It is understood that other arrangements are possible. In one embodiment, the camera 999 and the light source 998 may be incorporated into the door subassembly 908 and support member 910.

As shown, a computer 994 controls the components of instrument 900 such as, but not limited to, the plunging system 902, the components of the core subassembly 904, and components of the door subassembly. The computer 994 also controls the compressed gas source 995, and thus controls inflation of the window bladder 936. Each of these components is connected electrically, illustratively via cables 991, although other physical or wireless connections are within the scope of this invention. It is understood that computer 994 may be housed within instrument 900 or may be external. Further, computer 994 may include built-in circuit boards that control some or all of the components, and may also include an external computer, such as a desktop or laptop PC, to receive and display data from the optical array. An interface, illustratively a keyboard interface, may be provided including keys for inputting information and variables such as temperatures, cycle times, etc. Illustratively, a display 997 is also provided. Display 997 may be an LED, LCD, or other such display, for example.

It is understood that any of the illustrative components and subassemblies of instrument 900 may be used with instrument 800 or with other instruments as are known in the art. It is understood that this combination of components and subassemblies is illustrative only.

Fitment, Injection, and Sealbar

Figure 5:
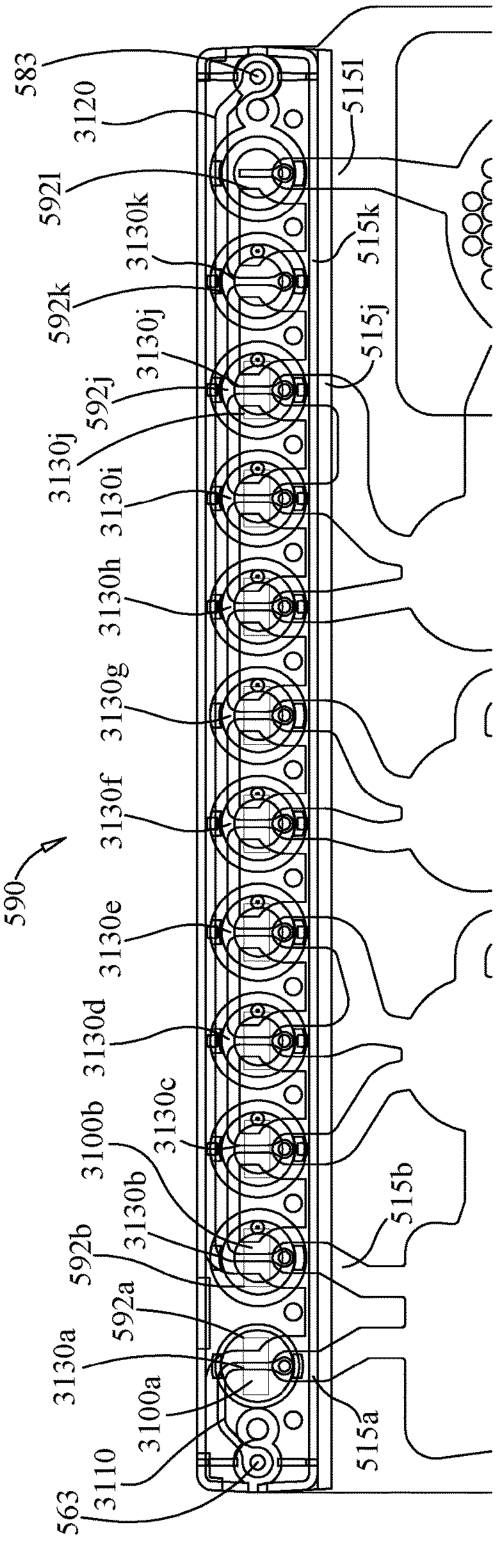
FIG. 5 is an end view of the fitment of the pouch of FIG. 2 illustrating a number of channels and seal locations, according to an embodiment of the present invention.

Referring to FIG. 5, in an illustrative method, the user injects the sample to be tested into the fitment 590 of pouch 500 by inserting an injection device (e.g., a cannula fluidly connected to a vial of sample) into sample injection opening 563. The sample fills sample chamber 592*a* by flowing through a first fill channel 3110 and through fill port 3130*a*, which fluidly connects sample chamber 592*a* to the sample injection port 563 and the first fill channel 3110. In the illustrative method, the reagents that were previously freeze dried in chambers 592*b*-592*k* are rehydrated by inserting a hydration device (e.g., a cannula fluidly connected to a vial containing a hydration solution such as water or buffer) into hydration injection port 583. The hydration solution hydrates the reagent in chambers 592*b*-592*k* by flowing down a second fill channel 3120 that is separate from fill channel 3110. The second fill channel 3120 is fluidly connected to fill ports 3130*b*-3130*k*, which are dedicated to filling chambers 592*b*-592*k*, respectively.

After injection, the sample may be moved from chamber 592*a* to pouch blister 522 (see FIG. 2) via injection channel 515*a* and the reagents may, at the appropriate times, be moved into the appropriate pouch blisters from chambers 592*b*-592*j* via injection channels 515*b*-515*j* (in the illustrated embodiment, chambers 592*k* and 592*l* are not used for injection into the pouch, but they may be utilized in some embodiments). However, in order to prevent fluid from flowing back out of the sample injection port 563 and the hydration injection port 583 and to prevent mixing of reagents between chambers, the fill ports 3130*a*-3130*k* may be sealed illustratively using a heat sealing device in the instrument prior to injection of sample and reagents into the pouch. Heat seals 3100*a*-3100*j* that may be applied to seal fill ports 3130*a*-3130*j* are shown in FIG. 5. The seals 3100*a*-3100*j* are positioned so that they seal off access to the fill ports 3130*a*-3130*j*, and optionally to seal off chambers 592*b*-592*j* from each other, without sealing access to injection channels 515*a*-515*j*. Thus, samples and reagents can be injected into the pouch without loss of sample or reagents through the sample injection port 563 or the hydration injection port 583 and without risk off mixing reagents between chambers 592*b*-592*j*.

Figure 6B:
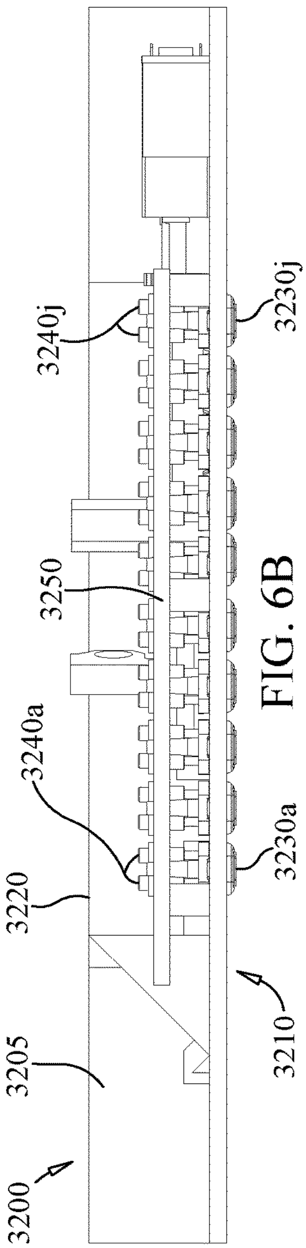
FIGS. 6A and 6B illustrate a heat sealing system for use with the pouch of FIG. 2, according to an embodiment of the present invention.
Figure 6A:
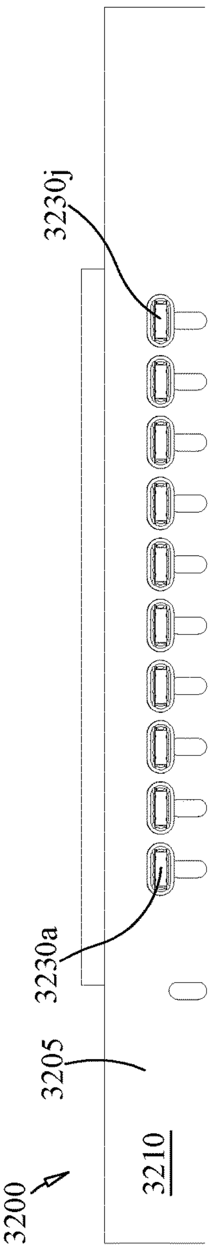

FIGS. 6A and 6B illustrate an embodiment of a heat sealing system 3200 that may be used with instrument 900 described herein. FIG. 6A illustrates a front view of the heat sealing system and FIG. 6B illustrates a top view of the heat sealing system rotated 90° relative to the view of FIG. 6A. It is understood that this heat sealing system is one illustrative sealing mechanism that may be used as seal bar 930, as shown in FIG. 3B, although other heat sealing devices are possible. The heat sealing apparatus 3200 includes a plate 3205 having an interior surface 3210 that may be pressed against one surface of the pouch 510 and an exterior surface 3220 opposite the interior surface. The plate 3205 may, for instance, be included in instrument 900 as an outer cover and the plate 3205 may include other components described herein, in addition to the heat sealing system, such as, but not limited to, a moving magnet system, heater(s) for one or more PCR steps, observation window(s), and the like. The plate 3205 may also include a variety of electrical connections, secondary covers, etc. that are not illustrated in FIGS. 6A and 6B.

The illustrated embodiment, the heat sealing system 3200 includes a number of individual heaters 3230*a*-3230*j*. As illustrated in FIG. 6B, each individual heater projects out of the face of the interior surface 3210 of plate 3205 so that the heaters can contact the fitment 590 of pouch 510 and produce the seals 3100*a*-3100*j* illustrated in FIG. 5 by providing sufficient heat to melt fill ports 3130*a*-3130*k* closed without compromising the integrity of fitment 590. It is understood that the amount of heat will depend upon the exact composition of the plastic used in fitment and the film. As further illustrated in FIG. 6B, each heater extends from the front surface 3210 to the back surface 3220 of plate 3205. The individual heaters 3230*a*-3230*j* each include electrical junctions illustrated at 3240*a*-3240*j* that are configured for connecting the individual heaters to an electrical source for heat production. In one embodiment, the individual heaters may be connected together to a single circuit or they may each be connected individually so that each heater element may be separately controlled and monitored. In the illustrated embodiment, the heaters 3230*a*-3230*j* are coupled to plate 3205 with the help of bar 3250. For instance, the individual heaters may be clipped, tied, or otherwise fastened to bar 3250.

Figure 7A:
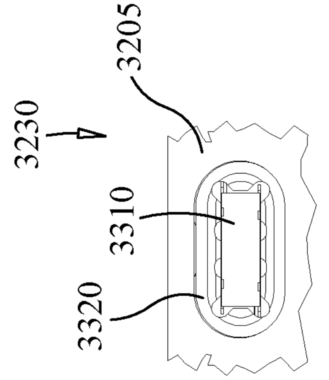
FIGS. 7A-7C illustrate views of heaters for use with the heat sealing system of FIGS. 6A and 6B, according to embodiments of the present invention.

Referring to FIG. 7A, an individual heater 3230 is illustrated. Each individual heater 3230 is disposed in plate 3205. Each individual heater 3230 includes an electric heater element 3310 and a housing 3320. The electric heater element 3310 may be any type of resistive heater element known in the art. For instance, typical resistance heaters may include, but are not limited to, resistance wire, ceramic, or etched foil heating elements. For instance, the electric heater element 3310 may include a nickel-chromium (i.e., nichrome) heating element or another typical resistance wire heating element. Etched foil elements are generally made from the same alloys as resistance wire elements, but are produced with a subtractive photo-etching process that starts with a continuous sheet of metal foil and ends with a complex resistance pattern.

In an illustrative embodiment, electric heater element 3310 may include a ceramic heating element, such as a positive thermal coefficient (PTC) heating element. PTC ceramic material is named for its positive thermal coefficient of resistance (i.e., resistance increases upon heating). While most metals do become slightly more resistant at higher temperatures, this class of ceramics (often barium titanate and lead titanate composites) has a highly nonlinear thermal response where the resistivity increases exponentially with increasing temperature, so that the PTC material becomes extremely resistive above a composition-dependent threshold temperature. This behavior causes the material to be self-regulating and to act as its own thermostat. "Self-regulating" means that every point of the heater independently keeps a constant temperature without the need of regulating electronics. "Self-limiting" means that the heater can generally not exceed a certain temperature at any point and requires no overheat protection.

Thus, current passes readily when PTC material is cool, and does not readily pass when the threshold temperature is reached. Due to the exponentially increasing resistivity, the heater cannot generally heat above the selected, composition-dependent threshold temperature. In one embodiment, the PTC heater element is configured to heat to a range of about 180° C. to about 220° C. (e.g., 200° C.) at 12V. In contrast to resistance wire materials that are typically controlled with a thermocouple and that can overheat if the heater or the thermocouple fails, PTC heaters cannot generally overheat. This is a relevant concern in the present case because if a heater overheats, the heater can melt through the plastic of pouch 510, which can cause the run to fail, and potentially contaminate the instrument with the pouch contents.

Figure 7B:
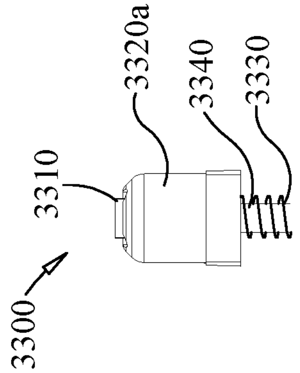
Figure 7C:
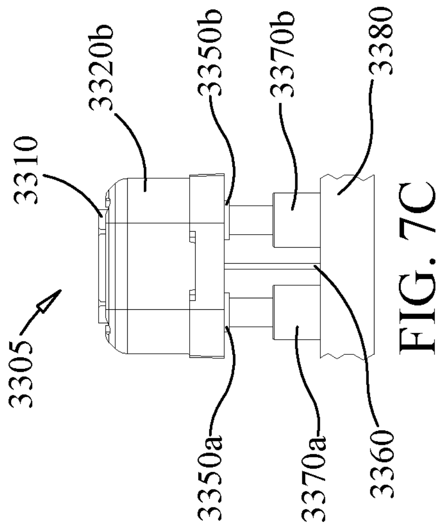

Referring now to FIGS. 7B and 7C, side views of two exemplary heater designs 3300 and 3305 are illustrated. Heater 3300 in FIG. 7B includes a heater element 3310, a composite holder 3320*a* (e.g., a thermally stable plastic) for the heater element 3310, and a base 3330 that may be used to connect the heater 3300 to plate 3205. In the illustrated embodiment, heater 3300 also includes spring member 3340 that wraps around the base 3330 and that allows the heater assembly 3300 to be flexibly mounted in the instrument. Heater 3305 illustrated in FIG. 7C is similar to heater 3300. Heater 3305 includes a heater element 3310 and a composite holder 3320*b* (e.g., a thermally stable plastic) for the heater element 3310. In the illustrated embodiment, the heater assembly 3305 may be coupled to base 3380 via a clip 3360.

In one embodiment, base 3380 may be part of plate 3205. In another embodiment, base 3380 may be part of circuit board, or the like, that may be attached to or integrally formed with plate 3205. In the illustrated embodiment, heater 3305 includes two electrical connections 3350*a* and 3350*b* that may be used to electrically connect the heater element 3310 to a power source. In the illustrated embodiment, the two electrical connections 3350*a* and 3350*b* are connected to two pins 3370*a* and 3370*b* that are electrically couple to the base 3380. The pins 3370*a* and 3370*b* in the illustrated embodiment are so-called 'pogo pins' that maintain electrical contact and include an internal spring member that allow the heater assembly 3305 to be flexibly mounted in the instrument.

In one embodiment, spring 3340 and the springs in the pins 3370*a* and 3370*b* may be selected to regulate the amount of pressure that the heaters apply to the pouch when the pouch is enclosed in an instrument. Likewise, the springs can control, at least in part, how far the heaters can penetrate into the plastic of the pouch. For instance, at a given temperature, there is a correlation between the pressure applied to the plastic of pouch 510 and how long it takes to melt/seal the plastic. In one illustrative example, the amount of pressure is selected to allow the heaters to seal the pouch in a temperature a range of about 180° C. to about 220° C. (e.g., 200° C.) illustratively within 1-5 seconds. In an example, the springs and the mounting of the heaters to the instrument are selected so that each heater applies about 0.5 to 2 pounds of pressure (e.g., about 1 lb of pressure) to each heat seal spot Referring now to FIG. 8, an embodiment of a heat sealing system 3200 that includes a cover 3400 over the heater array 3230*a*-3230*j* is illustrated. The heat sealing system 3200 includes a plate 3205 having an interior surface 3210; the heater array 3230*a*-3230*j* is disposed in plate 3205 and projects out of the plane of plate 3210. The cover 3400 includes a portion 3420 that is sized and configured to fit over the heater array 3230*a*-3230*j* and may include an adhesive portion 3430 that is sized and configured to adhere the cover 3400 to the plate. In one embodiment, the cover 3400 may be made from a heat resistant and heat conductive material. As such, the cover 3400 may be placed over the heater array 3230*a*-3230*j* to protect the heaters and to prevent melted plastic from sticking to the heaters if one or more heaters malfunction and melt through the pouch. In one embodiment, the cover may be made from a material (e.g., Teflon) that melted plastic will not adhere to in the event of malfunction. In one embodiment, the cover 3400 is a field replaceable (i.e., user replaceable) Teflon seal strip that is formed to fit over the heater array 3230*a*-3230*j*. Even if the heaters melt the plastic of the fitment 590, the melted plastic will not stick to the Teflon.

After sealing with the sealing system 3200, the sample may be moved from chamber 592*a* to into pouch blister 522 via injection channel 515*a*. Lysis blister 522 is provided with beads or particles 534, such as ceramic beads, and is configured for vortexing via impaction using rotating blades or paddles provided within the instrument. Bead-milling, by shaking or vortexing the sample in the presence of lysing particles such as zirconium silicate (ZS) beads 534, is an effective method to form a lysate. It is understood that, as used herein, terms such as "lyse," "lysing," and "lysate" are not limited to rupturing cells, but that such terms include disruption of non-cellular particles, such as viruses.

Plunging Systems

Figure 9:
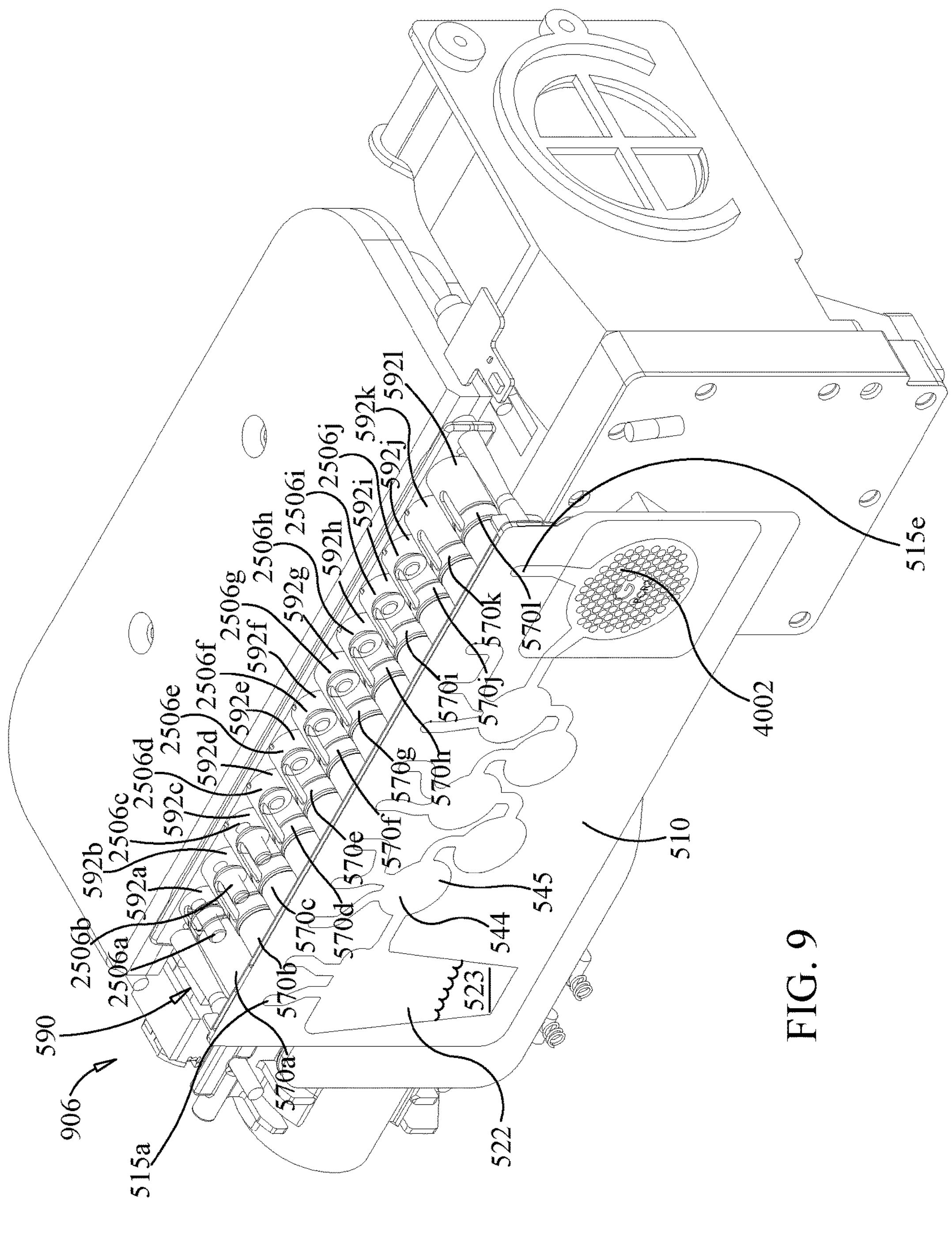
FIG. 9 illustrates a perspective view of a plunging system for moving fluids from the fitment into the blisters of the pouch of FIG. 2, according to an embodiment of the present invention.
Figure 9A:
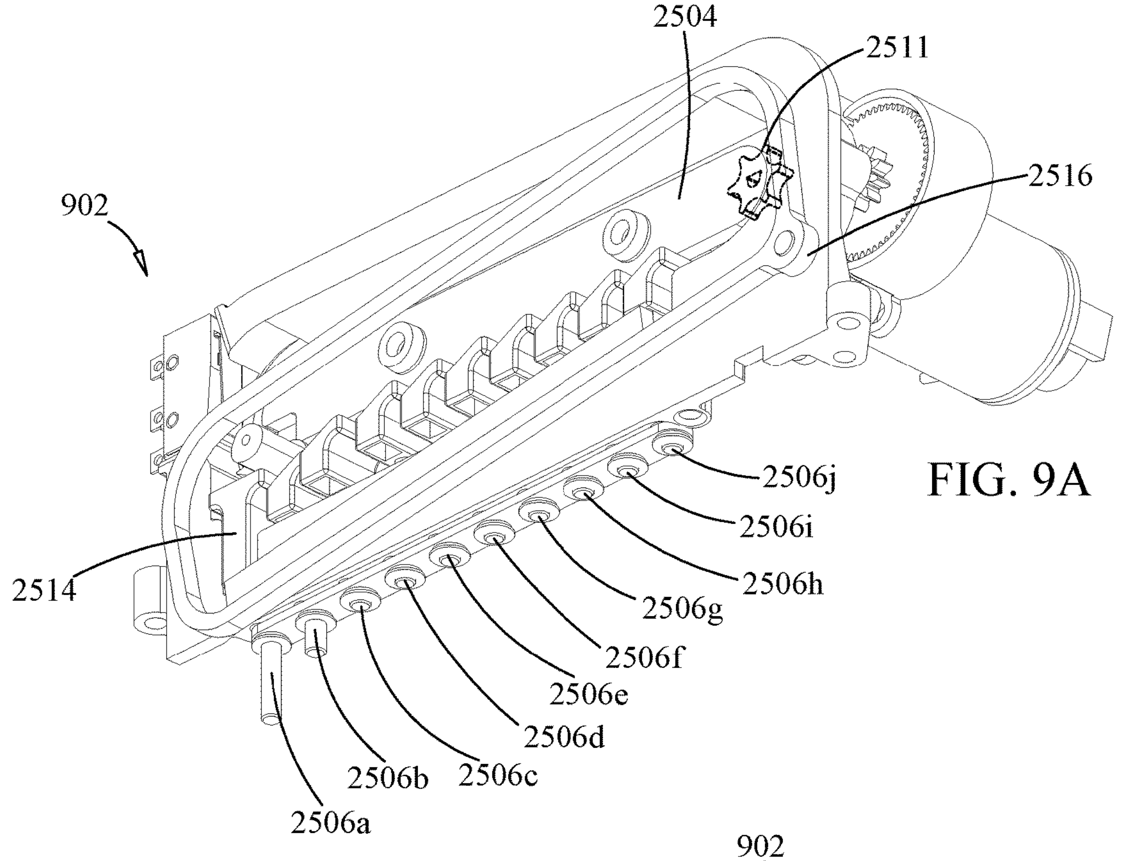
FIGS. 9A-9D illustrate views of a plunging system, according to an embodiment of the present invention.

FIGS. 9-9D, 10A-10C, 11A-11B, and 12A-12B illustrate four embodiments of plunging systems that include pistons or other similar mechanisms that may be employed to move fluids into the pouch. FIG. 9 illustrates an embodiment of a plunging system that was illustrated at 902 in FIG. 3B. Plunging system 902 may be used to move fluids (i.e., sample or reagents) from the fitment 590 into pouch 510. For clarity and context, plunging system 902 is shown in relation to support member 906, pouch 510, and fitment 590. However, it is understood that other arrangements are contemplated.

Fitment 590 comprises a plurality of chambers 592*a*-592*l* that are each connected to a plurality of entry channels 515*a*-515*l*. Any or all of chambers 592*a*-592*l* may contain a sample to be analyzed or freeze dried reagents; freeze dried reagents may be rehydrated with water or hydration buffer. Loading of sample and reagent rehydration are discussed in detail in Example 2 presented below. Sample and/or buffer may be moved into pouch 510 through entry channels 515*a*-515*j* during use. Plungers 570*a*-570*l* may be associated with pistons or other similar mechanisms from the plunger systems illustrated herein that may be employed to activate plungers 570*a*-570*l* to move fluids from chambers 592*a*-592*l* into pouch 510. In the illustrated embodiment, while chambers 592*k* and 592*l* include pistons 570*k* and 570*l*, entry channel 515*k* is not fluidly connected to blisters in the pouch and entry channel 515*l* may be used for overflow from second-stage PCR. As will be discussed in greater detail below, chambers 592*k* and 592*l* are not associated with injection pistons, although they may be provided with injection pistons in other configurations.

All of the components of the plunger systems illustrated herein used to move fluid from fitment 590 into pouch 510 may be fabricated by any means know in the art, such as, but not limited to, injection molding, die casting, or machining Each component may be made from any durable material known in the art, such as, but not limited to, metals (e.g., pot metal or aluminum), plastics (e.g., polyethylene, polypropylene, polystyrene, polycarbonate, ABS, PEEK, and the like), and metal and plastic composites.

Referring again to FIG. 9, when the pouch 510 is placed in an instrument (e.g., instrument 900), the pouch 510 can be contacted by the various systems and subassemblies of the instrument that, for example, position and confine the pouch 510 in relation to the various subsystems. For instance, when pouch 510 is placed in instrument 900, the pouch 510 may be contacted by support members 906 and 910 (not shown) and the fitment 590 may be arranged perpendicular to the pouch 510 and parallel to the plunging system 902. Plunging system 902 includes pistons 2506*a*-2506*j* that project into chambers 592*a*-592*j*. The pistons 2506*a*-2506*j* can be extended one or more at a time by the plunging system 902 in order to activate plungers 570*a*-579*j* to move fluids from the respective chambers into the pouch. The plunging system 902 is configured to extend pistons 2506*a*-2506*j*, one or more at a time, to move fluids at the appropriate time from the fitment 590 into the pouch 510.

This is schematically illustrated at chambers 592*a*-592*c* of FIG. 9. In chambers 592*a*-592*c*, pistons 2596*a*-2506*c* are extended to press down on plungers 570*a*-570*c*. The chambers 592*a*-592*j* and 592*l* of the illustrated fitment 590 are connected specific entry channels and blisters of the pouch 510. In the illustrated example, chamber 592*a* may include a sample and chambers 592*b*-592*c* may include reagent. Compression of plungers 570*a* and 570*b* can inject sample and a reagent (e.g., a lysis buffer) into blister 522 (shown schematically in blister 522 as liquid 523) and compression of plunger 570*c* can inject a reagent (e.g., a wash buffer) into blister 544 (shown schematically in blister 544 as liquid 545).

FIGS. 9A-9D illustrate the internal mechanism of one embodiment of the plunging system 902. The embodiment illustrated in FIGS. 9A-9D includes a chain mechanism 2502 and a return mechanism (e.g., cam 2516 and return pin 2512) that are configured for extending and retracting the individual pistons 2506*a*-2506*j*. Chain 2502, which may be similar to a bicycle chain, rotates around plate 2504 in groove 2510, in a substantially elliptical pattern. For the sake of clarity, only part of chain 2502 is illustrated in FIGS. 9A-9D but it is understood that chain 2502 extends in a loop all the way around in groove 2510. In the illustrated embodiment, chain 2502 is driven by a drive wheel 2511, which may be mechanically coupled to a motor or another power source and other mechanisms that cause drive wheel 2511 to rotate and move the chain, as will be understood by one of skill in the art. In the illustrated embodiment, chain 2502 includes a number of specially shaped links (e.g., links 2503*a*-2503*c* and 2512) that, respectively, are configured for generating downward forces to extend the individual pistons 2506*a*-2506*j* and configured for activating a mechanism to retract all of the pistons. The configuration of links 2503*a*-2503*c* and 2512 will be discussed in greater detail below.

In the illustrated embodiment, three links 2503*a*-2503*c* in chain 2502 are raised relative to the links around them in a direction that is substantially perpendicular to the axis of chain 2502. In the embodiment depicted in FIGS. 9A-9D, the plunging mechanism 902 further comprises columns 2514*a*-2514*j*, each of which is coupled to a respective plunger 2506*a*-2506*j* at their distal ends. Column 2514*a* comprises a substantially flat platform 2508*a* at its proximal end and piston 2506*a* at its distal end. Each of columns 2514*b*-2514*j* comprises angled portions 2508*b-j* at its proximal end and its respective piston 2506*b*-2506*j* at its distal end. Substantially flat platform 2508*a* and angled portions 2508*b*-2508*j* extend from columns 2514*a*-2514*j* in a direction that is substantially perpendicular to the direction in which the raised links 2503*a*-2503*c* extend from the link of chain 2502. One will appreciate that three links 2503*a*-2503*c* is merely illustrative and that a plunging mechanism that includes chain 2502 may have more or fewer raised links.

As chain 2502 rotates around plate 2504, one of raised links 2503*a*-2503*c* eventually comes in contact with the flat proximal end 2508*a* of column 2514*a*. At this point, the raised link applies pressure to the flat proximal end 2508*a* of column 2514*a*. The pressure forces column 2514*a* to move in the same direction as the raised link is moving (downward depicted in FIGS. 9A-9D). Specifically, in the embodiments shown in FIG. 9B, while raised link 2503*a* is moving around the curve at first end 2520 of plate 2504, raised link 2503*a* pushes downward on the flat platform 2508*a* of column 2514. It is understood that the directions downward and upward as used herein are in reference to the illustrations of FIGS. 9A-9D and that the devices and components thereof may be rotated into planes other than that shown in the Figures.

Figure 9B:
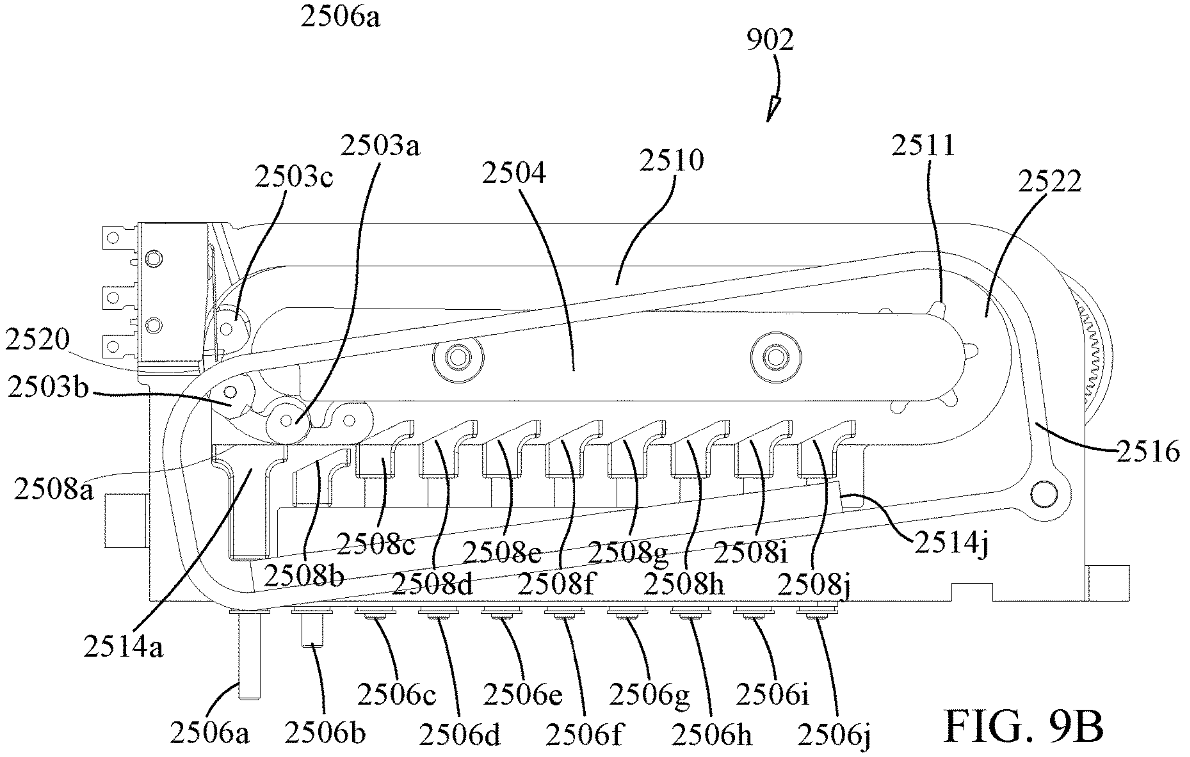
Figure 9C:
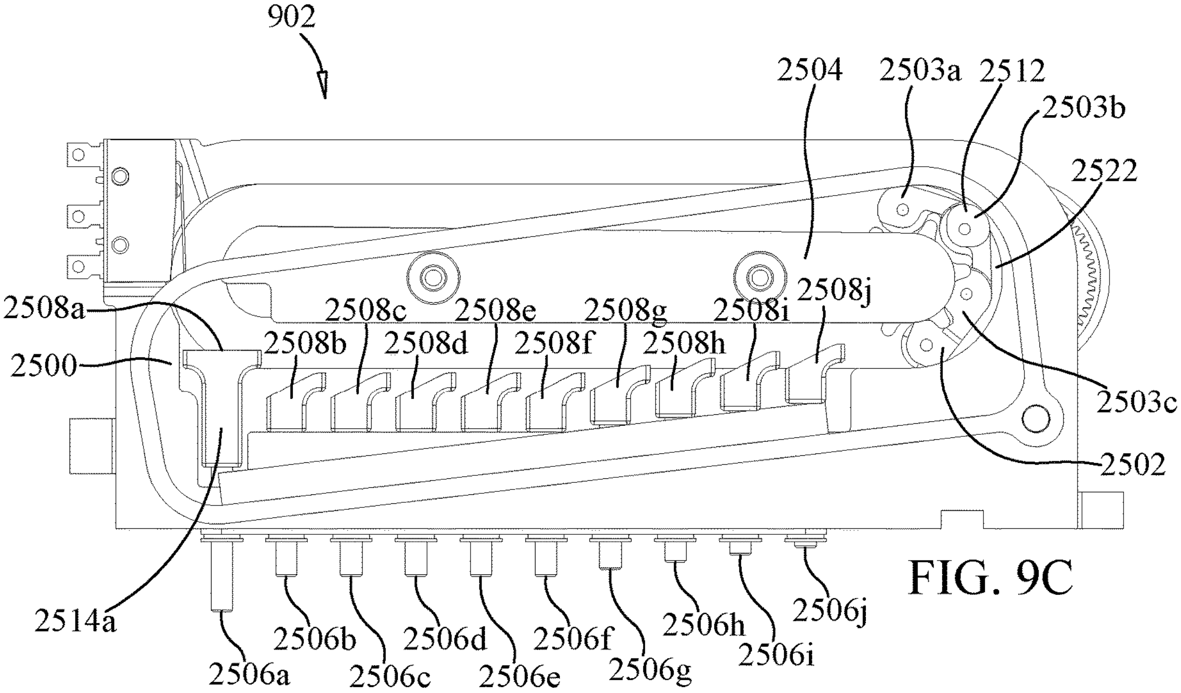
Figure 9D:
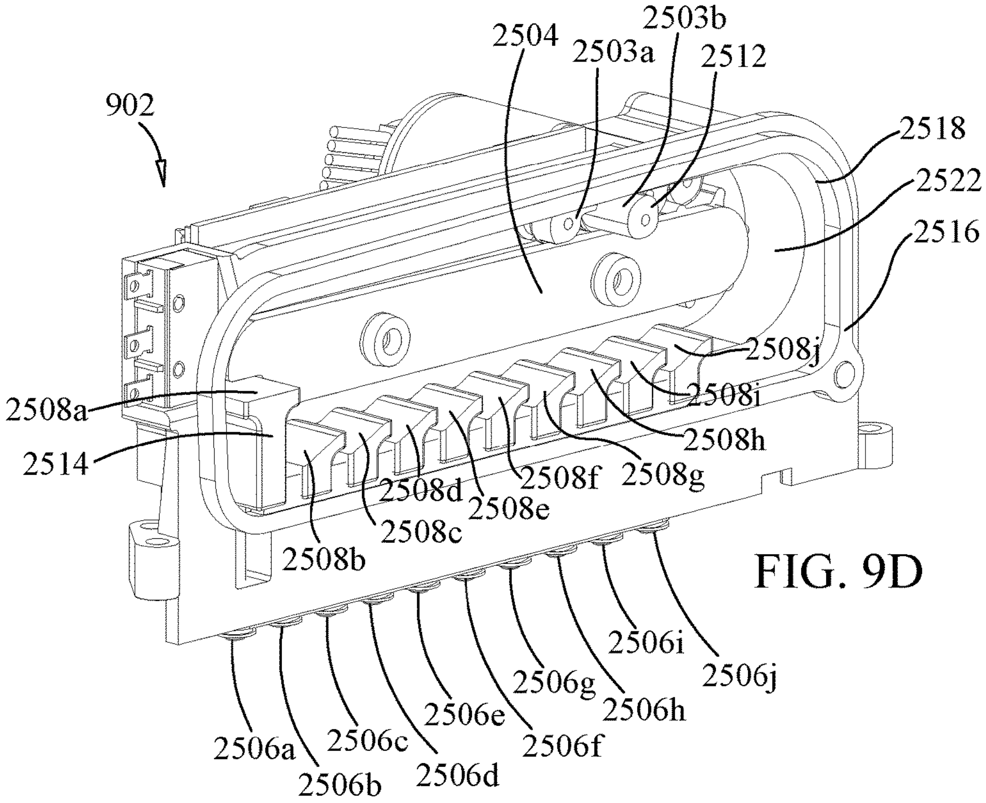

The embodiment of FIGS. 9A-9D further comprises pistons 2506*b-j*. Each of pistons 2506*b-j* may comprise one of angled platforms 2508*b-j* at its proximal end (see FIGS. 9B-9D). As illustrated in FIGS. 9B-9D, the lower side of each of angled platforms 2508*b-j* may be on the side nearest column 2514 (nearest first end 2520 of plate 2504) and the higher side of each of angled platforms 2508*b-j* may be nearest a second end 2522 of plate 2504. As the raised links 2503*a*-2503*c* move past column 2514*a* on chain 2502, one of the raised links may come in connection with and move laterally across the surface of angled platform 2508*b*, beginning at the lower end and moving towards the upper end of angled platform 2508*b*. As the raised links 2503*a*-2503*c* proceed toward the upper end of angled platform 2508*b*, raised link 2503*a* may apply pressure on angled platform 2508*b* (downward pressure as shown in FIGS. 9B-9D), which may actuate piston 2506*b*. This process may repeat as the raised links 2503*a*-2503*c* come in connection with each of angled platforms 2508*c-j* until all of pistons 2506*a-j* have been actuated. As chain 2502 is rotated around plate 2504, the leading raised link (i.e., link 2503*a*) may contact successive raised platforms 2508*a*-2408*j* and the following raised links (i.e., links 2503*b*-2503*c*) may contact the raised platforms behind, e.g., in the illustrated embodiment, raised links 2503*a*-2503*c* may contact up to three raised platforms 2508*a*-2408*j* and provide a plunging force to up to three pistons downward force to up to three pistons 2506*a*-2505*j*.

The embodiments of FIGS. 9A-9D further comprises cam 2516 that can be employed to retract all of the pistons 2506*a*-2505*j* after chain 2502 has made a full revolution around plate 2504. The cam 2516, as illustrated in FIGS. 9C and 9D, further comprises a shelf 2518 on its inner surface. While cam 2516 shown in FIGS. 9A-9D comprises a rectangular shape with rounded corners, one of skill in the art will understand that the cam may comprise of other shapes. For example, cam 2516 may comprise the shape of a different polygon.

Referring again to FIG. 9B, column 2514*a* pivots cam 2516 down as it comes in contact with the lower perimeter of cam 2516 as the chain deploys piston 2506*a*. As is illustrated in FIG. 9D, as chain 2502 tracks around plate 2504, pin 2512 slides along the inner perimeter of cam 2516; pin 2512 applies an upward pressure on cam 2516 that retracts pistons 2506*j*-2506*a* as the chain moves along the upper surface of plate 2504. As illustrated in FIGS. 9C and 9D, this occurs after pin 2512 moves past angled platform 2508*j* toward the upper right corner of cam 2516. Cam 2516 thus swings upward away from the pressure. As pin 2512 continues to rotate around plate 2504, pin 2512 moves along the upper perimeter of cam 2516 and, consequently, applies pressure to the upper perimeter of cam 2516. In response to this pressure, cam 2516 swings upward. In the embodiment of FIG. 9D, as cam 2516 swings upward, shelf 2518 catches the bottom surface of angled platform 2508*j* and moves angled platform 2508*j* upward. Alternatively, each of angled platforms 2508*b-j* may comprise of any type of extension know in the art which cam 2516 may catch as cam 2516 rotates upward. Accordingly, cam 2516 pushes upward on angled platform 2508*j* causing angled platform 2508*j* to return to the position it occupied prior to being pushed downward by pin 2512. Cam 2516 may continue to swing upward and the process is sequentially repeated with angled platforms 2508*i-a* in that order. Consequently, each of pistons 2506*a-j* may exit chambers 592*a*-1 of fitment 590 in reverse order relative to the order in which pistons 2506*a-j* entered chambers 592*a*-1. This process may be repeated causing pistons 2506*a-j* to be inserted into and removed from chambers 592*a*-1.

In the embodiment illustrated in FIGS. 9A-9D, raised link 2503*b* and return pin 2512 are located on the same chain link. However, one will appreciate that the return pin 2512 can be positioned on another link separate from the raised links 2503*a*, 2503*b*, or 2503*c* without affecting the principle of the deployment and retraction of the pistons described in reference to FIGS. 9A-9D.

FIGS. 10A-12B illustrate alternative embodiments of plunging systems. While the plunging systems illustrated in FIGS. 10A-12B use different mechanisms to generate plunging forces, the operating principle is similar to what was illustrated in FIGS. 9-9D. For instance, each of the embodiments illustrated in FIGS. 10A-12B uses mechanical pistons to provide plunging forces one at a time to the plungers 570*a*-570*j* of the fitment 590 (plungers 570*k* and 570*l* are not typically plunged, but they may be in some embodiments).

Figure 10A:
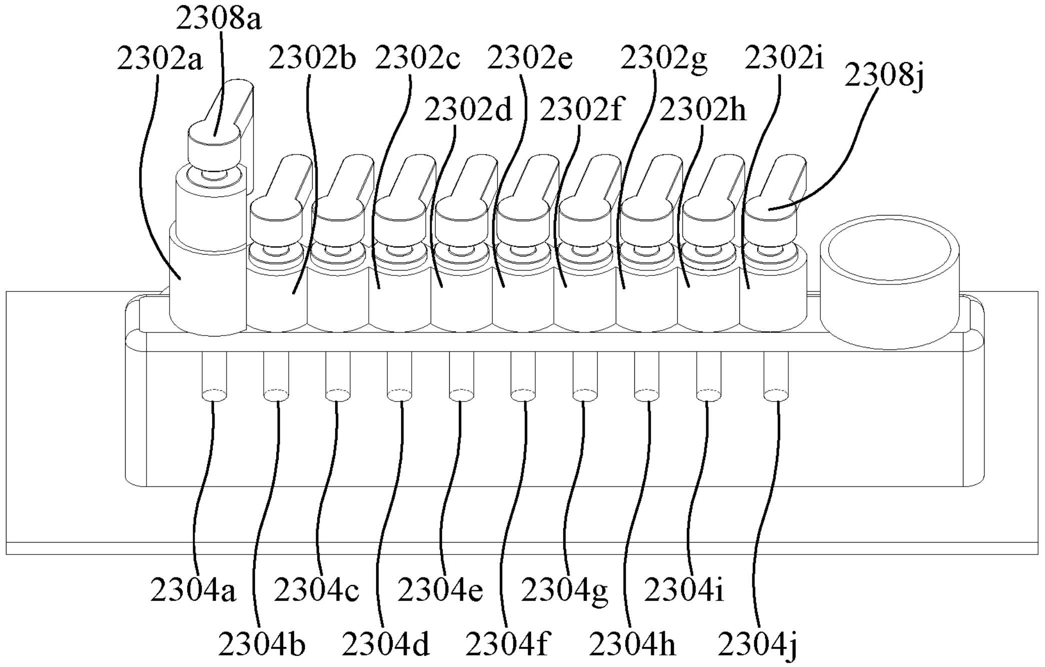
FIGS. 10A and 10B illustrate views of another plunging system, according to an embodiment of the present invention.
Figure 10B:
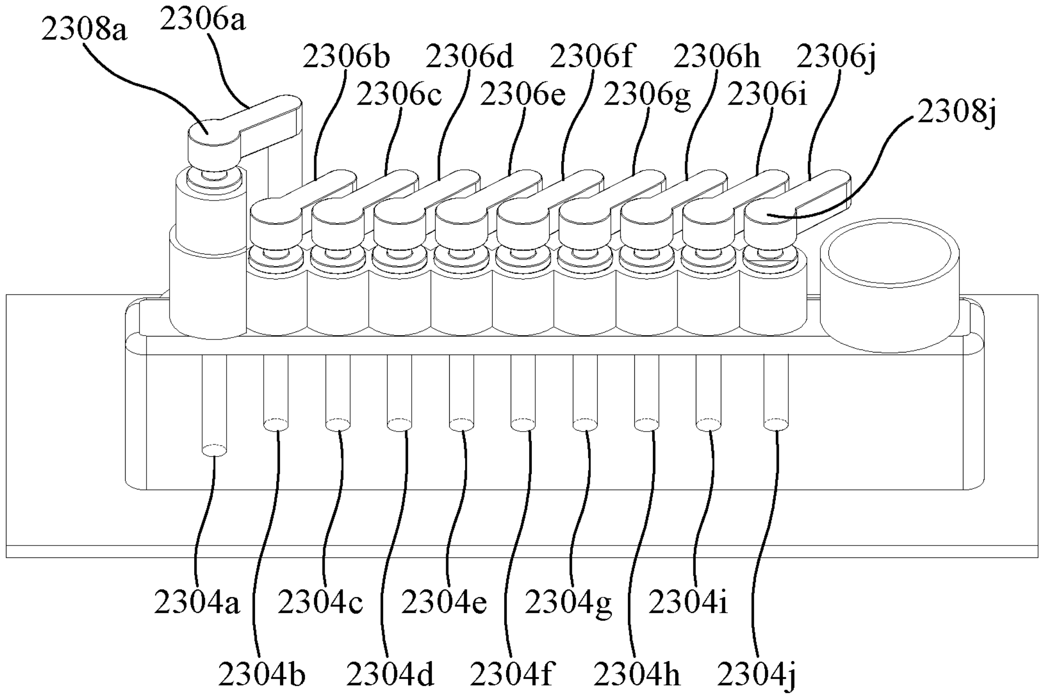

Referring now to FIGS. 10A and 10B, another embodiment of a device that may be used to move fluid from chambers 592*a*-1 into pouch 510. This embodiment comprises a plurality of bolts 2302*a*-2302*j* that include piston members 2304*a*-2304*j* at their distal ends. The bolts 2302*a*-2302*j* and their associated piston members 2304*a*-2304*j* may be moved from a retracted position to an extended position in order to plunge the individual plungers 570*a*-570*j* of the fitment 590. As was noted above, chambers 592*k* and 592*l* are not typically plunged, so the illustrated embodiment includes only ten piston members 2304*a*-2304*j* (i.e., one piston each for chambers 592*a*-592*l*). However, one will appreciate that other embodiments may include pistons for chambers 592*k* and 592*l*. In one embodiment, each of bolts 2302*a*-2302*j* may be threaded so that rotation causes the bolt to descend downward to extend the pistons 2304*a*-2304*j* that are connected to the bolts 2302*a*-2302*j*. Similar to the device illustrated in FIGS. 9A-9D, the distal ends of pistons 2304*a*-2304*j* may extend into chambers 592*a-j* of fitment 590, thereby contacting plungers 570*a*-570*j*, thus pushing sample or reagents through connected entry channels 515*a*-515*j* into blisters within pouch 510.

In the illustrated embodiment, the proximal ends 2308*a*-2308*j* of each of bolts 2302*a*-2302*j* is connected to a respective one of cross-bars 2306*a*-2306*j*. In one embodiment, downward movement of a selected bolt and its associated piston is produced by rotating a selected crossbar 2306*a*-2306*j* in a selected direction (e.g., a clockwise direction). That is, the bolts 2302*a*-2302*j* may be threaded such that movement of the cross-bars 2306*a*-2306*j* in an arc around an elongate axis defined by the bolts produces a downward (i.e., plunging) movement of the pistons 2304*a*-2304*j*. In one embodiment, the cross-bars 2306*a*-2306*j* may be of sufficient length such that as one of cross-bars 2306*a*-2306*j* is rotated as shown by the arrow in FIG. 10A, it comes in connection with the adjacent cross-bar. The adjacent cross-bar may then be rotated in the same direction as the first cross-bar causing its associated bolt to descend and push one of pistons 2304*a*-2304*j* into one of chambers 592*a*-1. Each time one of cross-bars 2306*a*-2304*j* is rotated, the bolt 2302*a*-2302*j* that is in connection with it also rotates and actuates one of pistons 2304*a*-2304*j*.

In the embodiment shown in FIGS. 10A and 10B, bolt 2302*a* is longer than bolts 2302*b-j* so as to accommodate a longer plunge stroke of chamber 592*a*, which accommodates a greater volume of fluid than chambers 592*b*-1. This is because, in one embodiment of fitment 590, chamber 592*a* receives the sample fluid in a volume larger than the hydration fluid needed to rehydrate the reagents housed in chambers 592*b*-1. It is understood that this configuration is illustrative only and in other embodiments of fitment 590, others of chambers 592*a*-1 may house larger volumes and be in connection bolts 2302*a*-2302*j* that are of greater length.

Figure 11A:
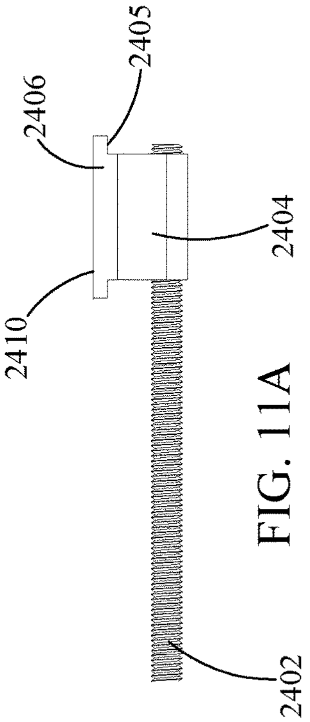
FIGS. 11A and 11B illustrate views of another plunging system, according to an embodiment of the present invention.
Figure 11B:
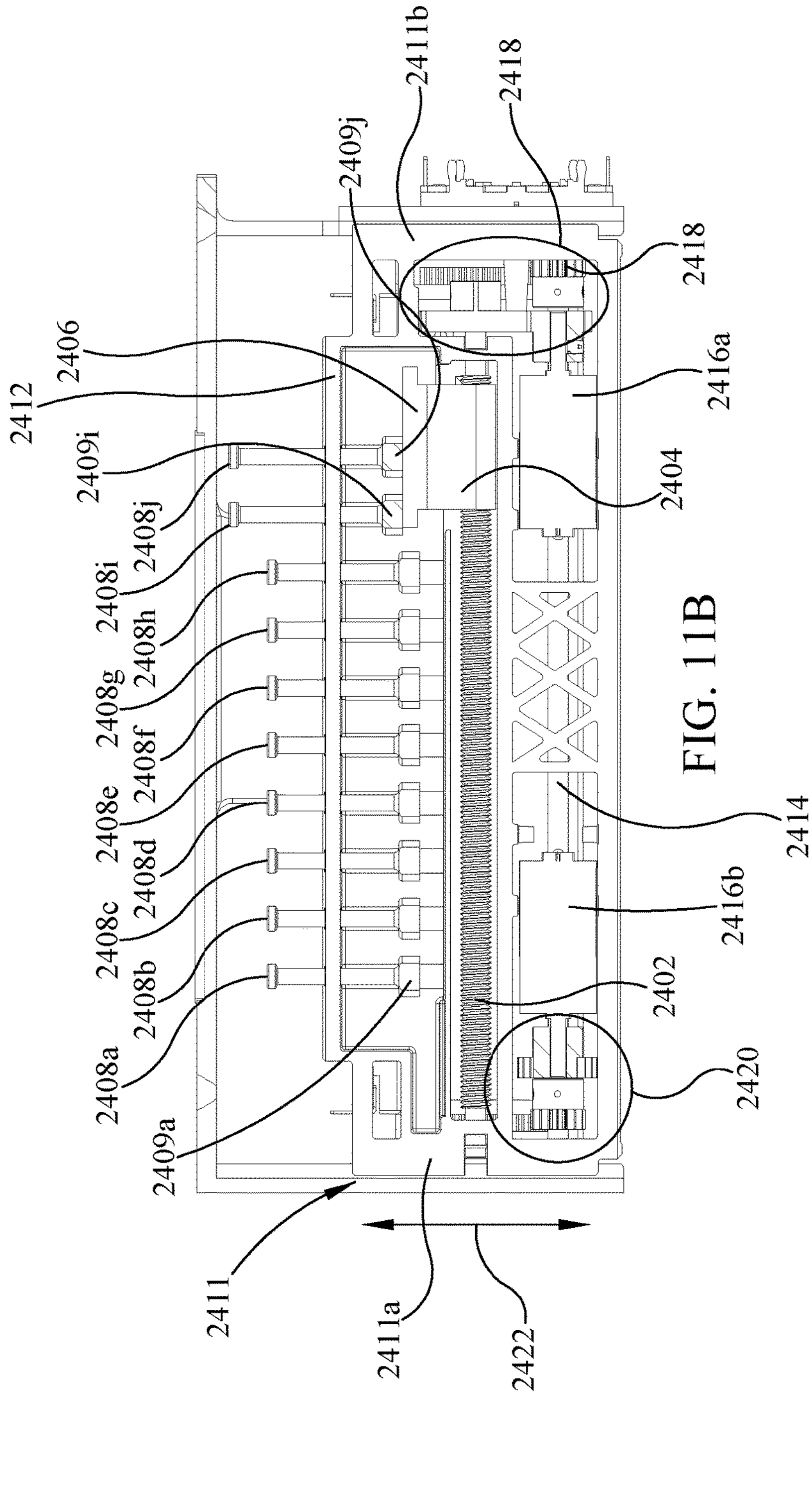

FIGS. 11A and 11B illustrate yet another embodiment of a device that may be used to move fluid from chambers 592*a*-592*j* of fitment 590 into pouch 510. The embodiment of FIGS. 11A and 11B includes a shuttle mechanism 2404 that is configured to moves along a threaded member 2402 such that the shuttle mechanism 2404 (e.g., a nut) can move individual pistons from a retracted position to an extended (i.e., plunge) position. Threaded member 2402 may be threaded to fit the shuttle mechanism 2404. A motor or other source of power may cause threaded member 2402 to rotate. Thus, the shuttle mechanism 2404 may be configured to move laterally along the length of threaded member 2402 as it rotates. FIGS. 11A-11B further depict connector 2406 which may comprise a first side 2405 as well as second side 2410 which may be opposite the first side 2405. The first side 2405 of connector 2406 may be in connection with shuttle mechanism 2404.

FIG. 11B further illustrates how shuttle mechanism 2404, threaded member 2402, and connector 2406 may actuate a plurality of pistons 2408*a*-2408*j*. As the threaded member 2402 is rotated, shuttle mechanism 2404 and connector 2406 may move along the threaded member 2402, allowing the second side of connector 2406 to come into contact with a distal end of one or more of pistons 2408*a*-2408*j*. Similar to the pistons illustrated by FIGS. 9 and 10, pistons 2408*a*-2408*j* may enter a proximal end of chambers 592*a*-592*l* of fitment 590 thus applying force which moves fluid out of chambers 592*a*-592*l* and into pouch 510. The device may be configured so that connector 2406 may come in connection with a single piston or multiple pistons at the same time. FIG. 11B illustrates the latter with pistons 2408*i* and 2408*j* being actuated simultaneously. This may be accomplished by adjusting the width of connector 2206 so that it simultaneously comes in contact with a defined plurality of pistons. In one embodiment, individual pistons 2408*a*-2408*j* may be spring-loaded such that the pistons will return to their retracted pistons when they are not in contact with the connector 2206. In another embodiment, the plunging mechanism illustrated in FIGS. 11A and 11B may include a retraction mechanism similar to the retraction mechanism illustrated in FIGS. 9A-9D.

Figure 12A:
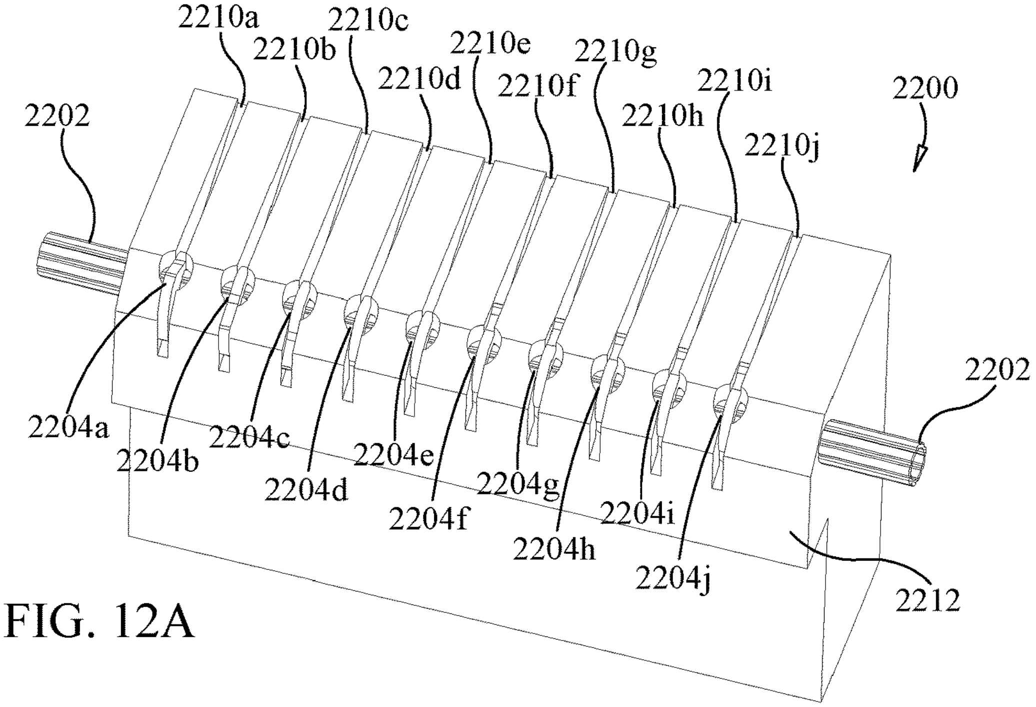
FIGS. 12A-12C illustrate views of components of another plunging system, according to an embodiment of the present invention.
Figure 12B:
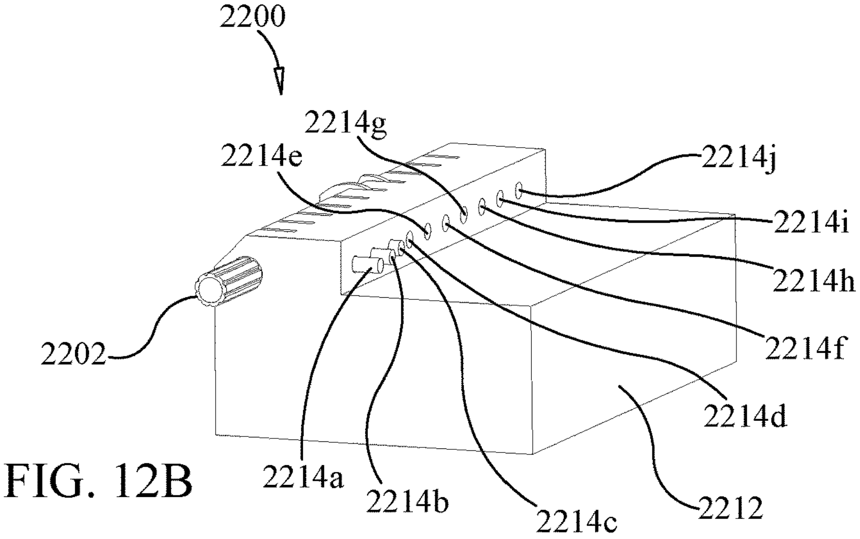
Figure 12C:
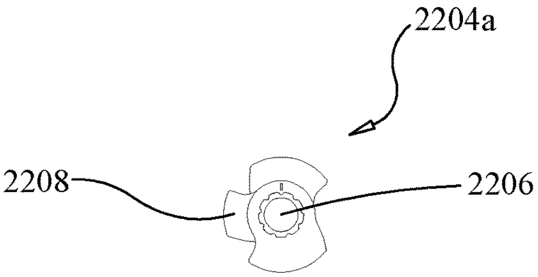

FIGS. 12A-12C illustrate yet another embodiment of a device 2200 that may be used to move fluid from chambers 592*a*-592*j* of fitment 590 into pouch 510. In the embodiment shown in FIGS. 12A-12C plunging forces may be generated by rotation of a cam shaft 2202 that includes a number of individual lobes that successively actuate a number of individual pistons. FIG. 12B illustrates a number of pistons 2214*a*-2214*j* that can be projected out of the housing 2212 of the device 2200 in response to rotating the cam shaft. Device 2200 comprises rod 2202 that may be rotated using a motor or other power source. Rotation of rod 2202 brings a plurality of cam lobes into contact with a proximal end (not shown) of individual pistons 2214*a*-2214*j*; as the cam lobes are rotated against the proximal ends, the cam lobes push the individual pistons 2214*a*-2214*j* out to produce a plunging movement. FIG. 12B illustrates two pistons 2214*a* and 2214*b* that have been pushed out such that they could extend into chambers 592*a* and 592*b* of fitment 590 to depress plungers 570*a* and 570*b* to move liquid from the fitment 590 into pouch 510. Such a process can be repeated for pistons 2214*c*-2214*j*.

In one embodiment, cam shaft 2202 may be inserted through holes 2206 approximately in the center of each of a plurality of lobes 2204*a*-2204*j*. FIG. 12C illustrates an embodiment of lobe 2204*a* and hole 2206 in more detail. Each of lobes 2204*a*-2204*j* may comprise tab 2208 that may extend from the lobe. Lobes 2204*b*-2204*j* may be shaped identically or include a tab 2208 that is located at a different position along the perimeter of the lobe relative to lobe 2204*a*. Cam shaft 2202 and lobes 2204*a*-2204*j* may be partially enclosed by housing 2212 that comprises slots

2210*a*-2210*j*. Each of lobes 2204*a*-2204*j* may be positioned adjacent to one of a plurality of slots 2210*a*-2210*j* such that the tab 2208 of each of lobes 2204*a*-2204*j* may move through one of slots 2210*a*-2210*j* as it turns on cam shaft 2202. Slots 2210*a*-2210*j* permit individual tabs to clear the upper wall of housing 2212 as lobes 2204*a*-2204*j* rotate on cam shaft 2202.

As lobes 2204*a*-2204*j* rotate, tab 2208 of each of lobes 2204*a*-2204*j* may come in connection with a proximal end of one of a plurality of pistons 2214*a*-2214*j*. Illustratively, as tab 2208 of lobe 2204*a* comes in connection with the proximal end of adjacent piston 2214*a*, the force thereby applied causes that piston to move from a retracted position to an extended position. This is schematically illustrated at FIG. 12B. When the piston is in the second position, its distal end may enter an opening in a proximal end of a chamber such as, but not limited to, chamber 592*a* of fitment 590, and apply pressure, illustratively on plunger 570*a*, which is disposed within chamber 592*a*. The pressure created by the plunger may subsequently force the liquid present in chamber 592*a* through entry channel 515*a* and into pouch 510. The process is repeated with lobe 2204*b* and its adjacent piston 2214*b* and so on through lobe 2204*j*. The location of tab 2208 may be at a different position on the perimeter of each of lobes 2204*a*-2204*j* so that each of the pistons may be actuated in a defined sequence.

In this embodiment, as tab 2208 of lobe 2204*a* rotates away from the distal end of the adjacent piston, the force is released from the piston and it returns to the first position. Alternatively, the pistons may be spring loaded such that they remain in the second position even after tab 2208 is no longer in connection with the piston. In the latter embodiment, fluid is prevented from moving backwards through the system.

It is understood that any of the illustrative embodiments disclosed herein may be used to operate the piston assembly 902 in instrument 900. It is also understood that these illustrative embodiments may be used in instrument 800 or in other instruments.

Bead Beater

FIG. 13 shows a bead beating motor 819, comprising blades 821 that may be mounted on a first side 811 of support member 802, of instrument 800 shown in FIG. 3A. Blades may extend through slot 804 to contact pouch 510. It is understood, however, that motor 819 may be mounted on other structures of instrument 800. While reference is made to instrument 800, it is understood that a bead beater may be similarly mounted in instrument 900 of FIG. 3B. In one illustrative embodiment, motor 819 is a Mabuchi RC-280SA-2865 DC Motor (Chiba, Japan), mounted on support member 802. In one illustrative embodiment, the motor is turned at 5,000 to 25,000 rpm, more illustratively 10,000 to 20,000 rpm, and still more illustratively approximately 15,000 to 18,000 rpm. For the Mabuchi motor, it has been found that 7.2V provides sufficient rpm for lysis. It is understood, however, that the actual speed may be somewhat slower when the blades 821 are impacting pouch 510. Other voltages and speeds may be used for lysis depending on the motor and paddles used. Optionally, controlled, small volumes of air may be provided into the bladder 822 adjacent lysis blister 522. It has been found that in some embodiments, partially filling the adjacent bladder with one or more small volumes of air aids in positioning and supporting lysis blister during the lysis process. Alternatively, other structures, illustratively a rigid or compliant gasket or other retaining structure around lysis blister 522, can be used to restrain pouch 510 during lysis. It is also understood that motor 819 is illustrative only, and other devices may be used for milling, shaking, or vortexing the sample.

While impaction using rotating blades or paddles is discussed above, it is understood that other embodiments for a bead milling component for shaking or vortexing the sample are contemplated. In one embodiment, beater bars may be replaced with bearings, including ball bearings and roller bearings. FIG. 14 illustrates an instrument subassembly 906*a* that is a simplified version of subassembly 906 of FIG. 3B. Subassembly 906*a* includes a bead beater assembly 912 that partially extends through a slot 914 in a compression plate 922. FIG. 14 also illustrates a pouch 510 with a lysis blister 522 in proximity to the compression plate 922 where the bead beater assembly 912 can contact the lysis blister 522 when the pouch 510 is installed in the instrument 900. FIG. 14A is a cross-sectional view along line A-A of FIG. 14

FIG. 14A shows a motor 719 driving a bead beating effector that includes spinning wheel 720. Spinning wheel 720 has a plurality of bearings 721 set therein. FIG. 14A shows six bearings 721. However, this number is illustrative only and any number of bearings may be used. In the illustrative embodiment, the bearings are seated loosely, allowing them to move in spinning wheel 720, such that as wheel 720 spins, centripetal force drives bearings 721 radially and bearings 721 extend radially from a perimeter 718 of spinning wheel 720. This permits bearings 721 to strike pouch 510, illustratively at or near blister 522. Optionally, bearings 721 may be spring loaded to bias them radially.

Figure 14B:
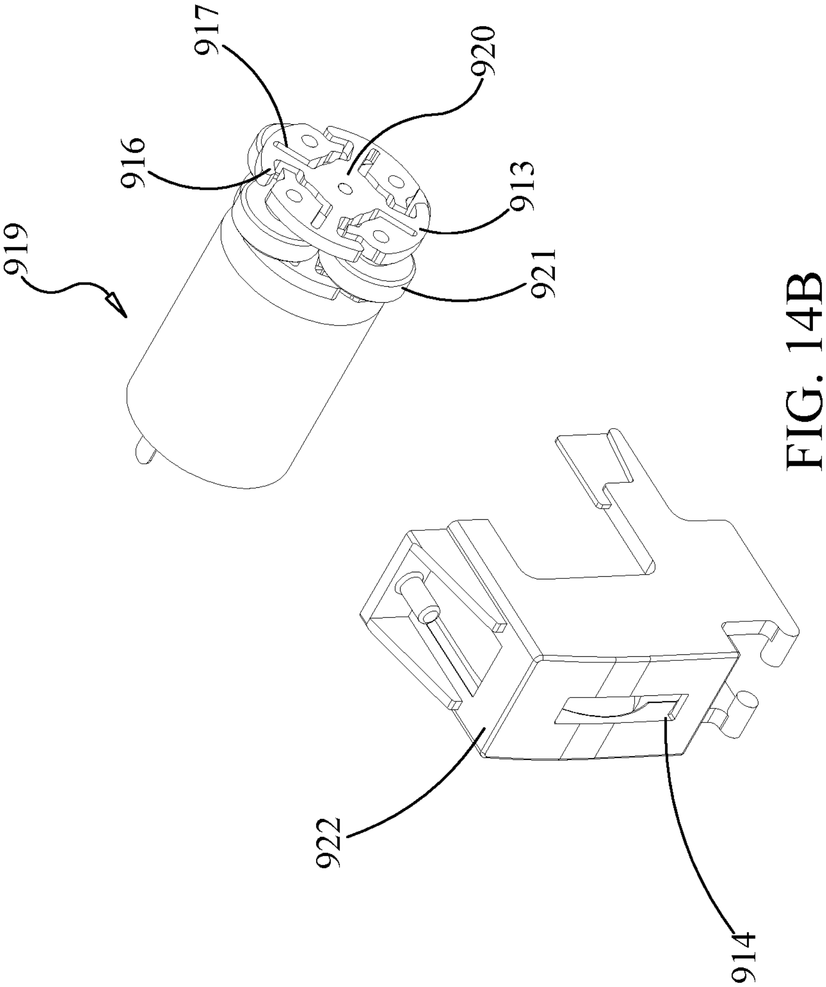
FIG. 14B shows an exploded perspective view of another alternative embodiment of a motor and compression plate that may be used in the instrument of FIGS. 3A and 3B.

FIG. 14B shows an embodiment similar to that of FIG. 14A. In this embodiment, spinning wheel 920 is driven by motor 919. In this embodiment, four roller bearings 921 are mounted on spinning wheel 920, but, as above, this number is illustrative only and any number of roller bearings are contemplated. Spinning wheel 920 is made of a flexible material and is provided with a plurality of grooves 917 defining a plurality of arms 913 upon which roller bearings 921 are mounted. As motor 919 drives spinning wheel 920, arms 913 flex outward, thereby allowing roller bearings 921 to move radially and contact pouch 510 (not shown). A plurality of tabs 916, also defined by grooves 917, are positioned to restrain roller bearings 921 from too much radial movement.

It is understood that the tension on any springs that may be provided to spring load bearings 721 of FIG. 14A and the amount of flexion provided to arms 913 upon which roller bearings 921 are mounted should be appropriate to bias the bearings 921 or 721 into contact with pouch 510 to provide significant movement of the lysing particles contained therein, without providing too much force such that the flexible material of pouch 510 may be torn. While motor 719 is shown as part of instrument 800 and motor 919 is shown as part of instrument 900, it is understood that this is illustrative only, and that any motor configuration may be used in any instrument for sample preparation.

In the embodiment shown in FIG. 3A, bladder 822 provides force upon blister 522 of pouch 510 on a side opposite the side that the blades strike blister 522 while extending through slot 804. In some embodiments, it may be desirable to have the impaction on blister 522 be on the same side as the compression member, such as bladder 822. However, in such embodiments, it may be desirable to replace bladder 822 with compression member that is less prone to tearing. Thus, a compression plate 922 may be used in addition to or instead of bladder 822. In the embodiments shown in FIGS. 14A-14B, compression plate 922 is provided with a slot 914, through which blades 21 or bearings 921 or 721 may extend to strike blister 522. Illustratively, bladder 822 or compression plate 922 may be pulsed while bearings 921 or 721, or blades 21 impact pouch 510. Such pulsing may help provide different and changing vortexes to improve mixing. Alternatively or additionally, the direction of the motor 919, 719, or 819 may be alternated.

Bead beating may be achieved by impacting pouch 510 with beater structures such as rotating blades, paddles, or bearings attached to an electric motor. The beater structures may impact the pouch at the lysis blister 522 or may impact the pouch near the lysis blister. As discussed above, the bead beater motor is configured to rotate at approximately 15,000 to 18,000 rpm (e.g., about 12,000 rpm). One way to increase the efficiency of bead beating is to increase the frequency with which the beater structures (e.g., blades, paddles, or bearings) strike the pouch. This can be accomplished by increasing the speed of the bead beater motor or increasing the number of beater structures so that the pouch is struck more times with every revolution of the motor. The bead beater embodiments illustrated in FIGS. 14A and 14B accomplish this by including six and four bearing structures, respectively.

Figure 14C:
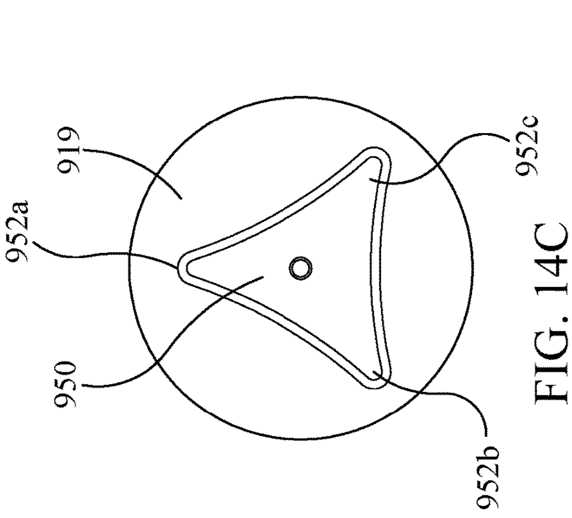
FIGS. 14C-14E shows alternative embodiments of motors that may be used in one illustrative embodiment of the instrument of FIGS. 3A and 3B.
Figure 14D:
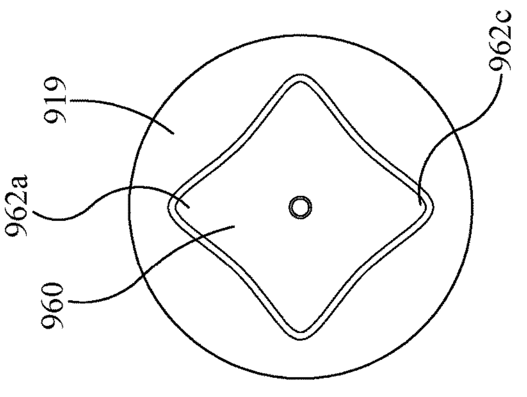
Figure 14E:
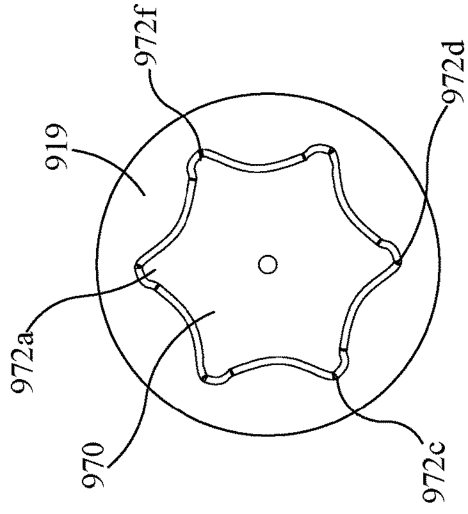

FIGS. 14C, 14D, 14E, and 14F illustrate alternative embodiments of a bead beater effector. These bead beater systems are similar to the rotating paddle system illustrated and described in U.S. Pat. No. 9,102,911, the entirety of which is incorporated herein by reference. FIG. 14C illustrates a bead beating motor 919, comprising a bead beating wheel 950 with three paddles 952*a*-952*c* projecting from the wheel 950. FIG. 14D illustrates a bead beating motor 919, comprising a bead beating wheel 960 with four paddles 962*a*-962*d* projecting from the wheel 960. FIG. 14E illustrates a bead beating motor 919, comprising a bead beating wheel 970 with six paddles 972*a*-972*f* projecting from the wheel 970. One will understand that the three, four, and six blades illustrated in FIGS. 14C-14E are illustrative only and that a bead beater wheel may have more or fewer blades.

Figure 14F:
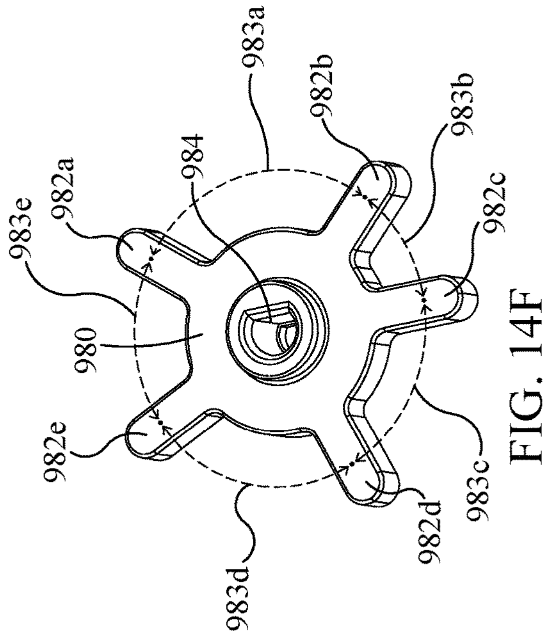
FIG. 14F shows an embodiment of an asymmetric bead beater effector.

FIG. 14F illustrates another embodiment of a bead beater effector 980. Effector 980 may be coupled to and driven by a bead beater motor similar to motor 919 illustrated in the previous examples. In the illustrated example, effector 980 may be coupled to a complementarily shaped motor shaft via center hole 984. In the illustrated embodiment, effector 980 has five bead beater arms 982*a*-982*e* that are arranged asymmetrically around a central axis defined by center hole 984. Preferably, arms 982*a*-982*e* are arranged to be weight balanced so that the center of mass of the effector 980 corresponds to the central axis defined by center hole 984. However, one will appreciate that the arms may be weight balanced by other modifications such as drilling portions out of the arms, removing or adding mass to selection portions of the arms, etc.

In one embodiment, the effector has five asymmetrically arranged arms. One will appreciate, however, that similar embodiments may have three or more asymmetrically arranged arms. If one or more balancing masses are included on the effector, an embodiment may have as few as two asymmetrically arranged arms. In the illustrated embodiment, bead beater arms 982*a*-982*e* are separated by angles of about 97° (983*a*), 45° (983*b*), 69° (983*c*), 86° (983*d*), and 63° (983*e*). One will appreciate that these angles are merely illustrative and that other angles with five illustrated arms and other angles with more or fewer arms are within the scope of this disclosure.

As in previously described embodiments, it is believed that increasing the number of bead beater arms may increase the efficiency of bead beating by increasing the number of hits on the sample preparation chamber (e.g., blister 522 of FIG. 2) per rotation of the effector 980. In one embodiment, the asymmetric spacing of the arms may change the tone produced by the bead beater so that the perceived volume is lower. For instance, non-periodic spacing of noise generating events has the effect reshaping noise-frequency spectra to provide reduced noise levels and the redistribution of the frequencies at which there is noise energy so as to generate fewer perceptible sounds. In contrast, pure tones of the same volume (sound-pressure level) are generally perceived to be noisier.

FIGS. 41A-42C illustrate an alternative embodiment of a bead beater system that uses a paddle-type bead beater to mix the sample during sample preparation. This provides different lysis motion than the bead beating systems described above and, for example, in U.S. Pat. Nos. 8,895,295 and 9,102,911, which are incorporated by reference elsewhere herein.

Figure 41A:
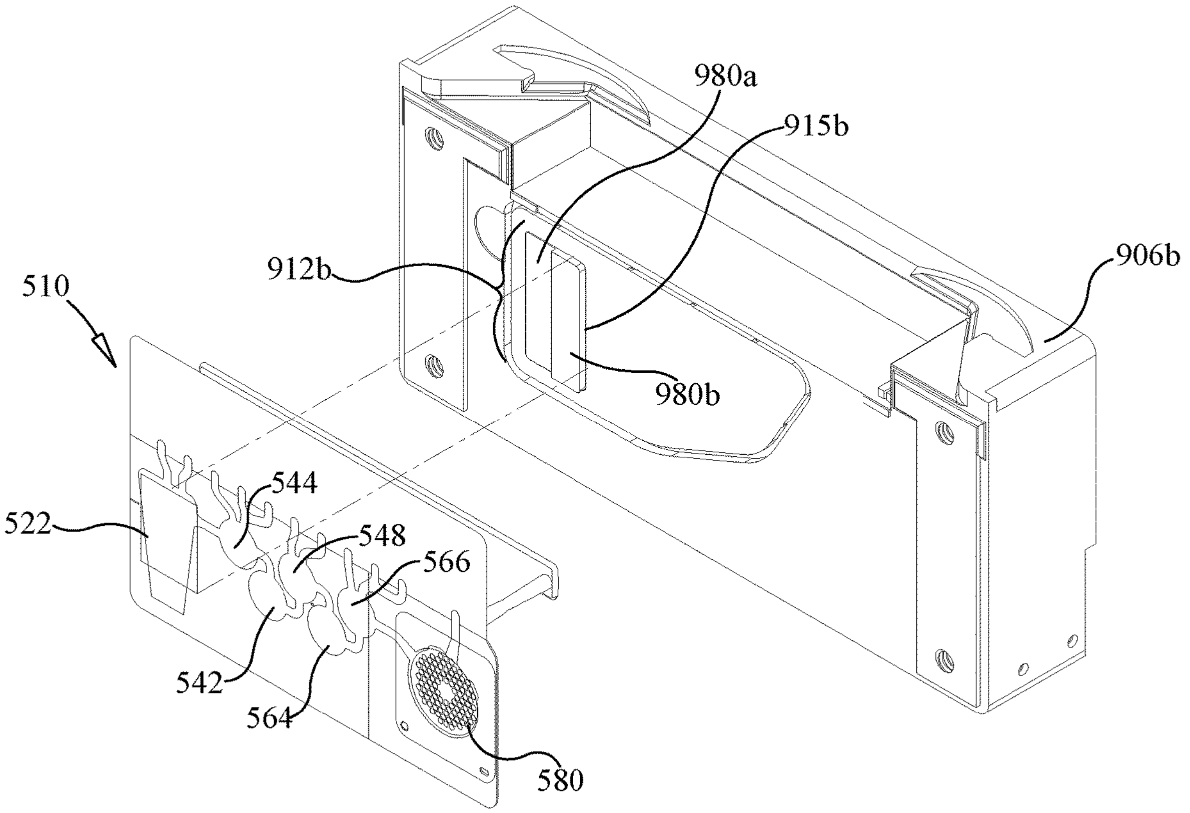
FIG. 41A is an isometric view of a paddle bead beater system in the context of an instrument subassembly and a pouch that could be run in the instrument.
Figure 41B:
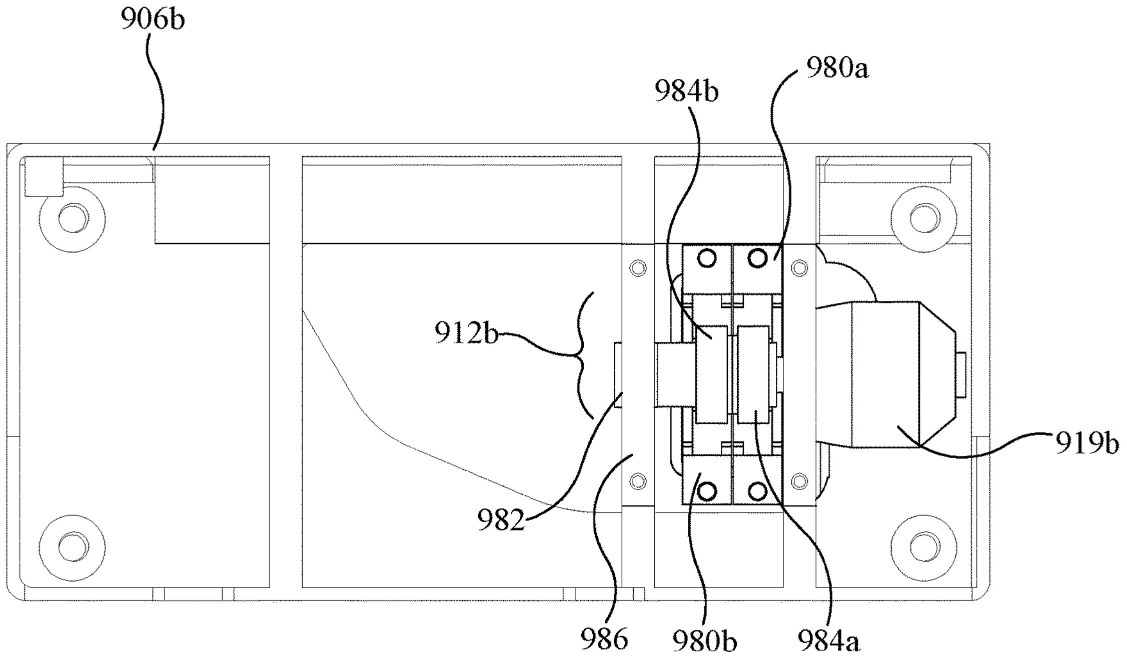
FIG. 41B is a rear view of the paddle bead beater system and instrument subassembly of FIG. 41A.

FIG. 41A shows a bead beater system 912*b* in the context of subassembly 906*b*, which is similar to subassembly 906 of FIG. 3B, but only showing parts relevant to cell lysis. It is understood that various heaters shown in FIG. 3B or other components may be used as part of or in addition to subassembly 906*b*. Illustratively, subassembly 906*b* may be included in instrument 800 or instrument 900 or a similar instrument. FIG. 41B shows a backside view of the same subassembly 906*b* and the bead beater system 912*b*. Bead beater system 912*b* comprises paddles 980*a* and 980*b* that are positioned to extend through slot 915*b* in subassembly 906*b* so that the paddles 980*a* and 980*b* can contact blister 522 of pouch 510, or a lysis or sample preparation blister of a similar pouch. Paddles 980*a* and 980*b* can be rapidly reciprocated to produce a lysate. When paddles 980*a* and 980*b* reciprocate, they repeatedly strike blister 522 and mix the contents (e.g., cells, lysis buffer, and zirconium lysis beads) of blister 522 back and forth in a motion that thoroughly agitates the samples and the lysis beads. Pouch 510 is shown in FIG. 41A in proximity to subassembly 906*b* for reference, as explained in greater detail elsewhere herein in reference to, for example, FIGS. 3A and 3B, and pouch 510 may illustratively be held in place adjacent to subassembly 906*b* and blister 522 may be held adjacent to paddles 980*a* and 980*b*. Illustratively, paddles 980*a* and 980*b* may be sized and positioned such that they are substantially the same area as blister 522. Likewise, paddles 980*a* and 980*b* may be larger or smaller than blister 522. In the illustrated embodiment, paddles 980*a* and 980*b* are substantially the same size as one another. One will appreciate, however, that the paddles may be sized differently in other embodiments. For instance, while paddles 980*a* and 980*b* are sized and shaped for blister 522, which is roughly rectangular, paddles may be sized and shaped for other blister shapes, such as, but not limited to, square or circular.

Referring now to FIG. 41B, which shows a backside of the bead beater assembly 912*b*, the bead beater includes a support member 986 that secures the bead beater assembly 912*b* in subassembly 906*b*, reciprocating paddles 980*a* and 980*b*, and a drive shaft 982 to drive reciprocal motion of the paddles 980*a* and 980*b*. In the illustrated embodiment, the drive shaft 982 and the paddles 980*a* and 980*b* are coupled to bearing members 984*a* and 984*b* that are in turn mechanically coupled to the drive shaft and to each respective paddle. FIG. 42C illustrates the axis of rotation 989 of the drive shaft 982 and two off-center, eccentric portions 982*a* and 982*b* that are coupled to the bearing members 984*a* and 984*b* to translate rotary motion of the shaft 982 into reciprocal, in and out motion of the paddles 980*a* and 980*b*. In the illustrated embodiment, rotary motion of the shaft 982 is driven by motor 919*b*. The motor 919*b* may also be secured to subassembly 906*b* to further support the bead beater assembly 912*b*. In one illustrative embodiment, motor 919*b* may be turned at 5,000 to 25,000 rpm, more illustratively 7,500 to 12,000 rpm, and still more illustratively approximately 8,000 to 10,000 rpm. It is understood, however, that the actual speed may be somewhat slower when the paddles 980*a* and 980*b* are impacting pouch 510. Likewise, other speeds may be used for lysis depending on the motor and paddles used and on sample type. It is also understood that motor 919*b* is illustrative only, and other devices may be used for actuating the paddles.

Figure 42B:
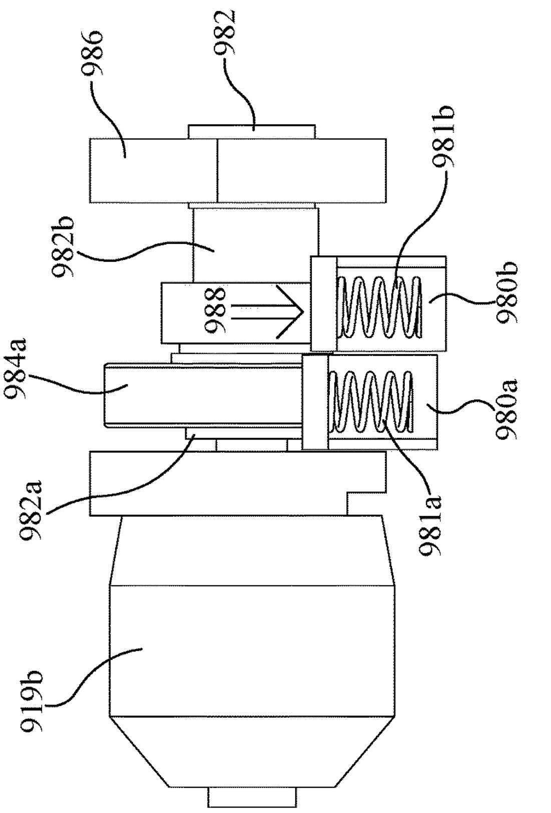
FIG. 42B is top view of the paddle bead beater system of FIG. 42A.
Figure 42A:
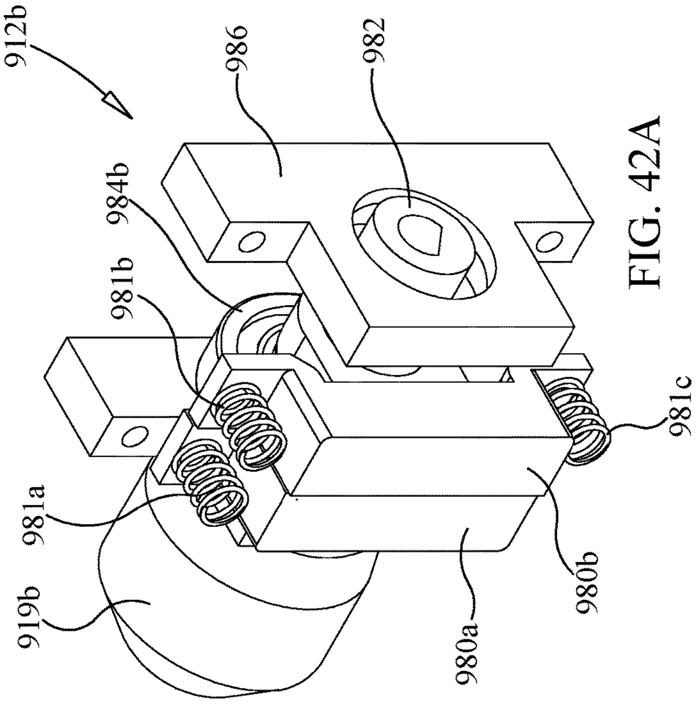
FIG. 42A is an isometric view of the paddle bead beater system of FIG. 41A.
Figure 42C:
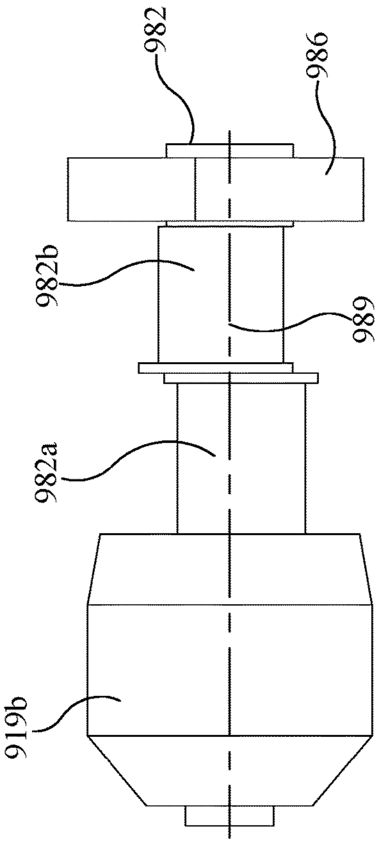
FIG. 42C is a top view of the drive system of the paddle bead beater system of FIGS. 42A and 42B.

Referring now to FIGS. 42A and 42B, further details of the bead beater assembly 912*b* are shown. Illustratively, the paddles 980*a* and 980*b* alternate in contacting the lysis blister during the cell lysis process. That is, the paddles contact the pouch one at a time. This allows the paddles to move the fluid (e.g., cells and/or viruses, lysis buffer, and lysis beads) in the lysis zone (i.e., blister 522) in a forceful side-to-side motion. One will appreciate, however, that other fluid motion patterns are possible with systems like 912*b*, such as, but not limited to, top-to-bottom, vortices, and the like. As mentioned above in reference to FIG. 3B and below in reference to FIGS. 22A-23B, in some embodiments there may be a gasket (e.g., front panel gasket 929) between the bead beater paddles and the pouch. Thus, the paddles may not contact the pouch directly, but the principle of operation is still the same.

FIGS. 42A and 42B also illustrate biasing members (e.g., springs) 981*a*-981*c* (a fourth biasing member is present on paddle 980*a* next to biasing member 981*c* but not shown due to the angle of view) that can placed between the ends of paddles 980*a* and 980*b* and the inner surface of subassembly 906*b* to bias paddles 980*a* and 980*b* toward the bearing members 984*a* and 984*b*. While coil springs are shown, one will appreciate that other spring members could be used, such as, but not limited to, leaf springs, elastomeric members, and the like.

FIG. 42B also schematically illustrates how the bead beater assembly 912*b* could be used to compress fluid out of blister 522 and into downstream blister, such as blister 544. Illustratively, motor 919*b* may be stopped with paddle 980*a* extended such that paddle 980*a* can press against blister 522 and force the fluid out of half of the blister 522. A mechanical actuator (e.g., a piston) indicated schematically at 988 can then press on paddle 980*b* so that it can press against blister 522 and plunge the fluid to a downstream blister. Alternatively, separate mechanical actuators may be associated with paddles 980*a* and 980*b* to press both paddles against blister 522 to plunge to fluid to a downstream blister. In another embodiment, a drive system may be employed (e.g., individually driven pistons) that individually extends and, optionally, retracts each paddle. In such an embodiment, the drive system may be used to extend both paddles together to press against blister 522 to plunge to fluid to a downstream blister.

In another embodiment, the relative arrangement of the biasing members (e.g., springs), the paddles, and inner surface of the instrument subassembly (e.g., subassembly 906*b*) may be switched such that the paddles are biased outward. In such a case, the sense of the drive mechanism may also be switched so that the so that the reciprocating action of the drive system can draw the paddles away from the pouch and the action of the biasing members causes the paddles to contact the lysis chamber. Since biasing members (e.g., springs) can be chosen to provide a selected amount impact force and/or pressure on the lysis blister, for example, a system that uses biasing members to bias the paddles to contact the pouch may provide predictable and reliable lysis forces. Likewise, since the paddles may default to pressing against the lysis blister, such a system may readily be used to plunge the contents of the lysis blister, for example, to a downstream blister. In an illustrative example, a paddle bead beater system with the paddles biased toward a lysis blister may plunge the contents of the blister by moving the drive member to a neutral position so that both paddles are pressed against the blister at the same time by the action of the biasing members. In another illustrative example, a paddle bead beater system with the paddles biased toward a lysis blister may plunge the contents of the blister to a downstream blister by using the drive system to bring the upstream blister into contact with the blister to force the fluid in the blister to the downstream side of the bister and then releasing the downstream paddle from the drive system so that the biasing member can press the second paddle against the blister to plunge the fluid to the downstream blister.

Figure 43A:
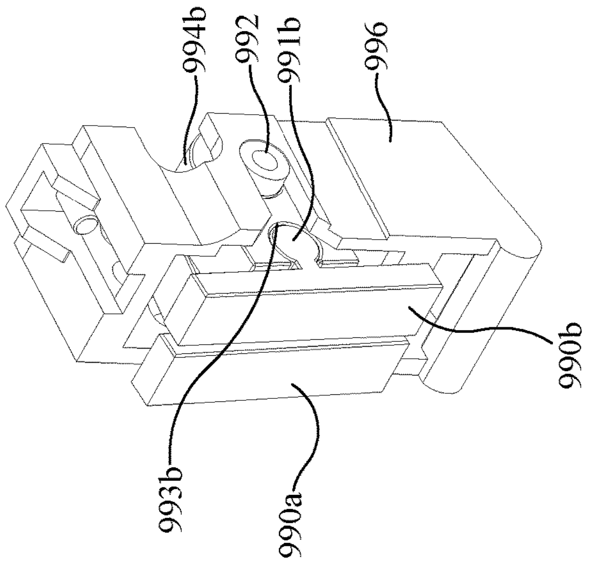
FIG. 43A is an isometric view of another embodiment of a paddle bead beater system.
Figure 43B:
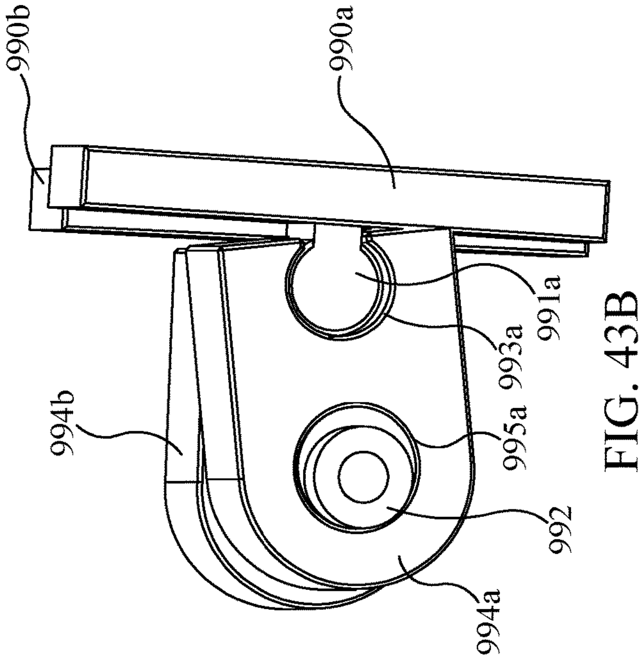
FIG. 43B is a side perspective view of the paddle bead beater system of FIG. 43A.
Figure 43C:
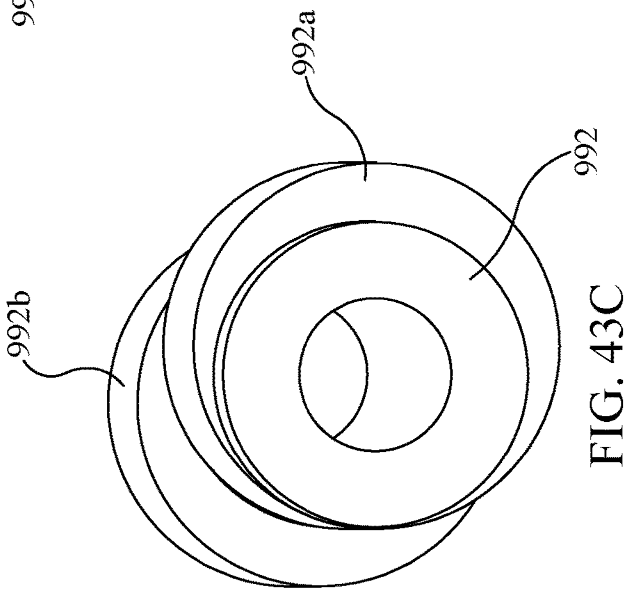
FIG. 43C is a side perspective view of the drive shaft of the paddle bead beater system of FIGS. 43A and 43B.

FIGS. 43A-43C illustrate another embodiment of a bead beater system 912*c*. Bead beater system 912*c* includes paddles 990*a* and 990*b*, a drive shaft 992, crank and slider mechanisms 994*a* and 994*b* that are, respectively, coupled to paddles 990*a* and 990*b* and to the drive shaft 992, and a support assembly 996 that can be used to couple the bead beater system 912*c* to an instrument subassembly. Bead beater system 912*c* may, for example, be used with subassembly 906 of FIG. 3B. Illustratively, bead beater system 912*c* may be included in instrument 800 or instrument 900 or a similar instrument. Bead beater system 912*c* comprises paddles 990*a* and 990*b* that may be positioned to contact blister 522 of pouch 510, or a similar blister of a similar pouch. Like paddles 980*a* and 980*b*, paddles 990*a* and 990*b* can be rapidly reciprocated to produce a lysate. Illustratively, paddles 990*a* and 990*b* may be sized and positioned such that they are substantially the same area as a corresponding blister on which they are positioned to act. Likewise, paddles 990*a* and 990*b* may be larger or smaller than a corresponding blister. In the illustrated embodiment, paddles 990*a* and 990*b* are substantially the same size as one another. One will appreciate, however, that the paddles may be sized or shaped differently in other embodiments.

Referring now to FIG. 43B, paddles 990*a* and 990*b* are illustratively pivotably coupled to crank and slider mechanisms 994*a* and 994*b* with tabs 991*a* and 991*b* on the paddles 990*a* and 990*b* that fit into corresponding slots 993*a* and 993*b* on the crank and slider mechanisms 994*a* and 994*b*. The crank and slider mechanisms 994*a* and 994*b*, which function like the bearings in systems 912*b*, are coupled to drive shaft 992 via openings 995*a* and 995*b*. As shown in FIG. 43C, drive shaft 992 includes off-center, eccentric portions 992*a* and 992*b* that drive the reciprocating motion of the paddles when the crank shaft 992 is rotated.

As with system 912*b*, system 912*c* may be coupled to a motor or a similar drive device to rotate crank shaft 992. In contrast to system 912*b*, because the crank shaft 992, the crank and slider mechanisms 994*a* and 994*b*, and paddles 990*a* and 990*b* are actively coupled together, system 912*c* does not need to include biasing members that retract the paddles 990*a* and 990*b*. However, one will appreciate that biasing members may still be included in some embodiment.

Figure 44A:
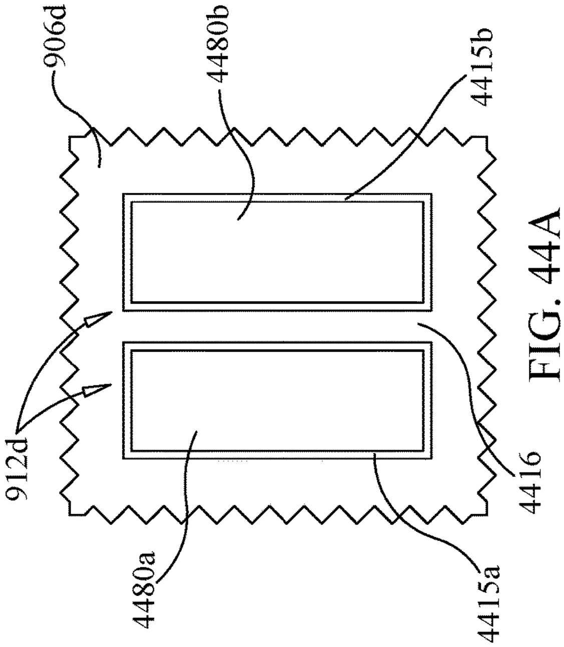
FIGS. 44A and 44B illustrate alternative embodiments of a paddle beat beater system.
Figure 44B:
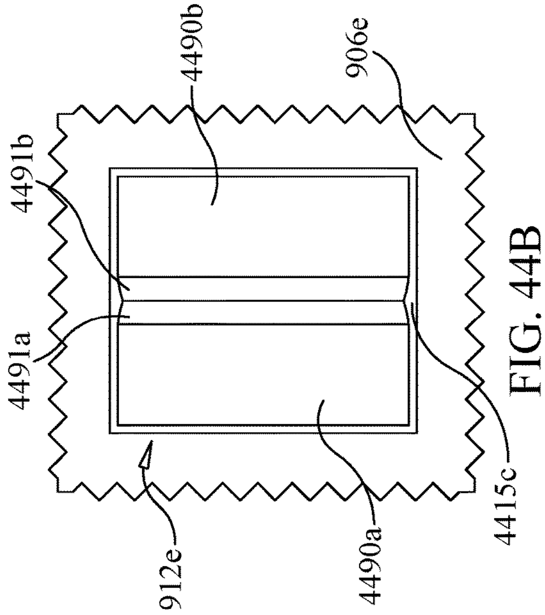

FIGS. 44A-46 illustrate various paddle beater embodiments with different paddle configurations and numbers of paddles. FIG. 44A illustrates a bead beater system 912*d* that includes paddles 4480*a* and 4480*b*. Bead beater system 912*d* is configured in the context of subassembly 906*d* and paddles 4480*a* and 4480*b* operate through openings 4415*a* and 4415*b*. In this illustrative embodiment, paddles 4480*a* and 4480*b* are separated by spacer 4416. Bead beater system 912*e* of FIG. 44B is similar to system 912*d*. System 912*e* includes paddles 4490*a* and 4490*b* that operate though opening 4415*c* of subassembly 906*e*. Paddles 4490*a* and 4490*b* include inwardly angled sections 4491*a* and 4491*b*. Systems 912*d* and 912*e* are similar in that spacer 4416 and inwardly angled sections 4491*a*, 4491*b* provide an open space between the paddles that can, illustratively, accommodate a swab or a similar inclusion in a lysis blister. It is also believed that that creating a space between the paddles in some embodiments may positively affect the agitation pattern (e.g., vortices may be created in the boundary area between the paddles), which in turn affects the movement of lysis beads and fluid and the effectiveness of the lysis process.

Figure 45:
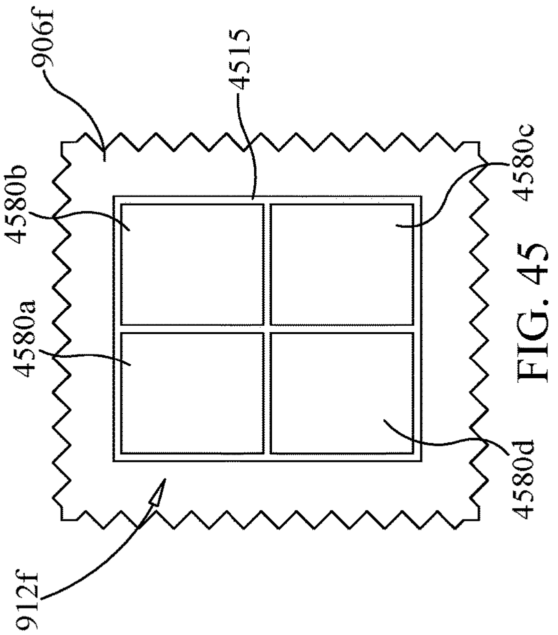
FIG. 45 illustrates an embodiment of a paddle bead beater system with four paddles.
Figure 46:
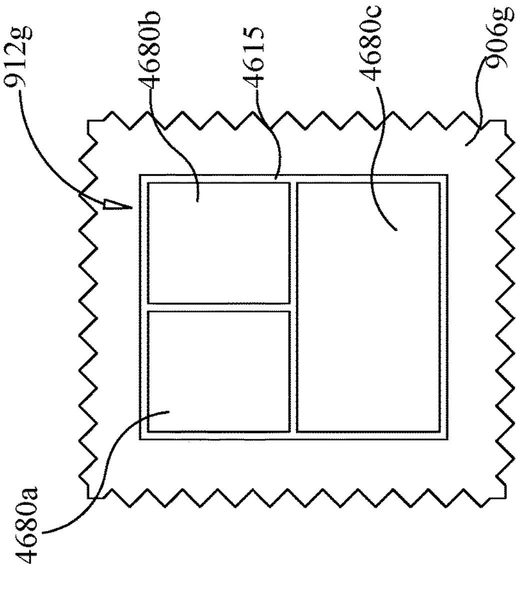
FIG. 46 illustrates an embodiment of a paddle bead beater system with three paddles.

FIG. 45 illustrates a bead beater system 912*f* that includes four paddles instead of the two used in the embodiments described above. FIG. 46 illustrates an embodiment of a bead beater system 912*g* that includes three paddles. In system 912*f* of FIG. 45 paddles 4580*a*-4580*d* are arranged in a square or rectangular arrangement. Paddles 4580*a*-4580*d* extend through opening 4515 in subassembly 906*f*. In FIG. 46, bead beater system 912*g* includes two vertically arranged paddles 4680*a* and 4680*b* and a horizontal paddle 4680*c*. Paddles 4680*a*-4680*c* are configured to operate in the context of subassembly 906*g* and extend through opening 4615. In one embodiment, the paddles of systems 912*f* and 912*g* may be actuated separately to create patterns, vortices, and the like in a lysis chamber. For instance, paddles 4580*a*-4580*d* may be actuated in sequence (e.g., 4580*a*, then 4580*b*, then 4580*c*, then 4580*d*, etc.) to create a vortex in the lysis. In another instance, paddles 4580*a*-4580*d* may be actuated in a cross pattern (e.g., 4580*a* and 4580*c* together followed by 4580*b* and 4580*d* together) to create a different lysis pattern. In another instance paddles 4680*a* and 4680*b* may be actuated one at a time similar to system 912*b*, for example, and paddle 4680*c* may be actuated in a timing not coupled to the actuation of paddles 4680*a* and 4680*b*. In yet another instance, paddles 4680*a*-4680*c* may be actuated in a circular manner (4680*a*, then 4680*b*, then 4680*c*, etc.). One will appreciate that the foregoing examples are merely illustrative and that other actuation patterns and lysis patterns are possible.

Components of bead beater systems 912*b*-912*g*, such as, but not limited to, the paddles, drive shafts, the crank and slider mechanisms 994*a* and 994*b*, etc. may be fabricated according to essentially any method known in the art. For example, components of bead beater systems may be fabricated from a durable and/or heat stable plastic material (e.g., Delrin® (polyoxymethylene), acrylonitrile butadiene styrene (ABS), Teflon, and the like) or from a metals material such as aluminum, stainless steel, titanium alloy, and the like. Illustratively, parts may be fabricated by injection molding, forging, machining, or the like. In one embodiment, one or more of the paddles of the bead beater systems described herein may include a temperature control element. For instance, a portion of one or more of the paddles that contacts a lysis blister may include a temperature control element that can illustratively be used for processes such as heated or cooled lysis, heated or cooled binding to magnetic beads, or thermal cycling. Illustrative examples of a temperature control element include, but are not limited to, heaters, coolers, Peltier devices, resistance heaters, induction heaters, electromagnetic heaters, thin film heaters, printed element heaters, positive temperature coefficient heaters, and combinations thereof. A temperature control element may include multiple heaters, coolers, Peltiers, etc. In one aspect, a given temperature control element may include more than one type of heater or cooler. For instance, an illustrative example of a temperature control element may include a Peltier device with a separate resistive heater applied to the top and/or the bottom face of the Peltier.

Performance of the paddle bead beater systems described herein is discussed below in Example 5 and is illustrated in reference to FIGS. 47-48C.

Figure 49:
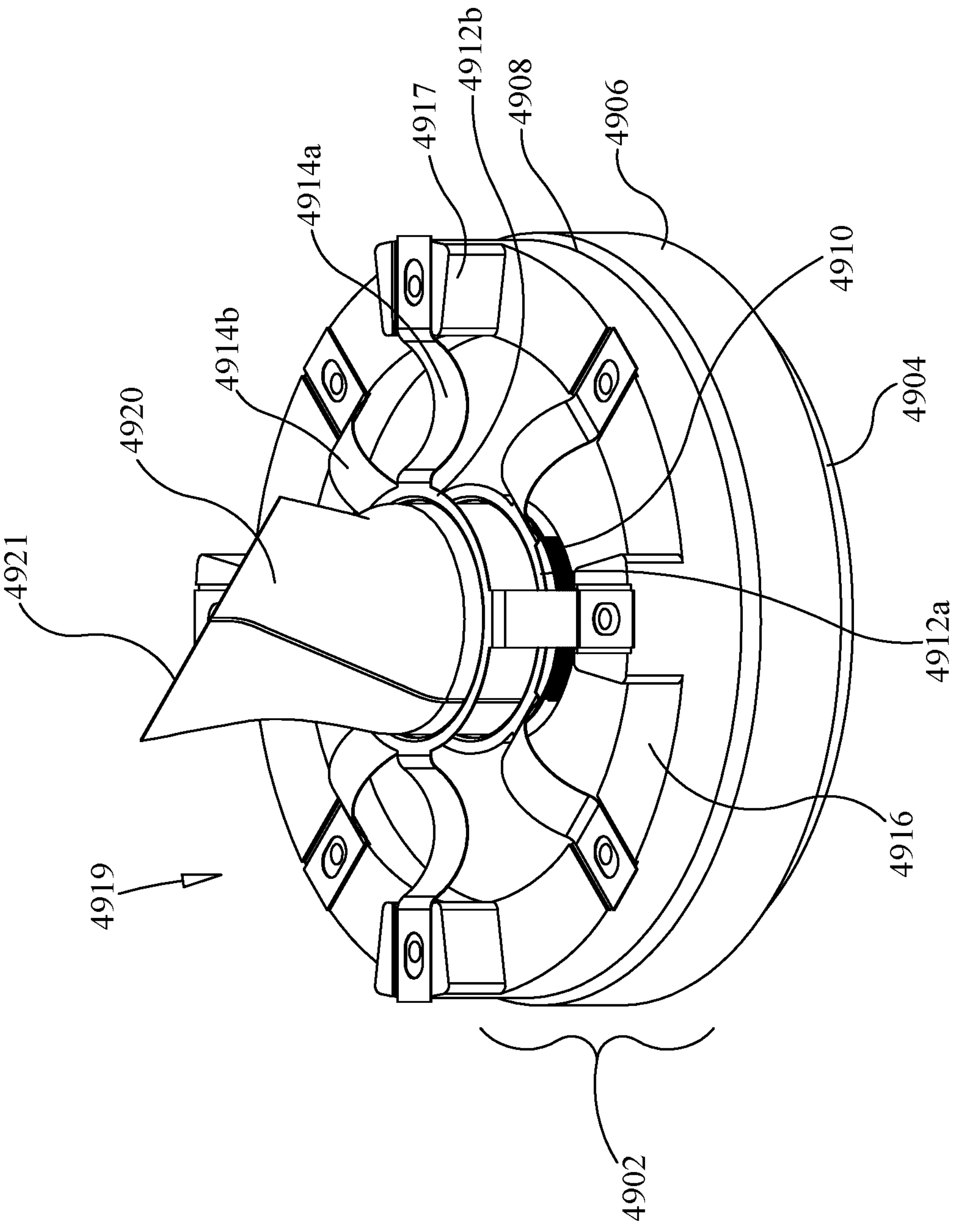
FIG. 49 illustrates an embodiment of a lysis apparatus driven by a voice coil motor, according to one embodiment of the present invention.

Referring to FIG. 49, a bead beater system 4919 is illustrated that includes an effector 4920 that is driven by a voice coil motor 4902. Voice coil motors are well known in the art. The illustrated voice coil motor 4902 includes permanent magnet 4906, a lower iron disc 4904, and an upper iron ring 4908, and a voice coil driver 4910. Types of voice coil drivers are well known in the art. For instance, a typical voice coil driver may include an annulus (not shown) (e.g., an aluminum or paper ring) that is wrapped with electrical wire to allow the voice coil driver to carry an electrical current. A typical voice coil driver may be supported on a post (not shown) and extends down into a narrow gap in the upper iron ring 4908. Passing an oscillating electrical current through the wire wrapped around the annulus causes an oscillating electrical field that causes the voice coil driver 4910 to oscillate up and down. The system 4919 may also include a number of support rings 4912*a* and 4912*b*, a support spider 4914*a* and 4914*b*, and additional supports and risers 4916 and 4917. And while the supports in the specific embodiment shown have a specific arrangements and structure, one will appreciate that this is merely illustrative and that other support arrangements are within the scope of this disclosure.

The effector 4920 is attached to the voice coil driver 4910 such that the effector oscillates up and down when the voice coil driver oscillates up and down. In the illustrated embodiment, the effector 4920 includes an edge 4921 that may be configured to contact the pouch (e.g., sample preparation blister 522) generally perpendicular to a surface 530 of pouch 510 to cause bead beating action. In one embodiment, the effector 4920 may be made from a variety of light materials such as, but not limited to, metal foils, plastics, and paper. For instance, a paper cylinder may be coupled to the annulus of the voice coil driver and then sealed at its end to form edge 4921. Properly shaped paper materials are very stiff and very light weight.

Voice coil drivers have low mass and they can generate high forces, but they are limited in displacement. Moreover, there is a tradeoff between frequency and displacement; i.e., the higher the frequency, the smaller the displacement of the voice coil driver. It was found, therefore, that the voice coil system 4919 could be driven for beat beating at frequencies of about 100-500 Hz (e.g., about 300 Hz, 400 Hz, or 500 Hz). This is comparable, for example, to the frequency of a bead beater of the type illustrated in FIG. 13, which operates at a bead beating speed, for example, of about 7,500-15,000 rpm, which translates to a frequency of blade 821 striking the pouch at about 250-500 Hz.

Figure 50A:
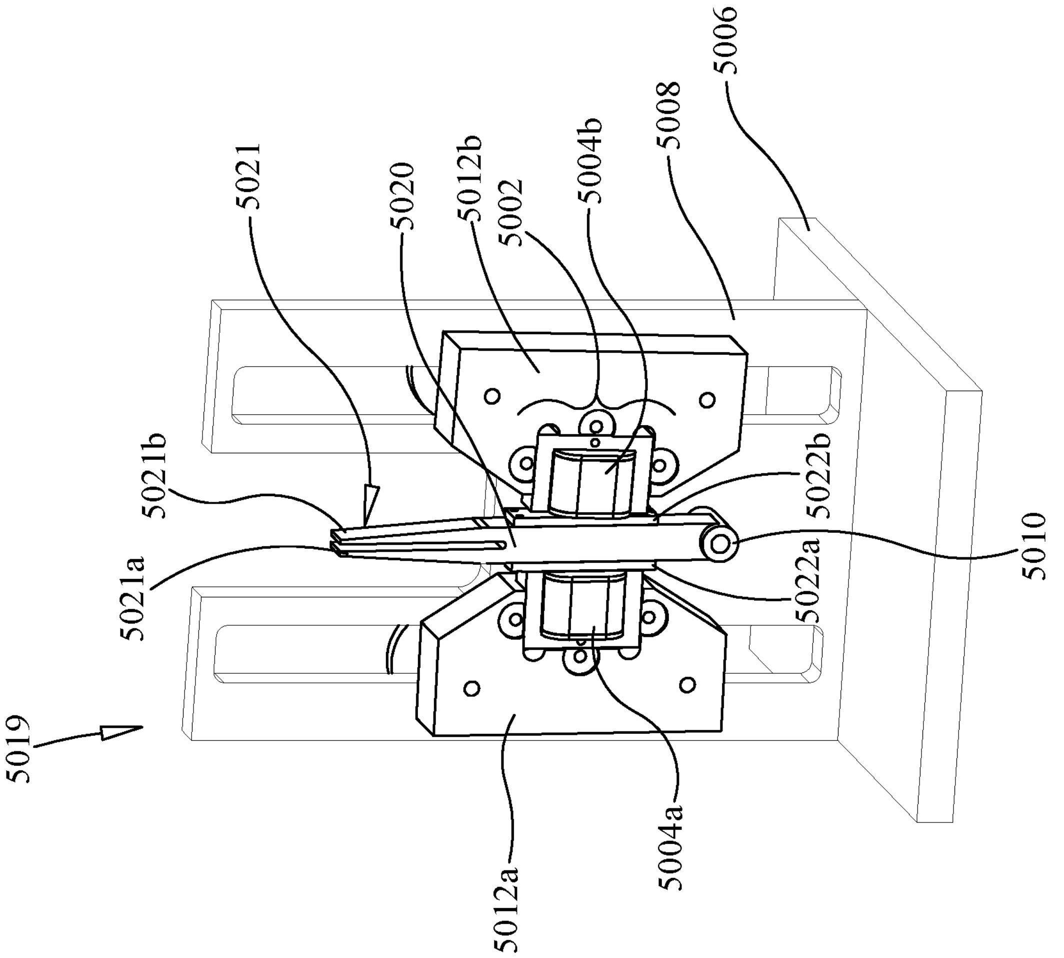
FIGS. 50A and 50B illustrate another embodiment of a lysis apparatus, according to one embodiment of the present invention.
Figure 50B:
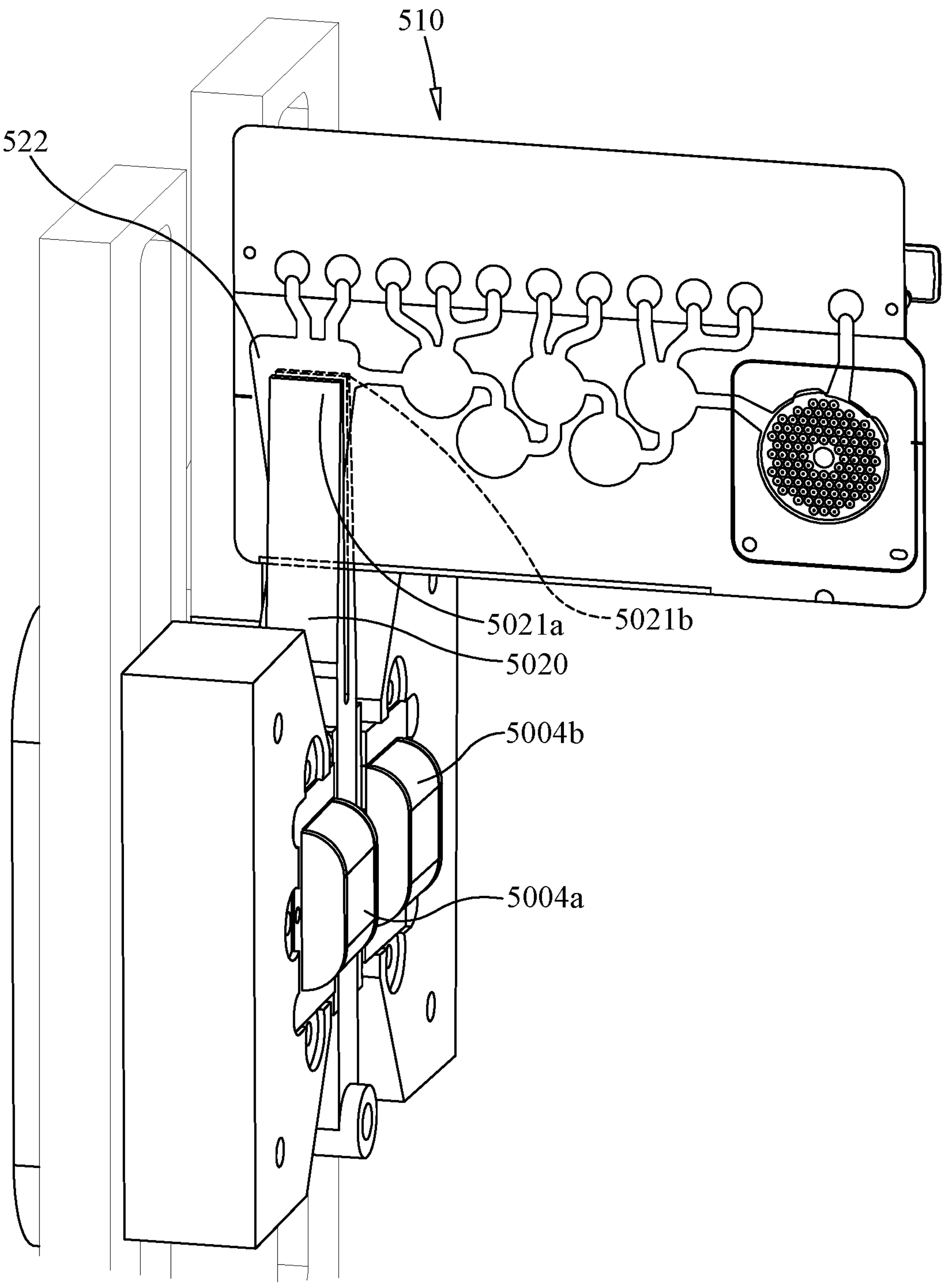

Referring now to FIGS. 50A and 50B, an embodiment of a prototype device 5019 that may be used for bead beating is illustrated. In the illustrated embodiment, the device 5019 has a fork-shaped effector 5020 with an end 5021 having a first half 5021*a* and second half 5021*b*. As illustrated in FIG. 50B, a pouch 510 can be placed between the ends 5021*a* and 5021*b* of the effector in the vicinity of the lysis blister 522. As will be described below, the effector 5020 can oscillate back and forth to aggressively mix the contents of the lysis blister 522, producing a bead beating action.

In the embodiment of a lysis apparatus illustrated in FIGS. 50A and 50B, the system 5019 includes an oscillator 5002 that is mounted on a base 5006 and a stand 5008. It is understood that this is illustrative only for and that system 5019 may be mounted within an instrument such as instrument 800. The oscillator 5002 is mounted on supports 5012*a* and 5012*b* that are alignably mounted on the stand 5008. The effector 5020 may be mounted to the stand 5008 at pivot 5010. In the illustrated embodiment, the oscillator 5002 includes two magnets including a first E core 5004*a* and a second E core 5004*b*. E cores, which are well known in the arts, are a type of magnetic core. A magnetic core is a piece of magnetic material with a high magnetic permeability used to confine and guide magnetic fields in electrical, electromechanical and magnetic devices such as electromagnets, transformers, electric motors, generators, inductors, magnetic recording heads, and magnetic assemblies. The E core gets its name because the core is formed by winding electrical wire around the central leg of a metallic E-shaped core. Other magnets may be used within the scope of this disclosure.

In one embodiment, E cores 5004*a* and 5004*b* are each configured to produce magnetic strong magnetic fields, one at a time, to cause the effector 5020 to oscillate back and forth between the E cores. As such, in the illustrated embodiment, the effector 5020 has magnetic plates 5022*a* and 5022*b* that may be attracted by the magnetic field produced by the E cores. In one embodiment, the E cores 5004*a* and 5004*b* may be coupled to an electrical circuit that powers E cores 5004*a* and 5004*b* one at a time. In an example embodiment, the electrical circuit may be a simple electrical device (e.g., a pair of diodes) that powers E cores 5004*a* and 5004*b* at the characteristic frequency of the alternating current power supply. In the United States, for example, alternating current has a frequency of 60 Hz. As such, system 5019 with E cores 5004*a* and 5004*b* can be configured for agitation for bead beating lysis without the need for complicated electronic control systems, firmware programming, or the like. E cores are also available in a number of sizes and power ratings. Thus, the power of system 5019 may be changed to increase or lower power to, for example, tune bead beating efficiency by changing E core size and/or power. In one embodiment, E core electromagnets may be replaced with mechanical actuators or the like that may strike the effector 5020 to cause the effector to oscillate back and forth.

In another embodiment, bead beading may be accomplished via sonication, as is known in the art. In still another embodiment, lysis is affected by placing pressure on the sample, illustratively by a scrubbing action. In this embodiment, a roller or slide may be placed against the surface 530 adjacent a portion of blister 522 and is moved along blister 522, illustratively lengthwise, although other movements are possible. The roller may illustratively move in an action similar to a steam roller, thereby crushing the sample against beads 534. Such an embodiment may use a peristaltic pump. A slide that does not roll may be employed similarly.

It is understood that any bead beater may be used with any other embodiment of a system disclosed herein.

Moving Magnet System

Referring now to FIGS. 15A-15K, an alternative embodiment of magnet system that can be used in combination with a series of sample preparation steps is illustrated. The sample preparation steps illustrated in FIGS. 15A-15K include magnetic bead hydration, dispersal of the magnetic beads in the cell lysate to facilitate nucleic acid recovery, magnetic bead recovery from the lysate, magnetic bead wash, and elution of the nucleic acid from the magnetic beads. FIGS. 15A-15K use the same numbering for pouch elements (i.e., blisters and magnetic beads) that were described in reference to FIG. 2, but only the relevant pouch elements are shown. In contrast to the previously described example that utilizes a retractable magnet located within the instrument adjacent to blister 546, the example illustrated in FIGS. 15A-15K utilizes a mechanism 1310 that includes a movable magnet 1320 that can be moved (e.g., along a circular or semi-circular path) to various blisters to facilitate movement and capture of the magnetic beads 546. The system illustrated in FIGS. 15A-15K can reduce the time needed for sample preparation in the pouch (i.e., nucleic acid recovery, magnetic bead recovery from the lysate, magnetic bead wash, and elution of the nucleic acid from the magnetic beads) by up to 10%, up to 15%, up to 20%, up to 25%, up to 30%, up to 35%, up to 40%, up to 45%, up to 50%, up to 55%, up to 60%, up to 65%, up to 70%, or by up to 75%.

Figure 15A:
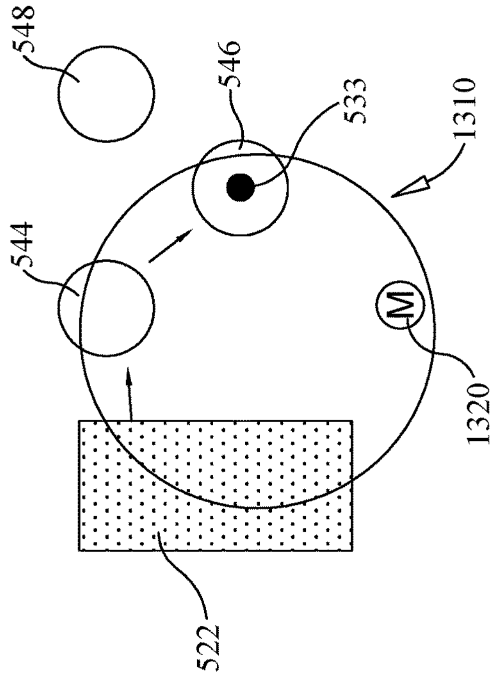
FIGS. 15A-15K schematically illustrate a method for magnetic bead rehydration, nucleic acid recovery, washing, and elution that employs a moving magnet system, according to an embodiment of the present invention.

Referring now to FIG. 15A, a portion of pouch 510 is schematically illustrated. The pouch 510 includes sample lysis blister 522 and downstream blisters 544, 546, and 548. The channels between blisters that were discussed in reference to FIG. 2 are omitted, but fluid movement between blisters is indicated by arrows. A mechanism 1310 that includes a movable magnet 1320 is also schematically illustrated. It is understood that mechanism 1310 illustratively may be mounted in door assembly 908 of instrument 900.

Figure 15B:
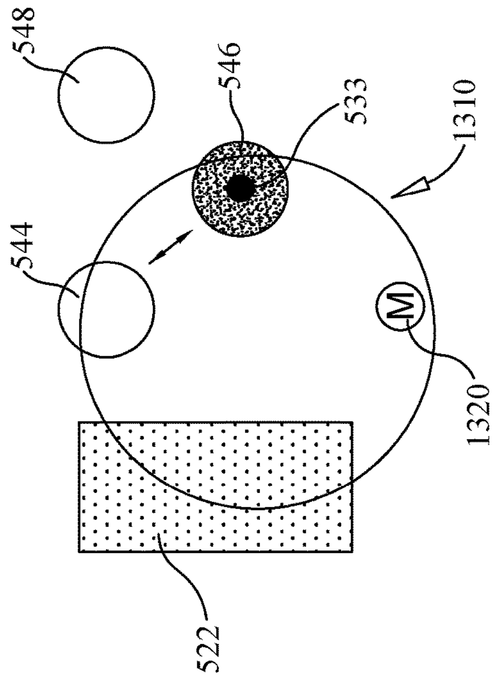
Figure 15C:
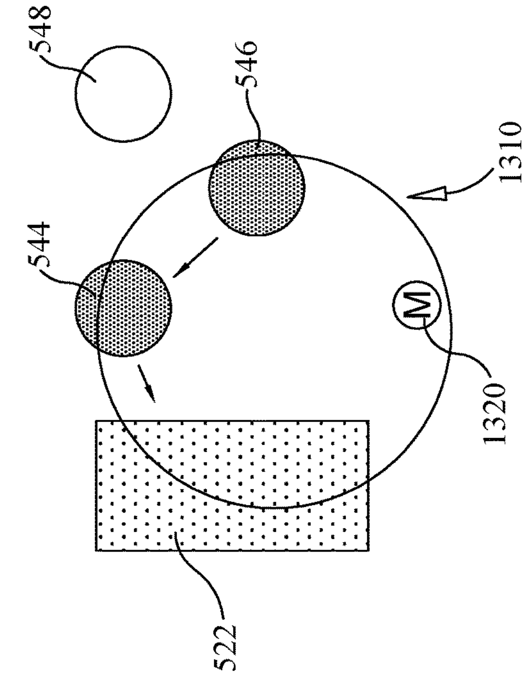
Figure 15D:
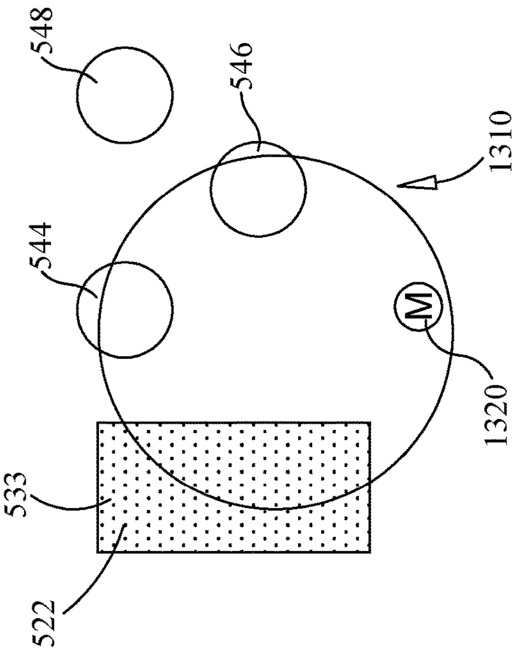

In a first step illustrated in FIGS. 15A and 15B, cell lysate is squeezed out of blister 522 and into blisters 544 and 546 to hydrate the magnetic beads 533. Fluid (i.e., cell lysate) may then be forced back and forth between blisters 544 and 546 to disperse the magnetic beads. In a second step illustrated in FIGS. 15C and 15D, substantially all of the fluid with the magnetic beads dispersed therein is squeezed from blister 546 to blister 544 and into blister 522 for recovery of the nucleic acids from the lysate in blister 522. As is schematically illustrated in FIG. 15D, the magnetic beads 533 are dispersed in substantially the entirety of the cell lysate in blister 522. For nucleic acid recovery, the magnetic beads 533 may be allowed to incubate in the lysate for a selected period of time. However, to improve dispersion and speed up nucleic acid recovery, the nucleic acid recovery step may include limited bead beating to further break up any clumps of beads and to more completely disperse the beads in the lysate.

Figure 15E:
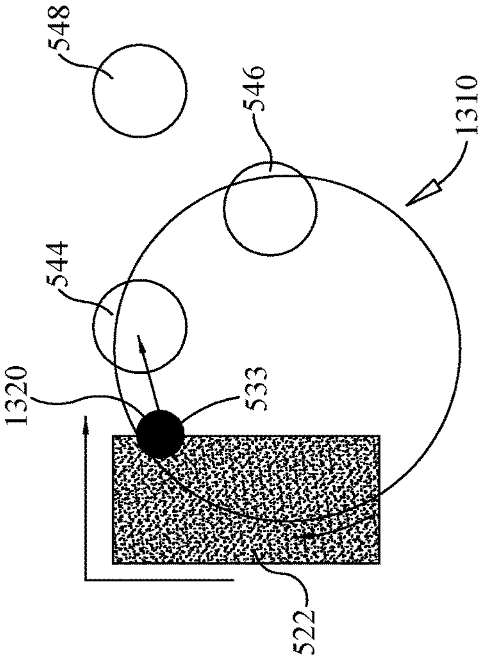

In the nucleic acid recovery protocol described above in reference to FIG. 3A, the magnetic beads are recovered by activating a retractable magnet at blister 546 and repeatedly forcing fluid back and forth between blisters 522 and 546 (via blister 544), while recovering additional magnetic beads each time fluid is moved to blister 546. While this may be an effective method for recovering the magnetic beads, it can be quite time consuming, requiring more than ten capture cycles. In contrast, with the moving magnet system illustrated in FIG. 15E, the magnet 1320 may be moved on a circular track of system 1310 into proximity of blister 522 and used to pick up the magnetic beads in a single step. As shown in FIG. 15E, the magnet 1320 is moved parallel to an outer surface of blister 522 and used to collect the magnetic beads 533 and bring them to an area near the channel between blisters 522 and 544. In the magnetic bead recapture embodiment described in reference to FIG. 3A, the magnet moves in and out (that is closer to and farther from the pouch) to capture and release the magnetic beads. In the magnetic bead recapture embodiment described in reference to FIGS. 15A-15K, the magnet 1320 may release the magnetic beads by rotating away from the blister where the beads are confined. In some embodiments, the magnet 1320 may not be able to carry a cluster of magnetic beads through the channels between the blisters, either because the magnet is not strong enough or the channel is not wide enough, or for other reasons. Thus, to aid in moving magnetic beads 533 through channel 538 (see FIG. 2), a pulse of liquid from blister 522 to 544 may be used to dislodge the beads from the magnet 1320 and flush them into blister 544.

In one embodiment, magnet 1320 is a small (e.g., a diameter of 1 cm-5 mm or less) powerful magnet. In general, magnets that are small in diameter relative to the size the blisters (e.g., blisters 522 and 544) may be desired because their magnetic force is more focused and fewer beads are lost when they are used for recovery of the magnetic beads. For instance, a small, powerful magnet forms a smaller pill of magnetic beads that can be "lifted" to the channel between blisters and 544 and then flushed to blister 544 with fluid from 522. If the magnet were larger, a larger pill would be formed and such a larger pill may not be flushed as effectively. Likewise, when the magnet confines the beads to a blister for washing away of cellular debris carried over from the lysis protocol or elution of recovered nucleic acids from the bead (discussed below), a smaller pill can be more efficiently moved away from the channels connecting the blisters so that the beads are not flushed away when the wash or elution solutions are flushed.

In one embodiment, the magnet 1320 is a rare earth magnet. Rare-earth magnets are strong permanent magnets that are typically made from alloys of neodymium and samarium. The magnetic field typically produced by rare-earth magnets can exceed 1.4 teslas, whereas ferrite or ceramic magnets typically exhibit fields of 0.5 to 1 tesla. Neodymium magnets are the strongest and most affordable type of rare-earth magnet. They are made of an alloy of neodymium, iron and boron ($Nd_2Fe_{14}B$), sometimes abbreviated as NIB. Samarium-cobalt magnets (chemical formula: $SmCo_5$) are less common than neodymium magnets because of their higher cost and weaker magnetic field strength. However, samarium-cobalt has a higher Curie temperature, creating a niche for these magnets in applications where high field strength is needed at high operating temperatures. In another embodiment, the magnet 1320 may be an electromagnet. In yet another embodiment (not shown), the system 1310 for moving the magnet 1320 may be replaced with an array of fixed electromagnets that can be turned on and off at selected locations for magnetic bead recovery, washes, etc.

Figure 15F:
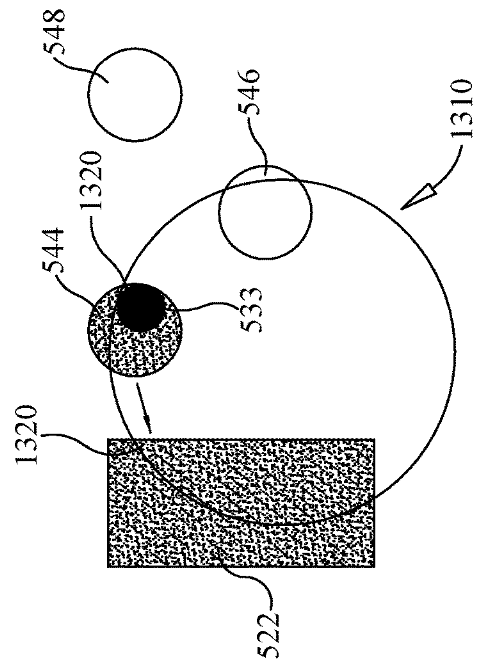

Referring now to FIG. 15F, after the magnetic beads 533 are flushed to blister 544, the magnet is moved to blister 544 and the magnetic beads 533 are captured in an area away from the channel between blisters 544 and 522 and the fluid is flushed away to blister 522. At this point, the nucleic acids have been recovered from the lysate and blister 522 may be used a waste receptacle. In some embodiments, it may be desirable to do additional collections of magnetic beads from blister 522.

Figure 15G:
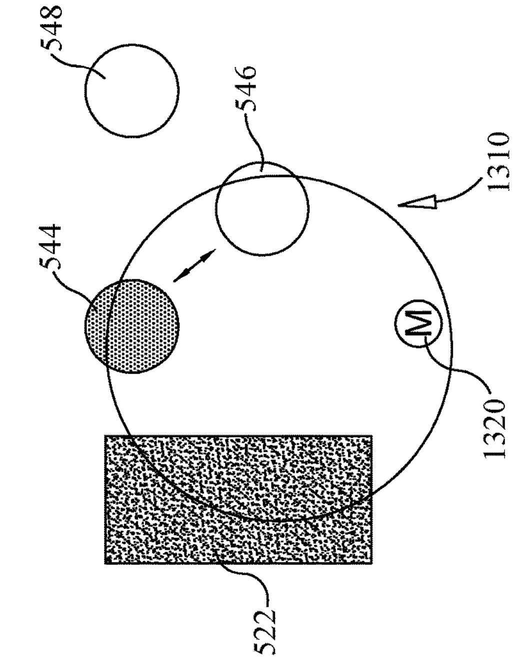
Figure 15H:
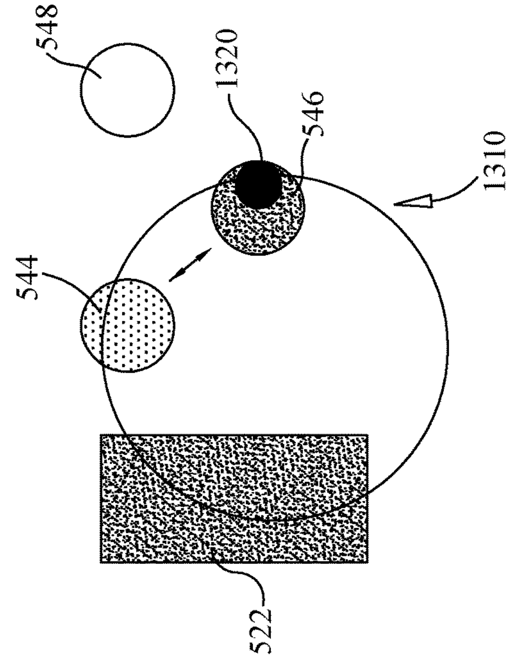

Referring now to FIG. 15G, the magnetic beads may be washed to remove cell fragments, lysis buffer and the like by moving the magnet 1320 away from the blisters and injecting a wash buffer solution from the fitment into blister 544 and squeezing the beads slowly between blisters 544 and 546. The magnet 1320 may then be moved to blister 546 and the fluid may be squeezed from blister 544 into blister 546 to recapture the beads. The wash solution may be squeezed away through blister 544 to blister 522. The wash sequence is optionally repeated at least once with fresh wash buffer.

Figure 15I:
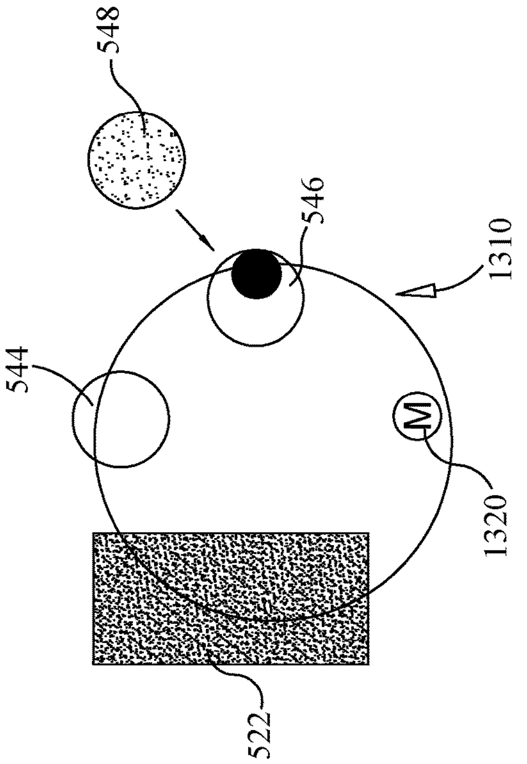
Figure 15J:
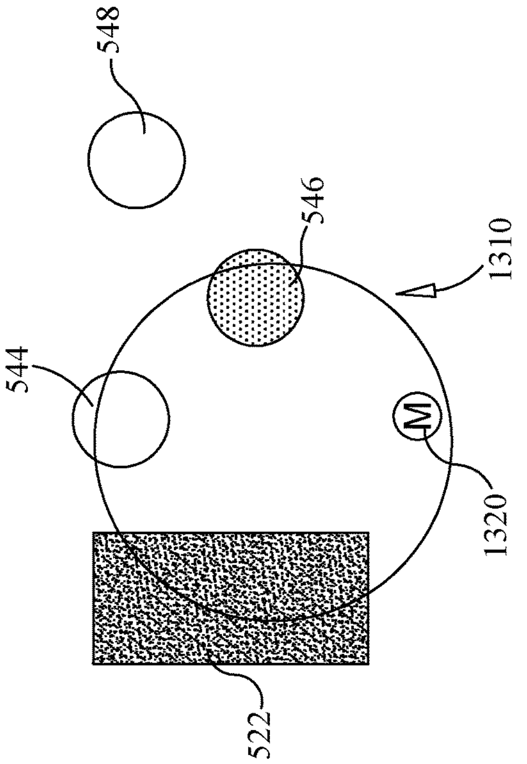
Figure 15K:
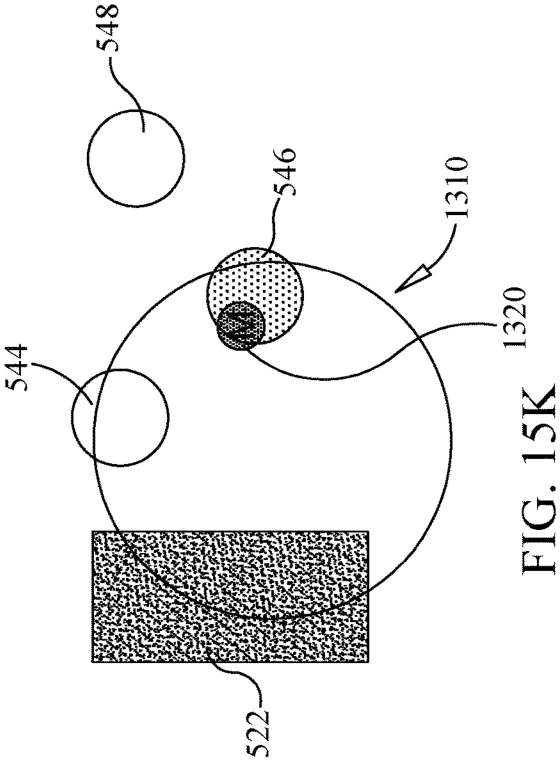

Referring now to FIGS. 15I-15K, nucleic acids may be eluted from the magnetic beads 533 by moving the magnet 1320 away from the blisters, injecting elution buffer from the fitment into blister 546 via blister 548. In the illustrated embodiment, the magnetic beads may be dispersed in the elution buffer to elute the nucleic acid by squeezing the fluid between blisters 544 and 546. Alternatively, the elution buffer may be added to blister 546 and elution will take place merely by waiting. In any case, the elution buffer and the beads are recollected in blister 546 by moving the magnet to blister 546 and collecting the beads away from the channel between 546 and 548. The eluted nucleic acids and the elution buffer are then moved away from the beads 533 to blister. The eluted nucleic acids are now ready for first-stage PCR in blisters 548 and 550.

Referring now to FIGS. 16A-19B, specific embodiments are illustrated of moving magnet systems. The specific devices illustrated in FIGS. 16A-19B are configured to work with pouch 510 and instrument 900 described herein and in other applications filed by the applicant, but it is understood that this is illustrative only, and these embodiments may be used in various instrument for use with various sample containers. The moving magnet systems illustrated in FIGS. 16A-19B may be used according to the schemes illustrated in FIGS. 15A-15K to facilitate, for example, magnetic bead recovery, washing away of cellular debris from the magnetic beads that is captured when the nucleic acids are recovered, elution of the nucleic acids off the beads, and isolation of the magnetic beads when the eluted nucleic acids are moved away for first-stage PCR.

Figure 16B:
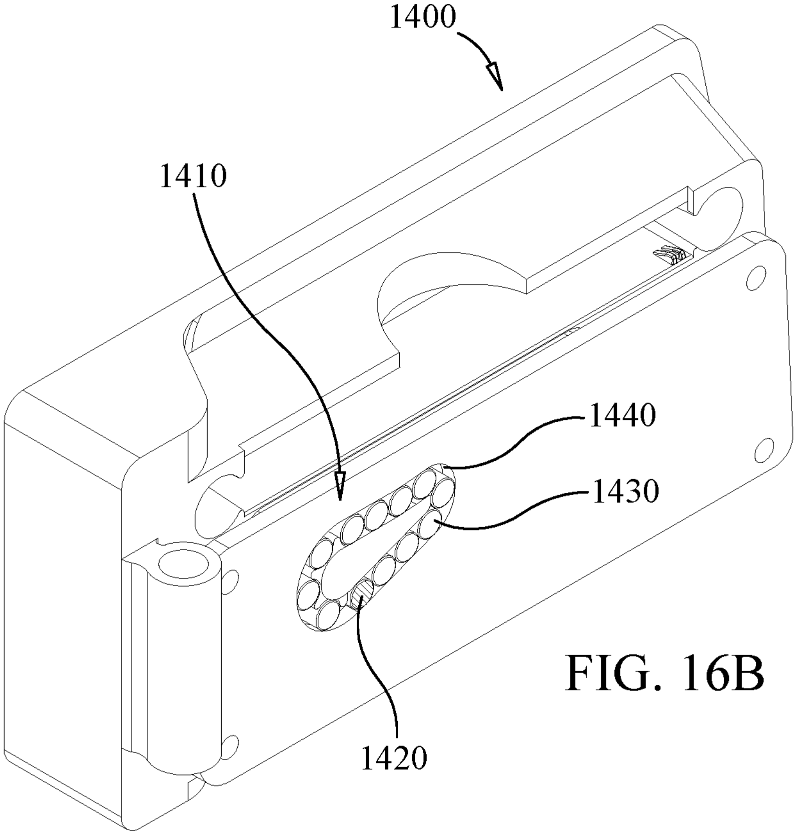
FIGS. 16A and 16B illustrate an embodiment of a moving magnet system, according to an embodiment of the present invention.
Figure 16A:
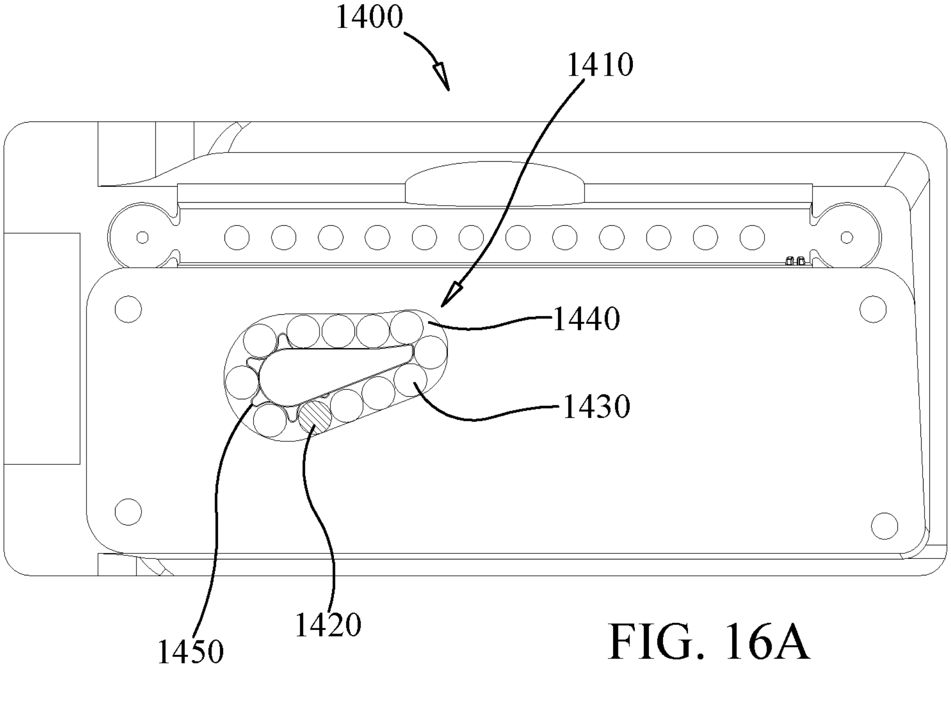

FIGS. 16A and 16B illustrate a moving magnet system 1410 that is housed in a plate 1400. The plate houses the moving magnet system 1410 and may be configured to be included in the instrument 900. For instance, the plate 1400 may comprise a structure that having a face that is pressed against pouch 510 in instrument 900. Plate 1400 may, for instance, comprise a structure that may be used to immobilize pouch 510 within instrument 900 and hold pouch 510 in relation to the plunging systems, compression members, seals, heaters, and the like described elsewhere herein.

The moving magnet system 1410 includes a magnet 1420 (e.g., a rare earth magnet). In the illustrated embodiment, the magnet 1420 is included in a chain structure 1430 that can be used to drive the magnet 1420 around a defined track 1440 by, for instance, turning drive cog 1450. Drive cog 1450 may be coupled to a drive motor or the like (not shown) for turning the drive cog 1450. By turning drive cog 1450 in a predetermined direction, the magnet 1420 of system 1410 may be moved around in track 1440 and positioned over the various blisters and channels described generally in FIGS. 15A-15K. For instance, to effect magnetic bead recovery, the magnet 1420 may be swept past blister 522, as schematically illustrated FIG. 15E. In an alternative to sweeping past blister 522, the magnet 1420 may be moved in a series of stepwise movements past the blister in order to separate the magnetic beads from the bead-beating beads and pick up the magnetic beads. Likewise, the magnet 1420 may positioned, for example, to facilitate the washing away of cellular debris from the magnetic beads that are captured when the nucleic acids are recovered, elution of the nucleic acids off the beads, and isolation of the magnetic beads when the eluted nucleic acids are moved away for first-stage PCR.

Figure 17A:
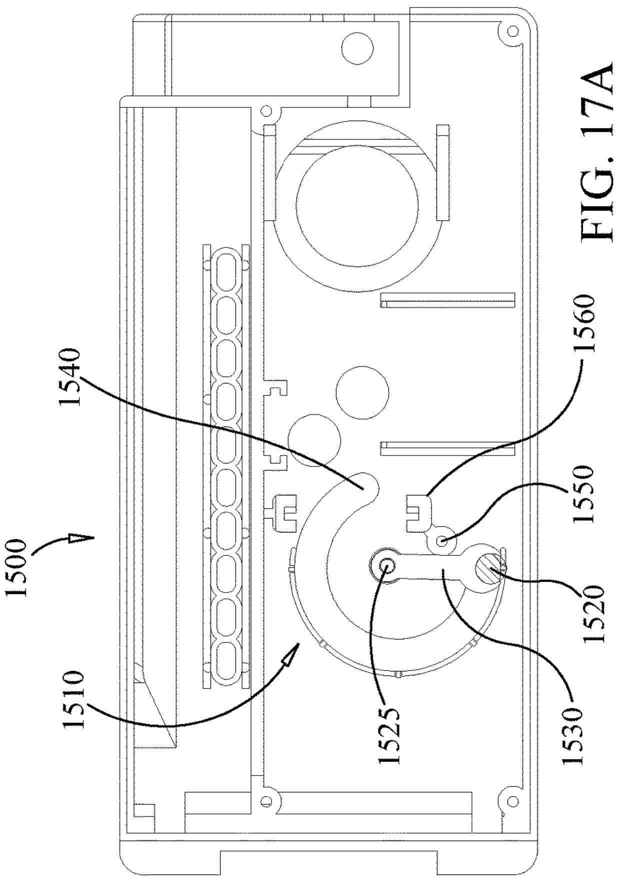
FIGS. 17A and 17B illustrate another embodiment of a moving magnet system, according to an embodiment of the present invention.
Figure 17B:
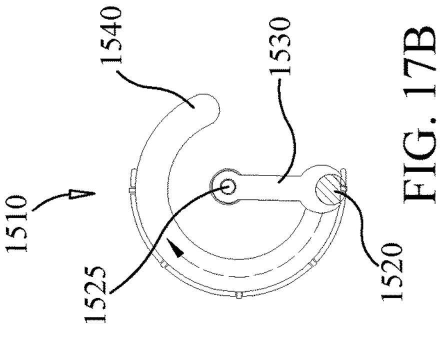

FIGS. 17A and 17B illustrate another moving magnet system 1510 similar to the system 1410 discussed previously. The moving magnet system 1510 may be housed in a plate 1500 that is configured to be included in instrument 900. As with plate 1400, plate 1500 may, for instance, comprise a structure such as support member 910 of FIG. 3B that is used to immobilize the pouch in the instrument and hold the pouch against the pistons, compression members, seals, heaters, and the like described elsewhere herein. However, in the illustrated view, the magnetic system 1510 is on the back side of plate 1500; the surface of plate 1500 that could be pressed against the pouch 510 (e.g., surface 944 of FIG. 3B) is not shown in this Figure.

The moving magnet system 1510 includes a magnet 1520 (e.g., a rare earth magnet) that is held in a wrench-shaped arm 1530. In the illustrated embodiment, the wrench-shaped structure 1530 is configured to swing around pivot 1525 in a defined arc-shaped path 1540. The moving magnet system 1510 also includes a first stop member 1550 and a second stop member 1560 that are positioned to stop the swinging of the arm 1530 at the ends of the arc shaped path 1540. In one embodiment, either the wrench-shaped structure 1530 or the pivot 1525 may be coupled to a drive motor or the like that can control the movement and positioning of the magnet 1520. By swinging the wrench-shaped arm 1530 around the arc path 1540, the magnet 1520 may be positioned over the various blisters and channels described generally in FIGS. 15A-15K. Like magnetic system 1410, the magnet 1520 of system 1510 may be positioned to facilitate recollection of the magnetic beads from the lysis blister, the washing, elution of the nucleic acids off the beads, and isolation of the magnetic beads when the eluted nucleic acids are moved away for first-stage PCR.

In one embodiment, the area of the plate 1500 defined by the path 1540 may be thinner than the rest of the plate. For instance, path 1540 may be machined or otherwise formed in plate 1500 by means known in the art. Forming the path 1540 in the plate 1500 may help to define and control the path of the magnet 1520, and one or both of stop members 1550, 1560 may be omitted. Likewise, because the magnet is on the back side of the plate 1500 away from the pouch and the magnetic force used to pick up the magnetic beads has to pass through the material of the plate, thinning the material of the path 1540 may increase the magnetic force experienced by the magnetic beads and reduce the diffusion (i.e., spreading) of the magnetic force. A stronger, more focused magnetic force may allow the magnet to better capture and isolate the magnetic beads. For example, stronger, more focused magnetic force may yield a more compact pellet of magnetic beads.

Figure 17C:
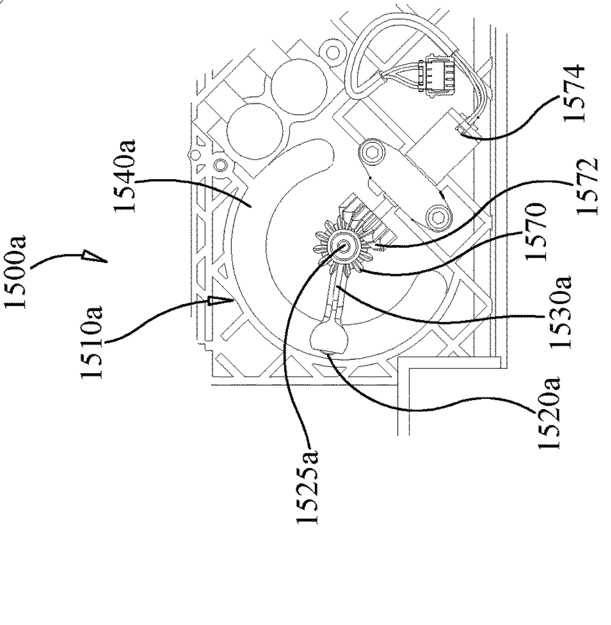
FIG. 17C illustrates an embodiment of a moving magnet system, according to an embodiment of the present invention.

FIG. 17C illustrates another embodiment of moving magnet system 1510*a* that is similar to the moving magnet system 1510 illustrated in FIGS. 17A and 17B. Like system 1510, moving magnet system 1510*a* may be housed in a plate 1500*a* that is configured to be included in instrument 900. The moving magnet system 1510*a* includes a magnet 1520*a* (e.g., a rare earth magnet) that is held in a wrench-shaped arm 1530*a*. In the illustrated embodiment, the wrench-shaped structure 1530*a* is configured to swing around pivot 1525*a* in a defined arc-shaped path 1540*a*. In the illustrated embodiment, the moving magnet system 1510*a* includes a drive motor 1574 and drive gears 1570 and 1572 that can control the movement and positioning of the arm 1530*a* and the magnet 1520*a*. The motor 1574 and drive gears 1570 and 1572 may, for example, be adapted to be included in the moving magnet system 1510 of FIGS. 17A and 17B.

By swinging the wrench-shaped arm 1530*a* around the arc path 1540*a*, the magnet 1520*a* may be positioned over the various blisters and channels described generally in FIGS. 15A-15K. Like magnetic system 1410, the magnet 1520*a* of system 1510*a* may be positioned to facilitate recollection of the magnetic beads from the lysis blister, the washing, elution of the nucleic acids off the beads, and isolation of the magnetic beads when the eluted nucleic acids are moved away for first-stage PCR.

Figure 18B:
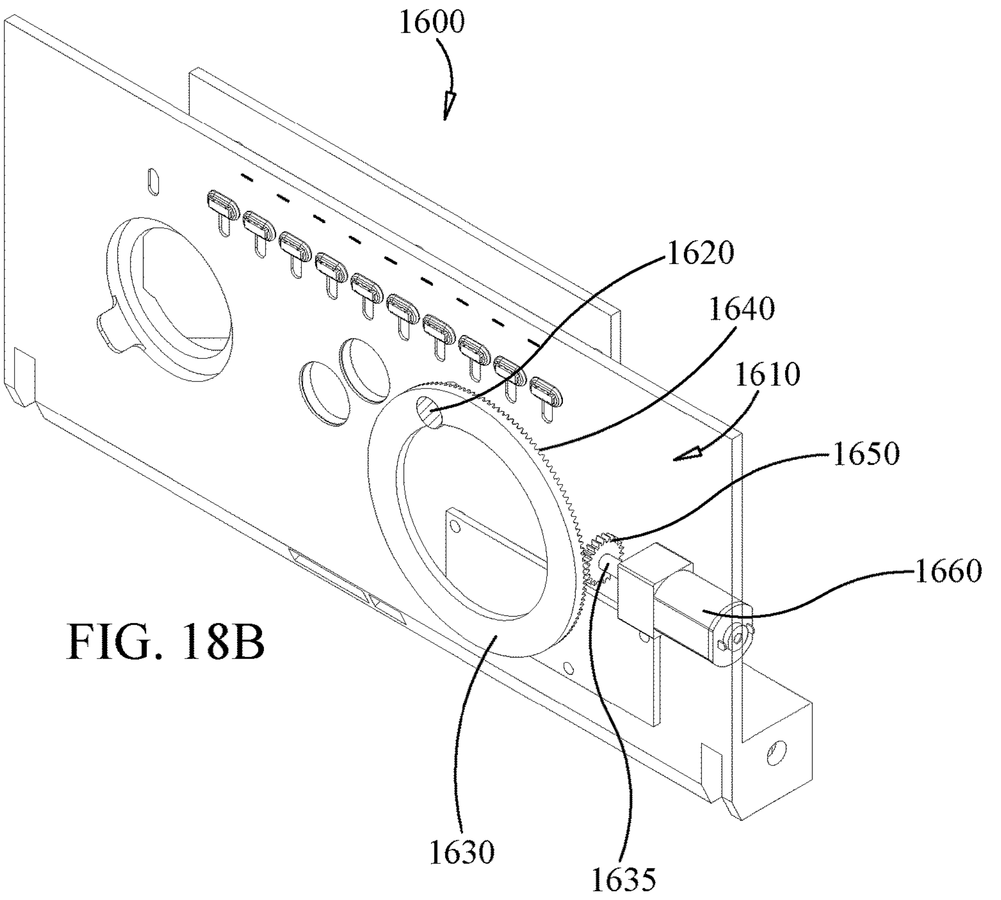
FIGS. 18A and 18B illustrate another embodiment of a moving magnet system, according to an embodiment of the present invention.
Figure 18A:
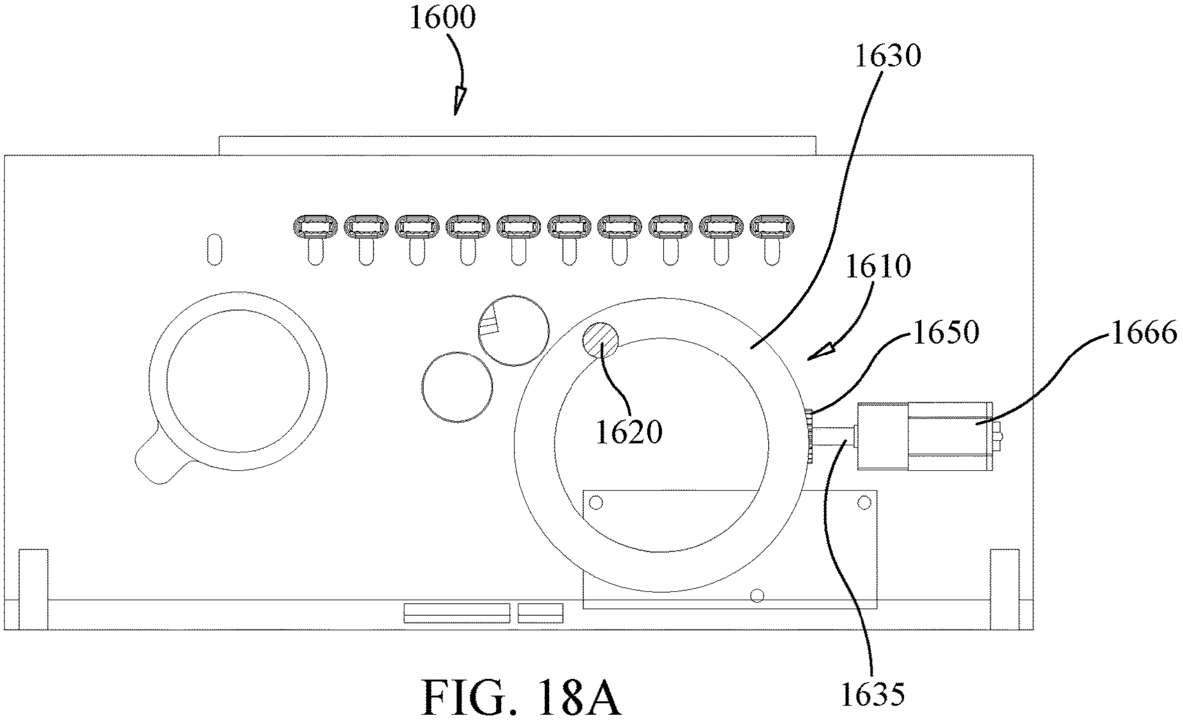

FIGS. 18A and 18B illustrate another embodiment of a moving magnet system 1610 similar to the systems discussed above. The moving magnet system 1610 is housed in a plate 1600 that is configured to be included in instrument 900. Plate 1600 is similar to plates 1400 and 1500 discussed above. Plate 1600 may include elements of the door subassembly 908 illustrated in FIG. 3B.

The moving magnet system 1610 includes a magnet 1620 (e.g., a rare earth magnet) and a rotatable ring 1630 that holds the magnet 1620 and that is configured to be rotated to position the magnet over the various blisters and channels described generally elsewhere to facilitate recollection of the magnetic beads from the lysis blister, the washing, elution of the nucleic acids off the beads, isolation of the magnetic beads when the eluted nucleic acids are moved away for first-stage PCR, and the like. In the illustrated embodiment, the rotatable ring 1630 is coupled to a drive motor 1660 via teeth 1640 on one surface of the rotatable ring 1630 and a drive shaft 1635 and a drive wheel 1650 that are attached to the drive motor 1660. Alternatively, the drive wheel 1650 may interface with the rotatable ring 1630 by friction instead of meshing gears on the drive wheel and the rotatable ring. Likewise, the drive wheel may be dispensed with and replaced with a worm gear that is positioned and configured to mesh with the teeth 1640 on the rotatable ring 1630.

The motor 1660 can be controlled such that the magnet 1620 can be positioned over the various blisters and channels of the pouch. For instance, the motor may be linked to a control system that includes programming to position the magnet where it needs to be in space and time so that the magnet can, for example, effect the steps with the magnetic beads that were illustrated in FIGS. 15A-15K.

Figure 19B:
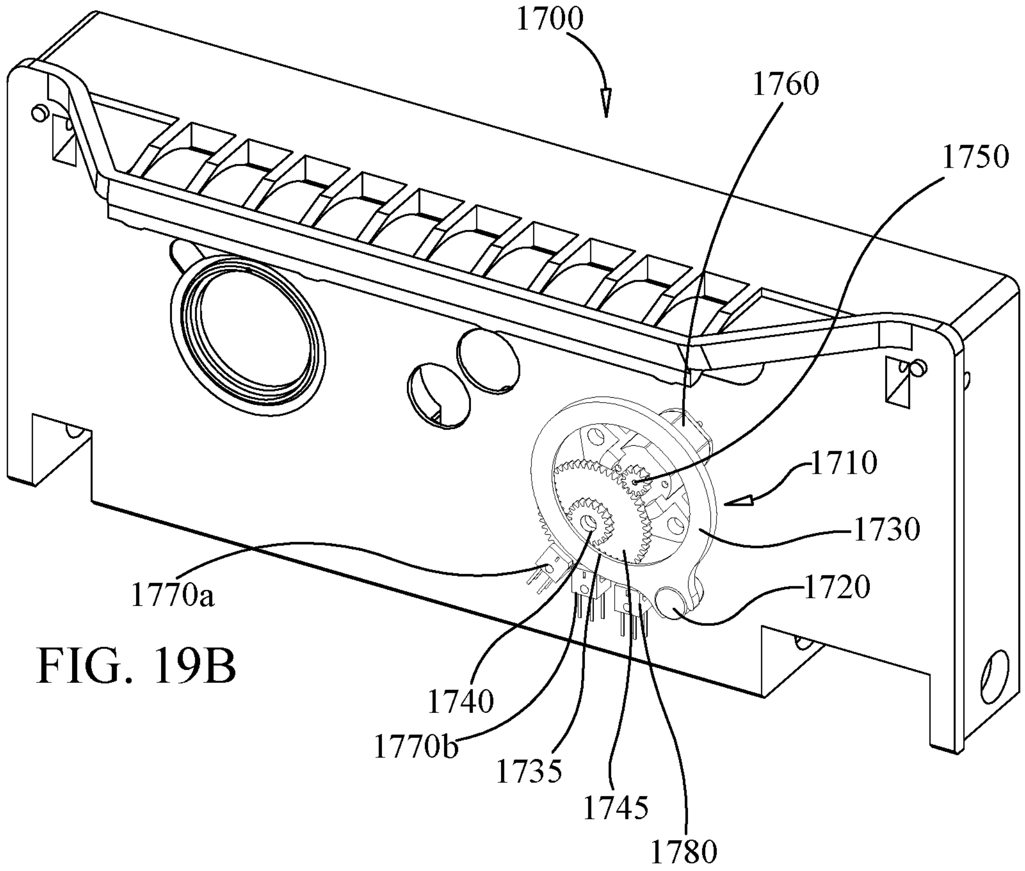
FIGS. 19A and 19B illustrate another embodiment of a moving magnet system, according to an embodiment of the present invention.
Figure 19A:
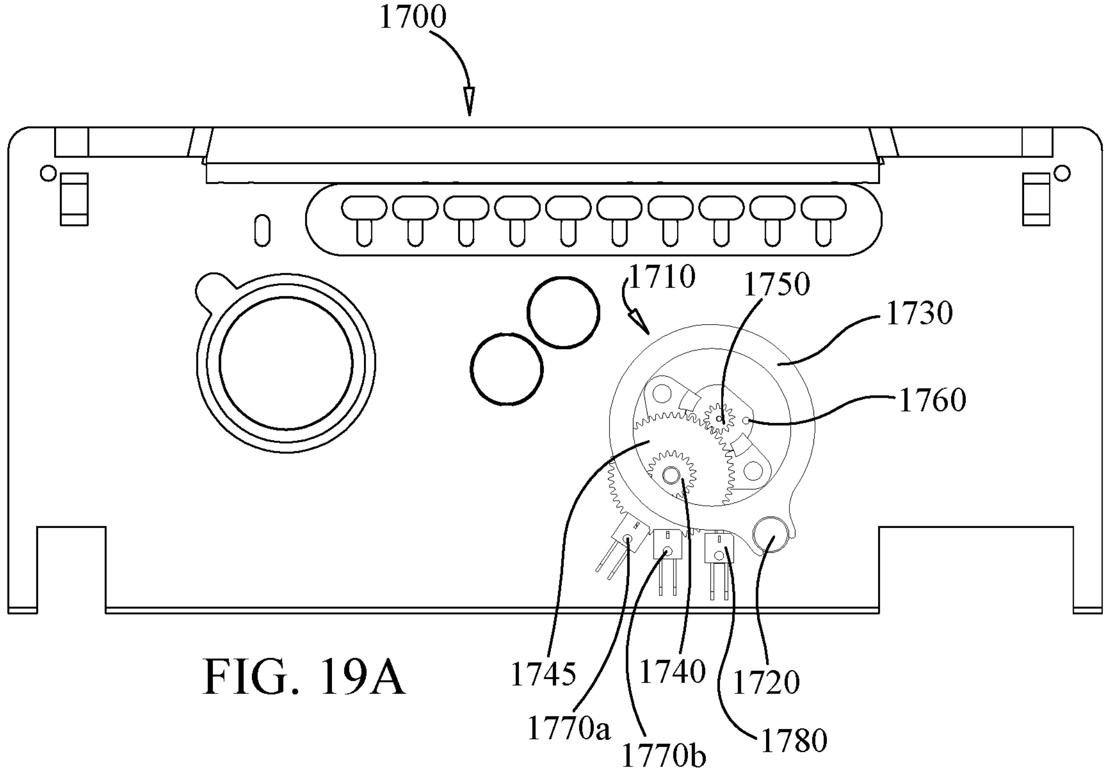

FIGS. 19A and 19B illustrate yet another embodiment of a moving magnet system 1710. As with the previously described systems, the moving magnet 1710 is housed in a plate 1700 that may form part of a structure that holds pouch 510 in place in the instrument 900. Plate 1700 may include some of the elements of the door subassembly 908 shown in FIG. 3B. The moving magnet system 1710 bears some similarity to the system 1610 illustrated in FIGS. 18A and 18B.

The moving magnet system 1710 includes a magnet 1720 housed in a rotatable ring 1730. The rotatable ring 1730 includes teeth 1735 on one face that intermesh with a drive gear system that is coupled to a motor 1760. The drive gear system includes a small drive gear 1740 that meshes with the teeth 1735 on the rotatable ring 1730. The small drive gear 1740 is coupled to a large drive gear 1745 that is meshed with a gear wheel 1750 that is in-line with the motor 1760. When the motor 1760 is turned, gear wheel 1750 turns the large 1745 and small 1740 drive gears, which causes the rotatable ring 1730 to rotate and position the magnet 1720.

In one embodiment, moving magnet system 1710 as well as the other moving magnet systems discussed herein may include a sensor system that can detect the state of the moving magnet system 1710 so that programming state can be updated dynamically with information about where the magnet is located. One embodiment of such a system is illustrated at 1770*a*, 1770*b*, and 1780. In the illustrated embodiment, sensors 1770*a*, 1770*b*, and 1780 are optical sensors that are configured to detect the relative positions large drive gear 1745 and the rotatable ring 1730. For instance, the rotatable ring may include a feature (not shown) that blocks optical sensor 1780. Such a feature could tell the system 1710 when the magnet 1720 is at its "home" position (i.e., roughly 6 o'clock in the illustrated embodiment). Sensors 1770*a* and 1770*b* may be optically coupled to the large drive 1745 gear to, for example, count passing teeth as the large drive 1745 is rotated. By integrating information from sensor 1780 and sensors 1770*a* and 1770*b*, the position of the magnet can be determined by the instrument so that the magnet can be positioned where it needs to be in space and time so that the magnet can, for example, effect the steps illustrated in FIGS. 15A-15K. While an optical sensing system was described in the foregoing, one will appreciate that a sensing system may alternatively or in addition include magnetic sensors that can directly detect the position of the magnet. Likewise, while the sensing system that includes sensors 1770*a*, 1770*b*, and 1780 has been described in reference to FIGS. 17A and 17B, one will appreciate that similar systems could be included with any of the moving magnet systems described herein.

Compression Members and Seals

FIGS. 20A-20H illustrate another system for moving fluid within a sample container such as pouch 510. The system is schematically illustrated in reference to a simplified pouch 1800 that shows a succession of blisters 1801-1807 and channels 1811*a*-1811*c* and 1809*a*-1809*c* that interconnect the blisters. For the sake of clarity, the pouch 1800 lacks many of the details that are depicted, for example, in pouch 510 of FIG. 2. While the system is depicted in conjunction with the simplified pouch 1800, one will appreciate that the system illustrated in FIGS. 20A-20H for moving fluid through the succession of blisters of a pouch is configured to operate with the pouch 510 illustrated in FIG. 2 and the other pouches and systems described herein and elsewhere, as are known in the art.

When the pouch 1800 is placed in an instrument (e.g., an instrument similar to instrument 900 of FIG. 3B), the pouch 1800 can be contacted by a series of mechanical compression members 1810, 1820*a*-1820*c*, and 1830*a*-1830*b* and a series of seals 1840*a*-1840*c*, 1850*a*-1850*c*, and 1860*a*-1860*e* and that can be used to selectively plunge liquid out of selected blisters and to control the directionality of fluid movement in the pouch 1800. Compression member 1810 is associated with blister 1801; compression members 1820*a*-1820*c* are associated with blisters 1802, 1804, and 1806; and compression members 1830*a*-1830*b* are associated with blisters 1803 and 1805. Seals 1850*a*-1850*c* are associated with channels 1811*a*-1811*c*; and seals 1840*a*-1840*c* are associated with channels 1809*a*-1809*c*. Seals 1860*a*-1860*e* are positioned to seal the entry channels coming from the fitment. Similar seals and entry channels are described in detail in reference to FIGS. 2 and 4. In one embodiment, seals 1860*a*-1860*e* may be spring-loaded seals that are configured to allow fluid to be injected from the fitment, through the entry channels, and into their corresponding blisters, but that restrict backward flow of liquid from the blisters into the fitment, without any active control.

In the embodiment illustrated in FIGS. 20A-20H, compression members 1820*a*-1820*c* are mechanically arranged so that they compress their respective blisters together and, likewise, compression members 1830*a*-1830*b* are mechanically arranged so that they compress their respective blisters together. That is, for example, if liquid is being moved from blister 1802 to 1803 via channel 1809*a*, blister 1802 will be plunged by compression member 1820*a*. However, even though blisters 1804 and 1806 are dry at this point in this example, blisters 1804 and 1806 will be compressed at the same time by compression members 1820*b* and 1820*c*. A similar arrangement is in place for blisters 1803 and 1805 and compression members 1830*a* and 1830*b*. For instance, if liquid in blisters 1803 is to be squeezed into blister 1802 or 1804, compression member 1830*a* will be actuated to squeeze the liquid out of blister 1080; even though blister 1805 is dry in this example, compression member 1830*b* will be actuated at the same time that compression member 1830*a* is actuated. It is understood that when empty blisters are compressed, the compression of that blister will have no effect on the flow of fluid through the pouch. By examining essentially all of the possible fluid movements within the pouch, including sample preparation, nucleic acid recovery, first-stage PCR, and second-stage PCR, it was found that this system of grouping the compression members together was mechanically simple and robust, and this "ganging" approach permitted the use of, for example, just three actuators (e.g., cams) for the compression members instead of there being a separate actuator for each compression member. One will appreciate, however, that reference to three actuators is merely illustrative and that the system could include more or fewer actuators for the compression members.

A similar approach is in place for seals 1840*a*-1840*c* and seals 1850*a*-1850*c*. The 1840 set and the 1850 set are each "ganged" together on a separate actuator, but, unlike the compression member example, each actuator (e.g., a cam) is configured so that the seals can be opened or closed individually. For example, the seals may be spring-loaded so that they default to a "closed" (i.e., sealed) position and the cam may be configured so that the seals are opened one at a time as the cam is rotated. In such an arrangement, the actuators for, for example, hard seals 1840*a*-1840*c* may be actuated by rotating a single cam, with means for opening each seal being arranged on the cam at different angles of rotation. The opposite arrangement may be used as well where the seals are defaulted to open and the seals close one at a time as, for example, the cam is rotated. To confine liquid within a particular blister or to control direction of flow within the pouch, the seals are activated (i.e., opened or closed) over the channels leading to and from the blister, such that the actuators function as pinch valves to pinch the channels shut.

Referring now to FIGS. 20B-20H, it is illustrated how the system of "ganged" compression members and seals can be used to move a volume of fluid from blister 1801 to blister 1807. And while fluid is shown only moving one direction in FIGS. 20B-20H, the principle illustrated in FIGS. 20B-20H can be used to move fluid backwards (e.g., from blister 1803 to 1802 to 1801) or to force fluid back and forth between two or more blisters to, for example, mix the contents of the blisters.

Figure 20A:
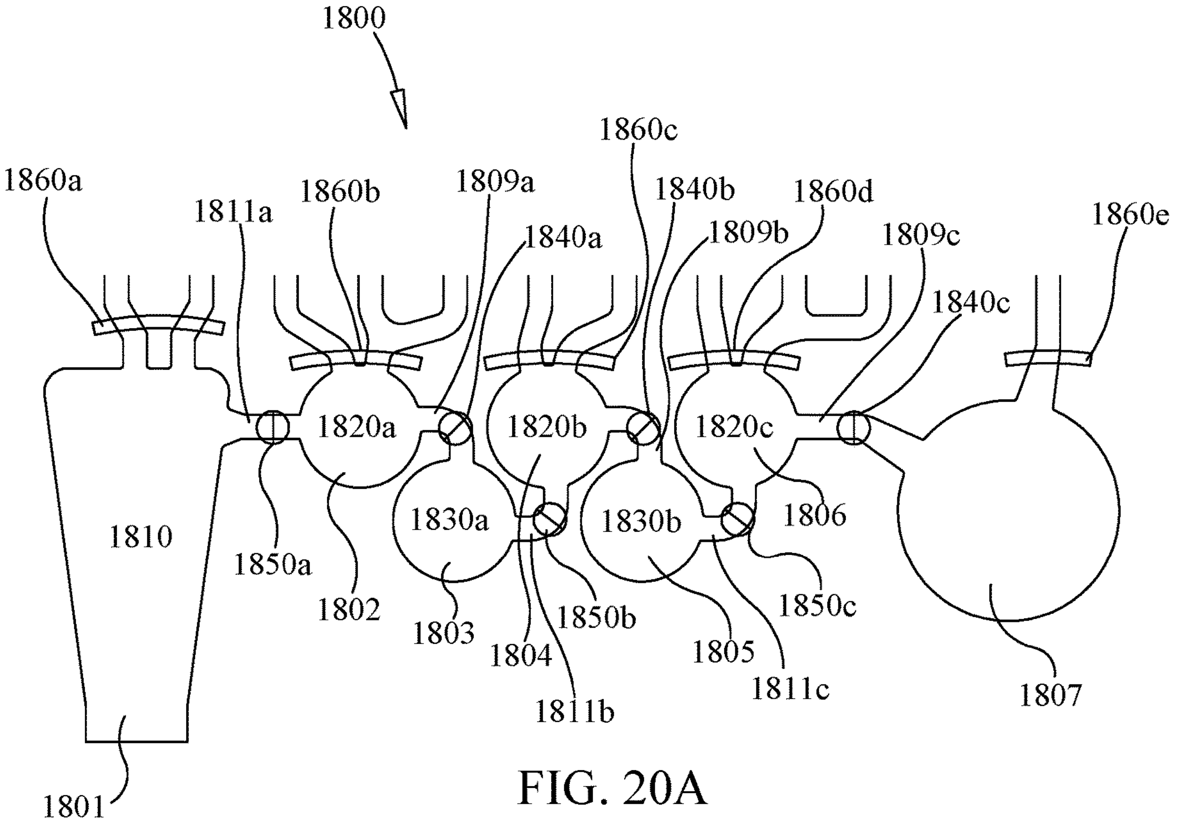
FIGS. 20A-20H schematically illustrate a method for moving fluid in a pouch of FIG. 2 that employs a series of linked compression members and seals, according to an embodiment of the present invention.
Figure 20B:
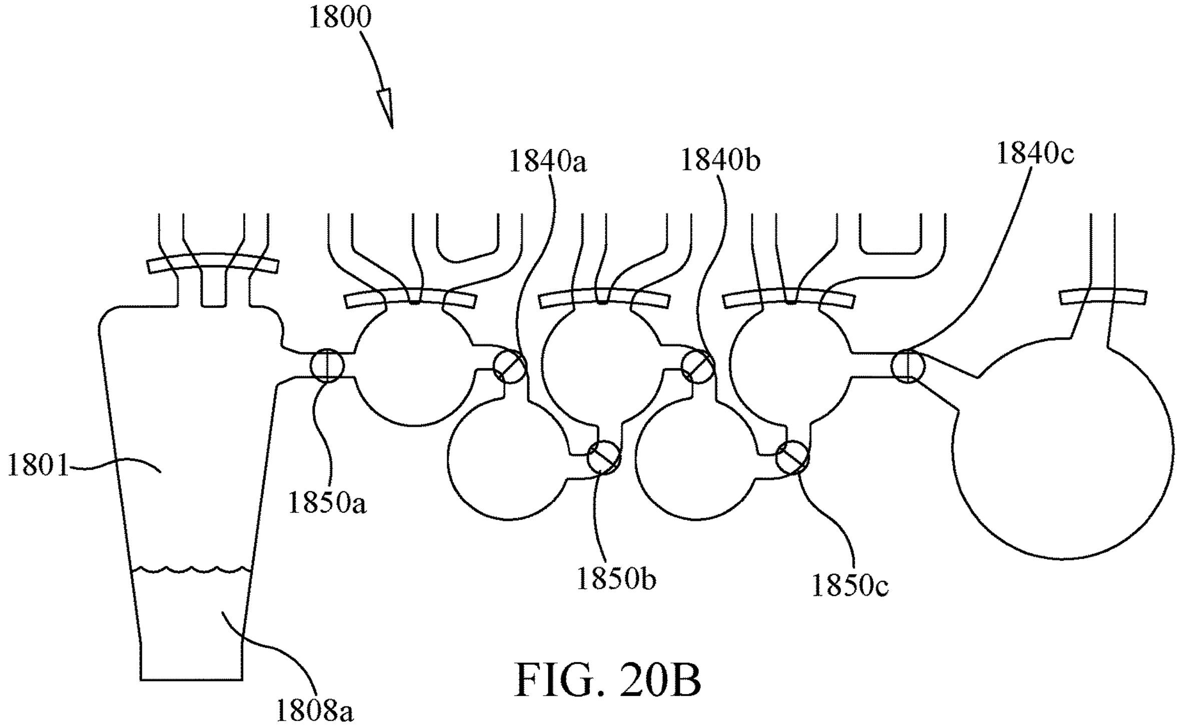

Referring now to FIG. 20B, a volume of liquid 1808*a* is present in blister 1801. The next series of FIGS. illustrate how that volume of liquid (e.g., water, buffer, cell lysate, etc.) can be moved through the succession of blisters and eventually to blister 1807 using the compression members and seals discussed in reference to FIG. 20A.

Figure 20C:
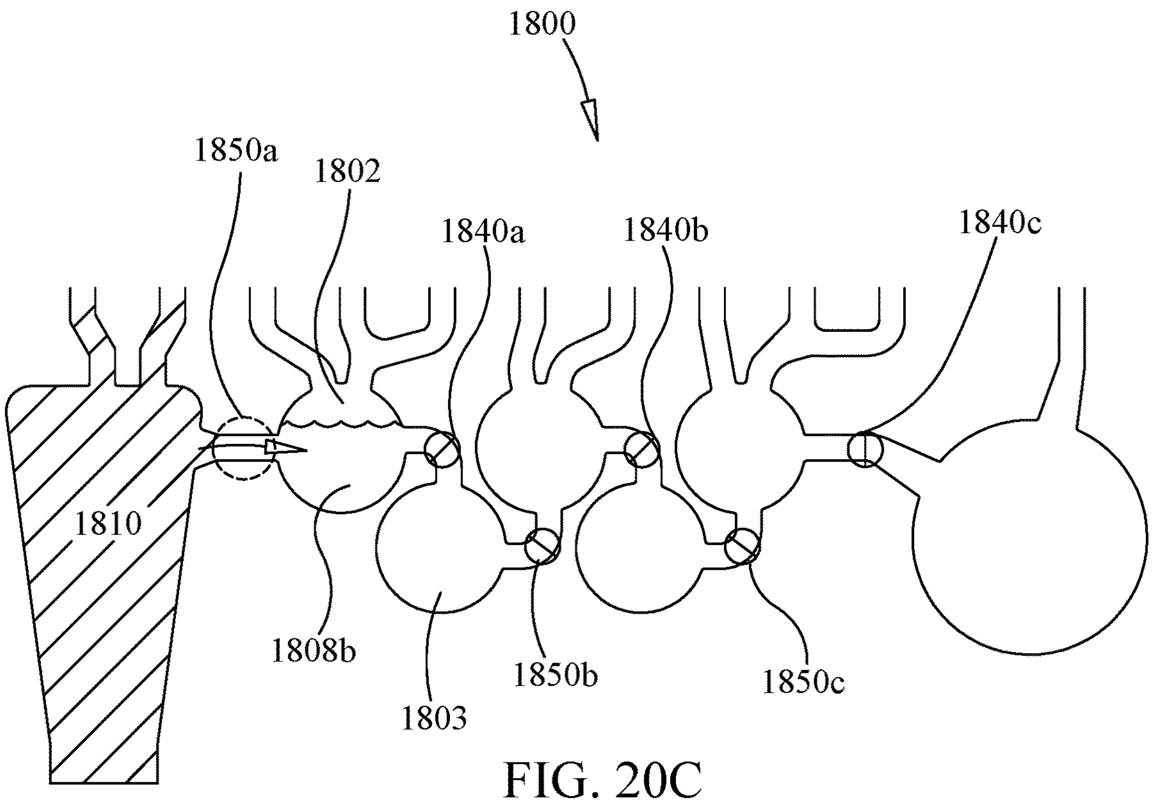

Referring to FIGS. 20B and 20C, the volume of fluid 1808*a* may be plunged from blister 1801 to 1802 by releasing seal 1850*a* and squeezing blister 1801 with compression member 1810 to force the liquid through channel 1811*a* into blister 1802. Seal 1850*a* and compression member 1810 may be actuated in succession (e.g., seal 1850*a* is released and then compression member 1810 is actuated, or vice-versa) or they may be actuated essentially simultaneously. In the illustrated embodiment, blister 1801 is associated with a standalone compression member 1810 (i.e., it is not "ganged") that may be actuated independently of the compression members used to purge fluid from the other blisters. In FIG. 20C, the volume of fluid moved from blister 1801 to 1802 is labeled 1808*b*.

Figure 20D:
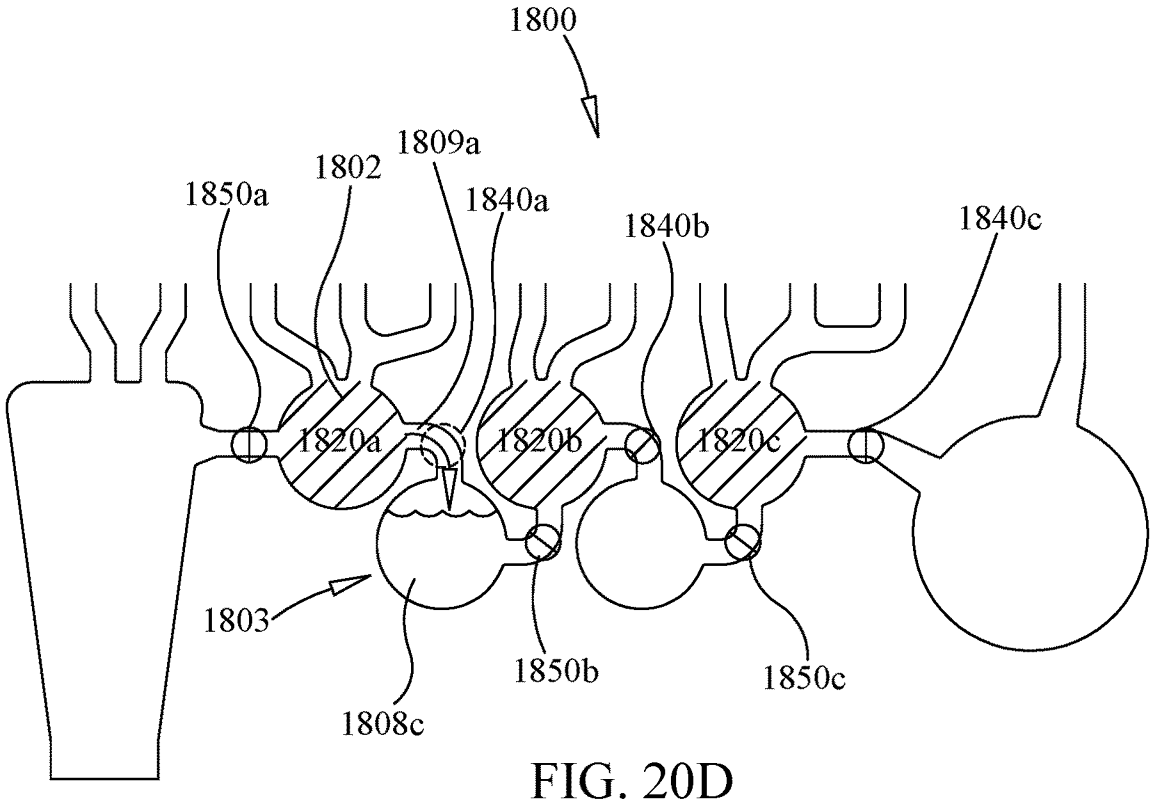

Referring to FIGS. 20C and 20D, the volume of fluid 1808*b* may be squeezed from blister 1802 to 1803 by releasing seal 1840*a* and actuating compression members 1820*a*, 1820*b*, and 1820*c*. As discussed above, in this example, there is only liquid in blister 1802 when compression members 1820*a*, 1820*b*, and 1820*c* are first actuated-compression member 1820*a* squeezes volume of liquid 1801*b* out of blister 1802 and into blister 1803 via channel 1809*a*, while compression members 1820*b* and 1820*c* are squeezing dry blisters. However, the system described in reference to FIGS. 20A-20H can still be used to create directional flow of fluid in the pouch 1800 even if there is fluid in multiple blisters, due to the action of the seals. That is, in this example, if there were fluid in one or both of blisters 1804 and 1806, the system described herein could isolate the fluid in one or both of blisters 1804 and 1806 and allow fluid to be moved from blister from 1802 to 1803 by only releasing seal 1840*a* and keeping the other seals in place while the compression members are actuated.

Figure 20E:
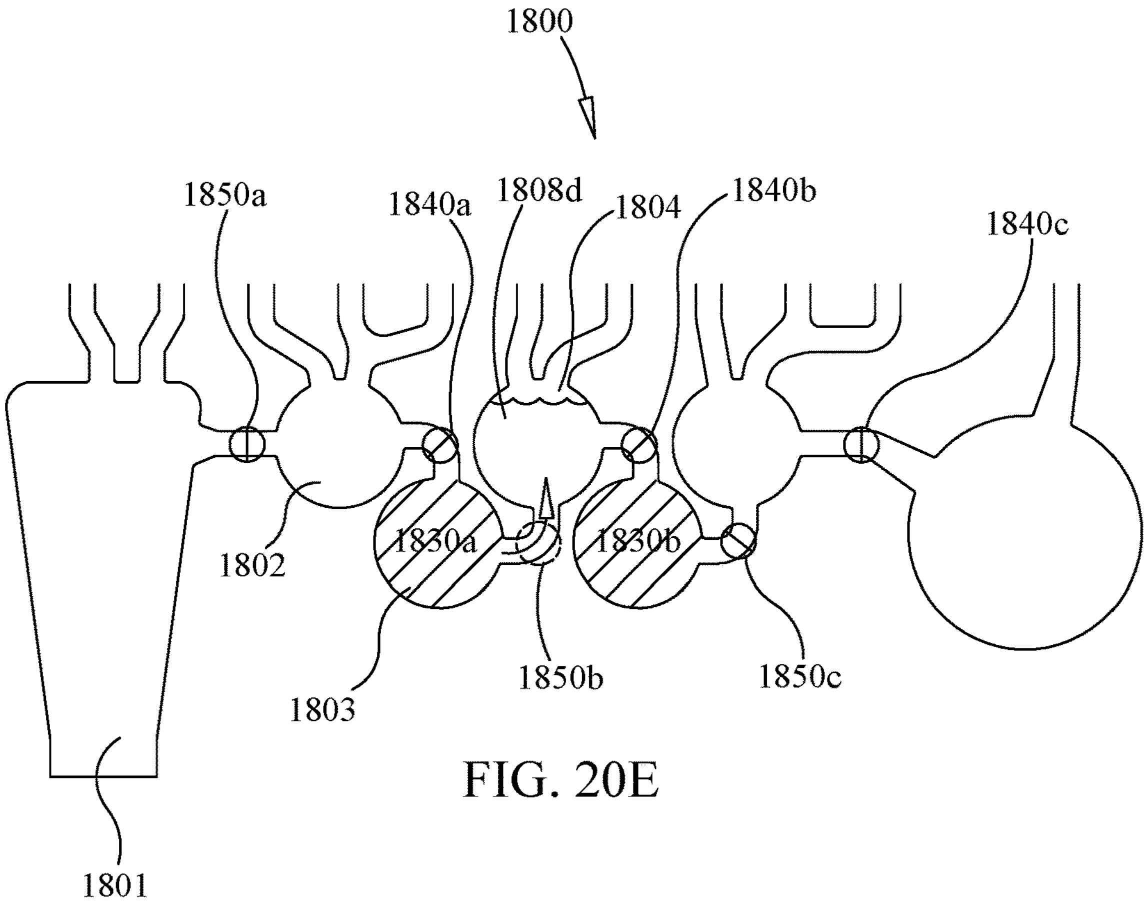

Referring to FIGS. 20D and 20E, the volume of fluid 1808*c* may be squeezed from blister 1803 to 1804 by releasing seal 1850*b* and actuating compression members 1830*a* and 1830*b*. As in the discussion of compression members 1820*a*, 1820*b*, and 1820*c*, compression member 1830*a* is actuated on a blister with fluid therein, while compression member 1830*b*, which is actuated at the same time, is actuated on a dry blister. Actuation of compression members 1830*a* and 1830*b* and opening of hard seal 1840*a* can also be used to move fluid back to blister 1802. Repeated successive actuation of compression members 1820*a*, 1820*b*, and 1820*c* and compression members 1830*a* and 1830*b* with, for example, the opening of seal 1840*a* can be used to mix the contents of blisters 1802 and 1803. Moving fluid back and forth between adjacent blisters is used at several steps in the methods described herein that utilize the pouch to, for example, perform nucleic acid recovery, hydrate and mix reagents, and perform washes. Likewise, opening seal 1840*a* and actuating compression members 1830*a* and 1830*b* followed by closing seal 1840*a*, opening seal 1850*a*, and actuating compression members 1820*a*, 1820*b*, and 1820*c* can be used, for example, to move fluid from blister 1803 to 1802 to 1801, as was described above in reference to the hydration of the magnetic beads and moving the hydrated magnetic beads to blister 1801 for DNA binding and recovery from the lysate in blister 1801.

Figure 20F:
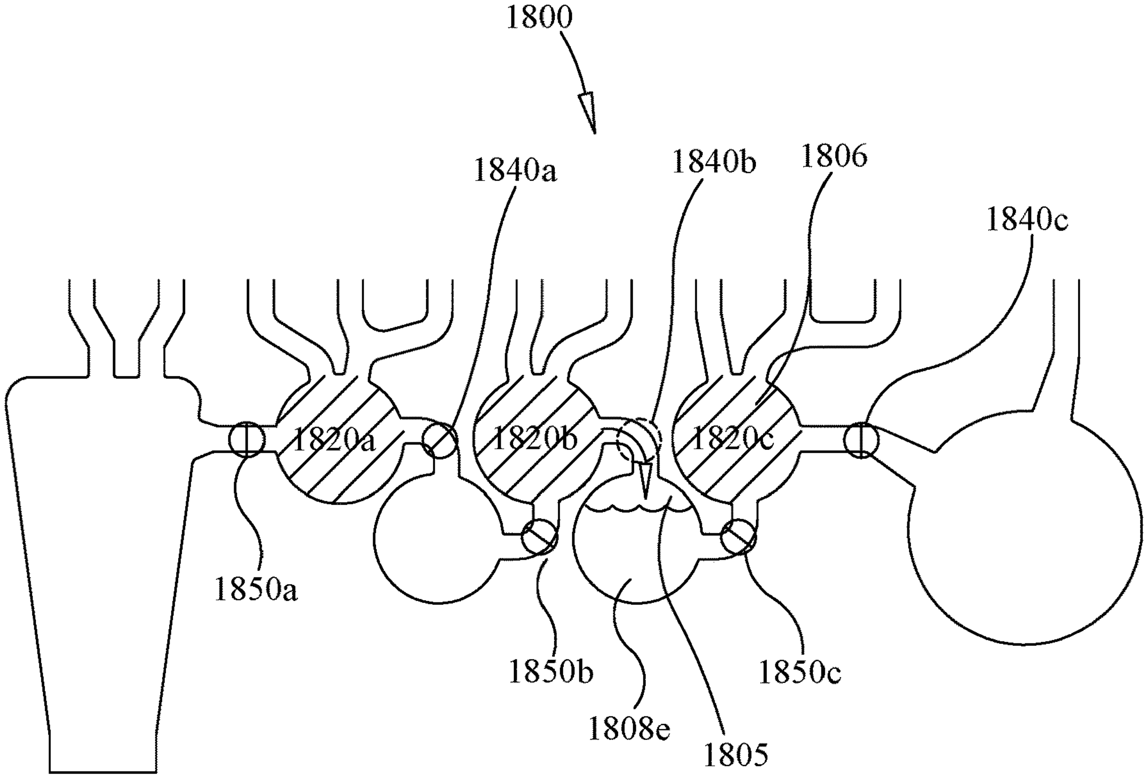
Figure 20G:
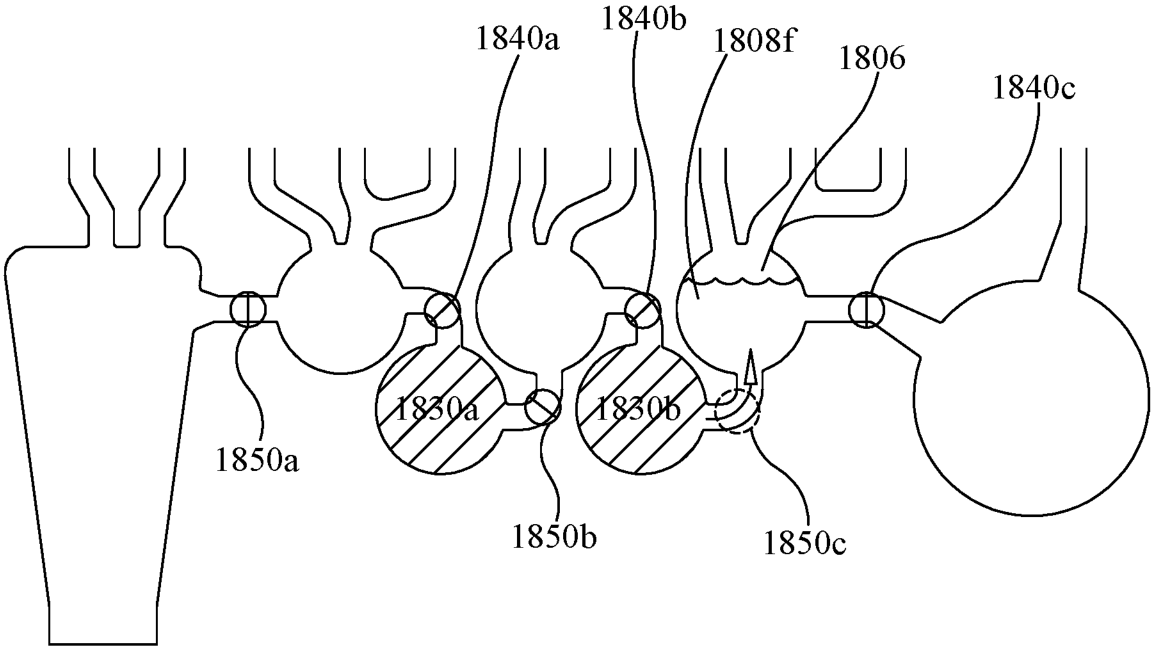
Figure 20H:
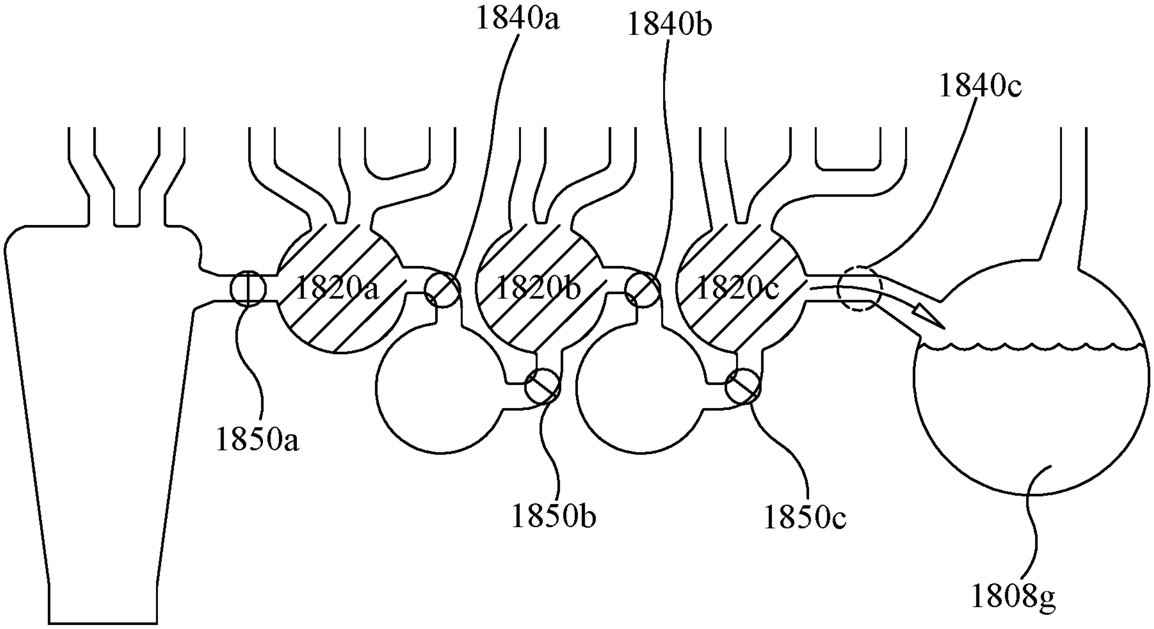

Referring to FIGS. 20E and 20F, the volume of fluid 1808*d* may be squeezed from blister 1804 to 1805 by releasing seal 1840*b* and actuating compression members 1820*a*, 1820*b*, and 1820*c*. Referring to FIGS. 20F and 20G, the volume of fluid 1808*e* may be squeezed from blister 1805 to 1806 by releasing seal 1850*c* and actuating compression members 1830*a* and 1830*b*. Referring to FIGS. 20G and 20H, the volume of fluid 1808*f* may be squeezed from blister 1806 to 1807 by releasing seal 1840*c* and actuating compression members 1820*a*, 1820*b*, and 1820*c*.

Figure 21A:
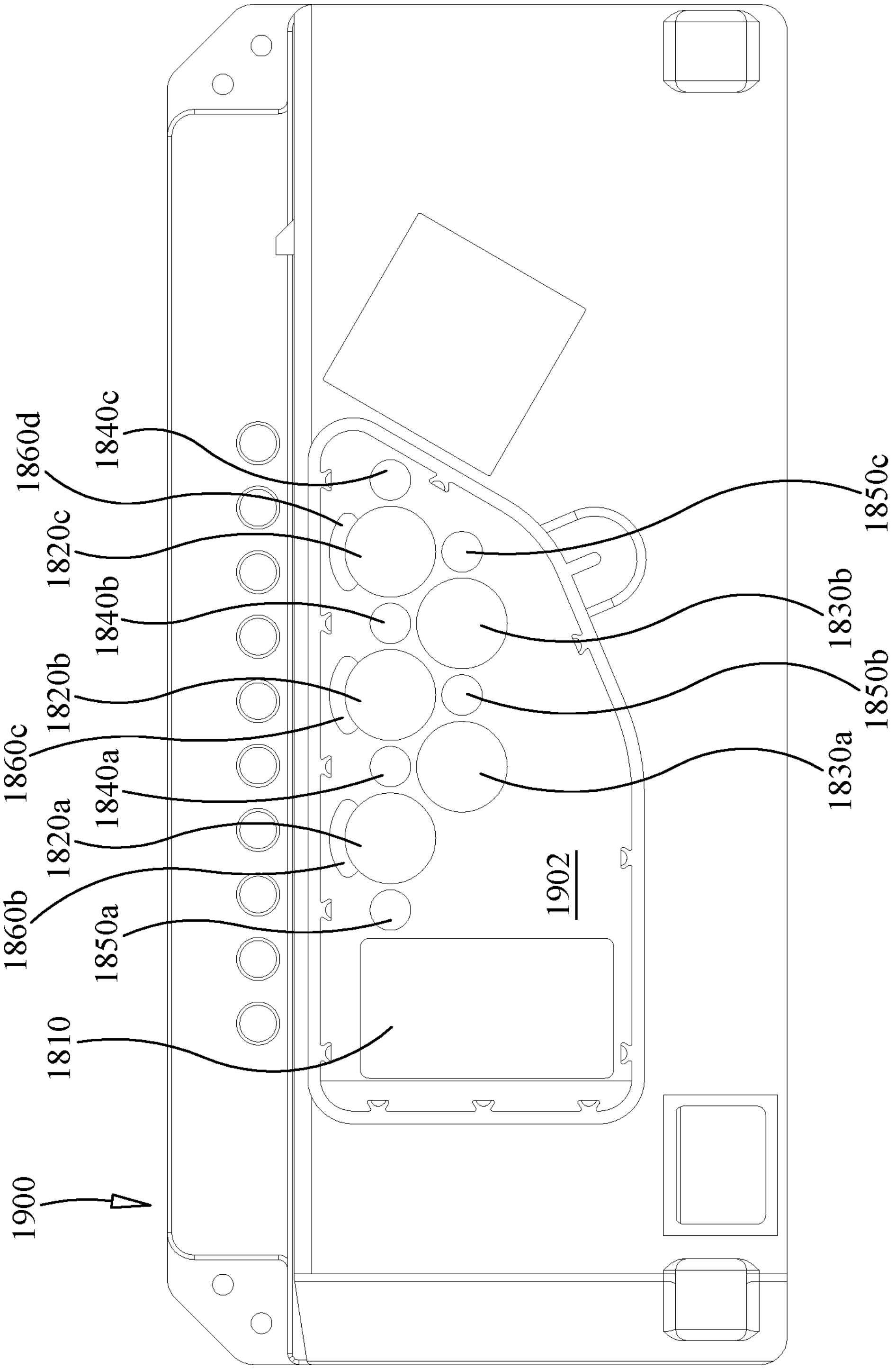
FIGS. 21A-21C illustrate the compression members and seals employed in FIGS. 20A-20H, according to an embodiment of the present invention.

FIG. 21A schematically illustrates a plate 1900 that encompasses a compression member/seal assembly 1902 that may be incorporated into instrument 900. Plate 1900, with compression members 1810, 1820*a*-1820*c*, and 1830*a*-1830*b* and seals 1840*a*-1840*c* and 1850*a*-1850*c*, forms a compression member/seal assembly 1902. Plate 1900 is configured to press against one face of the pouch when the pouch is placed in an instrument such that the compression members and seals can contact their respective blisters and channels, such that activation of the compression members may force liquid from one or more of the blisters of pouch and/or the seals may form pinch valves with one or more channels of pouch. The relationship between the blisters and channels of the pouch and the compression members and seals was illustrated in more detail above in FIGS. 20A-20H.

Figure 21B:
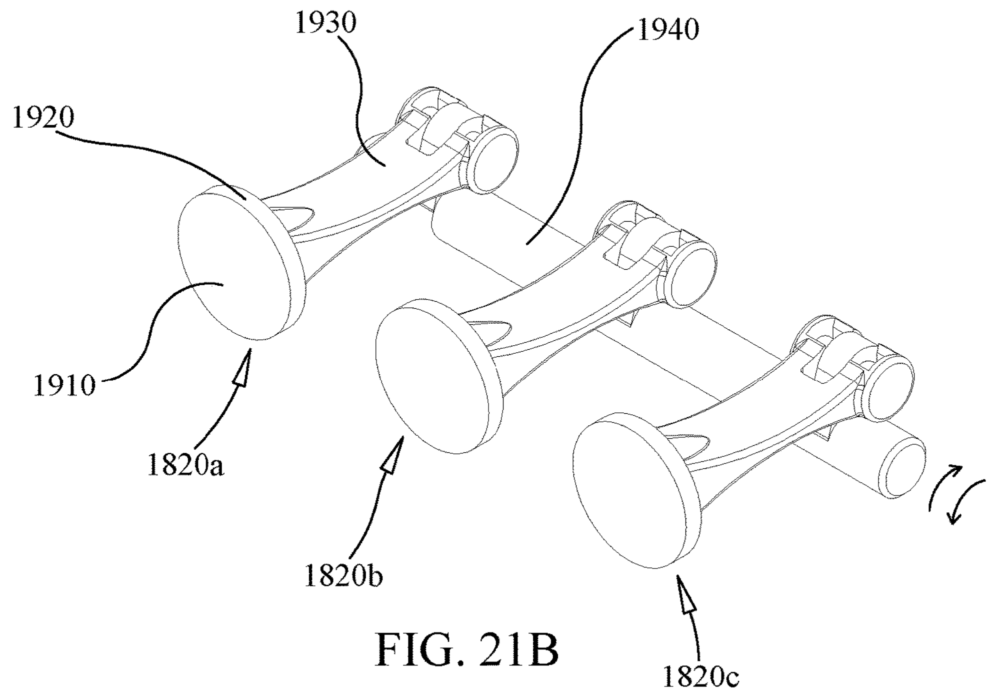
Figure 21C:
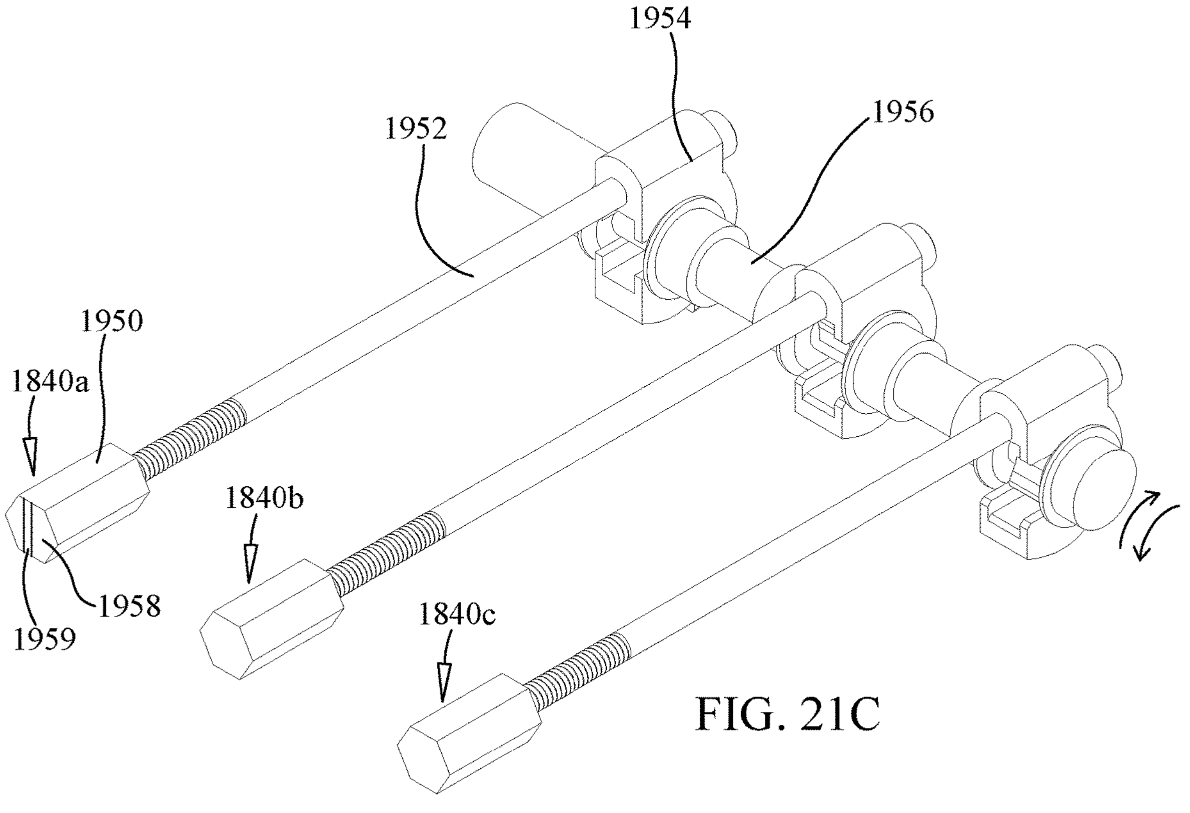
Figure 21D:
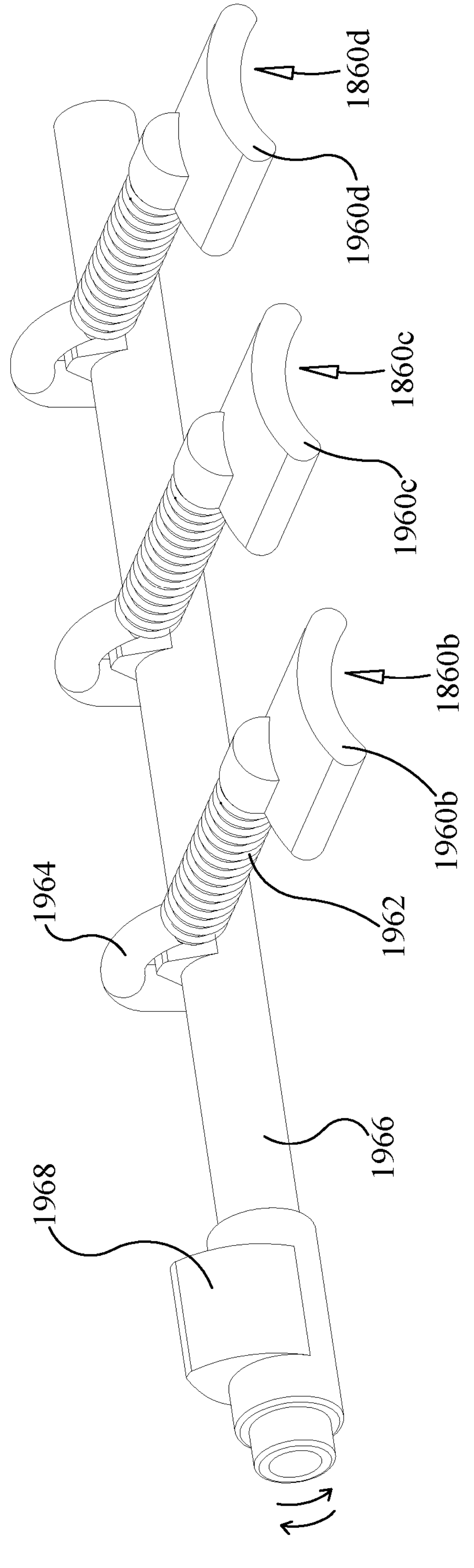
FIGS. 21D-21E illustrate top 'eyebrow' seals and a drive member, according to an embodiment of the present invention.

Referring now to FIGS. 21B, 21C, and 21D, partial cut-away views of exemplary embodiments of the compression members and seals and systems for actuating the compression members and seals are illustrated. In FIG. 21B, compression members 1820*a*-1820*c* that were discussed above are illustrated in greater detail. While compression members 1820*a*-1820*c* were selected for further illustration, one will appreciate that compression members 1830*a* and 1830*b* may be configured the same or similarly. In the illustrated embodiment, each compression member includes a compression member head 1910 and a compression member body 1920. The compression member body may be fabricated by any means know in the art, such as, but not limited to, injection molding, die casting, 3D printing, or machining. The compression member bodies 1920 may be made from any durable material known in the art, such as, but not limited to, metals (e.g., aluminum, aluminum alloys, pot metal, or the like), plastics (e.g., polyethylene, polypropylene, polystyrene, polycarbonate, ABS, PEEK, and the like), and metal and plastic composites. In the illustrated embodiment, the compression member bodies 1920 are substantially cylindrical and are configured to slide back and forth (i.e., toward the pouch 510 and away from the pouch 510) in a channel (not shown) formed in the plate 1900. Nevertheless, in other embodiments, the compression member bodies may have other profiles (e.g., oval) or they may be configured to key into the plate with, for example, a cross-shaped profile.

In one embodiment, the compression member head 1910 may be made from the same material as the compression member body 1920 or compression member 1910 and compression member body may be made from different materials. In one embodiment, the compression member head 1910 may be made from a resilient material such that the compression member head 1910 at least partially conforms to the blister when a blister is squeezed. This may, for instance, allow the compression member to squeeze more fluid out of the blister and make the transfer of fluid from the blister more efficient. Examples of resilient materials that may be used for the compression member head include, but are not limited to, neoprene, polyurethane foam, polyimide foam, and foam rubbers. If the compression member head 1910 is formed from a material different from that of the compression member body 1920, the different materials may be fabricated integrally or separately. In one example, the compression member head 1910 may be a resilient pad (e.g., a sticky-backed neoprene pad) that is adhered to the distal end of the compression member body 1920. Such a pad could, for example, be field replaceable and would protect the compression member body from wear and tear.

Still referring to FIG. 21B, the distal end of each compression member body 1920 is attached to a connecting rod 1930. The connecting rod 1930 is in turn connected to a cam 1940. The connecting rod 1930 and the cam 1940 may be configured such that rotation of the cam 1940 in one direction can cause the compression members to project out of the plate 1900 to contact the blisters of the pouch and to squeeze liquid out of selected blister(s). Likewise, the connecting rod 1930 and the cam 1940 may be configured such that rotation of the cam 1940 in the opposite direction can cause the compression members to be drawn away from the blisters of the pouch. In another embodiment (not shown), the cam 1940 may, for example, be a lobed cam that is configured such that rotation of the cam 1940 in one direction can cause the compression members to extend to contact the pouch and retract away from the pouch. One will appreciate, however, that the foregoing description is merely illustrative and that other configurations are possible. For instance, the compression members may be spring loaded so that they are biased in a position that does not contact the pouch. In such a configuration, a cam or a lever may be configured to press on the proximal-most end of the compression member body 1920 or the connecting rod 1930 to push the compression member forward to contact the pouch.

In one embodiment, a compression system that includes compression members 1820*a*-1820*c* and 1830*a*-1830*b* may include one or more of position sensors or a feedback control system to ensure that fluids are fully plunged from blister-to-blister. Because the compression members are actuated in groups (i.e., they are "ganged") and because a compression member in a ganged group may react differently to a fluid-filled blister as compared to empty blisters encountered by the 'gang,' position sensors and/or feedback control may improve the efficiency of moving fluid from blister-to-blister.

For instance, as a 'gang' of compression members 1820*a*-1820*c* or 1830*a*-1830*b* moves forward to force fluid from one blister to another the force begins to rise rapidly when a compression member encounters a fluid-filled blister. In one embodiment, the system may include force sensors, position sensors, and/or feedback programming that can signal the compression members and hard seals associated with the blister that fluid is being plunged to retract. Retracting the hard seals and the compression members in the opposite gang allows the fluid to move and the pressure to drop. However, in one embodiment, the compression movement may continue to ensure that the blister is completely emptied. As the plunge stroke continues (essentially compressing the pouch blisters against the instrument door), the force will continue to rise. When the force reaches a predefined threshold for a given period of time (control effort), the feedback system is programmed to determine that the compression is complete. Different system parameters may be programmed to include different predefined thresholds and different periods of time (i.e., different control efforts). Such programming, because it relies on force and time to determine compression efficiency, may be able to accommodate slight variations in pouch thickness, instrument dimensions, and the like.

Figure 51A:
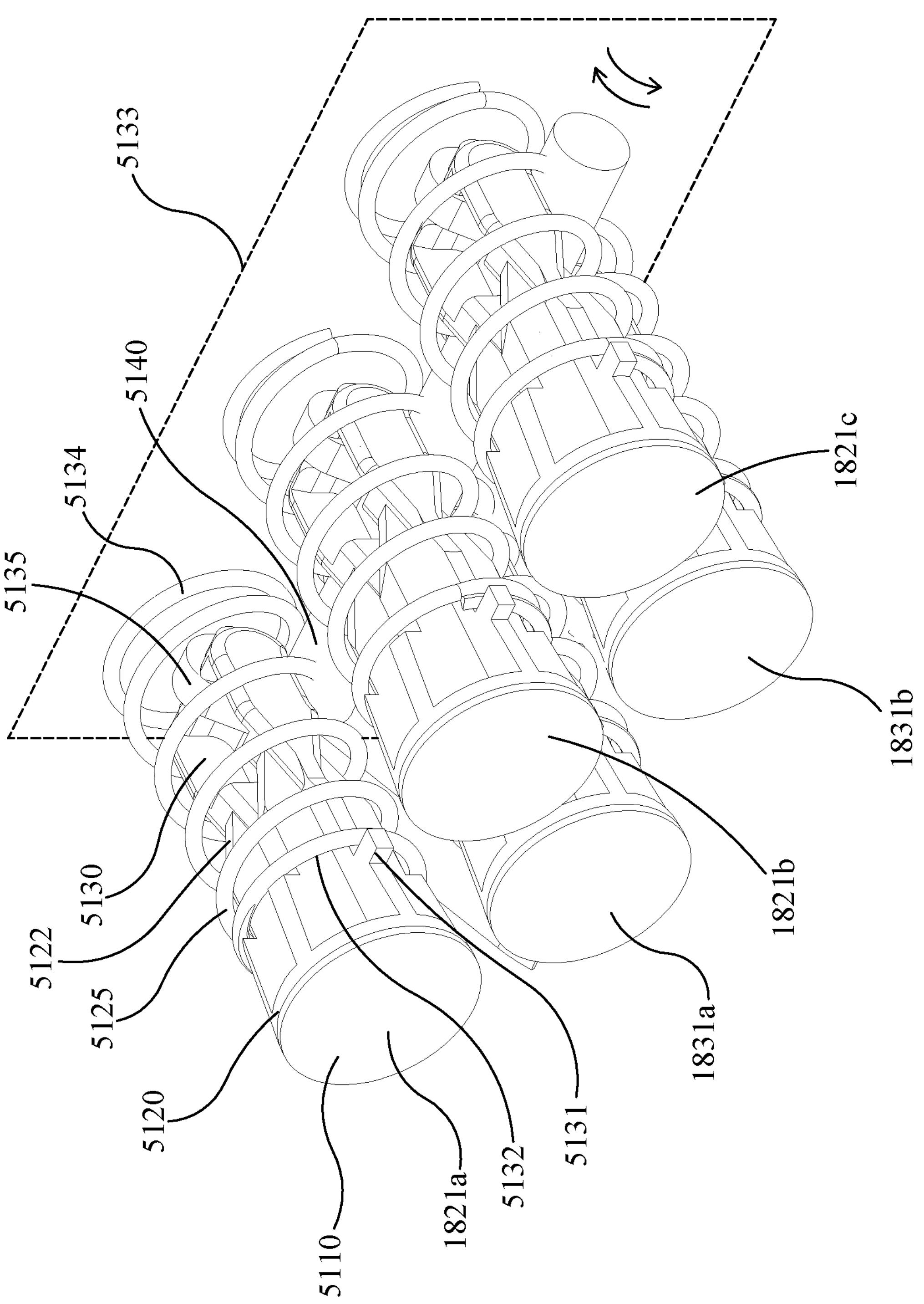
FIGS. 51A and 51B illustrate another embodiment of compression members that may be used in an instrument described herein, according to an embodiment of the present invention.

FIG. 51A illustrates another embodiment of a set of compression members 1821*a*-1821*c* and 1831*a*-1831*b* that may be used in an instrument described herein (e.g., in either instrument 800 of FIG. 3A or instrument 900 of FIG. 3B). In the illustrated embodiment, each compression member includes a compression member head 5110 and a compression member body 5120. The compression member body 5120 comprises an elongate shaft 5122 that connects the distal head end 5110 to a drive system; an embodiment of a drive system will be described below in reference to FIG. 51B. Each compression member includes a spring 5125 that can be configured to bias the compression members toward or away from the pouch. In the illustrated embodiment, springs 5125 are configured to bias the compression members toward the pouch so that compression force for squeezing fluid from blister-to-blister is a function of spring tension. Thus, fluid moving force may be adjusted by increasing or decreasing the size or stiffness of the springs 5125. In such a case, there is no need to change instrument programming or any other instrument parameters in order to increase or decrease compressing force. In the illustrated embodiment, the body shaft 5122 includes a first stop 5131 on the proximal end of the body associated with a proximal end 5132 of the spring 5125 and a spring base 5133, shown schematically, on the distal end of the body associated with a distal end 5134 of the spring 5125. In an example embodiment, the spring base 5133 may be a structure that is attached to the back of plate 1900 that provides a working surface (e.g., stops) to compress the springs to bias the compression members 1821*a*-1821*c* and 1831*a*-1831*b* toward the pouch.

The compression member body may be fabricated by any method know in the art; examples of fabrication methods and materials were discussed above with respect to FIG. 21B. In the illustrated embodiment, the compression member head 5110 is substantially cylindrical and is configured to slide back and forth (i.e., toward the pouch 510 and away from the pouch 510) in a channel formed in the plate 1900, as illustrated, for example, in FIG. 21A. Nevertheless, in other embodiments, the compression member head 5110 may have other profiles (e.g., oval) or they may be configured to key into the plate with, for example, a cross-shaped profile.

In one embodiment, the compression member head 5110 may be made from the same material as the compression member body 5120 or compression member 5110 and compression member body may be made from different materials. In one embodiment, the compression member head 5110 may be made from a resilient material such that the compression member head 5110 at least partially conforms to the blister when a blister is squeezed. This may, for instance, allow the compression member to squeeze more fluid out of the blister and make the transfer of fluid from the blister more efficient. Examples of resilient materials and how they may be attached to the body were discussed above with respect to compression member head 1910.

Still referring to FIG. 51A, the distal end of each compression member body 5120 is mechanically coupled to a drive shaft 5140 via a drive slot 5130 on the drive shaft 5140. As is illustrated schematically in FIGS. 20A-20H, compression members 1821*a*-1821*c* and 1831*a*-1831*b* may be configured to be actuated/retracted in an oppositely "ganged" arrangement. Thus, compression members 1821*a*-1821*c* may each be associated with corresponding drive members at one angular position on drive shaft 5140 and compression members 1831*a*-1831*b* may each be associated with corresponding drive members at another angular position on drive shaft 5140. In one example, the drive members for compression members 1821*a*-1821*c* and for compression members 1831*a*-1831*b* may be approximately 180° apart from each other on drive shaft 5140 so that the different sets of compression members can be actuated/retracted opposite to each other.

Figure 51B:
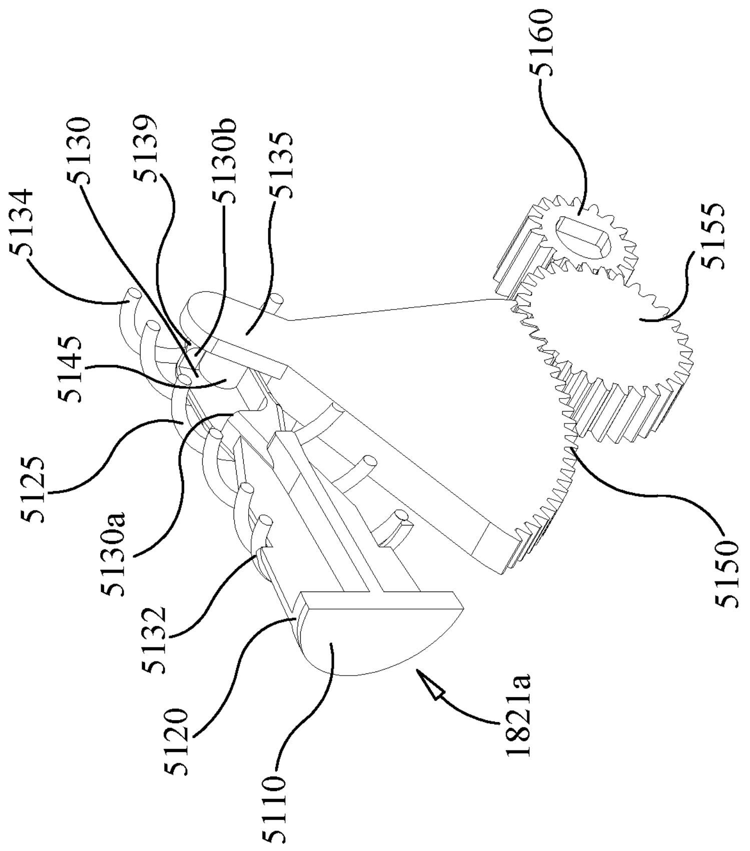

Referring now to FIG. 51B, a cutaway view of compression member 1821*a* is shown illustrating an embodiment of a drive system that may be used to actuate/retract compression the compression member. While only compression member 1821*a* is shown in FIG. 51B, one will appreciate that compression members 1821*a*-1821*c* and 1831*a*-1831*b* may be linked and that the drive system may be used to actuate/retract all of compression members 1821*a*-1821*c* and 1831a-1831b. In the illustrated embodiment, drive member 5135 fits into drive slot 5130; drive slot 5130 has a proximal end 5130a and a distal end 5130b. The drive member 5135 comprises a drive pin 5145 that extends from the drive member 5135 (in the cutaway view, half of the drive pin 5145 is shown) and fits in the slot 5130. The drive pin 5145 is moved back and forth to actuate/retract the compression member 1821a with drive gears 5150, 5155, and 5160 that may be coupled to a motor or the like (not shown).

In the illustrated embodiment, the springs, the drive members, and the drive slots are arranged in order to allow the compression members to partially decouple from the drive system as the compression members are actuated forward to force liquid from one blister to another. This may, for instance, reduce stress on the mechanical components of the system and allow the compression members to more completely plunge fluid from blister-to-blister. For example, if the compression members were moving fluid from blister 544 to 546 (FIG. 2), compression member 1821a could partially decouple from the drive system when it encountered the fluid filled blister at 544 while compression members 1821b and 1821c could be driven to the end of their stroke with having the drive system trying to drive against the fluid. Compression member 1821a could then remain in position until 1840a and compression members 1831a and 1831b are retracted, and then the spring provides the force to complete the plunging of fluid from blister 544 to blister 546. While this example is presented in reference to moving fluid from blister 544 to 546, one will appreciate that this principle applies to the other blisters plunged by compression members 1821a-1821c and 1831a-1831b.

One will appreciate, however, that the foregoing description is merely illustrative and that other configurations are possible. For instance, the compression members may be spring loaded so that they are biased in a position that does not contact the pouch. In such a configuration, a cam or a lever may be configured to press on the proximal-most end of the compression member body 5120 to push the compression member forward to contact the pouch. Likewise, while mechanical compression members are used in the foregoing embodiments, when the term "compression member" or "actuator" is used herein, it is understood that other actuators and other ways of providing pressure such as, but not limited to, pneumatic actuators, servos, switches, and the like may be used, depending on the configuration of the pouch and the instrument.

Referring now to FIG. 21C, seals 1850a-1850c were discussed above are illustrated in greater detail. While seals 1850a-1850c were selected for further illustration, one will appreciate that seals 1840a-1840c may be configured the same or similarly. In the illustrated embodiment, each seal includes a seal body 1950. As with the compression member bodies, the seal body may be fabricated by any means know in the art, such as, but not limited to, injection molding, die casting, or machining. The seal bodies 1950 may be made from any durable material known in the art, such as, but not limited to, metals (e.g., pot metal or aluminum), plastics (e.g., polyethylene, polypropylene, polystyrene, polycarbonate, ABS, PEEK, and the like), and metal and plastic composites. In the illustrated embodiment, the seal bodies 1950 are substantially cylindrical and are configured to slide back and forth in a channel (not shown) formed in the plate 1900. Nevertheless, in other embodiments, the seal bodies may have other profiles (e.g., oval) or they may be configured to key into the plate 1900 with, for example, a cross-shaped profile.

The proximal end of each seal body 1950 may be coupled to or integrally formed with an actuating rod 1952. The actuating rod 1952 that includes a structure 1954 that may be mechanically connected to a lobe (not shown) or similar structures set at different angles of rotation on a cam 1956 that allow the actuation of each of the seals one at a time as the 1956 cam is rotated. In one embodiment, the seals (e.g., seals 1850a-1850c) may be spring loaded such that actuation by rotation of the cam opens (i.e., releases) the seals such that fluid can flow freely through the channels between blisters. In another embodiment, the seals, the cam 1956, and the structures 1954 may be configured such that rotation of the cam 1956 in one direction can cause the seals to close over their associated channels one at a time. One will appreciate, however, that the foregoing description is merely illustrative and that other configurations are possible. For instance, the seals may be spring loaded so that they are biased in a position that does not contact the pouch. In such a configuration, a cam or a lever may be configured to press on the proximal-most end of the seal body 1950 or the actuating rod 1952 to push the seal forward to contact the pouch. Likewise, while mechanical seals are used in the presently disclosed embodiment, when terms such as "actuator" are used herein, it is understood that other actuators and other ways of providing pressure such as, but not limited to, pneumatic actuators, servos, switches, and the like may be used, depending on the configuration of the seals and the instrument.

In one embodiment, the seal head 1958 may be made from the same material as the seal body 1950 or it may be made from a different material. In one embodiment, the seal head 1958 may be made from a resilient material such that the seal head 1958 at least partially conforms to the material around the channel when the seal is actuated. This may, for instance, allow the seal to more completely seal the channel with less applied force. Examples of resilient materials that may be used for the seal head 1958 include, but are not limited to, neoprene, polyurethane foam, polyimide foam, and foam rubbers. If the seal head 1958 is formed from a material different from that of the seal body 1950, the different materials may be fabricated integrally or separately. As with the example of the compression member head 1910 discussed above, the seal head 1958 may be a resilient pad (e.g., a sticky-backed neoprene pad) that is adhered to the distal end of the seal body 1950. Such a pad could, for example, be field replaceable and would protect the seal body 1950 from wear and tear.

In one embodiment, the distal end of the seal body may be equipped with a seal head 1958 formed from a resilient material similar to the compression member head 1910 discussed above. Such a seal head 1958 may at least partially conform to the channel when the seal is actuated. This may, for instance, allow the seal to make a more effective seal on the channel In a related embodiment, the seal head 1958 may be formed with a raised ridge structure 1959, or the like. A raised ridge like 1959 may increase the localized seal pressure of the seal on a channel, increasing the efficiency of the seal. In addition, as discussed above, hard bead beater beads and magnetic beads can occasionally enter the channels between blisters in the process of a run and those particles can cause pin holes to form in the pouch if, for example, they are pressed upon by the by the seals. The resilient ridge structure 1959 may reduce the instance of such pin holes because the ridge 1959 can act as a sort of squeegee that can push the particles to the side or the thin ridge itself can be pushed aside by the particles so that the bead beater particles do not become compressed by the seal in between the layers of pouch material. Such a seal head 1958 could also, for example, be field replaceable.

Figure 52A:
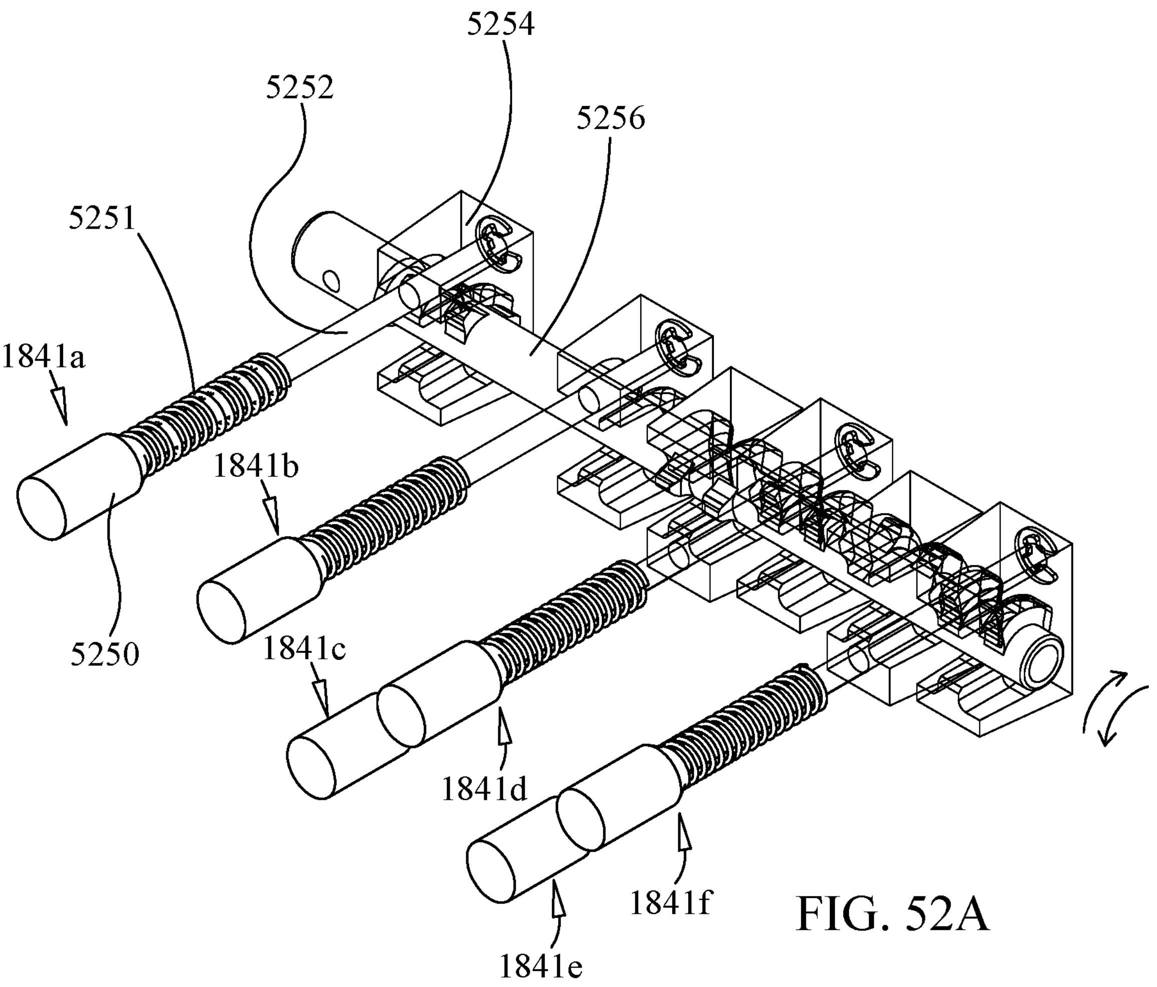
FIGS. 52A and 52B illustrate another embodiment of seals that may be used in an instrument described herein, according to an embodiment of the present invention.
Figure 52B:
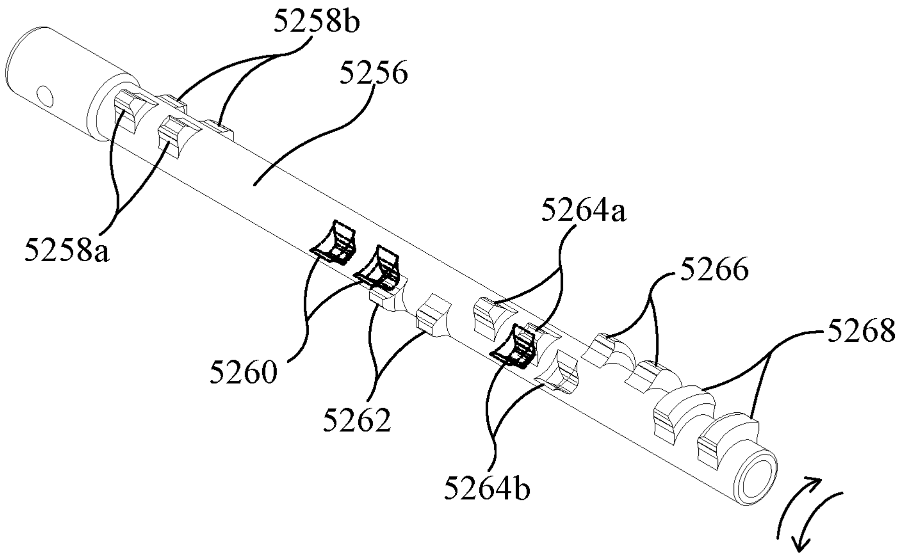

FIGS. 52A and 52B illustrate another embodiment of a seal system similar to seals 1850*a*-1850*c* illustrated in FIG. 21C. In contrast to seals 1850*a*-1850*c* and seals 1840*a*-1840*c*, seals 1841*a*-1841*f* illustrated in FIG. 52A are retracted/actuated by a single cam shaft 5256. Also in contrast to seals 1850*a*-1850*c* and seals 1840*a*-1840*c*, seals 1841*a*-1841*f* illustrated in FIG. 52A may be spring-loaded so that the seals are pressed against the pouch to seal the intrablister channels by spring action and the cam acts to retract the seal(s) to unseal the channels to permit liquid to flow. Referring to the blister numbering scheme of FIG. 20A, seal 1841*a* is positioned to seal the channel between blisters 1801 and 1802, seal 1841*b* is positioned to seal the channel between blisters 1802 and 1803, seal 1841*c* is positioned to seal the channel between blisters 1803 and 1804, seal 1841*d* is positioned to seal the channel between blisters 1804 and 1805, seal 1841*e* is positioned to seal the channel between blisters 1805 and 1806, and seal 1841*f* is positioned to seal the channel between blisters 1806 and 1807.

In the illustrated embodiment, each of seals 1841*a*-1841*f* includes a seal body 5250. As with the compression member bodies, the seal body may be fabricated by any means know in the art, such as, but not limited to, injection molding, die casting, or machining. As in the previous examples, the seal bodies 5250 may be made from any durable material known in the art. As in the previous examples, the seal bodies 5250 are substantially cylindrical and are configured to slide back and forth in a channel (not shown) formed in the plate 1900; nevertheless, the seal bodies may have other profiles. The proximal end of each seal body 5250 may be coupled to or integrally formed with an actuating rod 5252. In the illustrated embodiment, the seal body 5250 and the actuating rod 5252 are associated with a spring member 5251 that seals 1850*a*-1850*c* and seals 1840*a*-1840*c*, seals 1841*a*-1841*f* illustrated in FIG. 52A bias the seal body to press against the pouch to seal the intrablister channels by spring force. At its distal end, the actuating rod 5252 may be coupled to a cam follower structure 5254 that mechanically interacts with lobes (or similar structures) set at different angles of rotation on a cam shaft 5256 that allow the retraction of each of the seals one or more at a time as the is rotated. One will appreciate, however, that the foregoing description is merely illustrative and that other configurations are possible.

Referring now to FIG. 52B, an embodiment of the cam shaft 5256 is shown in greater detail. Cam shaft 5256 includes multiple lobes at various angular positions corresponding to the cam followers for actuating/retracting each of seals 1841*a*-1841*f*. In the illustrated embodiment, lobes 5258*a* and 5258*b* are positioned for actuation/retraction of seal 1841*a*, lobes 5260 are positioned for actuation/retraction of seal 1841*b*, lobes 5262 are positioned for actuation/retraction of seal 1841*c*, lobes 5264*a* and 5264*b* are positioned for actuation/retraction of seal 1841*d*, lobes 5266 are positioned for actuation/retraction of seal 1841*e*, and lobes 5268 are positioned for actuation/retraction of seal 1841*f*. The positions for seals 1841*a* and 1841*d* have more than one set of lobes and the positions for seals 1841*e* and 1841*f* have doubled lobes because in the illustrative embodiment these seals are opened more than once to accomplish the fluid movements in a pouch run.

The lobes on the cam shaft 5256 are positioned such that all of the seal openings needed for a pouch run can be accomplished with rotation of a single cam. Rotation of the cam 5256 permits blister-to-blister movement of fluids in a zigzag fashion in the simplified scheme illustrated in FIGS. 20A-20H and also permits more complex fluid movements like mixing between blisters for, for example, product/reagent mixing, dilution of the first-stage PCR product prior to second-stage PCR, etc. In the illustrated embodiment of the cam shaft 5256 and its lobes, there are six positions for seal retraction. Table 1 describes the illustrated embodiment of the lobe positions on cam shaft 5256 and the seals that are opened at each position. However, one will appreciate that this is only one example corresponding to the illustrated embodiment and that other arrangement and seal opening sequences are possible and within the scope of this description.

TABLE 1

| | Position | | | | | |
|---|---|---|---|---|---|---|
| | 1 | 2 | 3 | 4 | 5 | 6 |
| Seals Opened | 1841a and 1841f | 1841b and 1841d | All closed | 1841c | 1841a, 1841d, and 1841f | 1841e, and 1841f |

In one embodiment, all of the seal openings needed to accomplish all of the fluid movement steps, mixing steps between blisters, etc. in a pouch run may be accomplished by rotating cam shaft 5256 in a single direction. In another embodiment, the cam shaft 5256 may be rotated bidirectionally for some seal openings and fluid movements. In an illustrative but not limiting example, cam shaft 5256 may be moved from position 4 to 5 to 4 to 5 to 6 or another sequence for some fluid movement steps.

FIG. 21D illustrates an embodiment of seals 1860*b*-1860*d* that may be positioned to seal the entry channels coming from the fitment. Entry channels from the fitment into the blisters of the pouch and the seals in the instrument that can seal the entry channels are described, for example, in reference to FIGS. 2 and 4. In one embodiment, seals 1860*b*-1860*d* may be spring-loaded seals that are each biased to seal their respective entry channel(s) and that are retractable to allow fluid to be injected from the fitment, through the entry channels, and into their corresponding blisters, but that restrict backward flow of liquid from the blisters into the fitment.

In the illustrated embodiment, seals 1860*b*-1860*d* include 'eyebrow' shaped seal surfaces 1960*b*-1960*d* that may be shaped to seal the entry channels from the fitment. As is illustrated, for example, in FIG. 21A, seals 1860*b*-1860*d* may be associated with compression members 1820*a*-1820*c*. While other shapes (e.g., straight, oppositely arched, etc.) may be used, the arched shape of seals 1860*b*-1860*d* in the illustrated embodiment may be made to accommodate the shape of adjacent compression members.

Figure 21E:
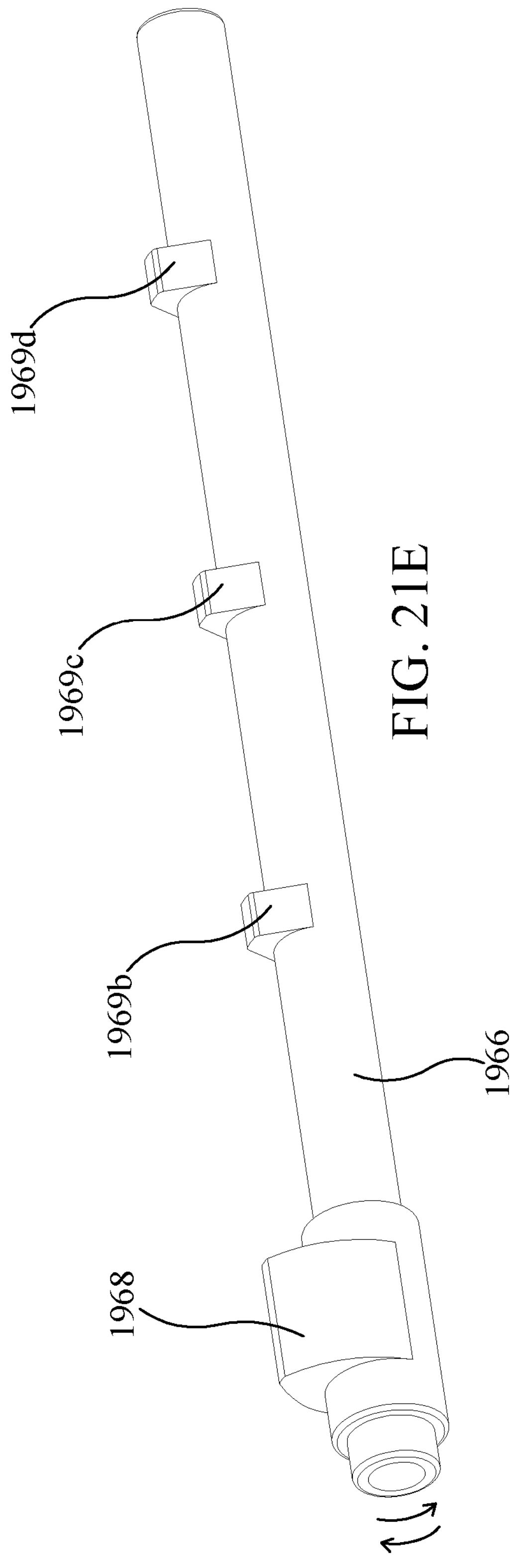

In the illustrated embodiment, each seal has an associated spring 1962 that may bias the seal to default to sealing the entry channels, and a structure 1964 that is mechanically coupled to a lobe on cam shaft 1966 that may retract seals 1860*b*-1860*d* when shaft 1966 is rotated. FIG. 21E illustrates the shaft 1966 in greater detail. In the illustrated embodiment, shaft 1966 includes lobes 1969*b*-1969*d* that are each associated with a respective seal 1860*b*-1860*d*. In the illustrated embodiment, lobes 1969*b*-1969*d* are all at the positioned at the same angle of rotation so that seals 1860*b*-1860*d* will all be retracted together. However, one will appreciate that other arrangements are possible. In the illustrated embodiment, shaft 1966 also includes a lobe 1968 that may be used to actuate compression member 1810.

Front Panel Gasket

Figure 22B:
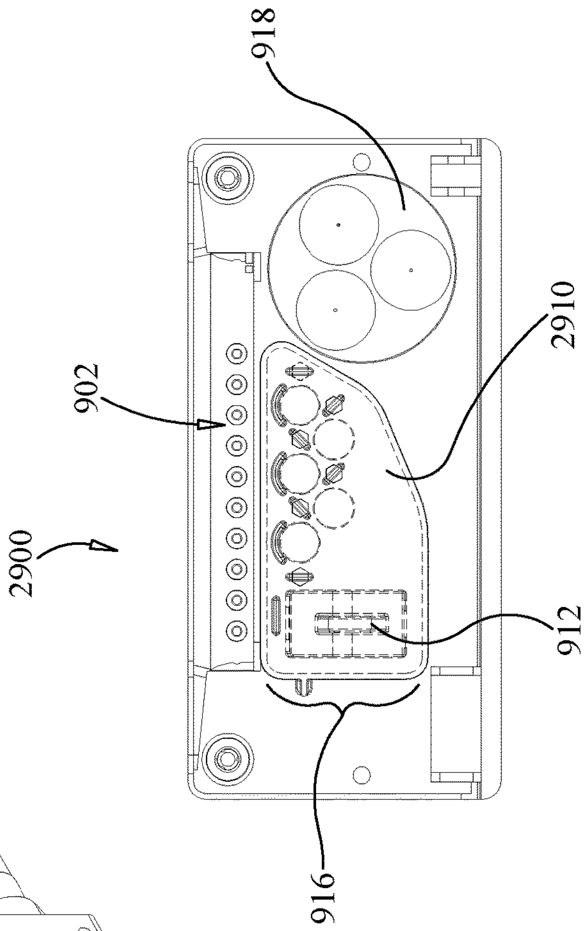
FIGS. 22A-B and FIGS. 23A-23B illustrate a front panel gasket, according to an embodiment of the present invention.
Figure 22A:
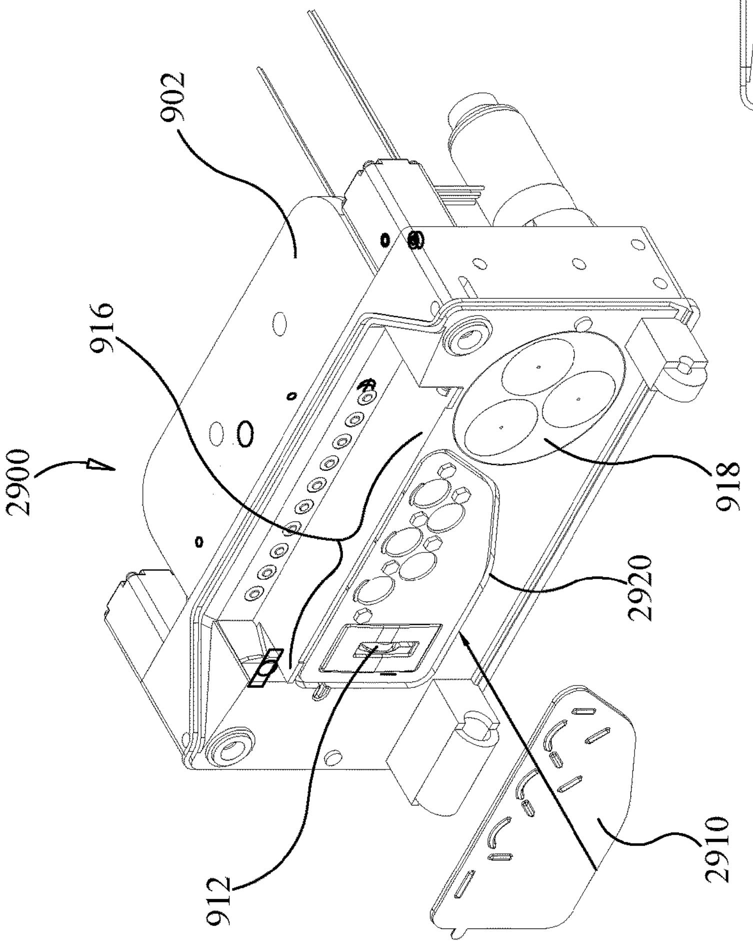
Figure 23B:
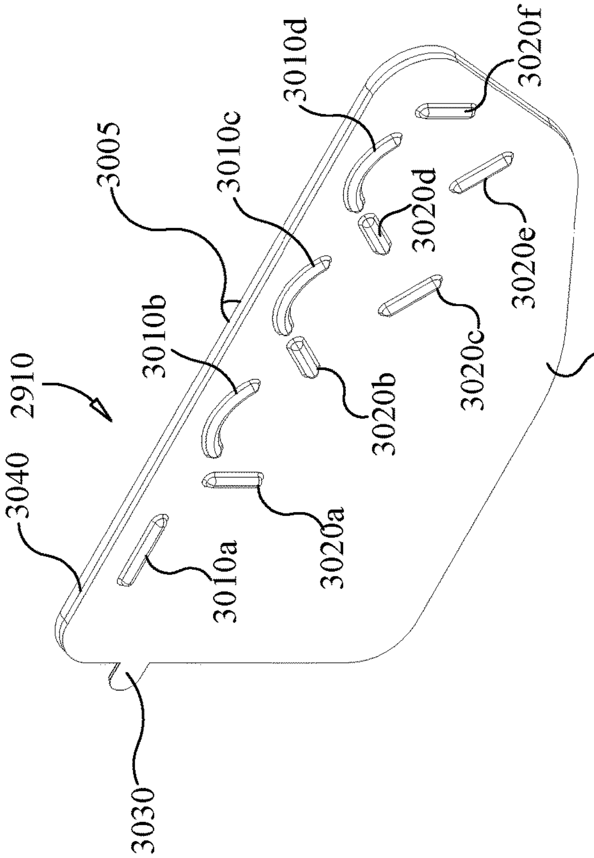

Referring now to FIGS. 22A-23B, a front panel gasket 2910 is illustrated. In FIGS. 22A and 22B, the front panel gasket 2910 is illustrated in the context of a sub-assembly 2900 of the instrument 900. FIGS. 23A and 23B illustrate plan and isometric views of the gasket 2910.

The illustrative sub-assembly 2900, which includes sub-assemblies 902, 904 and 906 of FIG. 3B (an illustrative embodiment of subassembly 906 is also shown, for example, at 1900 of FIG. 21A), includes the seal/compression member assembly 916, the plunging system 902 was discussed, for example, in reference to FIGS. 3B and 9-9D, a bead beater assembly 912 discussed, for example, in reference to FIGS. 14A and 14B, and an embodiment of a heater assembly 918 configured for second-stage PCR. The front panel gasket 2910 is sized and configured to fit over the seal/compression member assembly 916 and the bead beater assembly 912 of plate 1900 of sub-assembly 2900 to, for example, form a protective barrier between the pouch and the sensitive internal components of the instrument. For example, if a pouch leaks during a run, the front panel gasket 2910 can prevent the contents of the pouch from getting into and damaging the sensitive internal components of the instrument. Likewise, the front panel gasket 2910 can prevent amplified nucleic acids, live organisms, and the like from contaminating the instrument in the event of a pouch leak. Depending on the nature of a pouch leak, the front panel gasket 2910 can either be cleaned with conventional cleaners or replaced. In one embodiment, the front panel gasket 2910 is designed to be field replaceable (i.e., replaceable by an end user and not necessarily by an instrument service person).

Figure 23A:
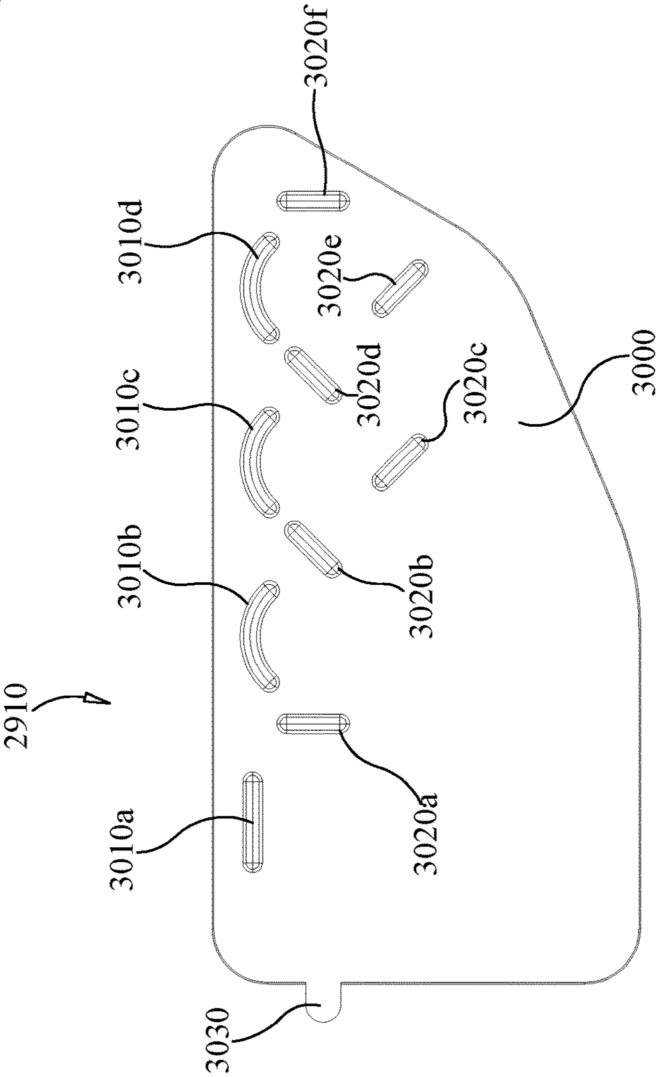

Referring now to FIGS. 23A and 23B, detailed views of the front panel gasket 2910 are shown. The front panel gasket 2910 includes a first surface 3000 and a second surface 3005. The first surface 3000 is the 'outer' surface that contacts the pouch and the second surface 3005 is the 'inner' surface that faces contacts the seal/compression member assembly 916 and the bead beater assembly 2906. The first surface 3000 includes projections 3010*a*-3010*d* and 3020*a*-3020*f* that are positioned to help the seals close off various channels of the pouch. Projections 3010*a*-3010*d* are positioned to work with seals 1860*a*-1860*e* that were illustrated, for example, in FIG. 20A. As was noted in reference to FIG. 20A, seals 1860*a*-1860*e* are usually spring-loaded, passive seals that are positioned to prevent fluid from flowing from the blisters back into the fitment. Projections 3020*a*-3020*f* are positioned to work with seals 1850*a*-1850*c* and 1840*a*-1840*c*. Projections 3010*a*-3010*d* and 3020*a*-3020*f* help the seals close off various channels of the pouch by focusing the pressing force of the seals on a small area that spans the channels.

Illustratively, the first surface 3000 of the front panel gasket 2910 further includes a pull tab 3030 that facilitates removal of the front panel gasket 2910 for cleaning and/or replacement. The front panel gasket 2910 also includes a ring 3040 (e.g., a molded ring) that is coextensive with the outer edge of the second surface 3005. The ring 3040 is sized and configured to mate with edge 2920 shown in FIG. 22A to couple the front panel gasket 2910 to the subassembly 2900.

Figure 23C:
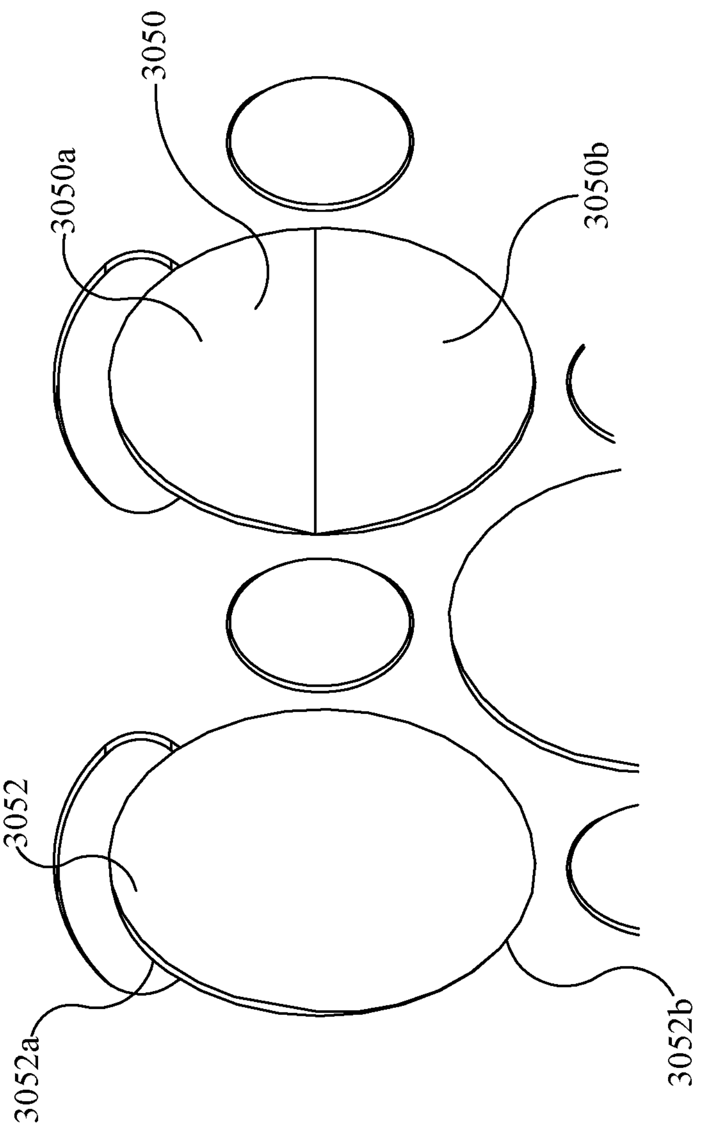
FIG. 23C illustrates embodiments of features that may be included on the front panel gasket of FIGS. 22A-B and FIGS. 23A-23B.

Referring to FIG. 23C, the back surface 3005 of front panel gasket 2910 may include features that may, for instance, help provide directionality to the plunging of fluid from blister-to-blister. As is illustrated in FIGS. 22A and 22B, the front panel gasket 2910 may be positioned over the compression members as an intermediate layer between the compression members and the pouch. Such directional features may, for example, help increase contact between the compression members and the pouch blisters and may help the compression members to more fully plunge fluid out of the blisters. In the illustrated examples, a compression member would tend to contact the raised end(s) of the features and move fluid towards the thinner ends. In a first example, feature 3050 includes a first semicircular wedge 3050*a* and a second semicircular wedge 3050*b* that may tend to cause a compression member to squeeze fluid first away from the thicker upper and lower edges of a fluid filled blister and toward the center of the blister and out of a central channel as the compression member is actuated. In a second example, feature 3052 is a circular wedge that may tend to cause a compression member to squeeze fluid away from the raised end 3052*a* and toward the thinner end 3052*b*. While these two examples are shown, one will appreciate that raised wedge features may be used in any combination to produce a desired fluid flow/press away pattern with cooperation between the front panel gasket and the compression members.

Window Bladder

Second-stage PCR occurs in the wells 582 of the array 580 (see, e.g., FIGS. 3A, 3B, and 4). To initiate second-stage PCR, a mechanical hot start is achieved by holding the second-stage PCR master mix/diluted template mixture at an elevated temperature (e.g., about 90° C.) optionally while the array 580 is also heated to an elevated temperature (e.g., about 75° C.). The array 580 and the wells 582 are then flooded with this mixture, which hydrates the individual second-stage PCR primers in their individual wells. To seal the PCR wells shut and to clear excess fluid from the second-stage array, a clear plastic bladder in the instrument, referred to herein as the "window bladder", may be inflated over the array after it is flooded. Inflation of this window bladder also has the effect of pressing the array gently against the second-stage PCR heater (918 in FIG. 3B) to facilitate heat transfer.

An example of a window bladder is illustrated at 936 in FIG. 3B. Bladder 936 is called "window bladder" because it comprises the area over the second-stage PCR array 582 where the camera 996 and the light source 998 are positioned for generation of and observation of fluorescence signal from the array 582. As such, in embodiments using fluorescence or other optical detection, it is preferable that the window bladder 936 be fabricated from a material that is optically transparent and minimally fluorescent. As will be discussed in greater detail below, a number of such materials are known in the art.

In addition to the foregoing, in some embodiments it may be preferable that the window bladder in the instrument is user replaceable. For instance, after a large number of instrument runs, the window bladder may become scratched or develop leaks. Rather than having to return the instrument for service in such a case, it may be preferable that the user is able to replace the window bladder.

Likewise, in addition to the foregoing, in one embodiment the window bladder can also efficiently and effectively clear excess fluid from the second-stage PCR array. For instance, clearing excess fluid from the second-stage array can lower PCR cycle time (i.e., smaller volumes of liquid can be cycled more quickly). Moreover, clearing excess fluid can help suppress cross talk between adjacent wells of the second-stage PCR array. As discussed in U.S. Pat. No. 8,895,295, which was already incorporated by reference herein, while the second-stage array is provided with a pierced overlay that allows filling of the second-stage wells and that largely suppresses cross talk, reducing the volume of excess liquid outside the wells with the window bladder may help enhance this effect.

Figure 24:
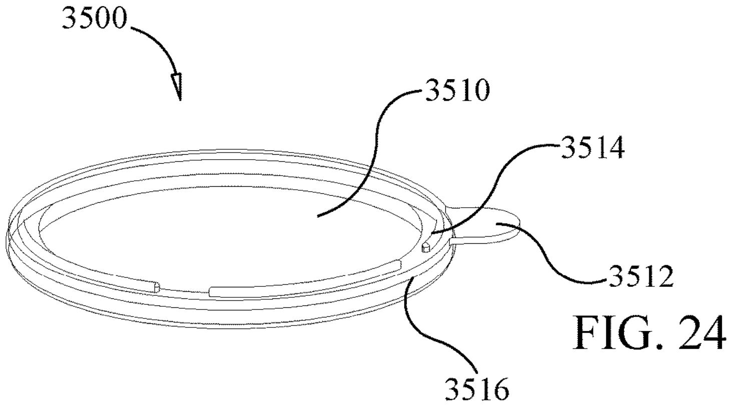
FIG. 24 illustrates an inflatable bladder that may be used in the instrument of FIG. 3B, according to an embodiment of the present invention.

Referring now to FIG. 24, a first example of a window bladder 3500 is illustrated. The window bladder 3500 includes a window 3510 comprised of one or more layers of optically transparent polymer material. Window bladder 3500 may include one or more tabs or the like (see, e.g., tab 3512) to facilitate installation and/or removal of the window bladder. Window bladder 3500 includes a sealing ring 3514 and a sealing surface 3516 that are configured to mate with a complementary surface on one of door subassembly 908 or support member 910. For instance, sealing ring 3514 and sealing surface 3516 may form a gas tight seal with door subassembly 908 with the sealing ring 3514, an adhesive on sealing surface 3516, one or more o-rings (not shown), or a combination thereof. Window bladder 3500 may be inflated via a gas line 978 (see, e.g., FIG. 3B) that may be, for instance, coupled to a channel (not shown) that is disposed in the door subassembly 908 and that fluidly connects to a space behind the window bladder 3500.

Figure 25A:
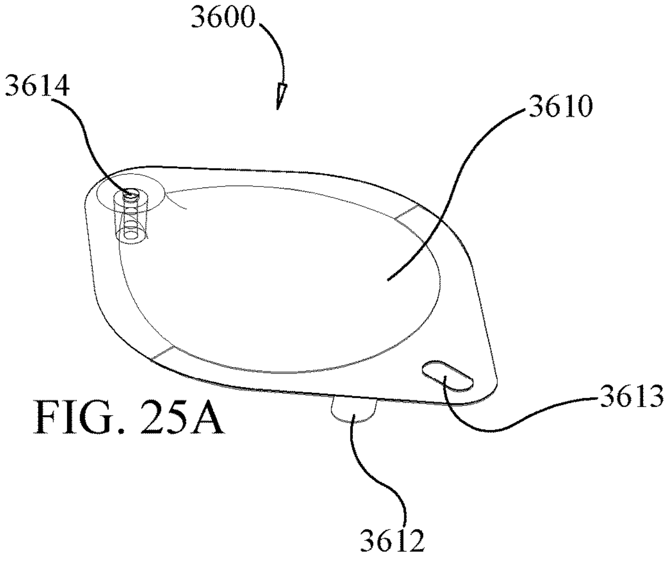
FIGS. 25A-25C illustrate another inflatable bladder that may be used in the instrument of FIG. 3B, according to an embodiment of the present invention.
Figure 25C:
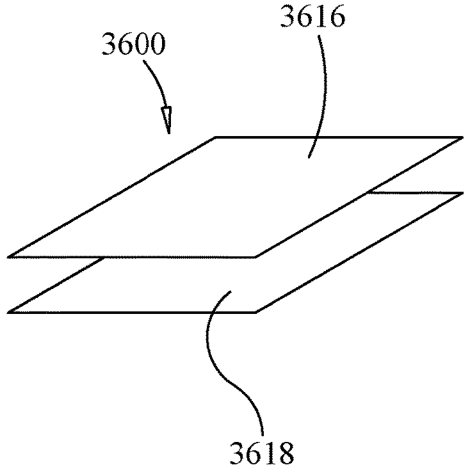
Figure 25B:
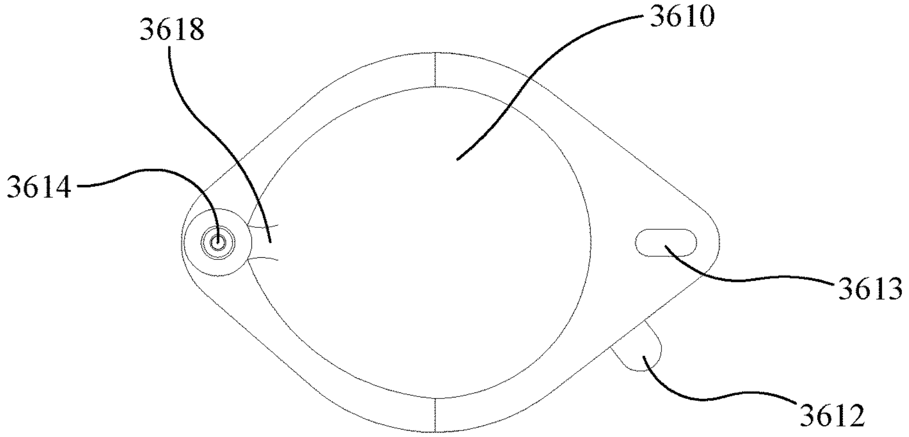

Referring now to FIGS. 25A and 25B, another embodiment of a window bladder 3600 is illustrated. Window bladder 3600 includes a clear window 3610 and a bonded area (e.g., laser, heat, or sonic welded) 3612 around the periphery of window bladder 3600. As is illustrated in FIG. 25C, window bladder 3600 is comprised of a first layer of material 3616 and a second layer of material 3618 that are bonded together on the edge to form an inflatable envelope between the two layers. The first and second layers of material 3616 and 3618 may be single layers of material or they each may include two or more layers of material that are bonded together. Suitable examples of material for the first and second layers 3616 and 3618 include, but are not limited to, a flexible plastic film or other flexible material such as polyester, polyethylene terephthalate (PET), polycarbonate, polypropylene, polymethylmethacrylate, and mixtures thereof. In one embodiment, window bladder 3600 is fabricated by laminating at least two layers of plastic film together in such a way that the inflatable bladder is formed.

Referring again to FIGS. 25A and 25B, window bladder 3600 includes a nipple 3614 that is fluidly connected to a fill channel 3618 and the envelope formed between the two layers. In one embodiment, the nipple 3614 may be connected to gas line 978 that is connected to compressed gas source 995 (see FIG. 3B) for inflation of the window bladder 3600.

Figure 26:
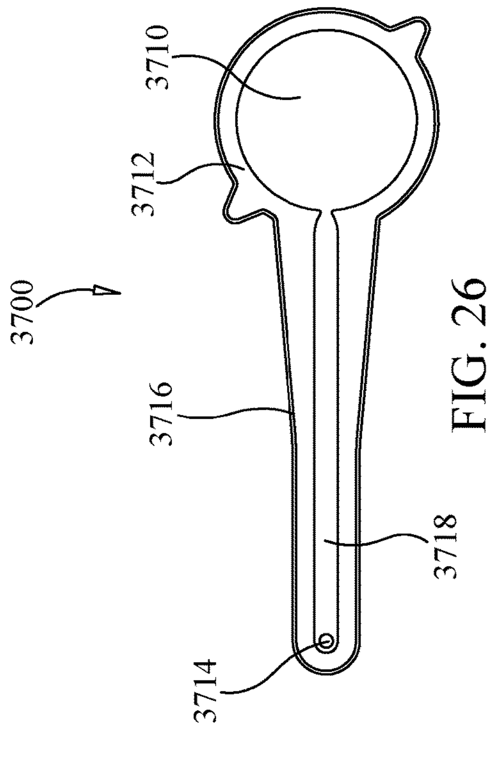
FIG. 26 illustrates another inflatable bladder that may be used in the instrument of FIG. 3B, according to an embodiment of the present invention.
Figure 27:
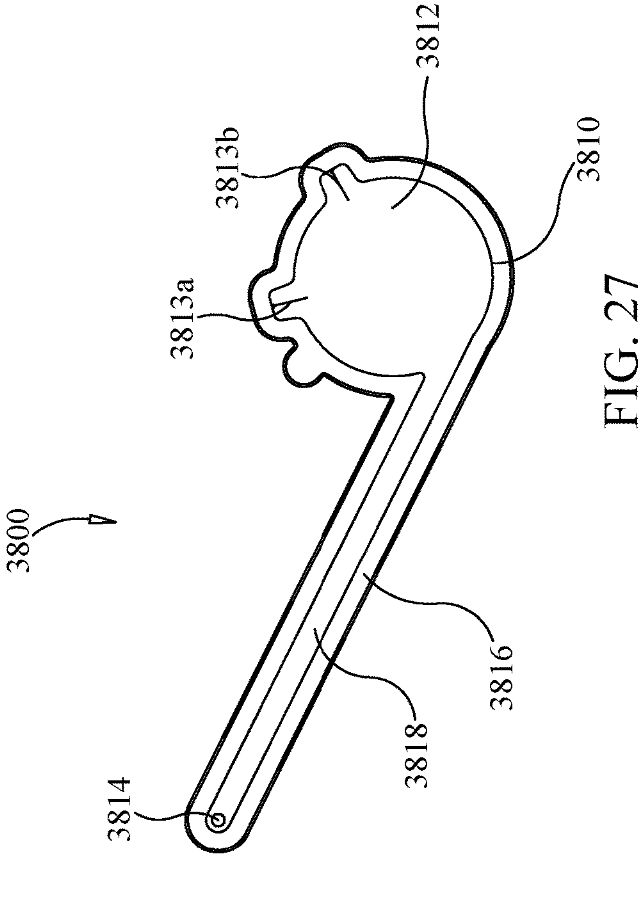
FIG. 27 illustrates another inflatable bladder that may be used in the instrument of FIG. 3B, according to an embodiment of the present invention.

Referring now to FIGS. 26 and 27, alternative embodiments of window bladders 3700 and 3800 are illustrated. Window bladders 3700 and 3800 include many of the features of window bladder 3600 and similar elements are numbered similarly. Window bladders 3700 and 3800 include transparent windows 3710 and 3810 and heat bonded areas 3712 and 3812. In contrast, window bladders 3700 and 3800 each include a long stem 3716 and 3816 that comprises a fill channel 3718 and 3818. Fill channels 3718 and 3818 may be fluidly connected to a nipple as in the previous example such as at 3714 or 3814. Alternatively, a gas line that may, for example, be directly connected to a compressed gas source may be inserted through holes 3714 or 3814 and bonded in stem 3716 or 3816. In addition to the foregoing, window bladder 3800 includes extra heat weld lines 3813*a* and 3813*b* that can create kinks in the bladder 3800 when inflated. Such kinks may, for instance, be positioned so that the inflated bladder cannot block the evacuation channels from the array (see, e.g., channel 565 of FIG. 2) when the bladder is inflated so as to facilitate evacuation of excess fluid from the array. Such welds lines or other structures to create selected kinks in the inflated window bladder could be included in the other window bladder embodiments described herein.

In one embodiment, window bladders 3600, 3700, or 3800 may be held in place on one of door subassembly 908 or second support member 910 over array 580 with an adhesive ring (not shown). For instance, an adhesive ring may correspond to the heat welded areas 3610, 3710, or 3810. As such, a user may access door subassembly 908 or second support member 910 and change the window bladder by peeling off the old bladder and affixing a new bladder in its place. In one embodiment, structures such as nipple 3614 and eyelet 3613 may be used to help align the window bladder relative to the one of the door subassembly 908 or the second support member 910 and relative to the array 580. In one embodiment, window bladders 3500, 3600, 3700, and 3800 may be sized and configured to be the same size as array 580 or slightly larger or slightly smaller than array 580.

Figure 28A:
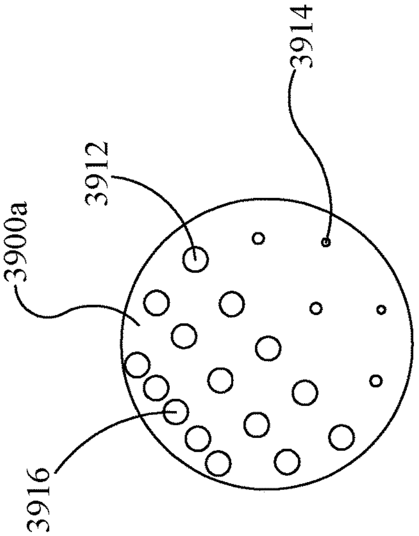
FIGS. 28A and 28B illustrate alternative embodiments of an inflatable bladder.
Figure 28B:
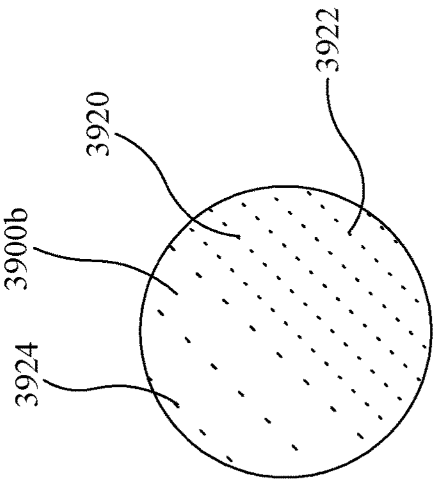

In addition to the foregoing, the inventors in this case have found that it may be desirable for the window bladder to be designed such that it can be opened in a controlled manner. For instance, if the bladder can open progressively, starting at one edge and moving across the bladder to the opposite edge in a wave-like fashion, the bladder can actually "wipe" fluid away from the array 580, resulting in a better evacuated array and possibly reduced cross-talk. FIGS. 28A and 28B schematically illustrate two examples of how this may be accomplished.

FIG. 28A schematically illustrates a window bladder 3900*a* that includes a series of welds 3912 (e.g., engineered sticky spots) in the inflatable envelope between the layers of material in gradient arrangement with relatively few welds at the bottom edge 3914 and a relatively greater number of welds at the top edge 3916. When bladder 3900*a* is inflated, the welds will tend to stick the bladder closed; the gradient of sticky welds will tend allow the bladder 3900*a* to open first at the bottom edge (i.e., 3914) with a wave progressing toward the top edge (i.e., 3916).

FIG. 28B schematically illustrates another window bladder 3900*b*. Bladder 3900*b* may be fabricated from a material that has an intrinsic tackiness that can partially adhere to itself. An example of a suitable material for a window bladder of this type is Ecdel, which is a material created by the Eastman chemical company. Ecdel is an elastomer copolymer material that is heat sealable, and optically transparent. In contrast to bladder 3900*a*, bladder 3900*b* may be fabricated with a gradient of dots 3920 (e.g., printed ink dots, laser modified spots, etc.) that counteract the intrinsic tackiness of the material such that the end with more dots 3922 can inflate first with a wave progressing toward the top edge 3924. Materials like Ecdel may also be desirable because they are somewhat elastic and the bladder can squeeze fluid out of the array 580 as the window bladder elastically deforms if it is overinflated against the surface of the pouch.

Second-Stage PCR Heater

Figure 29:
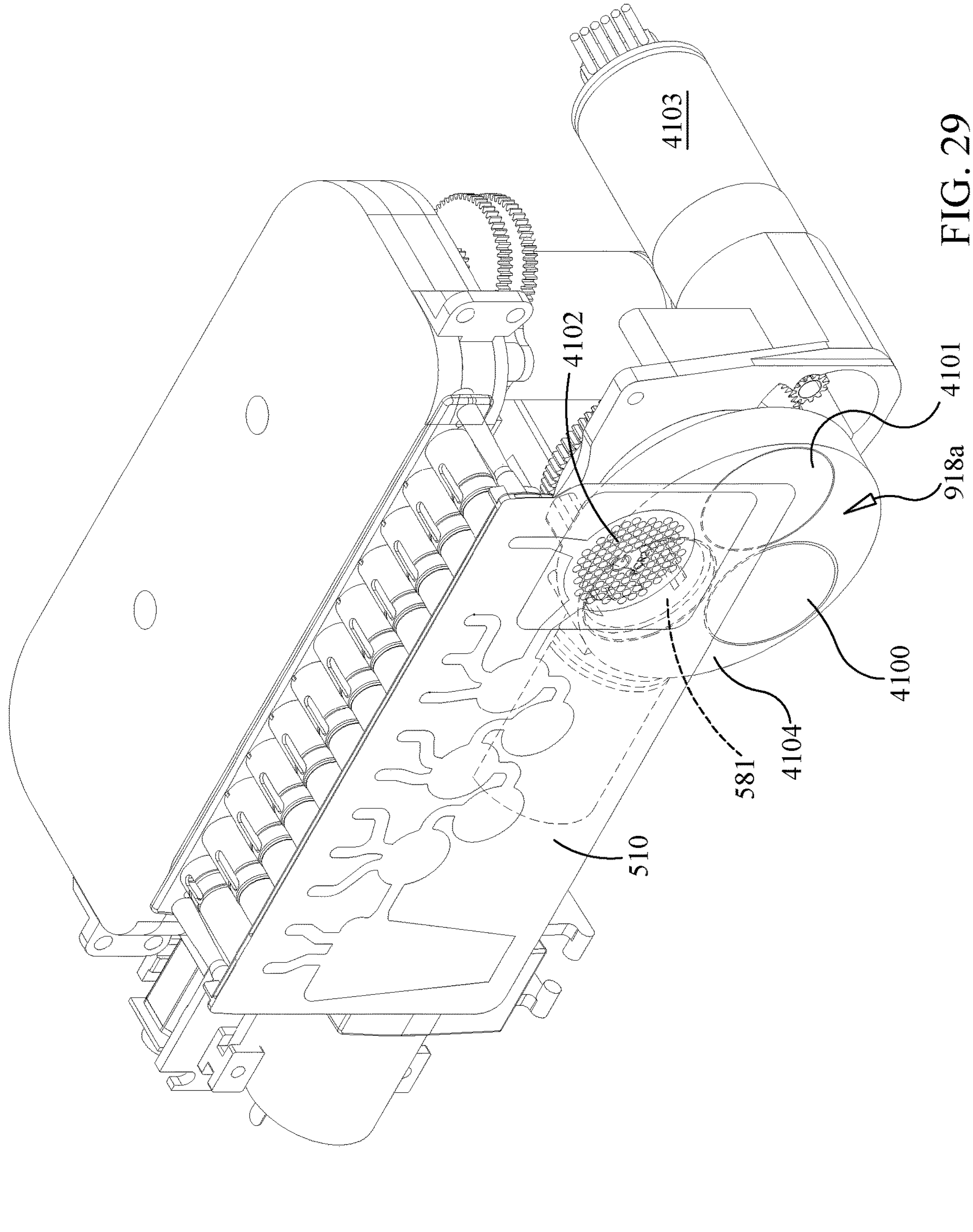
FIG. 29 illustrates a rotary heater that may be used with the instrument of FIG. 3B, according to an embodiment of the present invention.

FIG. 29 illustrates an embodiment of a second-stage PCR heater 918*a* that may be used in the instrument of FIG. 3B or another similar instrument. While Peltier heaters, which can thermocycle rapidly and accurately between two or more temperatures, are effective for PCR, it may be desirable in some embodiments to maintain heaters at a constant temperature. Illustratively, this can be used to reduce run time, by eliminating time needed to transition the heater temperature beyond the time needed to transition the sample temperature. Likewise, Peltier devices consume much of their power in the process of cycling between temperatures; a heater, be it a Peltier device or a standard resistance heater consumes much less power if it is held at a constant temperature.

Heater 918*a* is an alternative to the second-stage heater 888 shown in FIG. 3A or the second-stage heater 918*a* shown in FIG. 3B. Illustratively, heater assembly 918*a* includes three heaters 4100, 4101, and 4102, set in a circular mount 4104, driven circularly by motor 4103, so that one heater at a time contacts array 581 as each heater is moved sequentially into position adjacent array 581. Heaters 4100, 4101, and 4102 may be Peltier devices, resistance heaters, electromagnetic heaters, thin film heaters, printed element heaters, positive temperature coefficient heaters, or other heaters as are known in the art.

In one embodiment, heater 4100 may be set at an annealing temperature, illustratively 60° C., heater 4101 may be set at an elongation temperature, illustratively 72° C., and heater 4102 may be set at a denaturation temperature, illustratively 94° C. In another embodiment, heater 4100 may be set at an annealing temperature, illustratively 60° C., and heater 4102 may be set at a denaturation temperature, illustratively 94° C., while heater 4101 may be actively cooled to a low temperature, illustratively room-temperature or less. In such a case, rapid thermal cycling between a denaturation temperature and an annealing temperature may be accomplished by denaturing with heater 4102, rotating to heater 4101 to bring the temperature down as rapidly as possible, and rotating to heater 4100 for annealing. In such an embodiment, annealing and elongation may be set to occur at the same temperature. In another embodiment, heater 4100 may be configured for limited thermal cycling between an annealing temperature and an elongation temperature. For instance, heater may be seat at 63° C. for annealing and may by ramped to 68° C. for elongation. Such limited cycling by heater 4100 cycling can be rapid and the power consumption costs for cycling in such a limited temperature range are minimal In another embodiment, heater 4100 may be set at an elongation temperature (e.g., 68° C.) and annealing may be accomplished by allowing the reaction to overshoot (i.e., over cool) at the cooled heater 4101 and then rotating to heater 4100 to reheat the reaction through the annealing temperature and up to the elongation temperature. However, it is understood that these temperatures are illustrative only, and that other temperatures and other numbers of heaters may be used. Two heaters are sufficient for many applications. Because it is difficult to move array 581 within pouch 510, heaters 4100, 4101, and 4102 move to contact array 581. Mount 4104 may move in one direction only, with each of heaters 4100, 4101, and 4102 contacting array 581 in order, or mount may move in both clockwise and counterclockwise directions, illustratively changing direction after each PCR cycle.

While heaters 4100, 4101, and 4102 are provided in mount 4104 and are moved relative to array 581, it is understood that this illustrative only, and that two or more stationary heaters may be provided, and array 581 may be rotated relative to the heaters.

Example 1: High Density PCR

In one example, it is known that standard commercial immunofluorescence assays for the common respiratory viruses can detect seven viruses: adenovirus, PIV1, PIV2, PIV3, RSV, Influenza A, and Influenza B. A more complete panel illustratively would include assays for other viruses including: coronavirus, human metapneumovirus, rhinovirus, and non-HRV enterovirus. For highly variable viruses such as Adenovirus or HRV, it is desirable to use multiple primers to target all of the branches of the virus' lineage (illustratively 4 outer and 4 inner primer sets respectively). For other viruses such as coronavirus, there are 4 distinct lineages (229E, NL63, OC43, HKU1) that do not vary from one season to another, but they have diverged sufficiently enough that separate primer sets are required. The FilmArray® Respiratory Panel (BioFire Diagnostics, LLC of Salt Lake City, UT) includes Adenovirus, Coronavirus HKU1, Coronavirus NL63, Coronavirus 229E, Coronavirus OC43, Human Metapneumovirus, Human Rhinovirus/Enterovirus, Influenza A, Influenza A/H1, Influenza A/H3, Influenza A/H1-2009, Influenza B, Parainfluenza Virus 1, Parainfluenza Virus 2, Parainfluenza Virus 3, Parainfluenza Virus 4, and Respiratory Syncytial Virus. In addition to these viruses, the FilmArray® Respiratory Panel includes three bacteria: *Bordetella pertussis, Chlamydophila pneumonia*, and *Mycoplasma* pneumonia. The high density array 581 is able to accommodate such a panel in a single pouch 510. Other panels are available for the FilmArray®, each assaying for at least 20 pathogens.

Example 2: Pouch Loading

Figure 30:
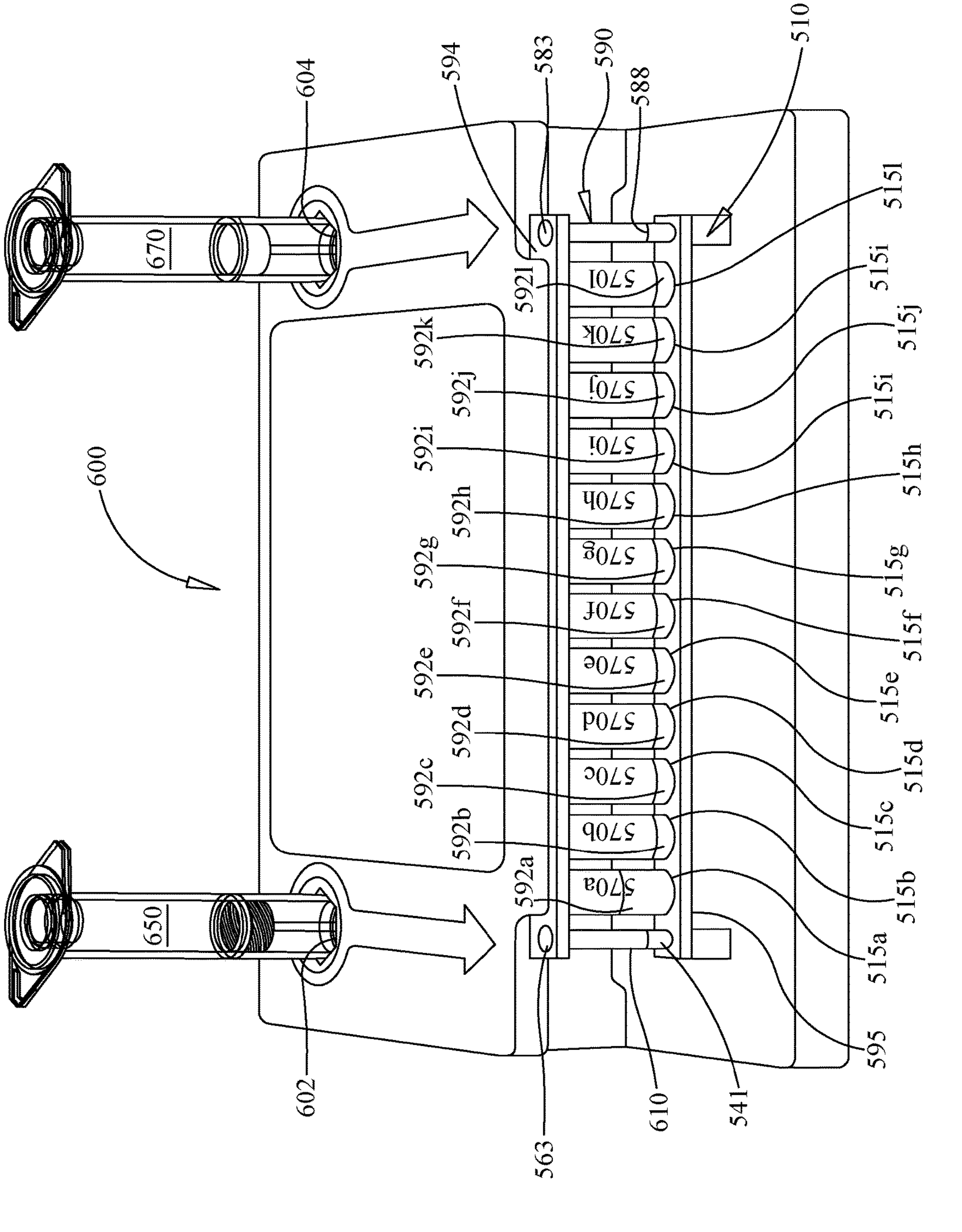
FIG. 30 shows a loading station for loading the pouch of FIG. 2, including the pouch of FIG. 2.

FIG. 30 shows a loading station 600. As shown, pouch 510 of FIG. 2 has been loaded into slot 610 of loading station 600, such that only fitment 590 of pouch 510 is visible. As shown, loading station 600 is provided with a sample vial receptacle 602 for holding sample vial 650 and hydration vial receptacle 604 for holding hydration vial 670. However, it is understood that the receptacles and vials are for aiding workflow and are illustrative only. Other configurations and use with other pouches and other devices are within the scope of this disclosure.

A sample is pipetted or otherwise loaded into sample vial 650. As discussed in more detail below, depending on workflow, sample vial 650 may already contain a buffer or other fluid 652 for receiving the biological sample, or the operator may add the biological sample in an appropriate buffer to sample vial 650. Optionally, the buffer may be provided in a separate ampoule, with an appropriate amount of buffer apportioned. Similarly, hydration vial 670 may be preloaded with water, buffer, or other fluid 672, or the operator may load hydration vial 670 with such fluid.

Illustrative fitment 590 includes an injection port 541 illustratively formed near second surface 595 of fitment 590. As shown, injection port 541 is located in sample injection opening 563, which is configured to receive a cannulated transfer vessel through first surface 594 of fitment 590, such as a cannulated syringe. In this illustrative configuration, injection port 541 is protected from accidental puncture and is not opened until a cannulated transfer vessel is placed into sample injection opening 563. Similarly, illustrative fitment 590 includes a second injection port 588 illustratively formed near second surface 595 of fitment 590, and is located in hydration fluid injection opening 583, which is configured similarly to sample injection opening 563. As configured in this illustrative embodiment, injection port 541 is for receiving the sample to be tested, which may be received into chamber 592*a* may be moved into the pouch 510 with plunger 570*a* or directly into lysis blister 522 (FIG. 2). Second injection port 588 is configured for receiving the hydration fluid 672 (displayed in FIG. 7), such as water or buffer, which hydration fluid 672 will be moved to chambers 592*b* through 592*l*, for subsequent movement through entry channels 515*b* through 515*l* by plungers 570*b*-570*l*. It is understood that the arrangement of injection ports 541 and 588 and openings 563 and 583 is illustrative and that other configurations are within the scope of this disclosure.

Figure 31:
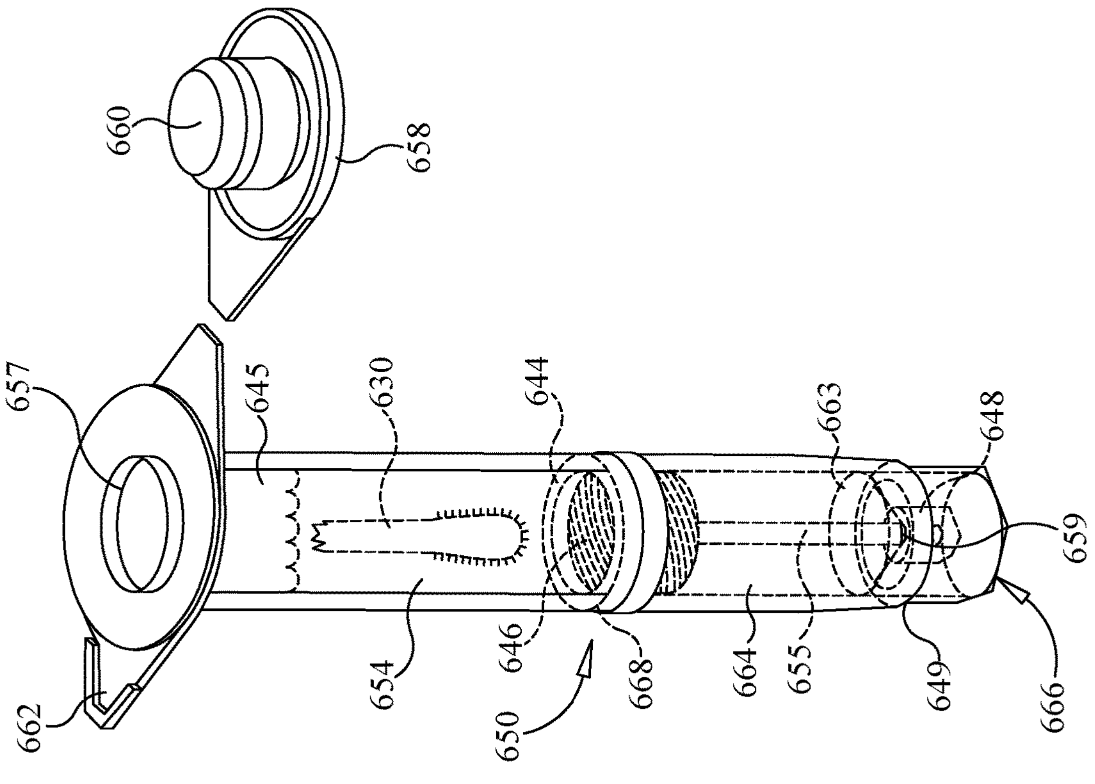
FIG. 31 shows a sample vial for loading a sample into the pouch of FIG. 2.

Illustrative sample vial 650, as best shown in FIG. 31, is comprised of a top surface 662, a vial body 654, and a cannula 655, in an arrangement similar to many cannulated syringes. In this illustrative embodiment, rather than the plunger found in many cannulated syringes, sample vial 650 is provided with a cap 658 for extending through top surface 662 for sealing body 654. Illustratively, the operator would pour, pipette, insert swab, scoop solid or semi-solid material, or otherwise transfer a fluid and/or other materials through opening 657 in top surface 662 and into vial body 654.

Depending on the type of sample to be tested, sample vial 650 may be provided with a filter 646, illustratively located at or near the hexagonal bottom surface 666 of vial body 654. As shown, filter 646 is held in place by o-ring 644. However, it is understood that filter 646 may be held in place by adhesive, by welding, by being press-fit into place, or by other means, as are known in the art. When cannula 655 is inserted into sample injection opening 563 and the sample is drawn into pouch 510, the sample material is filtered as it is pulled through filter 646 and into cannula 655. While the selection of filter material depends on the sample type and particle size, suitable filters for various biological samples include Pall 100 μm Absolute Ultipleat Polypropylene Melt Blown Media and Millipore 80 μm Polypropylene Net Filter. Most syringe filters are designed to exclude organisms of a certain size, thereby removing those organisms from the filtrate. Unlike such pre-existing filters, these illustrative filters were chosen based on their ability to exclude larger particulates found in stool, soil, powder, etc., while allowing target organisms (e.g., bacterial, viral, protozoan and fungal organisms) of approximately 60 μm in diameter or less to pass through in the filter. Also, the illustrative filter material is inert (i.e. does not bind organism or nucleic acid) and is relatively resistant to clogging. It is understood that these illustrative filters were chosen for samples that include protozoans as target organisms (up to about 60 μm). Because some pouch configurations may test only for smaller targets, filters with a smaller pore size may be desired, such as filters with pore sizes of 1-10 μm for bacteria and fungi, and pore sizes of less than 1 μm if only viral particles are to be detected. Of course, the larger pore size filter can still be used to filter smaller targets. Such filters may be particularly useful for sample types that have a large amount of particulate matter, such as soil, stool, and powder that may clog the fluid system. Further, it is understood that the pore size is chosen based on the materials to be filtered, and that other pore sizes are within the scope of this invention.

It is understood that one or more components useful for sample preparation may be provided dried in vial body 654. Such additives may include buffering agents, stabilizers, proteases, DNAses, DNAse inhibitors, RNases, RNase inhibitors, lysozymes, reducing agents, and the like. Alternatively, such components may be included in the sample buffer, or may be added downstream, after the sample has exited vial 650 for further processing. It is understood that the selection of such additives depends on the sample type and on the further processing desired. Additives that help reduce viscosity or aid in solubility, to allow the sample to pass through filter 646 are particularly helpful.

As shown, bottom cap 664 is provided with a hexagonal portion 666, which is configured to fit into the hexagonally shaped sample vial receptacle 602. While hexagonal portion 666 and sample vial receptacle are hexagonal in the illustrative embodiment, it is understood that other shapes may be used, and that the hexagonal or other mating or interlocking shapes may be provided to assist the operator in removing bottom cap 664. Alternatively, the operator may remove bottom cap 664 by other means, such as using two hands to twist bottom cap 664 from vial body 654. Bottom cap 664 may be press-fit on, threaded onto, or otherwise affixed to vial body 654.

In the illustrative embodiment, bottom cap 664 is provided with a seat 648, whereby a bottom end 659 of cannula 655 extends into seat 648. Illustratively, bottom end 659 of cannula 655 fits tightly into seat 648, such that seat 648 provides an airtight seal around the open bottom end 659 of cannula 655. Optionally, vents 649 are provided between bottom cap 664 and vial body 654.

Figure 32:
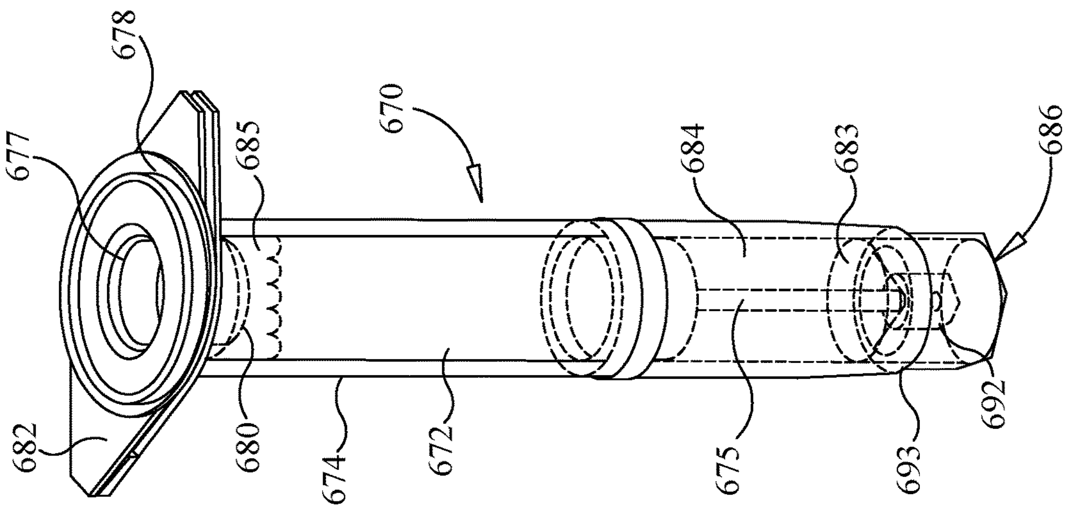
FIG. 32 shows a hydration vial for providing a hydration fluid to the pouch of FIG. 2.

Turning now to FIG. 32, hydration vial 670 may be configured similarly to sample vial 650. However, it may be desirable to preload hydration vial 670 with hydration fluid 672 and pre-seal the hydration fluid 672 in hydration vial 670, as shown in FIG. 32. Illustrative hydration vial 670, as shown in FIG. 32, is comprised of a top surface 682, a vial body 674, and a cannula 675, in an arrangement similar to that of sample vial 650. However, tongue 680 of cap 678 of illustrative hydration vial 670 is already press-fit into opening 677 of top surface 682, and cap 678 may be sealed to top surface 682, thereby preventing opening of hydration vial 670. This arrangement is illustrative only, and it is understood that other ways of sealing hydration fluid 672 within hydration vial 670 are envisioned herein. Illustratively, vial body 674 and cannula 675 may be provided completely full or essentially completely full of fluid, so that handling or rotating hydration vial 670 will not permit air to enter cannula 675. Alternatively, some air 685 or other gas may be present within vial body 674, and the operator may maintain hydration body in an upright position to prevent air from entering cannula 675. In yet another alternative embodiment, the air 685 may be provided under pressure, and removal of bottom cap 684 would result in hydration fluid being forced through cannula 675. As shown, hydration vial 670 is not provided with a filter, although one may be provided, if desired.

Bottom cap 684 may be provided to retain any fluid that might drip from cannula 675, as well as preventing contamination of hydration fluid 672 in cannula 675. A wiper 683 may be provided in bottom cap 684 to wipe excess fluid from the bottom of cannula 675. The conical shape of wiper 683 may also aid in retaining drips in bottom cap 684 during subsequent handling and disposal. In the illustrative embodiment, bottom cap 684 is provided with a hexagonal portion 686 for mating with the hexagonally shaped hydration vial receptacle 604, although other shapes are possible, as discussed above, with respect to sample vial 650. Hexagonal portion 686 of hydration vial 670 and hexagonally shaped hydration vial receptacle 604 may be of different dimensions and/or different shapes than hexagonal portion 666 of sample vial 650 and hexagonally shaped sample vial receptacle 602, such that only sample vial 650 will readily fit into sample vial receptacle 602 and only hydration vial 670 will readily fit into hydration vial receptacle 604, to reduce the chance of the operator confusing the sample vial 650 and hydration vial 670, so that the proper fluids are injected through ports 541 and 588. In addition, sample vial 650 and injection opening 563 may be partially or entirely provided in a matching specific color, illustratively red, while hydration vial 670 and injection opening 583 may be partially or entirely provided in a different matching specific color, illustratively blue, to provide the operator with visual assistance in providing the proper fluids in ports 541 and 588. To further minimize risk of inserting the wrong liquid into the wrong injection opening, the diameter of cannula 655 may differ from the diameter of cannula 675, and the diameters of sample injection opening 563 and hydration fluid injection opening 583 may similarly differ. Other configurations are within the scope of this disclosure.

Returning to FIG. 30, illustratively, to load pouch 510, the operator would place sample vial 650 into sample vial receptacle 602 and hydration vial 670 into hydration vial receptacle 604 on loading station 600. Pouch 510 would also be placed into slot 610. The sample would be placed into the sample buffer 652 in any way suitable for the sample type, including inserting a swab 630, pipetting a fluid sample, dripping blood from a patient directly into the vial body, and placing a solid or semi-solid sample such as stool into the vial body, with optional vortexing or other mixing, as is standard in the art. Depending on the sample type and desired target nucleic acids, the sample buffer may contain one or more additives or stabilizers, illustratively for treating a biological or environmental sample, such as proteases, DNases, DNase inhibitors, RNases, RNase inhibitors, lysozymes, and the like. Additionally or alternatively, these additives may be provided in the pouch 510. Preferably before vortexing or mixing, the operator would close sample vial 650 by placing the tongue 660 of cap 658 through opening 657. Inserting tongue 660 pressurizes the air contained within vial body 654. Illustratively, tongue 660 has a volume equal to or greater than the volume of cannula 655. Illustratively, when bottom cap 664 is removed, the airtight seal between seat 648 bottom end 659 of cannula 655 is broken, and substantially all air is forced out of cannula 655. If the volume of tongue 660 is greater than the volume of cannula 655, such would help ensure that the maximal amount of air is displaced from cannula 655. Any overflow in the amount of fluid forced into and potentially through cannula 655 can be captured in bottom cap 664 and removed from the bottom of cannula 655 by wiper 663. By completely or essentially completely filling cannula 655, the quantity of bubbles in pouch 510 upon loading of the pouch is minimized One or more vents 649 may aid in separation of bottom cap 664 from hydration vial 650.

Because bottom cap 664 is provided with a hexagonal portion 666, which is configured to fit into the hexagonally shaped sample vial receptacle 602, the operator can easily twist off bottom cap 654 while bottom cap is engaging receptacle 602, thereby exposing cannula 655. Cannula 655 is then inserted into sample injection opening 563 and is pushed in, opening injection port 541. A vacuum inside pouch 590 (or reduced pressure inside the pouch relative to atmospheric pressure or pressure outside the pouch) illustratively forces the sample through the filter (if present), with or without pressure from the vial body, may be used to draw the sample into pouch 510, illustratively into chamber **592*a* in fitment 590, for subsequent movement into lysis chamber 522. By assuring that cannula 655 is substantially filled with fluid 652, the amount of air or other gas moved from sample vial 650 into pouch 510 is minimized, thereby minimizing the size and quantity of bubbles. Furthermore, when a prior art syringe with a plunger is used and the vacuum inside pouch 590 draws fluid, the plunger is drawn down the syringe, thereby equilibrating the pressure inside the syringe. In the embodiment of FIGS. 30-31, because the opening at the top of each of the vial bodies is sealed, when the vacuum from inside pouch 590 draws fluid from the vial, the vial will also experience negative pressure and may degas the sample and draw some remaining air bubbles out of the pouch 590. Cannula 655 is then withdrawn from sample injection opening 563 and sample vial 650 and bottom cap 664 are disposed of according to protocols. Since the vial body 654 is under negative pressure, as cannula 655 is withdrawn, air bubbles that may have collected near injection port 541 may be drawn out of pouch 510**, further reducing air bubbles in the pouch.

Similarly, the operator twists off bottom cap 684 from hydration vial 670, thereby exposing cannula 675. If the contents of hydration vial 670 are provided under pressure, a small amount of hydration fluid may leak out into bottom cap 684 when cannula 675 is separated from seat 692. One or more vents 693 may aid in separation of bottom cap 684 from hydration vial 670. Cannula 675 is then inserted into hydration injection opening 583 and is pushed in, opening injection port 588. Vacuum from inside fitment 590 may be used to draw the hydration fluid into pouch 510, illustratively into chambers **592*b*-592*l*, for subsequent movement into various blisters of pouch 510. Cannula 675 is removed from hydration injection opening 583, pouch 510 is removed from loading station 600 and placed into instrument 800**, and the run started. It is understood that removal of the vials is illustrative only. If the configuration of the instrument and vials permit, the vials may be inserted permanently in the injection ports, thereby becoming part of the closed system of the pouch and minimizing contamination from the sample. In such an embodiment, a seal bar may not be needed.

In the illustrative embodiment of sample vial 650 discussed above, tongue 660 has a volume equal to or greater than the volume of cannula 655. In one exemplary embodiment where the pouch 510 has a fill volume of 1 ml, vial body 654 may be provided with 1.5 ml of sample fluid 652 and volume of 1 ml of air 645 above the sample fluid. Thus, the air is 40% of the volume of the vial body 654. However, it is understood that other percentages of air may be used, including 10%, 20%, 30% 50%, 60%, 70%, 80%, and amounts in between. When tongue 660 is inserted through opening 657, the air above the sample fluid is compressed, illustratively by about 50%, but compression in the range of 40-60%, 30-70%, 20-80%, and 10-90% are all possible. It is understood that choice of volume of air and sample fluid depends on size of sample, diameter of cannula, whether removal of the vials prior to running the fluidic reaction is desired, and on a number of other factors. For example, scooped or swabbed samples may need a significantly larger volume of sample fluid, regardless of the fill volume of the fluidic system.

Illustrative vial bodies 654 and 674 are cylindrical. However, since these illustrative vials are provided without plungers, it is understood that the vial bodies need not have circular cross-sections, and that any body shape is within the scope of this invention.

Figure 8:
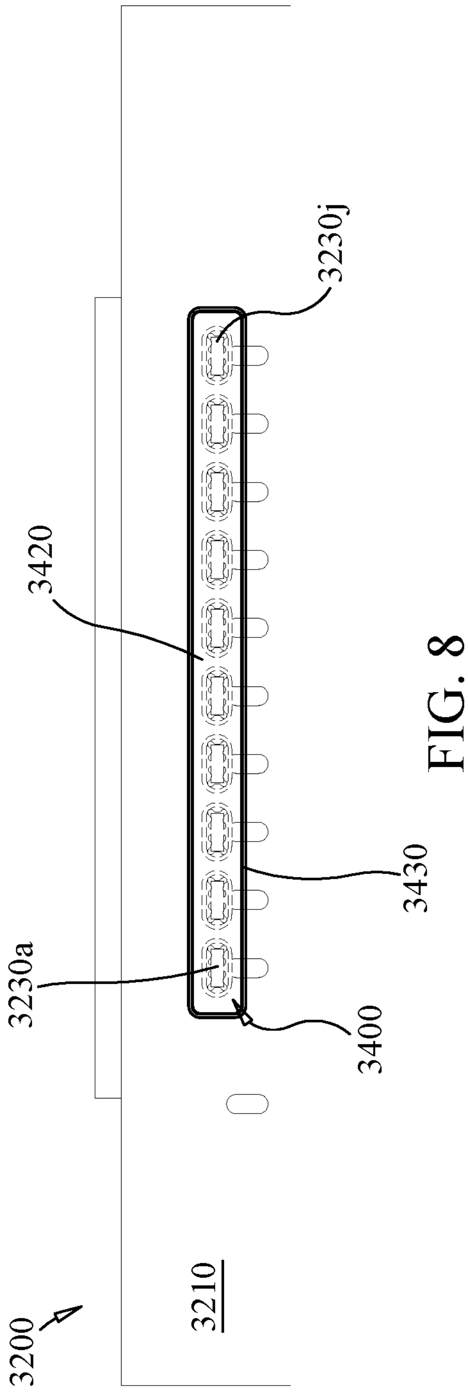
FIG. 8 illustrates an embodiment of the heat sealing system of FIGS. 6A and 6B with a cover, according to an embodiment of the present invention.
Figure 33:
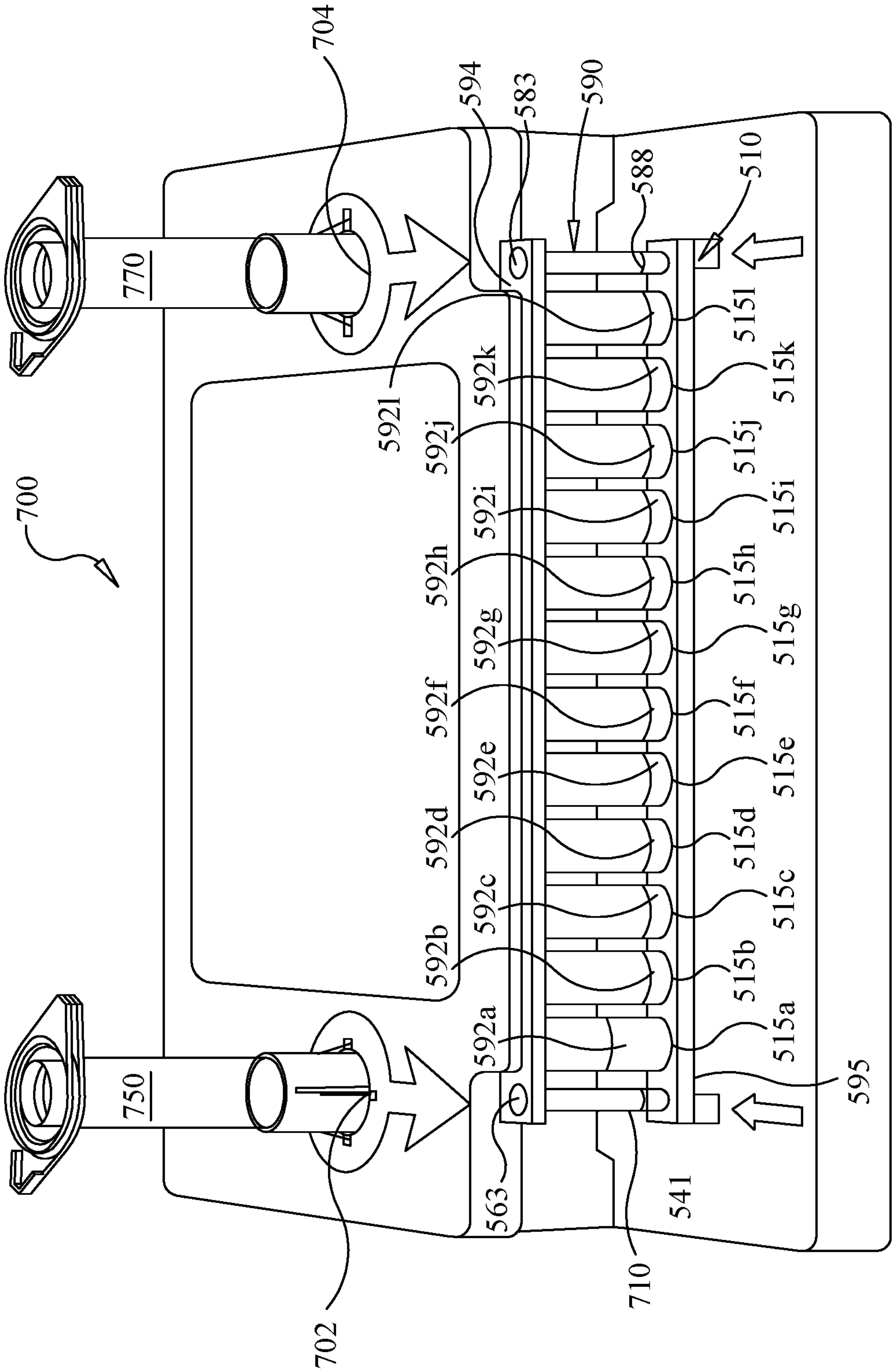
FIG. 33 shows a loading station comparable to FIG. 30, but displaying a different loading station configuration and vials for use with the loading station.
Figure 34:
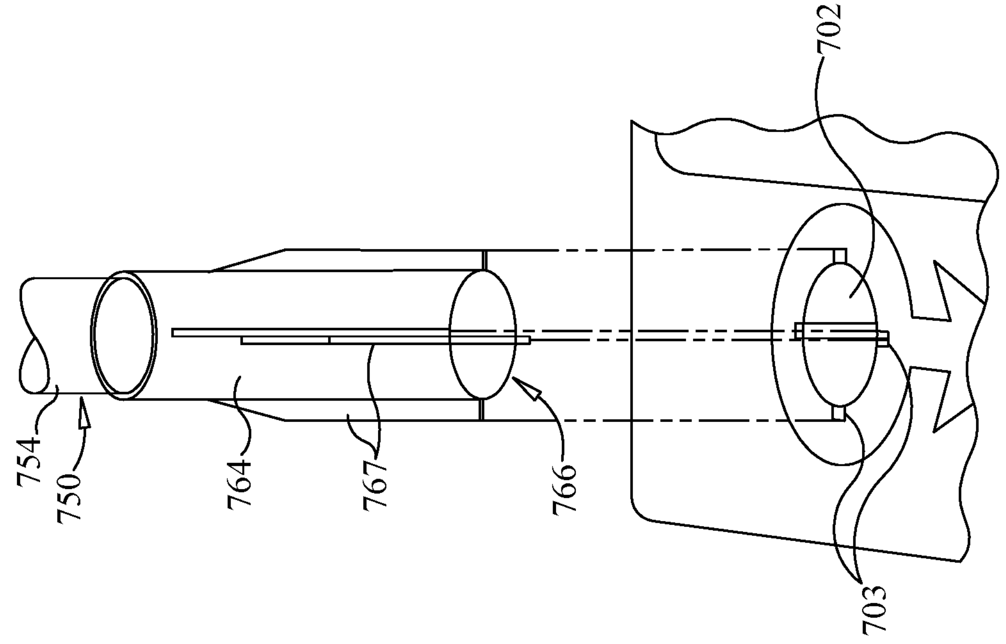
FIG. 34 shows a portion of the sample vial of FIG. 33 and how the sample vial keys to the sample vial receptacle of loading station of FIG. 33.
Figure 35:
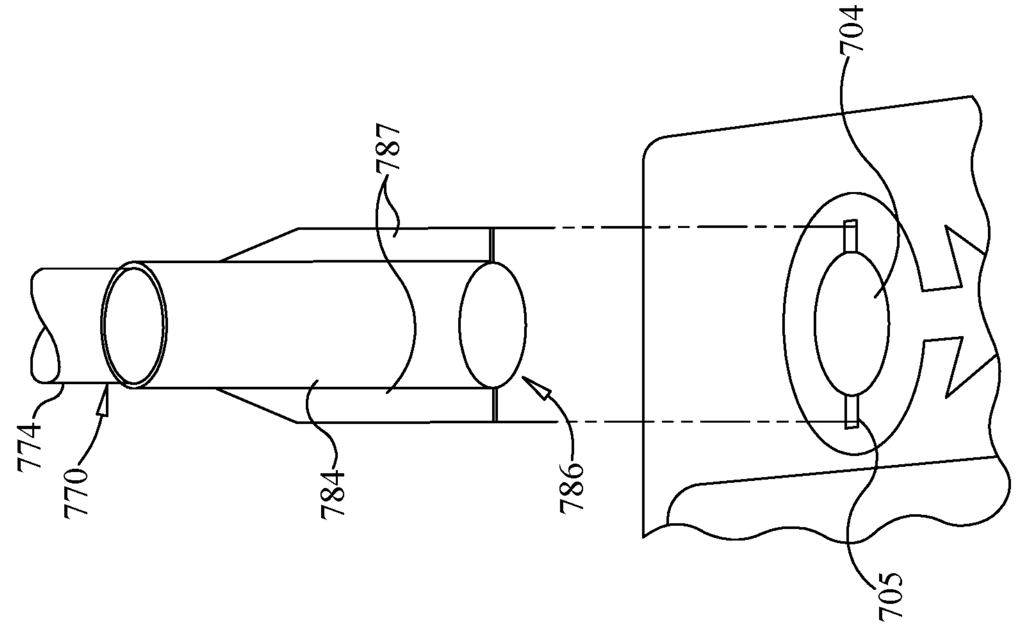
FIG. 35 shows a portion of a hydration vial of FIG. 33 and how the hydration vial keys to the hydration vial receptacle of loading station of FIG. 33.

FIGS. 33-35 show an alternative embodiment to loading station 600 and vials 650, 670, with like numbers indicating similar parts. Loading station 700, as shown in FIG. 8, may be similar to loading station 600, with sample vial receptacle 702 and hydration vial receptacle 704, and slot 710 for receiving pouch 510, similar to those shown in FIG. 2. However, according to at least one embodiment, the shape and location of the receptacles are significantly different between loading station 600 and loading station 700. For instance, in at least one embodiment, as compared to receptacles 602, 604 of loading station 600, receptacles 702 and 704 are closer to pouch 510. With this reduced distance, there is less opportunity for drips to occur upon loading pouch 510. Furthermore, as best seen in FIGS. 34 and 35, bottom cap 764 of sample vial 750 is provided with four relatively short fins 767 that fit within four matching slots 703 of sample vial receptacle 702, and bottom cap 784 of hydration vial 770 is provided with two relatively longer fins 787 that fit within two matching slots 705 of hydration vial receptacle 704. These fins replace the hexagonal portions 666 and 686 of vials 650 and 670, respectively. The larger number of fins 767 on bottom cap 764 prevents sample vial 750 from being placed in hydration vial receptacle 704, and the longer fins 787 of bottom cap 784 prevents hydration vial 770 from being placed in sample vial receptacle 702. However, it is understood that the use of fins of different sizes and numbers is illustrative only, and that different keying systems are within the scope of this disclosure. As discussed above with respect to loading station 600, the receptacles 702, 704 of loading station 700 may be used to assist with twisting off bottom caps 764, 784 from their respective vial bodies 754, 774, to aid with the loading process.

While sample vials 650, 750 and hydration vials 670, 770 are used in the illustrative example for loading of pouch 510, it is understood that these loading vials are suitable for loading any of the pouches disclosed herein, including loading attachment 3900 (see below). They are also suitable for loading other fluidic or microfluidic device, especially fluidic devices that are configured to draw liquid into the fluidic device using vacuum or suction.

Example 3: Filters Between Blisters

One of the problems associated with the use of beads in a closed system is that the beads can sometimes be carried downstream along with the desired sample components. For instance, bead beating beads (e.g., Zr beads) or magnetic beads used in, for example, pouch 510 can sometimes be carried downstream into the blisters used for nucleic acid recovery or PCR amplification. The magnetic bead recovery systems described in relation to, for example, FIGS. 15A-15K may be used to ameliorate this problem, but they do not always eliminate it.

Figure 36B:
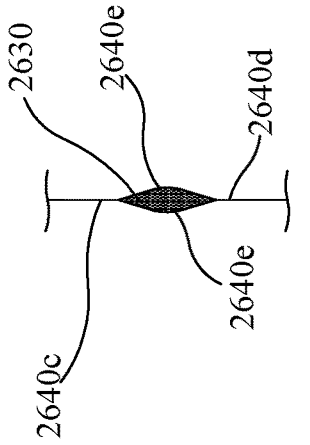
FIGS. 36A-38 schematically illustrate embodiments of a pouch of FIG. 2 with filter elements positioned between the blisters, according to an embodiment of the present invention.
Figure 36A:
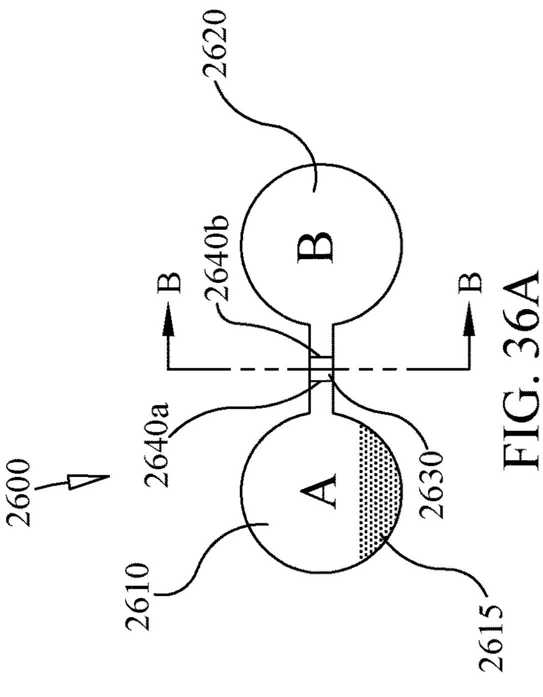

In one embodiment, beads can be prevented from flowing from blister to blister (and through the channels in between) by inserting a filter element in one or more channels in the pouch. Embodiments of such a pouch that includes filter elements are illustrated in FIGS. 36A and 36B, 37A and 37B, and 38. FIGS. 36A and 36B schematically illustrate a pouch 2600 with two illustrative blisters 2610 and 2620 and a filter element 2630 between. In the illustrated embodiment, the first blister 2610 includes a quantity of beads 2615 (e.g., Zr beads or magnetic beads). The filter 2630 is sealed in place such that the beads 2615 cannot be carried from blister 2610 to 2620. The filter 2630 is held in place in the pouch material with a number of seals 2640*a*-2640*e*.

While other containers may be used, illustratively, pouch 2600 is formed of two layers of a flexible plastic film or other flexible material such as polyester, polyethylene terephthalate (PET), polycarbonate, polypropylene, polymethylmethacrylate, and mixtures thereof. In one embodiment, the pouch 2600 is fabricated by laminating at least two layers of plastic film together in such a way that the blisters and channels are formed—e.g., by heat sealing. The selection of filter material depends on the sample type and desired pore size. In general, the pore size of the filter is chosen to be large enough to be able to pass all material in the liquid except the beads. In one embodiment, the pore size of the filter ranges from about 5 to 100 μm (e.g., 50-90 μm or 7-12 μm). Preferably, the filter element is made from a material that is compatible with the material(s) used to form the pouch such that the filter can be heat sealed in the channel without compromising either the pouch or the filter. Suitable filters include, but are not limited to, various polyethylene filters made by Porex (e.g., POR-4903 and XS-POR-7744).

Referring again to FIG. 36A, the filter element is sealed in the channel on both sides of the pouch at each end of the filter element at 2640*a* and 2640*b*. Referring to FIG. 36B, which shows a cross section along line B-B, it can be seen that filter element 2630 is sealed at the top 2640*c* and bottom 2640*d*, and over the surface of the filter 2640*e* to prevent liquid (and beads) from flowing around the filter 2630.

Figure 37B:
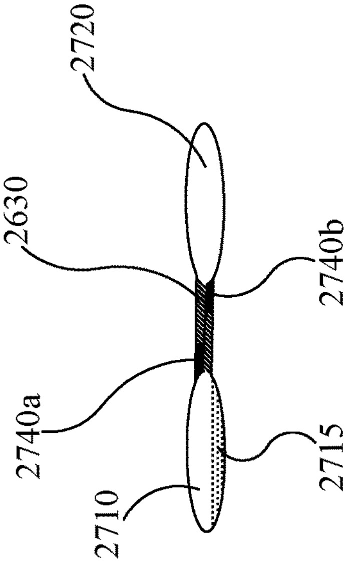
Figure 37A:
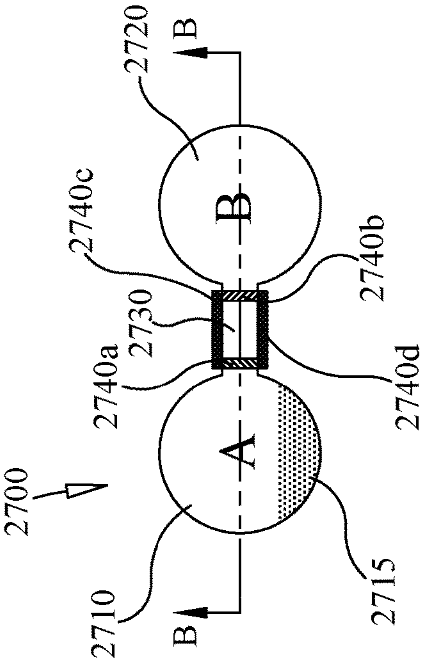

Referring to FIGS. 37A and 37B, another embodiment of a pouch 2700 with a filter element 2730 is illustrated. One potential drawback of the design illustrated in FIGS. 36A and 36B is that the surface area of the filter and, thus, flow rate is limited. The embodiment illustrated in FIGS. 37A and 37B attempts to address this drawback by sealing the filter element in the pouch 2700 differently. In the illustrated embodiment, the pouch includes a first blister 2710, a second blister 2720, and a quantity of beads 2715 (e.g., Zr beads or magnetic beads) that are kept in place by the filter element 2730.

The filter 2730 is sealed in place on the top 2740*c* and bottom 2740*d* as described above. The embodiment illustrated in FIGS. 37A and 37B effectively increases the surface area of the filter 2730 by sealing each end on only one side of the pouch—opposite sides are sealed. This is best seen in FIG. 37B, which is a cross section across the filter element 2730 along line B-B. Seal 2740*a* is applied to one surface of the pouch on one end of the filter element 2730 and seal 2740*b* is applied to the opposite surface of the pouch. By sealing the end on opposite sides of the pouch, liquid is prevented from flowing around the filter 2730 but liquid can flow through the whole surface of the filter.

Figure 38:
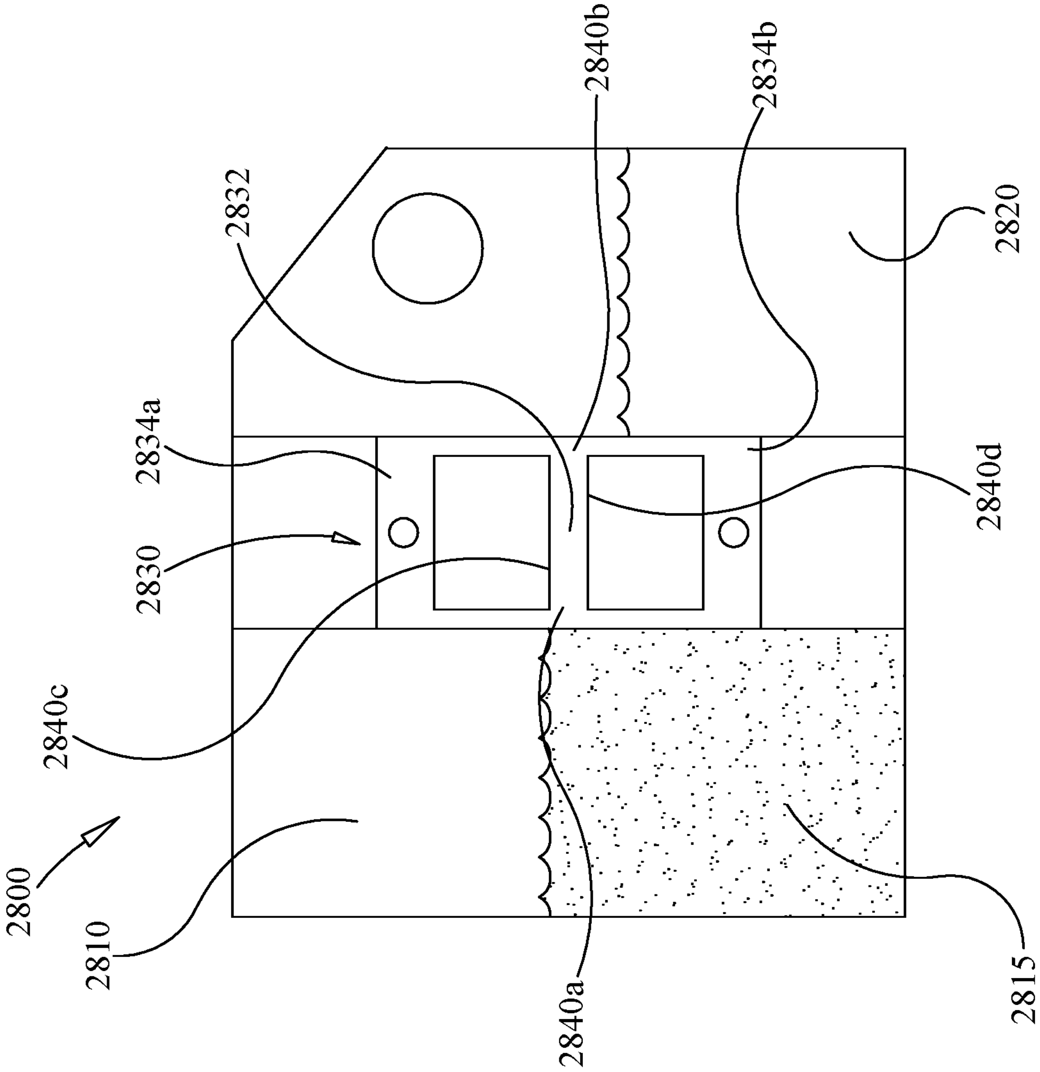

Referring to FIG. 38, another embodiment of a pouch 2800 with a filter element 2830 is illustrated. The embodiment of FIG. 38 is similar to FIG. 37, except the filter element 2830 includes some features that make it easier to place in the desired channel.

Pouch 2800 includes a first blister 2810, a second blister 2820, and a quantity of beads 2815 that are kept in place by the filter element 2830. The filter 2830 is sealed in place on the ends 2840*a* and 2840*b* and the top and bottom to form filter channel 2832, as described similarly above for FIGS. 37A and 37B. The filter element 2830 includes frame elements 2834*a* and 2834*b* at the top and bottom for facilitating placement of the filter element 2830.

In one embodiment, the filter element may be placed in a pouch (e.g., pouch 510 of FIG. 2) in between blisters 522 and 544 (i.e., between the lysis blister and the first downstream blister) and/or between blisters 546 and 548 (i.e., between the blister where the magnetic beads are held and the blister where reagents are mixed in preparation for first-stage PCR in blister 550). Placing a filter between blisters 522 and 544 would prevent bead beating beads from contaminating downstream blisters and channels. Placing a filter between blisters 546 and 548 would additionally prevent Zr beads and magnetic beads from contaminating the PCR amplifications.

Placing a filter between blisters 522 and 544 would alter the protocol described above with respect to moving the magnetic beads between blisters 522, 544, and 546 for nucleic acid recovery. However, because placement of the filter element would allow blister 522 to be completely emptied without fear of sending Zr beads downstream, it is possible that nucleic acid recovery could be rapidly and effectively accomplished by forcing the lysate and the magnetic beads between blisters 544 and 546 or by keeping the magnetic beads in blister 546 and collecting nucleic acids on the beads that are isolated in blister 546 by forcing the lysed sample into and out of blister 546.

Example 4: Alternative Pouch Loading Attachment

Figure 39A:
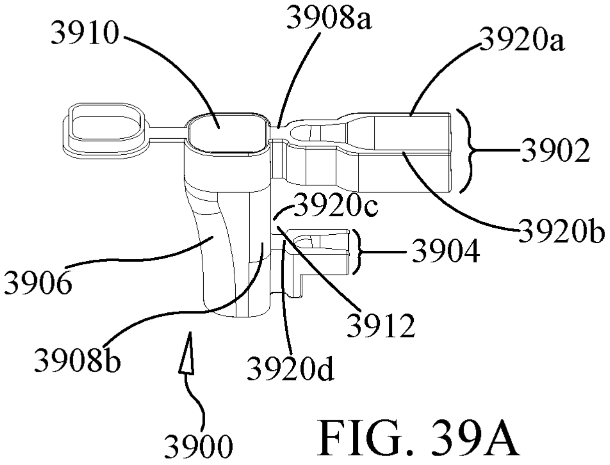
FIGS. 39A-C and 40A-D schematically illustrate a loading station comparable to FIG. 30, but displaying a different loading station configuration and vials for use with the loading station.

FIG. 39A illustrates loading attachment 3900 which may be used to load either samples or hydration fluid into a device including, but not limited to, that illustrated in FIG. 5 (fitment 590). Loading attachment 3900 represents an alternative to the use of sample vial 650 and hydration vial 670 as shown in FIG. 30. Loading attachment 3900 comprises a first clamp 3902 and a second clamp 3904. In the embodiment shown in FIGS. 39A and 39B, first clamp 3902 and second clamp 3904 comprise necks 3908*a* and 3908*b*. Each of necks 3908*a* and 3908*b* comprise a first end and a second end, the first end being in connection with the apex of a horseshoe-shaped member. The horseshoe-shaped members comprise arms 3920*a* and 3920*b* on first clamp 3902 while second clamp 3904 comprises arms 3920*c* and 3920*d*. Each of the arms extend from a curved section, the curved section comprising the apex of the horseshoe-shaped member. A second end of each of necks 3908*a* and 3908*b* connects to the shaft of loading cylinder 3906. One of skill in the art will readily understand that, in addition to necks 3908*a* and 3908*b*, other configuration may be used to form the connections between the two clamps (first clamp 3902 and second clamp 3904) and loading cylinder 3906, and that only one clamp may be needed in some embodiments. Clamps may also be replaced by other clips, clasps, fasteners, and the like known in the art to lock loading attachment 3900 onto the fitment. Loading cylinder 3906 further comprises an opening 3910 at a first end of loading cylinder 3906. Samples to be assayed or hydration fluid may be inserted into loading attachment 3900 through opening 3910. Loading attachment 3900 may be made of durable material known in the art, such as, but not limited to, metals (e.g., pot metal or aluminum), plastics (e.g., polyethylene, polypropylene, polystyrene, polycarbonate, ABS, PEEK, and the like), and metal and plastic composites.

In the illustrative embodiment, second clamp 3904 further comprises a beveled needle 3912. In the embodiment shown in FIG. 39A, beveled needle 3912 extends from the lumen of loading cylinder 3906, through the apex of the horseshoe-shaped member of second clamp 3904, although one of skill in the art will understand that beveled needle 3912 may be positioned elsewhere on loading cylinder 3906. As shown in the embodiment of FIG. 39A, tip 3918 of beveled needle 3912 protrudes from the inner surface of the apex of second clamp 3904.

Figure 39B:
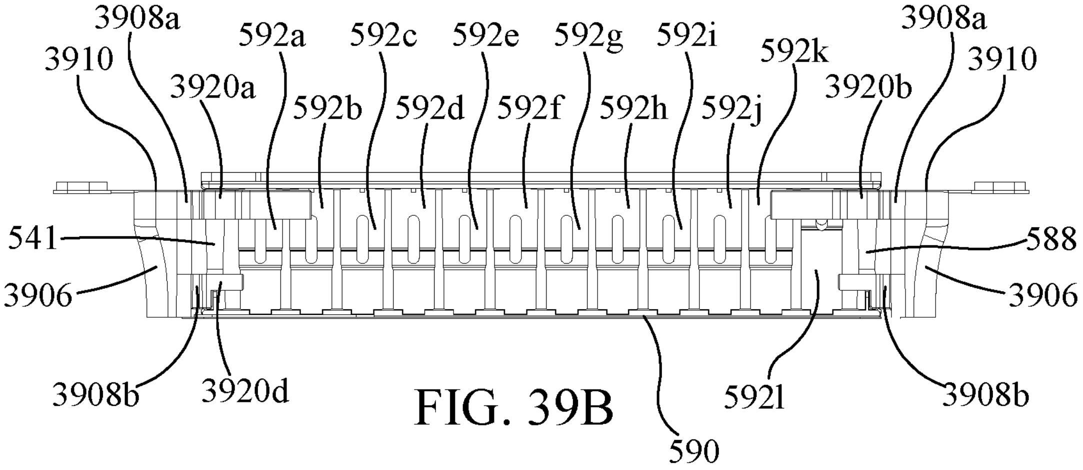
Figure 39C:
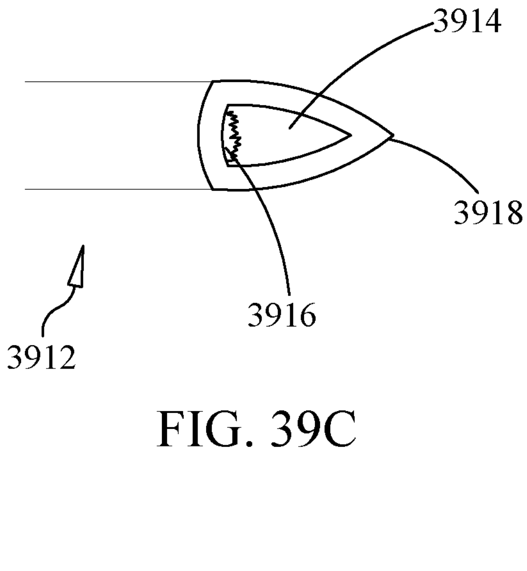

FIG. 39C provides a more detailed illustration of an embodiment of beveled needle 3912. Beveled needle 3912 further comprises opening 3914 which leads into the lumen of beveled needle 3912 and through which sample fluid or hydration fluid may travel when loading attachment 3900 is in connection with a device such as fitment 590. Beveled needle 3912 further comprises blunted heel 3916. In one illustrative method, the heel may be blunted by pressing a blunt tool (e.g., a flathead screwdriver) into the head of the bevel, although one of skill in the art will readily understand that other methods may be employed to blunt the heel of beveled needle 3912.

One embodiment of beveled needle 3912 was created using a 22 gauge standard needle on a syringe. The tip 3918 of the standard needle was ground to form a beveled tip using a Dremel® power tool with a fine abrasive cutting wheel which was fixture at approximately a 30° angle. Care was taken to grind some of the needles tested with a 'cross-face' grinding pattern. The ground face was de-burred using a leather strip. The lumen of the needle was cleared of debris by inserting a 0.015 inch wire in and out of the lumen to push out debris. Upon grinding the tip of the standard needle, blunted heel 3916 was formed inside the bore. As used herein, the heel of a beveled needle is defined as the non-leading edge of the bevel that defines a part of an opening that is opposite the tip of the needle.

Loading attachment 3900 may be connected to a device, such as fitment 590 illustrated in FIGS. 30 and 33, by snapping first clamp 3902 and second clamp 3904 onto fitment 590. Illustratively, FIG. 39B shows an embodiment in which each of arms 3920*a* and 3920*b* of first clamp 3902 and each of arms 3920*c* and 3920*d* of second clamp 3904 are snapped around injection ports 541 and 588, thus holding two of loading attachment 3900 in place. When attached to injection port 541, loading attachment 3900 may be used to transfer sample into fitment 590. FIG. 39B shows a second loading attachment 3900 which is snapped around injection port 588 in which case loading attachment 3900 may be used to transfer hydration fluid into fitment 590.

As each of the two loading attachments 3900 snap into place, beveled needle 3912 may pierce injection port 541 and injection port 588, thereby forming a pathway through which fluids loaded into opening 3910 of each loading cylinder 3906 may travel through the lumen of beveled needle 3912 and into injection ports 541 and 588. As previously discussed in reference to FIG. 30, for example, a vacuum inside pouch 510 (or reduced pressure inside pouch 510 relative to atmospheric pressure or pressure outside pouch 510) can illustratively draw the sample and the hydration fluid from loading cylinders 3906 of each of loading attachments 3900 that have been snapped to injection ports 541 and 588, through the lumen of beveled needle 3912, and into chamber 592*a* of fitment 590.

Figure 40A:
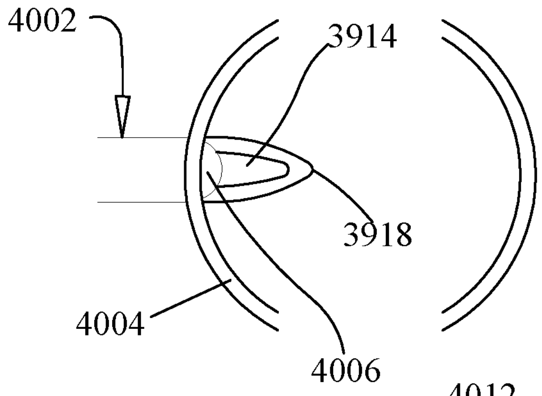
Figure 40B:
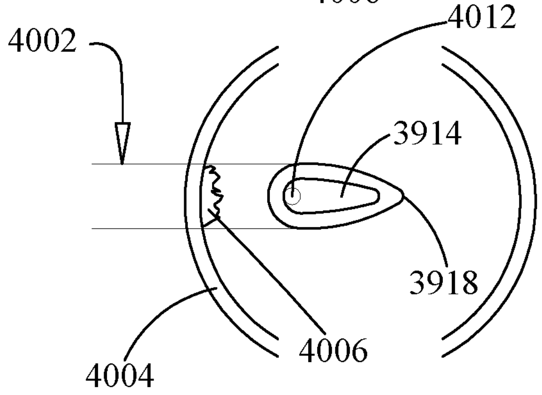
Figure 40C:
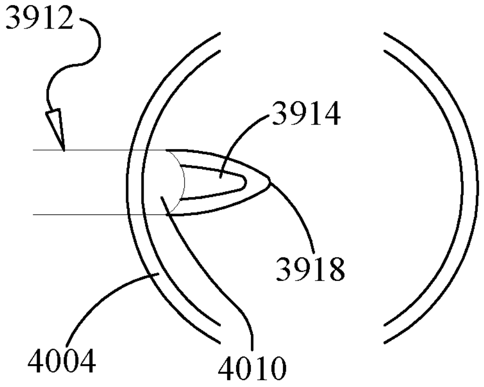
Figure 40D:
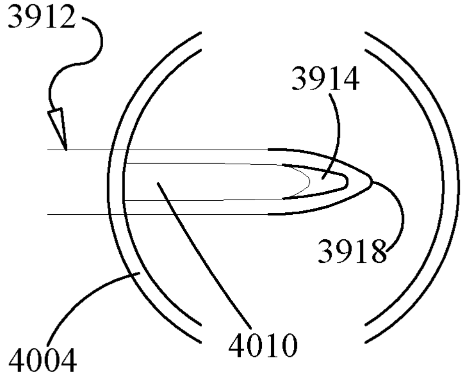

Blunted heel 3916 provides a safety feature by helping to prevent fluid leakage through the openings in injection ports 541 and 588 created by the needle punctures. FIGS. 40A-40D illustrate a comparison of a needle puncture in an injection port made with needles that have either a sharp heel (FIGS. 40A and 40B) or a blunted heel (FIGS. 40C and 40D). FIG. 40A illustrates the point of a needle 4002 that has a sharp heel puncturing wall 4004 of an injection port. The puncture site creates a plug 4006. As needle 4002 proceeds through the puncture site, the sharp heel slices through plug 4006 and may leave a fragment 4012 of plug 4006 adhered to the sharp heel. In this example, the remainder of plug 4006 slides backwards along the shaft of needle 4002. In the absence of the piece of plug 4006 that comprises fragment 4012, the opening created by the needle puncture is not fully covered by plug 4006. This results in an opening in wall 4004 through which fluid may leak out. In the case of injection port 541, such leakage may release infectious or toxic material which may contaminate the user and/or the environment. Furthermore, an opening in either of injection ports 541 or 588 would destroy the closed system by creating point of entry for contaminants. Such contaminants may impact the PCR reaction which may cause false results.

FIGS. 40C and 40D illustrate an embodiment of beveled needle 3912 that comprises a blunted heel and illustrates an example in which it punctures wall 4004 of an injection port. In this example, beveled needle 3912 creates plug 4010. As beveled needle 3912 first pierces wall 4004, the plug it creates is similar to that created by needle 4002 (compare FIGS. 40A and 40C). In contrast, as beveled needle 3912 proceeds through wall 4004, the blunt heel of beveled needle 3912 catches plug 4010 and does not slice through it as does needle 4002. Instead, the blunt heel of beveled needle 3912 may catch and stretch plug 4010 as beveled needle 3912 proceeds through wall 4004. Plug 4010 is not sliced or torn and is able to cover the opening created by the needle puncture and prevent leakage through wall 4004. The closed system is maintained preventing outside material from gaining access to the PCR reagents, preventing loss of reagents, and preventing potentially harmful sample from leaking out to expose the user and/or the environment. Furthermore, there are no used needles to dispose or potentially stick the user because loading attachment 3900 need not be removed from fitment 590 after use. Consequently, beveled needle 3912 remains unexposed after it comes in contact with samples and/or reagents.

Example 5: Alternative Bead Beater Systems

To better assess the paddle bead beater systems described herein above and in reference to FIGS. 41A-46, the performance of a prototype paddle bead beater system was compared to the performance of the present commercial FilmArray® bead beater system described, for example, in U.S. Pat. Nos. 8,895,295 and 9,102,911, the entireties of which were incorporated by reference elsewhere herein.

Figure 47:
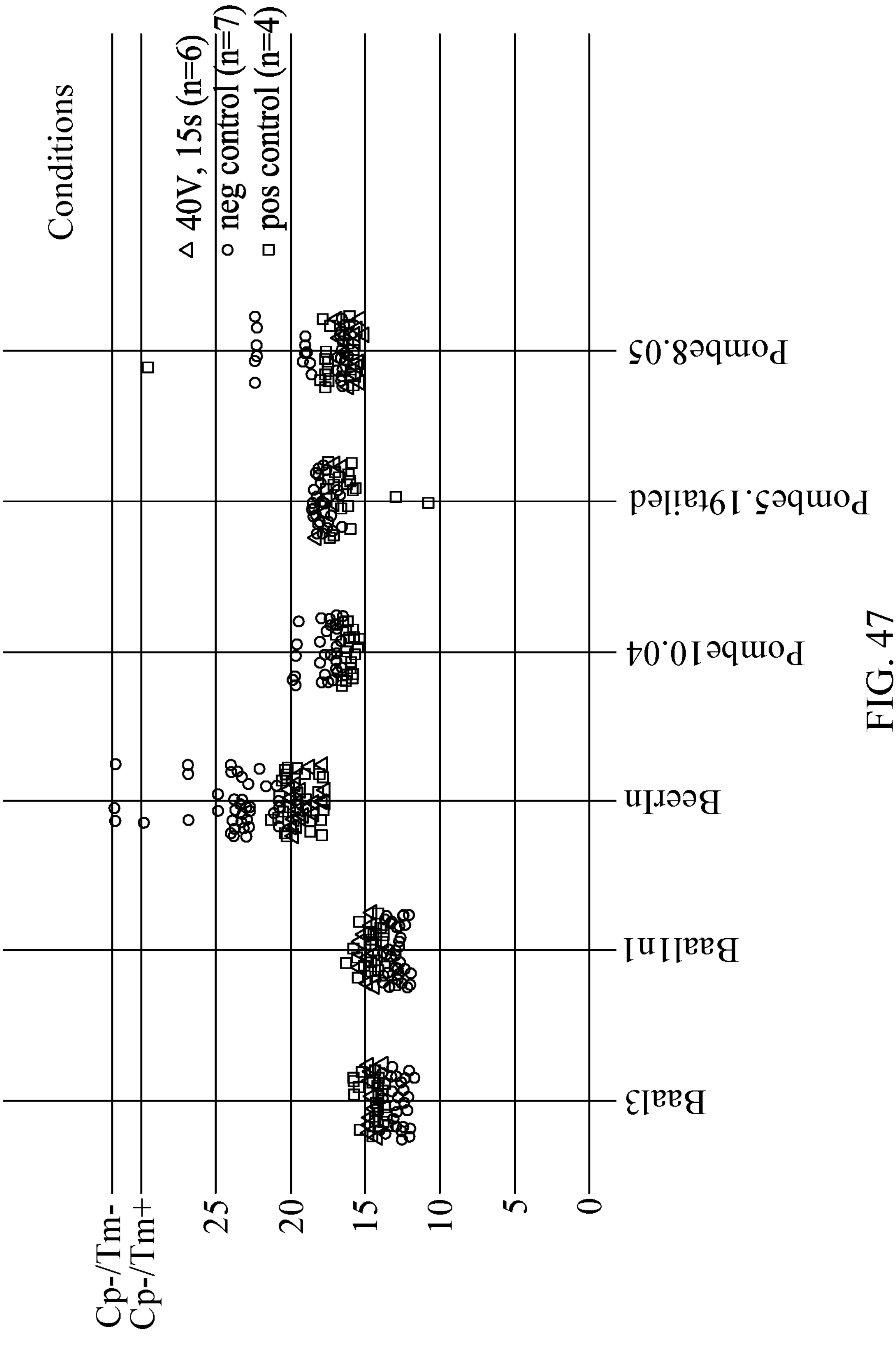
FIG. 47 is a graph illustrating crossing point (Cp) data for various sample targets as a function of bead beater type.

In a first experiment illustrated in FIG. 47, performance of the standard FilmArray® bead beater system (□), a paddle bead beater (Δ), and a no bead beater control (○) were compared with different DNA and RNA controls and intact purified yeast spores. The standard FilmArray® bead beater system is illustrated herein, for example, in FIGS. 3A, 3B, and 13 and a paddle bead beater system is illustrated, for example, in FIGS. 41A-42C. Yeast spores were chosen because they small and durable and are generally difficult to lyse. Thus, the extent of yeast spore lysing is a good measure of the ability of a bead beater system to lyse difficult sample types. The yeast spores in these experiments were DNase treated prior to preparation for lysis to remove any possibility of there being any free, amplifiable DNA in the sample. The DNA and RNA template controls, which are not contained in cells and do not need to be lysed to be amplified in the FilmArray pouch, serves to monitor for excessive lysis, which would be evidenced by degraded or destroyed DNA and RNA templates. The DNA and RNA templates also serve as internal quantification controls.

In the illustrative experiment, each pouch run was divided into two parts: (1) injection and bead beating (or lack thereof), and (2) the remaining run using a standard protocol, including nucleic acid template recovery, first-stage PCR, second-stage PCR, and fluorescent detection. Samples in FilmArray® bead beater pouches (n=4) were subjected to bead beating for one minute at approximately 12,000 RPM. Samples in paddle bead beater pouches (n=6) were subjected to beat beating for 15 seconds at 8800 RPM (40v). No bead beater control pouches (n=7) were bead beaten for 1 second in the FilmArray instrument. One second of bead beating is generally not considered to be a sufficient time to achieve any meaningful lysis, but it does serve as a control for any lysis that may occur by placing the pouch in the instrument for the first part of the experiment and removing it, and placing the pouch into a second instrument for the second part of the pouch run.

In the results illustrated in FIG. 47, amplification of the RNA template controls (Baal3 and BaalIn1) were not affected by FilmArray bead beating, paddle bead beating, or no bead beating. That is, in this illustrative example, all samples had similar crossing points (Cps) regardless of treatment. The pombe controls (pombe 10.04, pombe 5.19 tailed, and pombe 8.05) are different targets that are all amplified from freeze dried *Schizosaccharomyces pombe* cells, which are relatively easy to lyse (possibly due to the freeze drying) and were also relatively unaffected by the various lysis protocols. That is, all pombe assay had similar Cps regardless of treatment. Pombe 8.05 does appear to show some variability based on treatment, but because the pombe assays are all amplicons of the same organism, it is not clear if this variability is relevant to lysis or if it is artefactual. However, the yeast spores (BeerIn) show great variability depending on lysis protocol. The negative (i.e., no lysis) controls show poor lysis, a wide spread of crossing points, and a few failed assays. In contrast, FilmArray bead beating and paddle bead beating performed similarly with paddle bead beating possibly showing a tighter distribution of Cps. Surprisingly, paddle bead beating achieved comparable results with only 15 seconds of bead beating time versus one minute of bead beating in the FilmArray system.

Figure 48A:
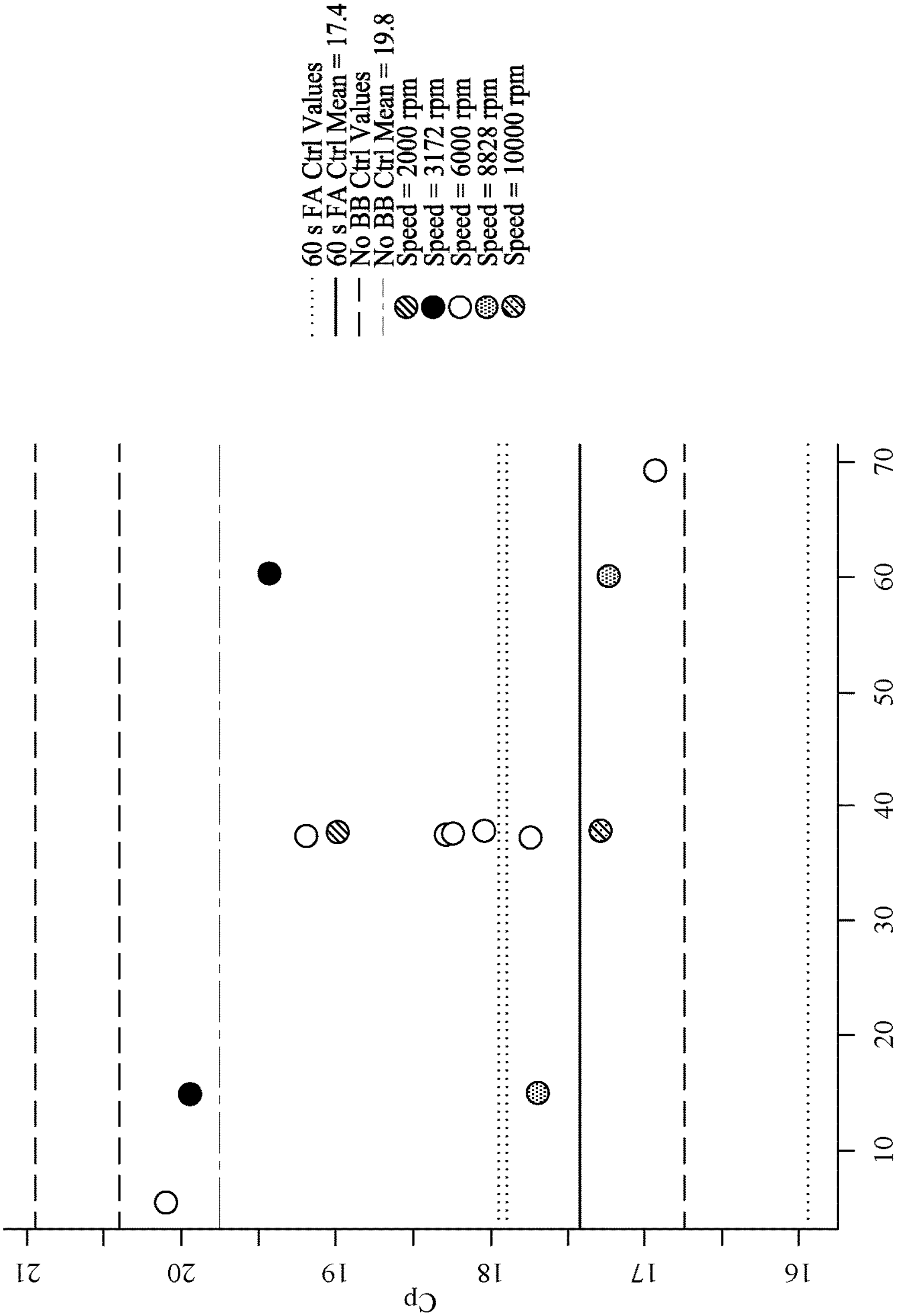
FIGS. 48A-48C are graphs illustrating crossing points (Cps) for different cells types lysed at different speeds of paddle bead beating as compared to compared to FilmArray bead beating and Cps.
Figure 48B:
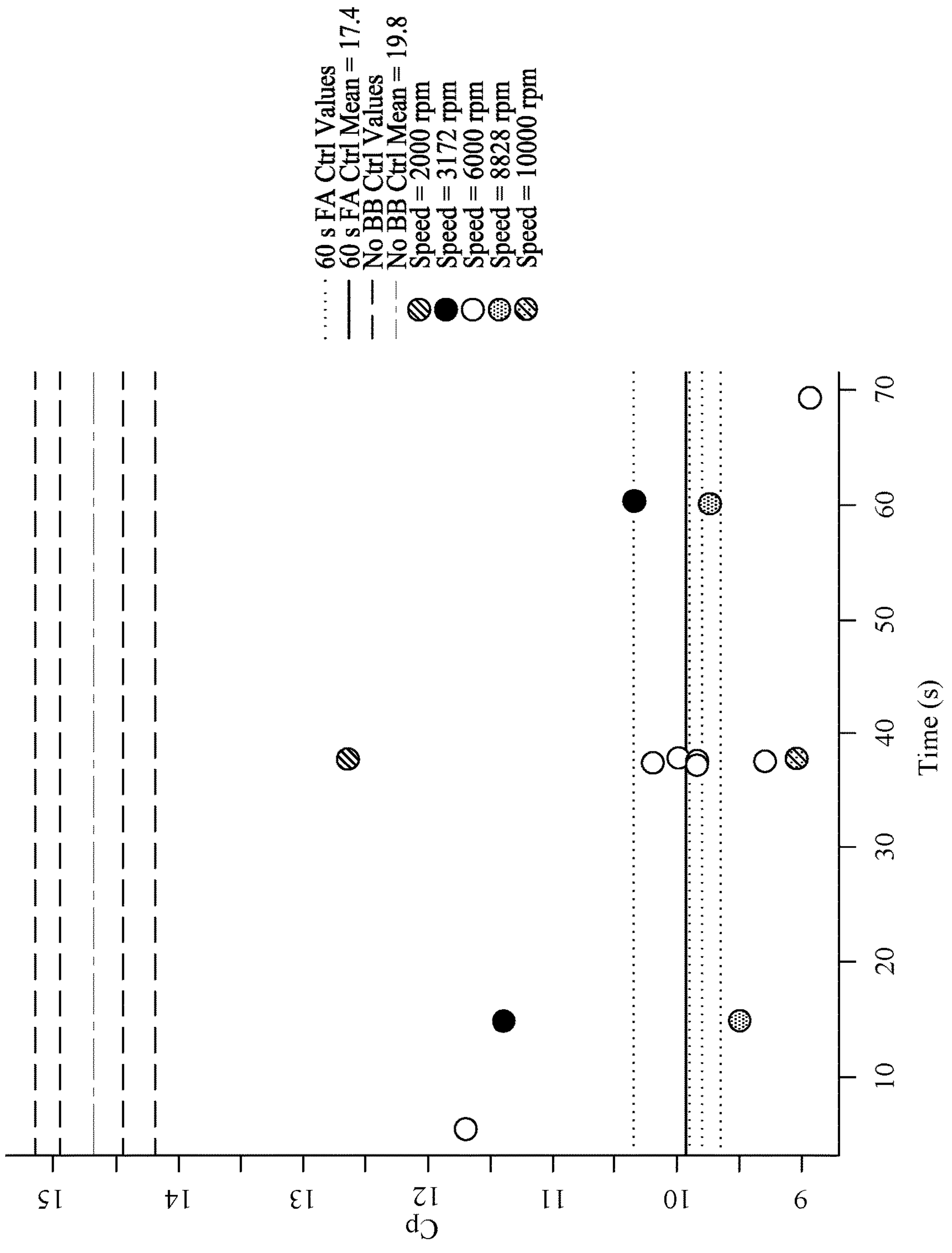
Figure 48C:
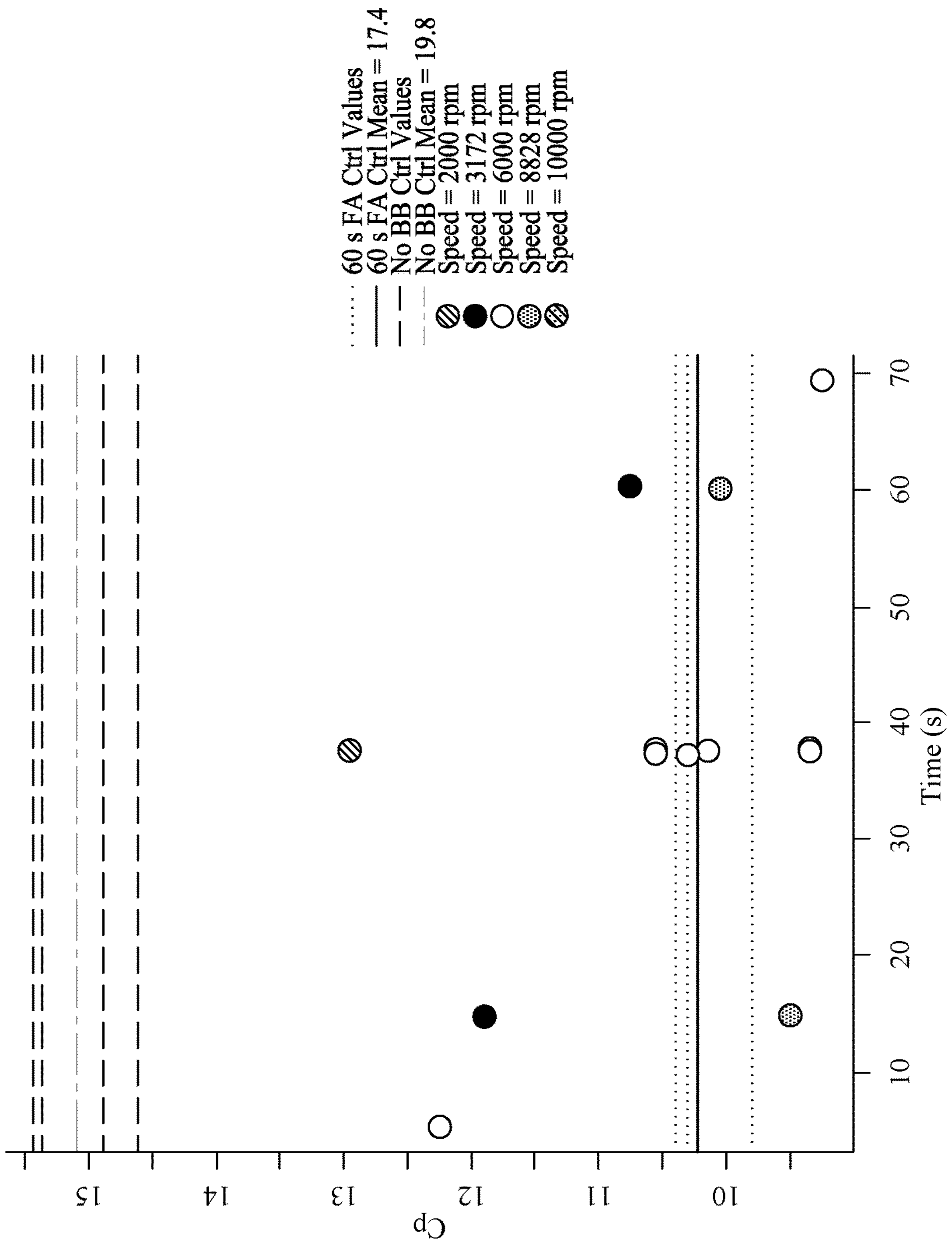

Referring now to FIGS. 48A-48C, the Cps for different cells types lysed at different speeds and different times of paddle bead beating were compared to FilmArray data. FIGS. 48A-48C are plots of Time versus Cp for each assay. The points in the plots are given symbols according to their speed (see legends); each point on the plot represents an n of 2. Horizontal lines represent control data and the horizontal lines mean either no bead beating or 60 seconds of FilmArray bead beating (see figure legends).

FIG. 48A illustrates bead beating results for yeast spores. Low paddle bead beater speeds (2000 rpm and 3172 rpm) produced poor results (i.e., late Cps). Higher speeds, at 8800 and 10000 rpm, and longer times of 60 and 69 seconds tended to produce the earliest Cps. It is noted that at 8800 rpm and 15 seconds of bead beating, results were comparable to and maybe even better than FilmArray bead beating conditions.

FIGS. 48B and 48C illustrate results for Anthrax spores (delta Sterne). Like yeast spores, anthrax spores are small and robust and are generally difficult to lyse. Again, low paddle bead beater speeds (2000 rpm and 3172 rpm) produced poor results (i.e., late Cps). Higher speeds, at 8800 and 10000 rpm, and longer times of 60 and 69 produced more satisfactory results and, again, 8800 rpm and 15 seconds of bead beating results were comparable to and maybe even better than FilmArray bead beating conditions. For all of these conditions, the paddle bead beater at higher speeds (i.e., 6000 rpm or higher) performs as well or better than the 60 second FilmArray control runs.

The present invention may be embodied in other specific forms without departing from its spirit or essential characteristics. The described embodiments are to be considered in all respects only as illustrative and not restrictive. The scope of the invention is, therefore, indicated by the appended claims rather than by the foregoing description. While certain embodiments and details have been included herein and in the attached invention disclosure for purposes of illustrating the invention, it will be apparent to those skilled in the art that various changes in the methods and apparatus disclosed herein may be made without departing from the scope of the invention, which is defined in the appended claims. All changes which come within the meaning and range of equivalency of the claims are to be embraced within their scope.

What is claimed is:

1. An instrument for processing a sample, comprising an opening for receiving a flexible reaction container between a first support member and a second support member, the flexible reaction container comprising:

a loading attachment comprising a plurality of reagent zones, a plurality of reaction zones, and a plurality of sealable flow paths, each having a first side connecting the loading attachment to one or more fill ports, at least one of which is configured for receiving the sample, and a second side connected to at least one of the plurality of reaction zones, the sealable flow paths providing the only access from the one or more fill ports to the plurality of reagent zones such that when the first side of all of the one or more sealable paths are sealed, the container is fully closed;

a heat sealing system comprising a plurality of heat seal elements provided on at least one of the support members so as to contact the loading attachment and the plurality of sealable flow paths, wherein the plurality of heat seal elements include a number of individually controlled ceramic heater elements associated with each one of the plurality of sealable flow paths, wherein the ceramic heater elements are self-regulating heater elements that include positive thermal coefficient (PTC) heating elements configured to heat to a temperature in a range of about 180° C. to about 220° C., each of the individually controlled ceramic heater elements further comprise a base affixing the individually controlled ceramic heater element to the support member and a spring member associated with the base, the spring member allowing each individually controlled ceramic heater element to be flexibly mounted to the support member, and wherein the spring members are selected such that the plurality of individually controlled ceramic heater elements are configured to seal each of the plurality of sealable flow paths within 1-5 seconds at the temperature in the range of about 180° C. to about 220° C. when the flexible reaction container is enclosed in the instrument.

2. The instrument of claim 1, wherein the PTC heating elements are self-limiting.

3. The instrument of claim 1, wherein the individually controlled heater elements are disposed on at least one of the support members and further comprise the self-regulating heater elements, a housing, and an electrical connection to a power source.

4. The instrument of claim 1, further comprising:

a plunging system including a plurality of pistons positioned and configured in the instrument for moving the sample from the loading attachment into the reaction zones, and wherein the container is sealed with the heat sealing system prior to actuation of the plunging system.

5. The instrument of claim 4, further comprising a sample preparation system associated with one of the first support member or the second support member, the sample preparation system including components to effect cell lysis and nucleic acid recovery in one or more of the reaction zones the flexible reaction container.

6. The instrument of claim 5, further comprising an optics system mounted in the instrument and positioned to produce and detect fluorescence in at least one of the reaction zones of the container.

7. The instrument of claim 6, further comprising:

a first heating/cooling device provided on one of the first support member or the second support member, the first heating/cooling device configured for thermal cycling contents of at least one of the reaction zones; and a second heating/cooling device provided on one of the first support member or the second support member, the second heating/cooling device configured for thermal cycling contents of another one of the reaction zones.

8. The instrument of claim 7, further comprising a computer for controlling at least one of the plurality of heat seal elements, the plunging system, the sample preparation system, the optics system, the first heating/cooling device, or the second heating/cooling device.

9. The instrument of claim 1, wherein the spring members are selected to regulate the amount of pressure that the individually controlled ceramic heater elements apply to the plurality of sealable flow paths when the flexible reaction container is enclosed in the instrument.

10. The instrument of claim 1, wherein the spring members are selected such that each individually controlled ceramic heater element applies about 0.5 to 2 pounds of pressure to each of the plurality of sealable flow paths when the flexible reaction container is enclosed in the instrument.

11. An instrument for processing a sample, comprising an opening for receiving a flexible reaction container between a first support member and a second support member, the flexible reaction container comprising:

a plurality of sealable flow paths providing the only access from one or more fill ports to one or more reagent zones such that when the plurality of sealable flow paths are sealed, access to the one or more reagent zones via the fill ports is closed, a heat sealing system comprising a plurality of heat seal elements provided on at least one of the support members so as to contact the plurality of sealable flow paths, wherein the plurality of heat seal elements include a number of individually controlled positive thermal coefficient (PTC) heating elements associated with each of the plurality of sealable flow paths, the PTC elements configured to heat to a temperature in a range of about 180° C. to about 220° C., wherein PTC heating elements are compressed against the plurality of sealable flow paths when the flexible reaction container is enclosed in the instrument with an amount of pressure selected to allow the PTC heating elements to seal each of the plurality of sealable flow paths within 1-5 seconds at the temperature in the range of about 180° C. to about 220° C., and wherein each of the individually controlled PTC heating elements is configured to apply about 0.5 to 2 pounds of pressure to each of the plurality of sealable flow paths when the flexible reaction container is enclosed in the instrument, and wherein, at about 0.5 to 2 pounds of pressure, the plurality of PTC heating elements are configured to irreversibly seal each of the plurality of sealable flow paths within 1-5 seconds at the temperature in the range of about 180° C. to about 220° C.

12. The instrument of claim 11, wherein the PTC heating elements are self-limiting.

13. The instrument of claim 11, wherein the PTC heating elements are disposed on at least one of the support members and further comprise a housing, and an electrical connection to a power source.

14. The instrument of claim 11, each of the PTC heating elements further comprise:

a base affixing each individually controlled PTC heating element to the support member and a spring member associated with the base, the spring member allowing each PTC heating element to be flexibly mounted to the support member, and wherein the spring members are selected to regulate the amount of pressure that the PTC heating elements apply to the plurality of sealable flow paths when the flexible reaction container is enclosed in an instrument between a first support member and a second support member.

15. The instrument of claim 14, wherein the spring members are selected such that each PTC heating element applies about 0.5 to 2 pounds of pressure to each of the plurality of sealable flow paths when the flexible reaction container is enclosed in the instrument.

16. An instrument for processing a sample, comprising:

a flexible reaction container, comprising:

a loading attachment comprising a plurality of reagent zones;

a plurality of reaction zones; and a plurality of sealable flow paths, each having a first side connecting the loading attachment to one or more fill ports, at least one of which is configured for receiving the sample, and a second side connected to at least one of the plurality of reaction zones, the sealable flow paths providing the only access from the one or more fill ports to the plurality of reagent zones such that when the first side of all of the one or more sealable paths are sealed, the container is fully closed;

the instrument for processing the sample, comprising:

an opening for receiving a flexible reaction container between a first support member and a second support member; and a heat sealing system comprising a plurality of heat seal elements provided on at least one of the support members so as to irreversibly seal each of the plurality of sealable flow paths, the plurality of heat seal elements including a number of individually controlled ceramic heater elements associated with each one of the plurality of sealable flow paths;

wherein the ceramic heater elements are self-regulating heater elements that include positive thermal coefficient (PTC) heating elements configured to heat to a temperature in a range of about 180° C. to about 220° C.

* * * * *